(12) United States Patent
Liu et al.

(10) Patent No.: US 8,618,212 B2
(45) Date of Patent: Dec. 31, 2013

(54) FUNCTIONALIZED MATRICES FOR DISPERSION OF NANOSTRUCTURES

(71) Applicant: Nanosys, Inc., Palo Alto, CA (US)

(72) Inventors: Mingjun Liu, Campbell, CA (US); Robert S. Dubrow, San Carlos, CA (US); William P. Freeman, San Mateo, CA (US); Adrienne D. Kucma, Dublin, CA (US); J. Wallace Parce, Palo Alto, CA (US)

(73) Assignee: Nanosys, Inc., Milpitas, CA (US)

( * ) Notice: Subject to any disclaimer, the term of this patent is extended or adjusted under 35 U.S.C. 154(b) by 0 days.

(21) Appl. No.: 13/633,769

(22) Filed: Oct. 2, 2012

(65) Prior Publication Data

US 2013/0043433 A1    Feb. 21, 2013

Related U.S. Application Data

(62) Division of application No. 12/799,813, filed on Apr. 29, 2010, now Pat. No. 8,283,412.

(60) Provisional application No. 61/215,054, filed on May 1, 2009.

(51) Int. Cl.
*C08L 83/04*   (2006.01)
*H01B 1/12*    (2006.01)

(52) U.S. Cl.
USPC .......................................... 524/588; 252/500

(58) Field of Classification Search
None
See application file for complete search history.

(56) References Cited

U.S. PATENT DOCUMENTS

| 2,381,366 | A |   | 8/1945  | Patnode                  |
|-----------|---|---|---------|--------------------------|
| 3,627,724 | A | * | 12/1971 | Lambert ............ 523/211 |
| 4,093,777 | A |   | 6/1978  | Heine et al.             |
| 4,130,708 | A | * | 12/1978 | Friedlander et al. ... 528/28 |

(Continued)

FOREIGN PATENT DOCUMENTS

| WO | 9927584    | 6/1999  |
| WO | 03092081   | 11/2003 |
| WO | 2005022120 | 3/2005  |
| WO | 2008013780 | 3/2008  |

OTHER PUBLICATIONS

Technical data sheet for ZnO-350 from Sumitomo Osaka Cement, 1995, 3 pages.*

(Continued)

*Primary Examiner* — Robert S Loewe
(74) *Attorney, Agent, or Firm* — Andrew L. Filler

(57) ABSTRACT

Matrixes doped with semiconductor nanocrystals are provided. In certain embodiments, the semiconductor nanocrystals have a size and composition such that they absorb or emit light at particular wavelengths. The nanocrystals can comprise ligands that allow for mixing with various matrix materials, including polymers, such that a minimal portion of light is scattered by the matrixes. The matrixes are optionally formed from the ligands. The matrixes of the present invention can be used as refractive index matching components, filters and antireflective coatings on optical devices and as down-converting layers. Processes for producing matrixes comprising semiconductor nanocrystals are also provided. Nanostructures having high quantum efficiency, small size, and/or a narrow size distribution are also described, as are methods of producing indium phosphide nanostructures and core-shell nanostructures with Group II-VI shells.

21 Claims, 43 Drawing Sheets

(56) References Cited

U.S. PATENT DOCUMENTS

| | | |
|---|---|---|
| 4,181,753 A | 1/1980 | Fischer |
| 4,258,080 A | 3/1981 | Sonoda et al. |
| 4,263,339 A | 4/1981 | Fischer |
| 4,426,431 A * | 1/1984 | Harasta et al. .................. 430/14 |
| 5,023,139 A | 6/1991 | Birnboim et al. |
| 5,124,278 A | 6/1992 | Bohling et al. |
| 5,126,204 A | 6/1992 | Tono et al. |
| 5,196,229 A | 3/1993 | Chau |
| 5,230,957 A | 7/1993 | Lin |
| 5,260,957 A | 11/1993 | Hakimi et al. |
| 5,262,357 A | 11/1993 | Alivisatos et al. |
| 5,330,791 A | 7/1994 | Aihara et al. |
| 5,376,307 A | 12/1994 | Hagiwara et al. |
| 5,396,148 A | 3/1995 | Endo et al. |
| 5,505,928 A | 4/1996 | Alivisatos et al. |
| 5,518,808 A | 5/1996 | Bruno et al. |
| 5,532,023 A | 7/1996 | Vogel et al. |
| 5,537,000 A | 7/1996 | Alivisatos et al. |
| 5,595,593 A * | 1/1997 | Burns et al. .................. 106/499 |
| 5,645,752 A | 7/1997 | Weiss et al. |
| 5,707,139 A | 1/1998 | Haitz |
| 5,744,233 A | 4/1998 | Opitz et al. |
| 5,751,018 A | 5/1998 | Alivisatos et al. |
| 5,777,433 A | 7/1998 | Lester et al. |
| 5,853,887 A | 12/1998 | Yoshimoto et al. |
| 5,882,779 A | 3/1999 | Lawandy |
| 5,892,084 A | 4/1999 | Janeiro et al. |
| 5,958,591 A | 9/1999 | Budd |
| 5,985,173 A | 11/1999 | Gray et al. |
| 5,990,479 A | 11/1999 | Weiss et al. |
| 6,084,250 A | 7/2000 | Justel et al. |
| 6,114,038 A | 9/2000 | Castro et al. |
| 6,147,363 A | 11/2000 | Udagawa |
| 6,153,123 A | 11/2000 | Hampden-Smith et al. |
| 6,179,912 B1 | 1/2001 | Barbera-Buillem et al. |
| 6,180,029 B1 | 1/2001 | Hampden-Smith et al. |
| 6,207,229 B1 | 3/2001 | Bawendi et al. |
| 6,225,198 B1 | 5/2001 | Alivisatos et al. |
| 6,251,303 B1 | 6/2001 | Bawendi et al. |
| 6,278,135 B1 | 8/2001 | Srivastava et al. |
| 6,294,800 B1 | 9/2001 | Duggal et al. |
| 6,306,610 B1 | 10/2001 | Bawendi et al. |
| 6,322,901 B1 | 11/2001 | Bawendi et al. |
| 6,326,144 B1 | 12/2001 | Bawendi et al. |
| 6,344,520 B1 | 2/2002 | Greene |
| 6,350,552 B1 * | 2/2002 | Livengood et al. ...... 430/108.22 |
| 6,353,073 B1 | 3/2002 | Biggs et al. |
| 6,426,513 B1 | 7/2002 | Bawendi et al. |
| 6,429,583 B1 | 8/2002 | Levinson et al. |
| 6,440,213 B1 | 8/2002 | Alivisatos et al. |
| 6,468,808 B1 | 10/2002 | Nie et al. |
| 6,482,672 B1 | 11/2002 | Hoffman et al. |
| 6,501,091 B1 | 12/2002 | Bawendi et al. |
| 6,573,535 B2 | 6/2003 | Hori et al. |
| 6,576,291 B2 | 6/2003 | Bawendi et al. |
| 6,602,671 B1 | 8/2003 | Bawendi et al. |
| 6,607,829 B1 | 8/2003 | Mikulec et al. |
| 6,617,583 B1 | 9/2003 | Bawendi et al. |
| 6,660,281 B1 * | 12/2003 | Nakanishi et al. ............ 424/401 |
| 6,682,596 B2 | 1/2004 | Zehnder et al. |
| 6,696,299 B2 | 2/2004 | Empedocles et al. |
| 6,711,426 B2 | 3/2004 | Benaron et al. |
| 6,713,586 B2 | 3/2004 | Greene |
| 6,734,465 B1 | 5/2004 | Taskar et al. |
| 6,781,166 B2 | 8/2004 | Lieber et al. |
| 6,783,855 B1 | 8/2004 | Dobson et al. |
| 6,788,453 B2 | 9/2004 | Banin et al. |
| 6,803,719 B1 | 10/2004 | Miller et al. |
| 6,815,064 B2 | 11/2004 | Treadway et al. |
| 6,819,692 B2 | 11/2004 | Bawendi et al. |
| 6,855,202 B2 | 2/2005 | Alivisatos et al. |
| 6,861,155 B2 | 3/2005 | Bawendi et al. |
| 6,864,626 B1 | 3/2005 | Schlamp et al. |
| 6,870,311 B2 | 3/2005 | Mueller et al. |
| 6,884,478 B2 | 4/2005 | Alivisatos et al. |
| 6,921,496 B2 | 7/2005 | Anderson et al. |
| 6,933,535 B2 | 8/2005 | Steigerwald et al. |
| 6,949,206 B2 | 9/2005 | Whiteford et al. |
| 7,060,243 B2 | 6/2006 | Bawendi et al. |
| 7,091,656 B2 | 8/2006 | Murazaki et al. |
| 7,175,778 B1 | 2/2007 | Bhargava et al. |
| 7,267,875 B2 | 9/2007 | Whiteford et al. |
| 7,326,908 B2 | 2/2008 | Sargent et al. |
| 7,332,701 B2 | 2/2008 | Van Arendonk et al. |
| 7,374,807 B2 | 5/2008 | Parce et al. |
| 7,420,005 B2 * | 9/2008 | Hojo et al. ...................... 522/81 |
| 7,432,642 B2 | 10/2008 | Murazaki |
| 7,645,397 B2 | 1/2010 | Parce et al. |
| 7,834,121 B2 | 11/2010 | Mowrer et al. |
| 8,071,079 B2 | 12/2011 | DeCaire et al. |
| 2002/0066401 A1 | 6/2002 | Peng et al. |
| 2002/0071952 A1 | 6/2002 | Bawendi et al. |
| 2002/0105004 A1 | 8/2002 | Hori et al. |
| 2002/0130311 A1 | 9/2002 | Lieber et al. |
| 2003/0066998 A1 | 4/2003 | Lee |
| 2003/0175004 A1 | 9/2003 | Garito et al. |
| 2003/0185771 A1 * | 10/2003 | Kamei et al. .................... 424/59 |
| 2003/0186003 A1 * | 10/2003 | Nakano et al. ............... 428/32.1 |
| 2003/0226498 A1 | 12/2003 | Alivisatos et al. |
| 2004/0007169 A1 | 1/2004 | Ohtsu et al. |
| 2004/0033270 A1 | 2/2004 | Kropf et al. |
| 2004/0178390 A1 | 9/2004 | Whiteford et al. |
| 2004/0245912 A1 | 12/2004 | Thurk et al. |
| 2005/0161666 A1 | 7/2005 | Park et al. |
| 2005/0179364 A1 | 8/2005 | Murazaki |
| 2005/0234416 A1 | 10/2005 | Kropf et al. |
| 2006/0001119 A1 | 1/2006 | Liu et al. |
| 2006/0040103 A1 | 2/2006 | Whiteford et al. |
| 2006/0157686 A1 | 7/2006 | Jang et al. |
| 2007/0034833 A1 | 2/2007 | Parce et al. |
| 2007/0185261 A1 | 8/2007 | Lee et al. |
| 2007/0213492 A1 | 9/2007 | Mowrer et al. |
| 2008/0090947 A1 | 4/2008 | Shin et al. |
| 2008/0118755 A1 | 5/2008 | Whiteford et al. |
| 2010/0006005 A1 | 1/2010 | Roesch et al. |
| 2010/0140551 A1 | 6/2010 | Parce et al. |
| 2011/0189102 A1 | 8/2011 | Kairdolf et al. |

OTHER PUBLICATIONS

Information sheet for Cab-O-Sil HS-5 from Cabot Corporation, 1 page, 2008.*

Xu, L. et al. "Reduced photo-instability of luminescence spectrum of core-shell CdSe/CdS nanocrystals" J. Mater. Sci (2000) 35:1375-1378.

Xu, S. et al. "Rapid synthesis of high-quality InP nanocrystals" J. Am. Chem. Soc. (2006) 128-1054-1055.

Gelest catalog entitled "Reactive Silicons: Forging New Polymer Links" (2004) 4 pages.

Akcora, P. et al. "Structural and magnetic characterization of norbornene-deuterated norbornene dicarboxylic acid diblock copolymers doped with iron oxide nanoparticles" Polymer (2005) 46(14):5194-5201.

Alivisatos, A.P. "Semiconductor clusters, nanocrystals, and quantum dots" Science (1996) 271:933-937.

Battaglia, D. et al. "Formation of high quality InP and InAs nanocrystals in a noncoordinating solvent" Nano Lett (2002) 2(9):1027-1030.

Bharali, D.J. et al. "Folate-receptor-medicated delivery of InP quantum dots for bioimaging using confocal and two-photon microscopy" J. Am. Chem. Soc. (2005) 127:11367-11371.

Bullen et al. "The effects of chemisoprtion on the luminescence of CdSe quantum dots" Langmuir (2006) 22:3007-3013.

Cao, L. et al. "Luminescence enhancement of core-shell ZnS:Mn/ZnS nanoparticles" Appl Phys Lett (2002) 80 (23):4300-4302.

Cao, YW. et al. "Colloidal synthesis and properties of InAs/InP and InAs/CdSe core/shell nanocrystals" Mat. Res. Soc. Symp. Proc. (2000) 571:75-80.

Cao, YW. et al. "Growth and Properties of Semiconductor Core/Shell Nanocrystals with InAs Cores" J. Am. Chem. Soc. (2000) 122:9692-9702.

(56) References Cited

OTHER PUBLICATIONS

Chen, H-S et al. "Colloidal ZnSe, ZnSe/ZnS, and ZnSe/ZnSeS quantum dots synthesized from ZnO" J. Phys. Chem. B. (2004) 108:17119-17123.

Clay, R.T. et al. "Synthesis of Cu and CuO nanoclusters within microphase-separated diblock copolymers" New J. Chem. (1998) 22(7):745-748.

Clay, R.T. et al. "Synthesis of metal nanoclusters within microphase-separated diblock copolymers: ICP-AES analysis of metal ion uptake" Supramolecular Science (1997) 4(1-2):113-119.

Dabbousi, B.O. et al., "(CdSe)ZnS core-shell quantum dots: Synthesis and characterization of a size series of highly luminescent nanocrystallites" J. Phys. Chem. B (1997) 101:9463-9475.

Ebenstein et al. "Fluorescence quantum yield of CdSe/ZnS nanocrystals investigated by correlated atomic-force and single-particle fluorescence microscopy" Appl Phys Lett 80(21):4033-4035, (2000).

Gelest, Inc. Catalog "Reactive silicones: forging new polymer links" (2004) pp. 26-33.

Guzelian, A.A. et al., "Colloidal chemical synthesis and characterization of InAs nanocrystal quantum dots" App. Phys. Lett (1996) 69:1432.

Guzelian, A.A. et al., "Synthesis of size-selected, surface-passivated InP nanocrystals" J. Phys. Chem. (1996) 100:7212-7219.

Haubold, S. et al. "Strongly luminescent InP/ZnS core-shell nanoparticles" Chem. Phys. Chem. (2001) 5:331-334.

Hines, M.A. et al. "Bright UV-blue luminescent colloidal ZnSe nanocrystals" J. Phys. Chem. B. (1998) 102 (19):3655-3657.

Hirai, T. et al., "Composite nano-CdS-polyurethane transparent films" J. Mater. Chem. (1999) 9:1217-1219.

Hirai, T. et al., "Effects of thiols on photocatlytic properties of nano-CdS-polythiourethane composite particles," J. Chem Eng. Jap. (1998) 31(6):1003-1006.

Hirai, T. et al., "Preparation of nano-CdS-polyurethane composites via in situ polymerization in reverse micellar systems" J. Mater. Chem. (2000) 10:2234-2235.

Hirai, T. et al., "Preparation of semiconductor nanoparticle polyurea composites using reverse micellar systems via an in situ diisocyanate polymerization" J. Phys. Chem. (1999) 103:10120-10126.

Kane, R.S. et al. "Synthesis of doped ZnS nanocrystals within block copolymer nanoreactors" Chem. Mat. (1999) 11 (1):90-93.

Korgel, B.A. et al. "Controlled synthesis of mixed core and layered (Zn,Cd)S and (Hg,Cd)S nanocrystals within phosphatidylcholine vesicles" Langmuir (2000) 16:3588-3594.

Kyprianidou-Leodidou, T. et al., "Size variation of PbS particles in high-refractive-index nanocomposites" J. Phys. Chem. (1994) 98:8992-8997.

Lee et al. "Full color emission from II-VI semiconductor quantum dot-polymer composites" Adv Mater (2000) 12 (15):1102-1105.

Li, S.L. et al. "High quality ZnSe and ZnS nanocrystals formed by activating zinc carboxylate precursors" Nano Lett (2004) 4(11):2261-2264.

Li, Y. et al. "White-light-emitting diodes using semiconductor nanocrystals" Microchem Acta (2007) 159:207-215.

Lu, C. et al., "High refractive index thin films of ZnS/polythiourethane nanocomposites" J. Mater. Chem. (2003) 13:526-530.

Lucey, D.W. et al. "Monodispersed InP quantum dots prepared by colloidal chemistry in a noncoordinating solvent" Chem. Mater. (2005) 17:3754-3762.

Malik, M.A. et al. "Synthesis and characterization of CdSe/CdS Core-shell and CdSe/CdS composites" Mat. Res. Soc. Symp. Proc. (2000) 581:291-296.

Malik, M.A. et al. "Synthesis and characterization of Mn doped CdS quantum dots from a single source precursor" Mat Res. Soc. Symp. Proc. (2000) 581:133-138.

Mews, A. et al. "Preparation, characterization and photophysics of the quantum dot quantum well system CdS/HgS/ CdS" J. Phys. Chem. (1994) 98:934-941.

Mews, A. et al. "Structural and spectroscopic investigations of CdS/HgS/CdS quantum-dot quantum wells" Phys. Rev. B. (1996) 53(20):R13242-R13245.

Micic, O.I. et al. "Synthesis and characterization of InP, GaP, and GaInP2 quantum dots" J. Phys. Chem. (1995) 99:7754-7759.

Micic, O.I. et al., "Core-shell quantum dots of lattice-matched ZnCdSe2 chells on InP cores: experiment and theory" J. Phys. Chem. B (2000) 104:12149-12156.

Mulligan, R.F. et al. "Synthesis and characterization of ZnO nanostructures templates using diblock copolymers" J Appl Polymer Sci (2003) 89:1058-1061.

Mulligan, R.F. et al. "Synthesis of self-assembled metal-oxide nanostructures in diblock copolymer matrix and integration onto semiconductor surfaces" Mat. Res. Soc. Symp. Proc. (2001) 642:J2.11/1-J2.11/5.

Murray, C.B. et al., "Synthesis and Characterization of Nearly Monodisperse CdE (E+S, Se, Te) Semiconductor Nanocrystallites" J. Am. Chem. Soc. (1993) 115:8706-8715.

Ogata, S. et al. "New preparation method for organic-inorganic layered compounds by organo derivatization reaction of Zn(OH)2 with carboxylic acids" J. Mat. Chem. (2000) 10(2):321-327.

Peng, X. et al., "Epitaxial growth of highly luminescent CdSe/CdS core/shell nanocrystals with photostability and electronic accessibility" J. Am. Chem. Soc. (1997) 119:7019-7029.

Qi, L. et al. "Synthesis and characterization of mixed CdS-ZnS nanoparticles in reverse micelles" Colloids and Surfaces (1996) 111:195-202.

Reid, E.E. et al., Organic Chemistry of Bivalent Sulfer, New York, Chemical Publishing Co., Inc. (1985) vol. 1, p. 33.

Robinson, H.D. et al. "Lateral coupling of self-assembled quantum dots studied by near-field spectroscopy" Mat. Res. Soc. Symp. Proc. (2000) 571:89-94.

Shiojiri, S. et al., "Immobilization of semiconductor nanoparticles formed in reverse micelles into polyurea via in situ polymerization of diisocyanates" Chem. Commun. (1998) 1439-1440.

Shiojiri, S. et al., "Thiol-mediated immobilization of photocatalytic metal sulfide ultrafine particles formed in reverse micellar systems in polythiourethane" J. Chem. Eng. Jap. (1998) 31(3):425-433.

Smith et al. "Minimizing the hydrodynamic size of quantum dots with multifunctional multidentate polymer ligands" JACS (2008) 130(34):11278-11279.

Sohn, B.H. et al. "Processible optically transparent block copolymer films containing superparamagnetic iron oxide nanoclusters" Chem. Mat. (1997) 9(1):264-269.

Talapin, D.V. et al. "Etching of colloidal InP nanocrystals with fluorides: photochemical nature of the process resulting in high photoluminescence efficiency" J. Phys. Chem. B. (2002) 106:12659-12663.

Tolbert, S.H. et al., "High-pressure structural transformation in semiconductor nanocrystals" Annu. Rev. Phys. Chem. (1995) 46:595.

* cited by examiner

1H NMR - Carboxylic Acid

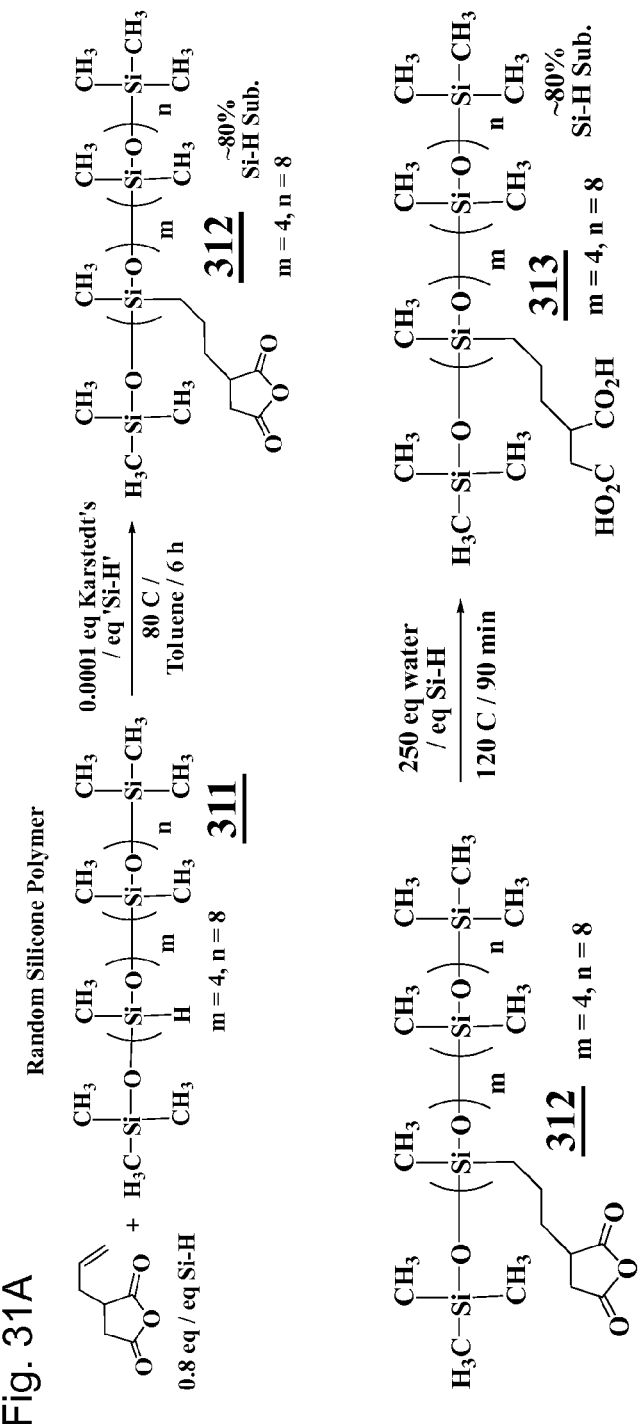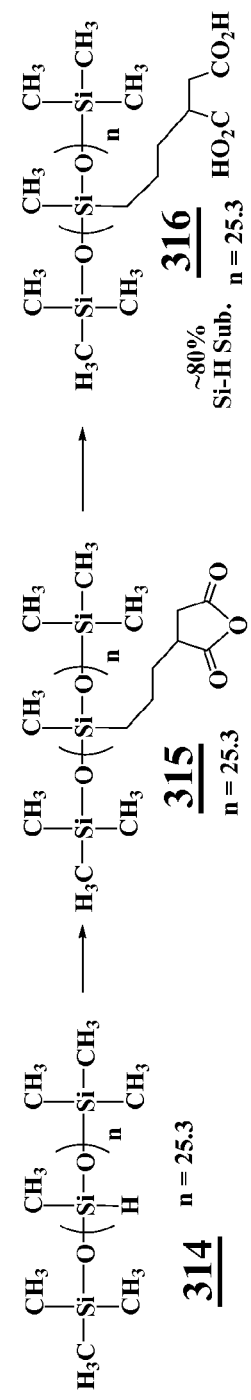
Fig. 31A
Fig. 31B

FUNCTIONALIZED MATRICES FOR DISPERSION OF NANOSTRUCTURES

CROSS-REFERENCE TO RELATED APPLICATIONS

This application is a division of U.S. Ser. No. 12/799,813, filed Apr. 29, 2010, which is a non-provisional utility patent application claiming priority to and benefit of the following prior provisional patent application: U.S. Ser. No. 61/215,054, filed May 1, 2009, entitled "Functionalized Matrixes for Dispersion of Nanostructures" by Mingjun Liu et al., which are each incorporated herein by reference in their entirety for all purposes.

FIELD OF THE INVENTION

The present invention relates to nanostructure ligands, particularly polymeric silicone ligands having alcohol or primary and/or secondary amine nanostructure binding moieties. The invention also relates to nanocomposites, particularly composites having silicone matrixes formed from such ligands and/or including nanostructures bearing such ligands. Processes for preparing nanocomposites are also featured.

BACKGROUND OF THE INVENTION

High performance down-converting phosphor technologies will play a prominent role in the next generation of visible light emission, including high efficiency solid-state white lighting (SSWL). In addition, such technologies are also applicable to near infrared (NIR) and infrared (IR) light emitting technologies. Down-conversion from ultraviolet (UV) or blue light emitting semiconductor light emitting diodes (LEDs) into blue, red and green wavelengths offers a fast, efficient and cost-effective path for delivering commercially attractive white light sources. Unfortunately, existing rare-earth activated phosphors or halophosphates, which are currently the primary source for solid-state down-conversion, were originally developed for use in fluorescent lamps and cathode ray tubes (CRTs), and therefore have a number of critical shortfalls when it comes to the unique requirements of SSWL. As such, while some SSWL systems are available, poor power efficiency (<20 light lumens/watt Om/WA poor color rendering (Color Rendering Index (CRI)<75) and extremely high costs (>$200/kilolumen (klm)) limit this technology to niche markets such as flashlights and walkway lighting.

Furthermore, LEDs often suffer from reduced performance as a result of internal reflection of photons at the chip/coating interface. Typically, LEDs are encapsulated or coated in a polymeric material (which may comprise phosphors) to provide stability to the light-emitting chip. Currently these coatings are made by using an inorganic or organic coating that has a very different refractive index than the base material (i.e., the chip), which results in a detrimental optical effect due to the refractive index mismatch at the interface between the two materials. In addition, the temperature of the LED can reach in excess of 100° C. To allow for the expansion and contraction that can accompany this temperature rise, a compliant polymeric layer (e.g., silicone) is often placed in contact with the chip. In order to provide additional stability to the LED, this compliant layer is often further coated with a hard shell polymer.

The resulting LED structure suffers loss of light at the chip/compliant polymer interface due to the lower refractive index of the polymer coating in relation to the LED. However, if the refractive index of the compliant layer is increased, even greater loss will occur due at the high refractive index/low refractive index interface between the compliant polymer and the hard shell polymer due to internal reflection.

There are several critical factors which result in poor power efficiencies when using traditional inorganic phosphors for SSWL. These include: total internal reflection at the LED-chip and phosphor layer interface resulting in poor light extraction from the LED into the phosphor layer; poor extraction efficiency from the phosphor layer into the surroundings due to scattering of the light generated by the phosphor particles as well as parasitic absorption by the LED chip, metal contacts and housing; broad phosphor emission in the red wavelength range resulting in unused photons emitted into the near-IR; and poor down-conversion efficiency of the phosphors themselves when excited in the blue wavelength range (this is a combination of absorption and emission efficiency). While efficiencies improve with UV excitation, additional loss due to larger Stokes-shifted emission and lower efficiencies of LEDs in the UV versus the blue wavelength range makes this a less appealing solution overall.

As a result, poor efficiency drives a high effective ownership cost. The cost is also significantly impacted from the laborious manufacturing and assembly process to construct such devices, for example the heterogeneous integration of the phosphor-layer onto the LED-chip during packaging (DOE and Optoelectronics Industry Development Association "Light emitting diodes (LEDs) for general illumination," Technology Roadmap (2002)). Historically, blue LEDs have been used in conjunction with various band edge filters and phosphors to generate white light. However, many of the current filters allow photon emission from the blue end of the spectrum, thus limiting the quality of the white LED. The performance of the devices also suffer from poor color rendering due to a limited number of available phosphor colors and color combinations that can be simultaneously excited in the blue. There is a need therefore for efficient nanocomposite filters that can be tailored to filter out specific photon emissions in the visible (especially the blue end), ultraviolet and near infrared spectra.

While some development of organic phosphors has been made for SSWL, organic materials have several insurmountable drawbacks that make them unlikely to be a viable solution for high-efficiency SSWL. These include: rapid photo-degradation leading to poor lifetime, especially in the presence of blue and near-UV light; low absorption efficiency; optical scattering, poor refractive index matching at the chip-interface, narrow and non-overlapping absorption spectra for different color phosphors making it difficult or impossible to simultaneously excite multiple colors; and broad emission spectra. There exists a need therefore for polymeric layers that aid production of high quality, high intensity, white light.

Among other benefits, the present invention fulfills these needs by providing polymeric nanocomposites that function as down-converting layers, photon-filtering layers and/or refractive index matching layers, by taking advantage of the ability to tailor nanocrystals to maximize their emission, absorption and refractive index properties.

SUMMARY OF THE INVENTION

Dispersion of nanostructures in a polymer matrix is desirable for a number of applications, for example, application of quantum dots to light-emitting devices, where dispersion in an appropriate matrix can stabilize the quantum dots, enhance quantum yield, and facilitate device fabrication. Novel ligands that enhance dispersion of nanostructures in polymer matrixes are described herein, as are silicone matrixes formed from the ligands.

In one aspect, the invention provides a variety of polymeric molecules including alcohol nanostructure binding moieties that are useful as nanostructure ligands. Accordingly, one general class of embodiments provides a composition that includes a nanostructure and a polymeric ligand, where the ligand comprises a silicone backbone and one or more alcohol moieties coupled to the silicone backbone. The silicone backbone is typically linear but is optionally branched. Particularly useful ligands include one or more dicarbinol moieties coupled to the silicone backbone.

Generally, the polymeric ligand is bound to a surface of the nanostructure. Not all of the ligand in the composition need be bound to the nanostructure, however. In some embodiments, the polymeric ligand is provided in excess, such that some molecules of the ligand are bound to a surface of the nanostructure and other molecules of the ligand are not bound to the surface of the nanostructure. The excess ligand can optionally be polymerized into a silicone matrix in which the nanostructure is embedded, as described in greater detail hereinbelow. The composition can include a solvent, a crosslinker, and/or an initiator (e.g., a radical or cationic initiator), e.g., to facilitate such incorporation.

In one class of embodiments, the polymeric ligand comprises at least two different types of monomer units, at least one of which comprises the alcohol (e.g., dicarbinol) moiety and at least one of which lacks the alcohol moiety. The number and/or percentage of monomers including the alcohol group can be varied. For example, monomer units comprising the alcohol (e.g., dicarbinol) moiety are optionally present in the ligand at a molar percentage between 0.5% and 20%, and more preferably between 0.5% and 10%. In embodiments in which the ligand comprises a dicarbinol nanostructure binding group, monomer units comprising the alcohol moiety optionally comprise a single dicarbinol moiety per monomer unit. Also in embodiments in which the ligand comprises a dicarbinol nanostructure binding moiety, the ligand optionally comprises 1-200 dicarbinol moieties per ligand molecule.

Subunits lacking the alcohol moiety can be, e.g., diphenylsiloxane, phenylmethylsiloxane, or dimethylsiloxane groups, as just a few examples. As another example, the monomer units lacking the alcohol group can include an alkyl group, a polymerizable group, an epoxide group, an amine group, or a carboxylic acid group. A number of exemplary ligands are described herein.

The nanostructures are optionally nanocrystals or quantum dots, e.g., inorganic, semiconductor, or metal nanocrystals. Optionally, the nanostructures are core-shell nanostructures.

A related general class of embodiments provides methods of making a composite material. In the methods, a population of nanostructures having a polymeric ligand bound to a surface of the nanostructures is provided, where the polymeric ligand comprises a silicone backbone and one or more alcohol (e.g., dicarbinol) moieties coupled to the silicone backbone. The polymeric ligand is incorporated into a silicone matrix in which the nanostructures are embedded.

The matrix is preferably formed from the ligand. Thus, in one class of embodiments, the methods include providing an excess of the polymeric ligand, which excess polymeric ligand is not bound to the surface of the nanostructures, and incorporating the excess polymeric ligand and the polymeric ligand bound to the nanostructures into the silicone matrix. In embodiments in which no other precursors of the silicone matrix are provided, the matrix optionally consists essentially of the polymeric ligand and/or a cross-linked or further polymerized form thereof, as well as any residual solvent, crosslinker, initiator, and the like.

In some embodiments, to incorporate the polymeric ligand into the silicone matrix the population of nanostructures and the excess polymeric ligand are mixed with at least one solvent. The solvent is then evaporated, e.g., after application of the mixture to the desired location of the composite in or on a device. The polymeric ligand bound to the nanostructures and the excess polymeric ligand not bound to the nanostructures form the silicone matrix. In some embodiments, a crosslinker is provided and reacted with hydroxyl moieties on the ligand. Similarly, an initiator (e.g., a radical or cationic initiator) can be provided.

For polymeric ligands comprising at least two different types of monomer units, at least one of which comprises the nanostructure binding moiety and at least one of which lacks the nanostructure binding moiety but comprises a polymerizable group or an epoxide group, incorporating the polymeric ligand into the silicone matrix includes reacting the polymerizable or epoxide groups on different molecules of the polymeric ligand with each other.

Exemplary nanostructures and ligands are described herein. Essentially all of the features noted for the compositions above apply to these methods as well, as relevant.

In another aspect, the invention provides a variety of polymeric molecules including amine nanostructure binding moieties that are useful as nanostructure ligands. Accordingly, one general class of embodiments provides a composition that includes a nanostructure and a polymeric ligand, where the ligand comprises a silicone backbone and one or more primary and/or secondary amine moieties coupled to the silicone backbone. The silicone backbone is typically linear but is optionally branched.

As for the embodiments above, the polymeric ligand is optionally provided in excess, such that some molecules of the ligand are bound to a surface of the nanostructure and other molecules of the ligand are not bound to the surface of the nanostructure. The excess ligand can optionally be polymerized into a silicone matrix in which the nanostructure is embedded, as described in greater detail hereinbelow.

Monomer units comprising the amine moiety optionally comprise a single primary amine moiety per monomer unit. In one class of embodiments, monomer units comprising the amine moiety comprise a single primary amine moiety and a single secondary amine moiety per monomer unit.

In one class of embodiments, the polymeric ligand comprises at least two different types of monomer units, at least one of which comprises the amine (e.g., primary and/or secondary) moiety and at least one of which lacks the amine moiety. The number and/or percentage of monomers including the amine group can be varied. For example, monomer units comprising the amine moiety are optionally present in the ligand at a molar percentage between 0.5% and 20%. In one exemplary embodiment, the ligand includes 1-20 primary amine moieties per ligand molecule, and optionally also includes an equal number of secondary amine moieties per ligand molecule.

The composition optionally includes a mixture of ligands. For example, in one class of embodiments, the composition also includes a second polymeric ligand, which second polymeric ligand comprises a silicone backbone and one or more primary and/or secondary amine moieties coupled to the terminal subunits of the second polymeric ligand.

A number of exemplary ligands are described herein. Exemplary nanostructures are also described. The nanostructures are optionally nanocrystals or quantum dots, e.g., inorganic, semiconductor, or metal nanocrystals. Optionally, the nanostructures are core-shell nanostructures.

The composition can also include a crosslinker and/or an initiator, e.g., for incorporation of the ligand and nanostructures into a silicone matrix. In one class of embodiments, the crosslinker is an epoxy crosslinker, e.g., an epoxycyclohexyl or epoxypropyl crosslinker. The crosslinker is optionally an epoxy silicone crosslinker, which can be, e.g., linear or branched. In certain embodiments, the crosslinker is a linear epoxycyclohexyl silicone or a linear epoxypropyl silicone.

A related general class of embodiments provides methods of making a composite material. In the methods, a population of nanostructures having a polymeric ligand bound to a surface of the nanostructures is provided. The polymeric ligand comprises a silicone backbone and one or more primary and/or secondary amine moieties coupled to the silicone backbone. The polymeric ligand is incorporated into a silicone matrix in which the nanostructures are embedded.

In one class of embodiments, the methods include providing an excess of the polymeric ligand, which excess polymeric ligand is not bound to the surface of the nanostructures, and incorporating the excess polymeric ligand and the polymeric ligand bound to the nanostructures into the silicone matrix. In embodiments in which no other precursors of the silicone matrix are provided, the matrix optionally consists essentially of the polymeric ligand and/or a cross-linked or further polymerized form thereof, as well as any residual solvent, crosslinker, initiator, and the like.

Optionally, a second polymeric ligand is provided and incorporated into the silicone matrix along with the polymeric ligand. In one exemplary embodiment, the second polymeric ligand comprises a silicone backbone and one or more primary and/or secondary amine moieties coupled to the terminal subunits. The first polymeric ligand generally has amine moieties coupled to internal subunits.

In some embodiments, a crosslinker is provided and reacted with amine moieties on the ligand (e.g., primary or secondary amine moieties). Similarly, an initiator (e.g., a radical or cationic initiator) can be provided.

Exemplary nanostructures and ligands are described herein. Essentially all of the features noted for the compositions above apply to these methods as well, as relevant.

Composite materials produced by any of the methods herein are also a feature of the invention, as are devices comprising the composite materials (e.g., LEDs) and the novel ligands themselves. Composites of the invention optionally exhibit high quantum yields and improved fluorescence stability of the nanocrystals, particularly under conditions of high temperatures and high light flux.

Additional features and advantages of the invention will be set forth in the description that follows, and in part will be apparent from the description, or may be learned by practice of the invention. The advantages of the invention will be realized and attained by the structure and particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will now be described with reference to the accompanying drawings. In the drawings, like reference numbers indicate identical or functionally similar elements.

DETAILED DESCRIPTION

Figure 1:
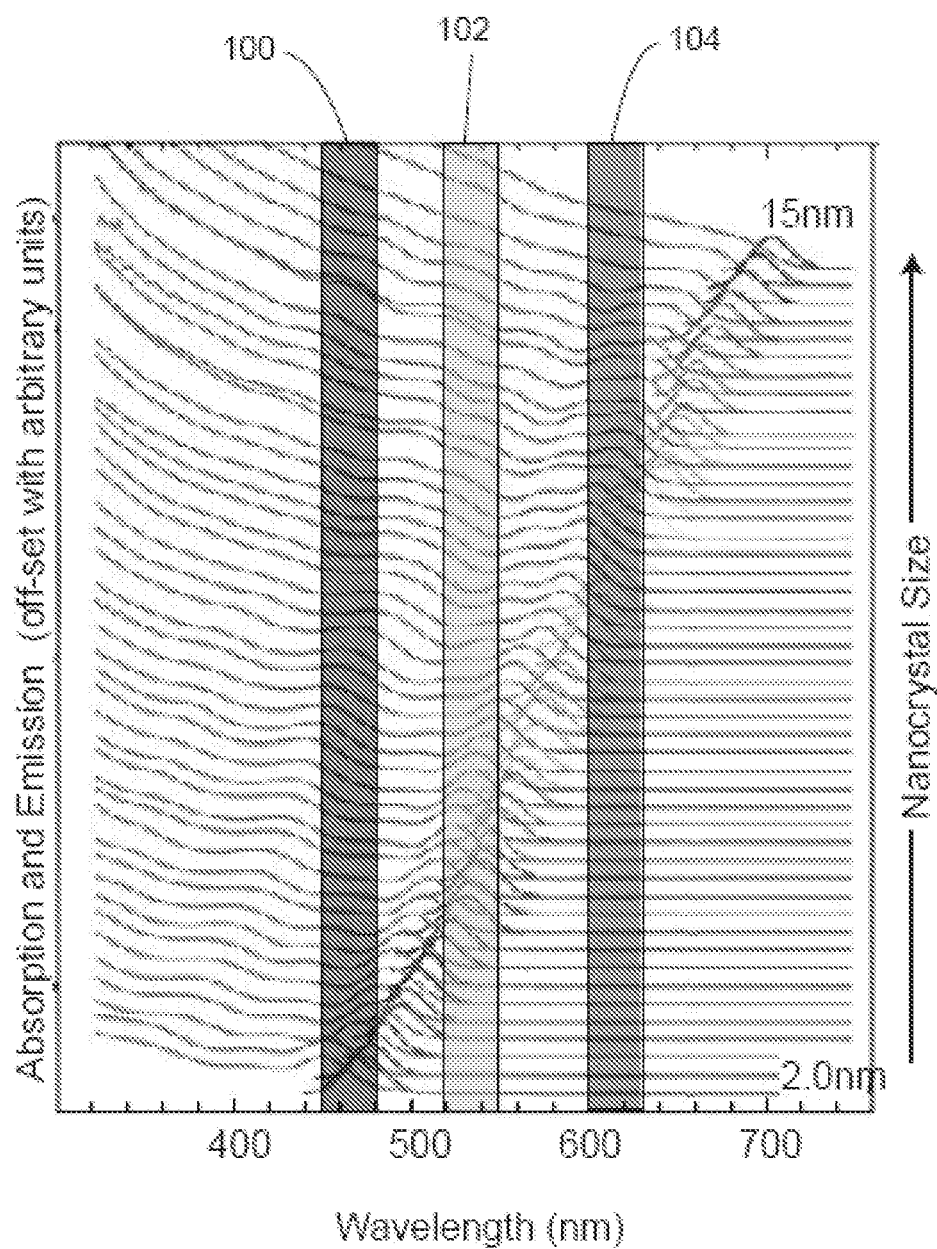
FIG. 1 shows absorption and emission spectra for various nanocrystal radii showing continuous tailoring of the emission and absorption wavelengths.

It should be appreciated that the particular implementations shown and described herein are examples of the invention and are not intended to otherwise limit the scope of the present invention in any way. Indeed, for the sake of brevity, conventional electronics, manufacturing, semiconductor devices, and nanocrystal, nanowire (NW), nanorod, nanotube, and nanoribbon technologies and other functional aspects of the systems (and components of the individual operating components of the systems) may not be described in detail herein. It should further be appreciated that the manufacturing techniques described herein can be used to create any semiconductor device type, and other electronic component types. Further, the techniques would be suitable for applications in electrical systems, optical systems, consumer electronics, industrial or military electronics, wireless systems, space applications, or any other application.

The present invention provides various polymeric nanocomposites comprising polymeric materials with embedded nanocrystals. The various properties of the nanocrystals, including their absorption properties, emission properties and refractive index properties, are utilized to create nanocomposites that can be tailored and adjusted for various applications. In one embodiment, the present invention provides applications of semiconductor nanocrystals that utilize their emission properties in down-conversion applications. Another application combines two, non-electronically active properties of the same nanocrystals, by using the high absorption coefficient and relatively sharp band edge of the nanocrystals to filter light as a cutoff filter. In another embodiment, the high refractive index of nanocrystals can also be used when mixed into low refractive index materials to create substantially transparent nanocomposites with effective refractive indexes matched to the substrates they are coating. In further embodiments, the refractive index of the nanocomposite can be matched to a second, further encapsulating material. The present invention also provides for nanocomposites that combine two or more of these various properties in different configurations into the same nanocomposite.

One aspect of the present invention provides novel nanostructure ligands, including, for example, ligands that enhance the miscibility of nanostructures in solvents or polymers, increase quantum efficiency of nanostructures, and/or preserve nanostructure luminescence when the nanostructures are incorporated into a matrix. Methods of making indium phosphide nanostructures and core-shell nanostructures, as well as nanostructures having high quantum efficiency, small size, and/or a narrow size distribution are also described.

As used herein, the term "nanocrystal" refers to nanostructures that are substantially monocrystalline. A nanocrystal has at least one region or characteristic dimension with a dimension of less than about 500 nm, and down to on the order of less than about 1 nm. As used herein, when referring to any numerical value, "about" means a value of ±10% of the stated value (e.g. about 100 nm encompasses a range of sizes from 90 nm to 110 nm, inclusive). The terms "nanocrystal," "nanodot," "dot" and "quantum dot" are readily understood by the ordinarily skilled artisan to represent like structures and are used herein interchangeably. The present invention also encompasses the use of polycrystalline or amorphous nanocrystals.

Typically, the region of characteristic dimension will be along the smallest axis of the structure. Nanocrystals can be substantially homogenous in material properties, or in certain embodiments, can be heterogeneous. The optical properties of nanocrystals can be determined by their particle size, chemical or surface composition. The ability to tailor the nanocrystal size in the range between about 1 nm and about 15 nm enables photoemission coverage in the entire optical spectrum to offer great versatility in color rendering. Particle encapsulation offers robustness against chemical and UV deteriorating agents.

Additional exemplary nanostructures include, but are not limited to, nanowires, nanorods, nanotubes, branched nanostructures, nanotetrapods, tripods, bipods, nanoparticles, and similar structures having at least one region or characteristic dimension (optionally each of the three dimensions) with a dimension of less than about 500 nm, e.g., less than about 200 nm, less than about 100 nm, less than about 50 nm, or even less than about 20 nm or less than about 10 nm. Typically, the region or characteristic dimension will be along the smallest axis of the structure. Nanostructures can be, e.g., substantially crystalline, substantially monocrystalline, polycrystalline, amorphous, or a combination thereof.

Nanocrystals (or other nanostructures) for use in the present invention can be produced using any method known to those skilled in the art. Suitable methods are disclosed in U.S. patent application Ser. No. 10/796,832, filed Mar. 10, 2004, and U.S. Pat. Nos. 6,949,206 and 7,267,875, the disclosures of each of which are incorporated by reference herein in their entireties. The nanocrystals (or other nanostructures) for use in the present invention can be produced from any suitable material, suitably an inorganic material, and more suitably an inorganic conductive or semiconductive material. Suitable semiconductor materials include those disclosed in U.S. patent application Ser. No. 10/796,832 and include any type of semiconductor, including group II-VI, group III-V, group IV-VI and group IV semiconductors. Suitable semiconductor materials include, but are not limited to, Si, Ge, Sn, Se, Te, B, C (including diamond), P, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and an appropriate combination of two or more such semiconductors.

In certain aspects, the semiconductor nanocrystals or other nanostructures may comprise a dopant from the group consisting of: a p-type dopant or an n-type dopant. The nanocrystals (or other nanostructures) useful in the present invention can also comprise II-VI or III-V semiconductors. Examples of II-VI or III-V semiconductor nanocrystals and nanostructures include any combination of an element from Group II, such as Zn, Cd and Hg, with any element from Group VI, such as S, Se, Te, Po, of the Periodic Table; and any combination of an element from Group III, such as B, Al, Ga, In, and Tl, with any element from Group V, such as N, P, As, Sb and Bi, of the Periodic Table.

Other suitable inorganic nanostructures include metal nanostructures. Suitable metals include, but are not limited to, Ru, Pd, Pt, Ni, W, Ta, Co, Mo, Ir, Re, Rh, Hf, Nb, Au, Ag, Ti, Sn, Zn, Fe, FePt, and the like.

The nanocrystals (or other nanostructures) useful in the present invention can also further comprise ligands conjugated, cooperated, associated or attached to their surface as described throughout. Suitable ligands are described herein. Additional ligands are disclosed in U.S. Pat. Nos. 7,645,397, 6,949,206, and 7,267,875. Use of such ligands can enhance the ability of the nanocrystals to incorporate into various solvents and matrixes, including polymers. Increasing the miscibility (i.e., the ability to be mixed without separation) of the nanocrystals in various solvents and matrixes allows them to be distributed throughout a polymeric composition such that the nanocrystals do not aggregate together and therefore do not scatter light. Such ligands are described as "miscibility-enhancing" ligands herein.

As used herein, the term nanocomposite refers to matrix materials comprising nanocrystals distributed or embedded therein. Suitable matrix materials can be any material known to the ordinarily skilled artisan, including polymeric materials, organic and inorganic oxides. Nanocomposites of the present invention can be layers, encapsulants, coatings or films as described herein. It should be understood that in embodiments of the present invention where reference is made to a layer, polymeric layer, matrix, or nanocomposite, these terms are used interchangeably, and the embodiment so described is not limited to any one type of nanocomposite, but encompasses any matrix material or layer described herein or known in the art.

I. Down-Converting Nanocomposites

In order to become competitive with traditional lighting from fluorescent and incandescent lights, significant improvements must be made in solid-state white lighting (SSWL). Improvements not just in the quantum efficiency of the phosphors, but in all aspects of the down-conversion system that relate to efficiency, color-rendering and overall system cost are needed. In one embodiment, the present invention provides a complete down-conversion system based on engineered nanocomposite materials for use with currently available blue LED excitation sources that dramatically improve the overall cost, performance and efficiency of SSWL. The down-converting nanocomposites of the present invention utilize the emission properties of nanocrystals that are tailored to absorb light of a particular wavelength and then emit at a second wavelength, thereby providing enhanced performance and efficiency of active sources (e.g., LEDs). As such, the nanocrystals utilized in the down-converting applications of the present invention will be constructed and tailored so as to be highly emitting. In one embodiment, this system produces SSWL that exceeds performance of the best traditional fluorescent and incandescent bulbs, with color rendering of greater than 80 and power efficiency of greater than 200 lm/W, at a cost of less than one U.S. dollar/klm.

Performance Characteristics of SSWL Devices

To evaluate the performance characteristics of solid-state white lighting (SSWL) devices, three primary attributes are commonly used: (1) luminous efficiency, (2) Correlated Color Temperature (CCT) and (3) Color Rendering Index (CRI). DOE and Optoelectronics Industry Development Association "Light emitting diodes (LEDs) for general illumination," Technology Roadmap (2002).

The luminous efficiency (measured in lm/W) is the efficiency of the conversion from electrical power (W) to optical power (W), combined with the efficiency of the conversion from optical power (W) to the luminous flux. The luminous efficiency is influenced by a number of factors, and can, in general terms, be written as a contribution of several separate efficiencies:

$$E_{luminous} = \eta_{wp} \times \eta_{lum} \times \eta_{ss} \times \eta_{IQE} \times \eta_{package}(E_{os}, E_{pa}, E_{TIR}, E_{exp}) \times \ldots$$

where $\eta_{wp}$ is the wall plug efficiency, $\eta_{lum}$ is the photopic efficiency/response of the human eye, $\eta_{iss}$ is the stokes shift efficiency from converting a blue photon to a longer wavelength photon, $\eta_{IQE}$ is the internal quantum efficiency of the phosphor, and $\eta_{package}$ is overall package efficiency and accounts for losses in light extraction efficiency from optical scattering ($E_{os}$), parasitic scattering ($E_{ps}$), total internal reflection ($E_{TIR}$), external packaging like the lead frame and submount ($E_{exp}$), etc.

CCT or correlated color temperature refers to the human eye property of being optimally adapted to the sunlight spectral content. The relative intensities of the blue (B), red (R) and green (G) colors, for the desired white color, referred to as chromaticity coordinates, optimally reproduce those in the visible sunlight, which corresponds to a blackbody spectral distribution of 6000 Kelvin (K). For optimum illumination the chromaticity coordinates for R, G and B must fall near the black body radiation, for temperatures between 2000° C. and 8000° C. Higher or lower than "optimum" temperatures register to the eye as too "cold" or too "warm" color hues.

Color rendering has to do with the appearance of various object colors under a given source illumination, compared to that from a reference source. A collection of 14 sample colors of different saturation is customarily used for the color rendering index (CRI), which provides a quantitative measure on a scale of 1 to 100. Two sources of similar color temperature may produce widely varying CRIs. Low CRIs make colors unacceptable for illumination, while high CRI (>80) are acceptable for general illumination purposes.

Procedure for Providing an Optimized White Light Emitting Device

In one embodiment, the present invention provides processes comprising:

(1) A simulation model can be used to determine optimized nanocrystal mixtures for CRI, CCT, and luminous efficiency with targets of CRI>80, CCT about 4,000 K and efficiency of 200 lm/W.

(2) Nanocrystals and nanocrystal component mixtures are synthesized with emission peak widths, peak maximums, and intensity ratios determined by simulation.

(3) A controlled nanocrystal phosphor nanocomposite is developed, including: (a) a surface ligand capable of achieving high (about 20% or more) loading density in the selected composite is produced; (b) a ligand exchange process to incorporate a 3-part ligand onto the nanocrystal is performed; (c) a homogeneous, non-phase separated $TiO_2$ nanocomposite with nanocrystal loading densities up to 20% by volume is produced; (d) quantum yield (QY) dependence on nanocrystal loading density in the nanocomposite is determined; (e) an index of refraction dependence on loading density in the nanocomposite and index-matching of the nanocomposite to blue LED substrate (e.g., sapphire and/or SiC) is determined; and (f) a relationship of loading density and film thickness to optimize refractive index matching and nanocomposite optical density is determined.

Simulations for Determining Optimum Nanocrystal Component Mixture for High Color Rendering, Color Temperature and High Efficiency In order to predict and maximize CRI, CTT and luminous efficiency of nanocrystal mixtures, a dynamic and robust simulation model is used. A super-convergent, random-search, parameter optimization algorithm is used to find the maximum performance point, subject to the imposed constraints. The model allows calculation of these performance characteristics based on actual experimental colorimetric and optical characteristics of nanophosphor components and mixtures. In turn, this model is used to aid the design and fabrication of optimal nanocomposite SSWL devices.

The simulation program incorporates an algorithm to determine the optimum spectral emission characteristics of nanocrystal component mixtures for simultaneous maximization of color rendering, color temperature and overall efficacy for production of white light. The approach provides a super-convergent, random search, optimization algorithm in the phosphor parameter space. The program seeks a combination of emission wavelengths that simultaneously maximizes luminous efficacy, color rendering (CRI) and color temperature (CCT), subject to the white-light chromaticity constrains calculated using standard CIE (Commission Internationale de l'Eclairage). The measured nanocrystal quantum efficiency, peak wavelength and emission spectral width are input parameters. Performance boundaries, as for example, efficacy no less than 90%, or CRI>90, can also be applied for flexibility in the design. The number of required wavelengths (i.e., nanocrystal sizes) is a variable that allows a determination of trade-offs between performance and manufacturing cost.

A validation procedure with iteration cycles is adopted, whereby mixtures of nanocrystal components, of size, composition peak maximum, peak widths, mixture abundance, and internal quantum efficiency predicted by the simulation are manufactured. The resulting values of CRI and CCT are determined experimentally and compared with the predictions and adjustments are made as appropriate. The luminous efficiency is determined based on optical parameters including stoke shift efficiency, internal quantum efficiency and photopic response.

The output of this procedure is the optimum number of emission colors, the precise center wavelengths of each color, the precise spectral width of each color and the exact relative intensity of each and the corresponding concentration based on excitation by, for example, a selected blue LED (about 460 nm).

The simulations described throughout can determine suitable emission characteristics for the nanocrystal. In addition, it is useful to (1) synthesize the materials with the prescribed spectral characteristics and (2) use the materials to validate the model. To achieve this objective, available solution phase synthetic techniques are used to fabricate core/shell nanocrystal phosphors and characterize mixtures as determined by the theoretical model.

Based on current methods, nanocrystal batches are fabricated with spectral characteristics generated by the theoretical model. Each distinct wavelength is synthesized separately and combined to produce the final mixture. Specific attention is paid to the center wavelength and the peak-width of each sample. In particular, narrow emission in the red avoids efficiency loss in the IR. In order to accomplish this, a solution-phase mixture of nanocrystals is produced and characterized that has the appropriate composition to produce white light with CRI and CTT, matching that of the theoretical model when illuminated with blue excitation and total down-conversion efficiency comparable to that predicted by the model, assuming zero loss to other mechanisms in the process. These measurements can be made in the solution-phase using a standard visible fluorometer and fluorescence standards with excitation matching the blue-LED.

Nanocrystal Phosphors

While any method known to the ordinarily skilled artisan can be used to create nanocrystal phosphors, suitably, a solution-phase colloidal method for controlled growth of inorganic nanomaterial phosphors is used. See Alivisatos, A. P., "Semiconductor clusters, nanocrystals, and quantum dots," *Science* 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," *J. Am. Chem. Soc.* 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," *J. Am. Chem. Soc.* 115:8706 (1993). This manufacturing process technology leverages low cost processability without the need for clean rooms and expensive manufacturing equipment. In these methods, metal precursors that undergo pyrolysis at high temperature are rapidly injected into a hot solution of organic surfactant molecules. These precursors break apart at elevated temperatures and react to nucleate nanocrystals. After this initial nucleation phase, a growth phase begins by the addition of monomers to the growing crystal. The result is freestanding crystalline nanoparticles in solution that have an organic surfactant molecule coating their surface.

Utilizing this approach, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape. The ratio of surfactants to monomer, surfactants to each other, monomers to each other, and the individual concentrations of monomers strongly influence the kinetics of growth.

In suitable embodiments, CdSe is used as the nanocrystal material, in one example, for visible light down-conversion, due to the relative maturity of the synthesis of this material. Due to the use of a generic surface chemistry, it is also possible to substitute non-cadmium-containing nanocrystals.

Core/Shell Nanocrystals

In semiconductor nanocrystals, photo-induced emission arises from the band edge states of the nanocrystal. The band-edge emission from nanocrystals competes with radiative and non-radiative decay channels originating from surface electronic states. X. Peng, et al., *J. Am. Chem. Soc.* 30:7019-7029 (1997). As a result, the presence of surface defects such as dangling bonds provide non-radiative recombination centers and contribute to lowered emission efficiency. An efficient and permanent method to passivate and remove the surface trap states is to epitaxially grow an inorganic shell material on the surface of the nanocrystal. X. Peng, et al., *J. Am. Chem. Soc.* 30:7019-7029 (1997). The shell material can be chosen such that the electronic levels are type I with respect to the core material (e.g., with a larger bandgap to provide a potential step localizing the electron and hole to the core). As a result, the probability of non-radiative recombination can be reduced.

Core-shell structures are obtained by adding organometallic precursors containing the shell materials to a reaction mixture containing the core nanocrystal. In this case, rather than a nucleation-event followed by growth, the cores act as the nuclei, and the shells grow from their surface. The temperature of the reaction is kept low to favor the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials. Additionally, the spherical shape acts to minimize interfacial strain energy from the large radius of curvature, thereby preventing the formation of dislocations that could degrade the optical properties of the nanocrystal system.

In suitable embodiments, ZnS can be used as the shell material using known synthetic processes, resulting in a high-quality emission. As above, if necessary, this material can be easily substituted, e.g., if the core material is modified. Additional exemplary core and shell materials are described herein and/or known in the art.

Optical Properties of Core-shell Nanocrystals

Due to the finite size of the core-shell nanocrystals, they display unique optical properties compared to their bulk counterparts. The emission spectrum is defined by a single Gaussian peak, which arises from the band-edge luminescence. The emission peak location is determined by the core particle size as a direct result of quantum confinement effects. For instance, by adjusting the particle diameter in the range of 2 nm and 15 nm, the emission can be precisely tuned over the entire visible spectrum (FIG. 1). FIG. 1 represents the absorption and emission peaks for nanocrystals of increasing size (2 nm to 15 nm). The initial peak (lower wavelength) indicates the absorption wavelength and the later peak (higher wavelength) the emission wavelength in nm. With increasing size of the nanocrystals, the absorption and emission peak wavelengths shift from about 450 nm to about 700 nm, and can be tuned over this range. The vertical shaded bars on FIG. 1 indicate visible light wavelengths in the blue 100, green 102 and red 104 ranges.

The width of the emission peak is determined by the size distribution of the sample. Peak widths down to 20 nm full width at half maximum (FWHM) can be achieved. Conversely, the absorption spectrum of nanocrystals is very broad and intense, as typical of the bulk material, which is characteristically different than organic phosphors. Absorption coefficients are in excess of 55,000/cm (in the blue range of the spectrum) over the entire range of crystal sizes. In addition, core-shell nanocrystals can be made with quantum efficiencies as high as 90% (this does not take into account energy loss due to Stokes shift, but is simply the ratio of photons-out to photons-in).

Figure 2:
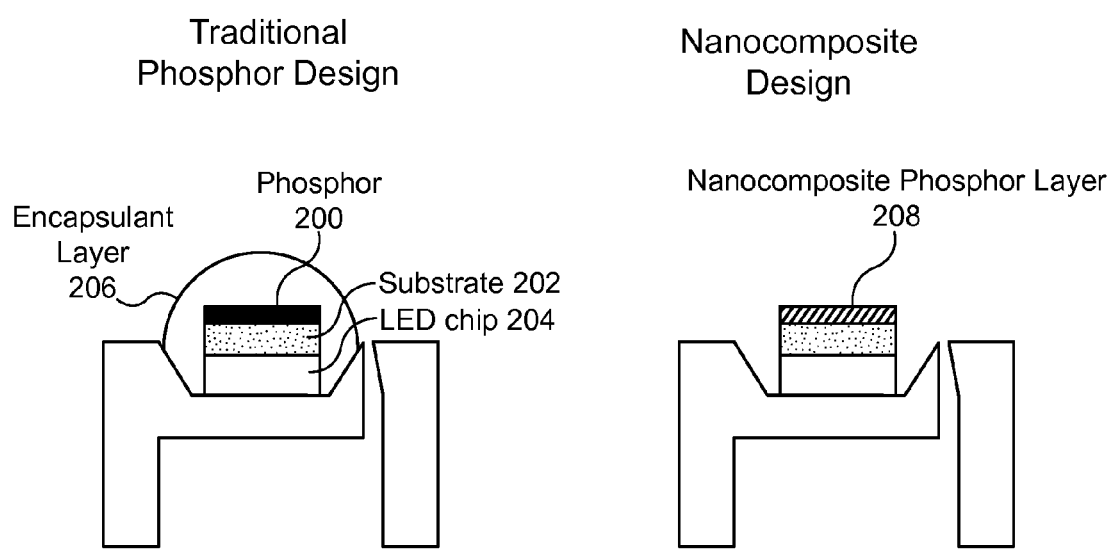
FIG. 2 shows a comparison of traditional thick phosphors integrated during packaging, and a nanocomposite down-converting layer integrated prior to dicing, according to one embodiment of the present invention.

In one embodiment, the present invention provides an engineerable down-converting system (see FIG. 2). Systems according to the present invention can comprise a nanocomposite down-converting layer that can be coated directly onto an LED wafer prior to dicing and packaging, eliminating the need for heterogeneous integration of the phosphor layer during packaging. The nanocomposite down-converting layer is suitably engineered from three components, including: (1) Semiconductor nanocrystal phosphors of one or more, suitably two or more, sizes tuned to emit at the required wavelength(s) and with the required spectral characteristics to optimize the color rendering index (CRI) and power conversion efficiency in the final device; (2) A host matrix (e.g., a polymer) selected for high index of refraction (generally about 1.5 or greater), low UV degradation and matched thermal expansion to the LED chip; and, (3) A unique nanocrystal surface chemistry that acts as the interface between the nanocrystals and the host matrix, allowing each element to be independently selected and tailored without impacting the other component. As shown in FIG. 2, such a down-converting nanocomposite phosphor layer 208 will take the place of phosphor 200 and phosphor encapsulant layer 206.

By independently selecting and tuning each of these three components, it is possible to simultaneously: (1) engineer a specific composite emission spectrum that can be tailored to optimize between CRI and down-conversion efficiency; (2) refractive index match the composite layer to the LED chip to reduce light-extraction losses prior to down conversion; (3) reduce scattering in the down-conversion layer, thereby minimizing light-extraction losses from the phosphor layer; (4) produce down-conversion with a quantum efficiency greater than about 20% (e.g., 40%, 60%, 80%, 100%) at any wavelength with simultaneous and efficient absorption of light (about 300 nm) (depending upon size and composition of the nanoparticles); and (5) minimize loss of efficiency due to photons emitted into the near-infra-red (near-IR) through the use of extremely sharp emission spectra in red light wavelengths (about 20 nm FWHM). This approach makes it possible to achieve overall power-conversion efficiencies greater than 200 μm/W, with CRI greater than 80, and overall chip brightness of greater than 100 Watts/chip at a cost of less than one U.S. dollar/klm.

| Nanocomposite System Features | Benefit to SSWL |
|---|---|
| High quantum efficiency (as high as 90%) | No loss of photons upon down conversion resulting in 2-fold increase in overall power-conversion efficiency over traditional phosphors. |
| Continuous, tunable emission spectrum | The emission peak wavelength and width can be precisely tuned so mixtures of different sized nanocrystals can be formed with precise emission characteristics to achieve maximum emission efficiency, CRI, CTT. |
| Narrow and Sharp Emission | Sharp emission allows tailoring of emitted light at wavelengths where the luminous efficiency of photopic vision of the eye is high. |

-continued

| Nanocomposite System Features | Benefit to SSWL |
|---|---|
| High photo- and chemical stability | Nanocrystals are not susceptible to bleaching effects and environmental sensitivities (UV, moisture, oxygen) as traditional organic phosphors offering long operating lifetimes. |
| Mixtures of nanocrystals in host matrix | Mixtures of nanocrystals can be embedded in a host matrix of virtually any material at high-loading densities (e.g., 20% by volume) with precise control over relative concentration ratios through modification of surface chemistry. |
| Non-scattering composites | Due to the small particle size and capability to make homogenous dispersion of the nanocrystals, optical scattering as well as parasitic absorption can be minimized or eliminated to improve light extraction efficiency and hence the device luminous efficiency. |
| Tunable refractive index | By selecting the proper host matrix material and tailoring the loading density, the index of refraction of the nanocomposite layer can be precisely tuned from about 1.5 to about 2.5 to minimize or even eliminate total internal reflection at the LED-nanocomposite interface, potentially increasing overall power conversion efficiency. Loading density and thickness can be traded-off to simultaneously optimize index of refraction and optical density of the composite layer while maintaining film thicknesses. |
| High absorption coefficients (as high as 55,000/cm) | At a high loading density, the nanocomposite down-conversion layer can be on the order of a single micron in thickness. This allows direct incorporation at the wafer-level using traditional thin film processing, dramatically reducing overall manufacturing costs for SSWL relative to thick-film phosphor layers that are incorporated at the package level. |

Figure 3:
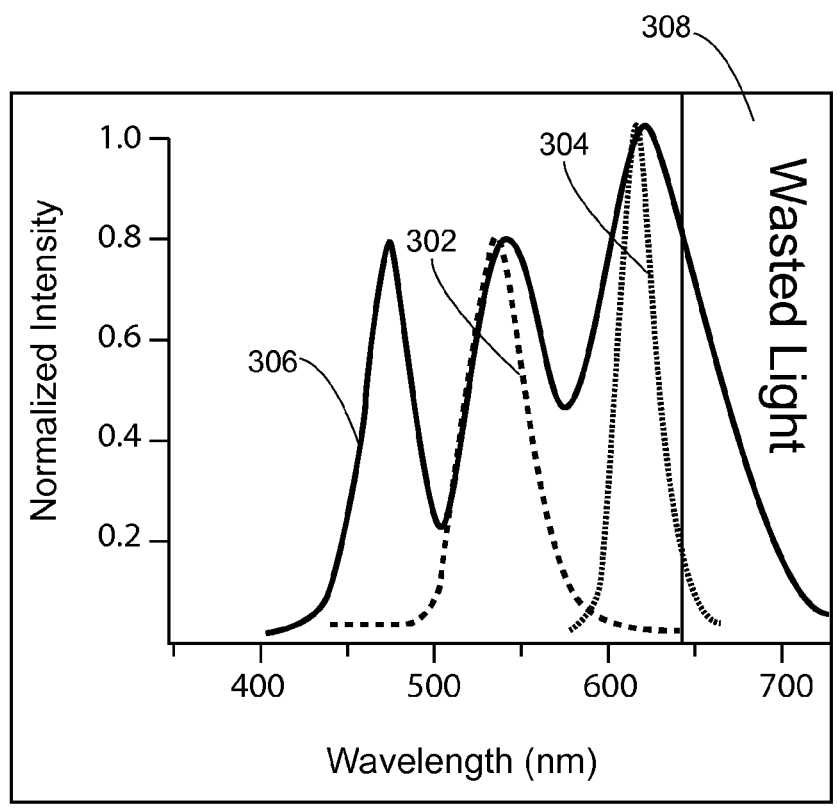
FIG. 3 shows the elimination of wasted light at the edges of the visible spectrum by using phosphor nanocrystals, compared to traditional phosphor edge losses.

FIG. 3 illustrates the emission range of the down-converting nanocomposites of the present invention, in the red region of a 2-color phosphor mix, compared to that resulting from traditional inorganic phosphors for white. Emission peaks 302 and 304 represent the emission spectra of a 2-color phosphor mix according to one embodiment of the present invention. Spectrum 306 represents the emission spectrum of traditional inorganic phosphors. Not only does the narrow emission prevent photon waste at the edges of the visible spectrum by the eye, but it also allows a superior optimization of color rendering index and power conversion efficiency. Wasted light region 308 demonstrates light emitted from traditional inorganic phosphors at the edges of the visible spectrum that is cut out by using the sharp emission peak 304.

Figure 4:
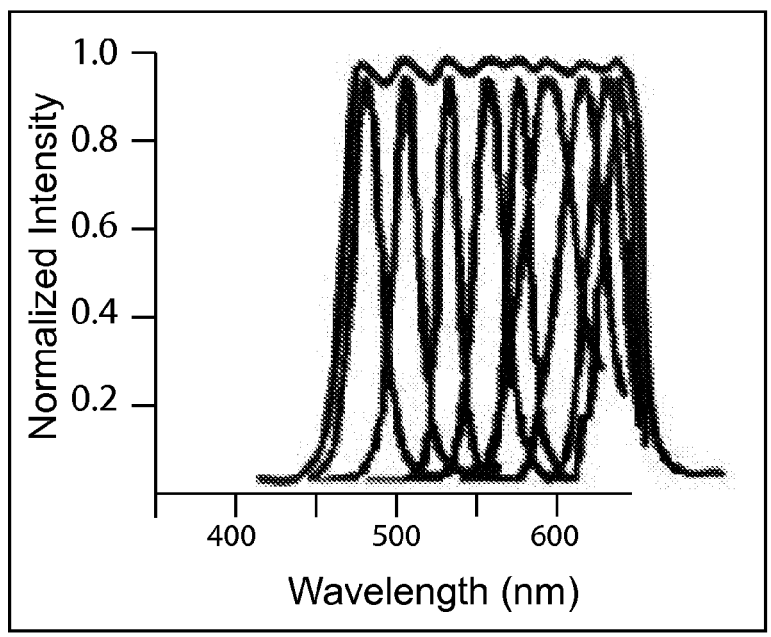
FIG. 4 shows the normalized intensity generated by mixing a continuum of nanocrystal sizes, creating broad-band white light.

FIG. 4 illustrates the concept of fine-tuning the emission by using more than three emission colors, each with a specific, narrow, emission peak, to generate an overall emission spectrum with a superior color rendering index that can be as high as 100 for any color temperature. Between the two extremes of extremely broad emission and extremely narrow emission, however, is a balance between efficiency and CRI. The exact number of colors, center wavelengths, relative concentrations and spectral widths can be determined theoretically to optimize both parameters simultaneously.

Figure 5:
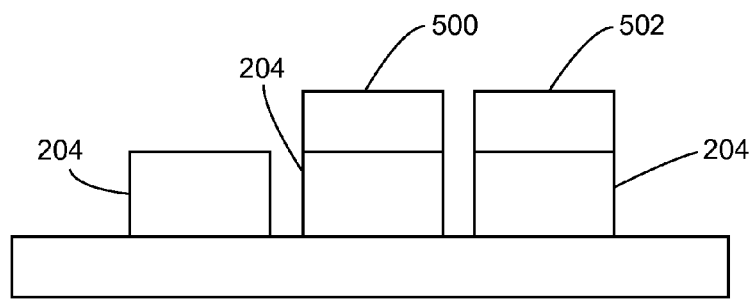
FIG. 5 shows a three color emitting LED in accordance with one embodiment of the present invention.

By using standard thin-film and lithographic processing techniques, as shown in FIG. 5, green 500 and red 502 down-conversion layers can be patterned across LED chips 204 prior to dicing. This allows low-cost fabrication of 3-color emitting LEDs integrated into a single die, such that a single chip can be used to dynamically tune emission of the LED from monochromatic to white for any color temperature. As such, the present invention provides formation of an integrated chip-level 3-color mixing-based SSWL for all lighting applications, at a cost point competitive with traditional lighting, but with far superior efficiency, performance and color engineering capability.

Suitable matrixes for use in all embodiments of the present invention include polymers and organic and inorganic oxides. Suitable polymers for use in the matrixes of the present invention include any polymer known to the ordinarily skilled artisan that can be used for such a purpose. In suitable embodiments, the polymer will be substantially translucent or substantially transparent. Such polymers include, but are not limited to, poly(vinyl butyral):poly(vinyl acetate), silicone and derivatives of silicone, including, but not limited to, polyphenylmethylsiloxane, polyphenylalkylsiloxane, polydiphenylsiloxane, polydialkylsiloxane, fluorinated silicones and vinyl and hydride substituted silicones.

The nanocrystals used the present invention can be embedded in a polymeric (or other suitable material, e.g., waxes, oils) matrix using any suitable method, for example, mixing the nanocrystals in a polymer and casting a film, mixing the nanocrystals with monomers and polymerizing them together, mixing the nanocrystals in a sol-gel to form an oxide, or any other method known to those skilled in the art. As used herein, the term "embedded" is used to indicate that the nanocrystals are enclosed within the polymer that makes up the majority component of the matrix.

The thickness of the layers of the present invention can be controlled by any method known in the art, such as spin coating and screen printing. Such methods are especially useful when coating optical devices such as lenses or mirrors with the polymeric layers. While the various polymeric layers of the present invention can be any thickness required, suitably, the layers will be less than about 100 mm in thickness, and down to on the order of less than about 1 mm in thickness. In other embodiments, the polymeric layers of the present invention can be on the order of 10's to 100's of microns in thickness. In one embodiment, the present invention provides nanocrystal doped layers that are greater than about 0.5 mm in thickness, and suitably will scatter only a minimal portion of light that enters the layer (see later for a discussion of scattering). In other embodiments, the layers will be between about 0.5 mm and about 50 mm in thickness. In all embodiments of the present invention, the nanocrystals can be embedded in the various matrixes at any loading ratio that is appropriate for the desired function. Suitably, the nanocrystals will be loaded at a ratio of between about 0.001% and about 75% by volume depending upon the application, matrix and type of nanocrystals used. The appropriate loading ratios can readily be determined by the ordinarily skilled artisan and are described herein further with regard to specific applications.

II. Photon-Filtering Nanocomposites

In another embodiment, the present invention provides polymeric layers comprising a polymer and nanocrystals embedded within the polymer, such that the layers act as photon-filtering nanocomposites. Suitably, the nanocrystals will be prepared from semiconductor materials, but any suitable material described throughout can be used to prepare the nanocrystals. In certain embodiments, the nanocrystals will have a size and a composition such that the nanocrystals absorb light of a particular wavelength or over a range of wavelengths. As such, the nanocrystals utilized in these embodiments are tailored such that their absorption characteristics are enhanced or maximized, while their emission characteristics are minimized, i.e. they will absorb light in a highly efficient manner, but suitably will emit only a very low level, or preferably no light. In other embodiments, however, the photon-filtering nanocomposites can also comprise nanocrystals that have high emission properties and emit light at a particular wavelength as discussed throughout. As such, the present invention provides nanocomposites that comprise different types of nanocrystals such that the nanocomposites exhibit several, or all, of the properties discussed throughout, in a layer.

Figure 6:
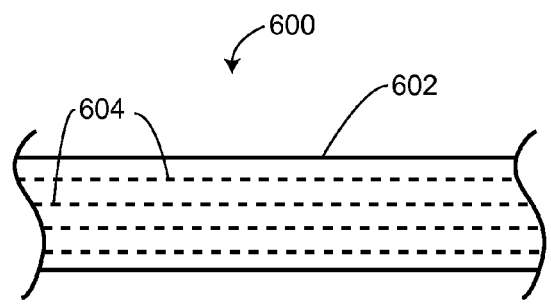
FIG. 6 is a cross-sectional view of a polymeric layer in accordance with one embodiment of the present invention.

A photon-filtering nanocomposite in accordance with one embodiment of the present invention is shown in FIG. 6. FIG. 6 is a cross-sectional view of a polymeric layer 600 showing nanocrystals 604 embedded in polymer 602. Note that nanocrystals 604 are not to scale and are visibly represented for illustrative purposes only. The polymeric layers and nanocomposites of the present invention can also comprise nanocrystals of different sizes and compositions within the same layer.

Figure 7:
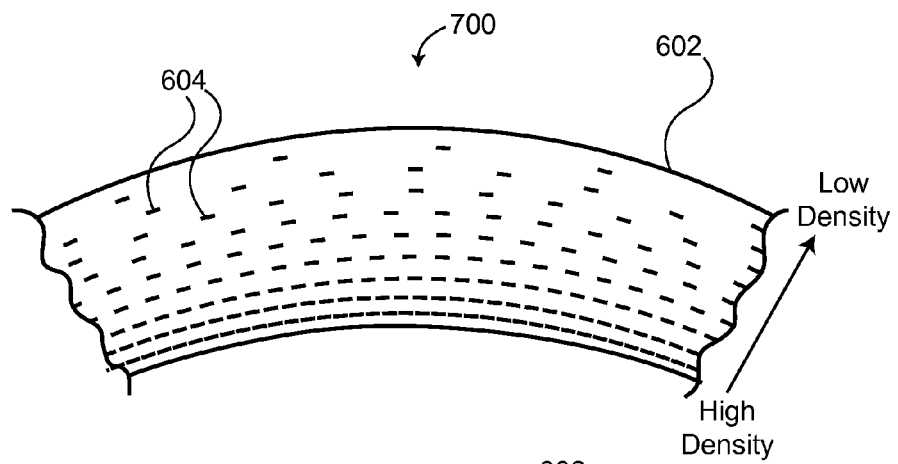
FIG. 7 is a cross-sectional view of a polymeric layer having a nanocrystal density gradient in accordance with one embodiment of the present invention.

In suitable embodiments, the nanocrystals can be distributed homogenously throughout the polymeric layer and nanocomposites (see FIG. 6). In other embodiments, the nanocrystals can be randomly distributed. In further embodiments, the nanocrystals can be distributed throughout the layer such that they form a nanocrystal density gradient throughout the layer (as discussed further in the refractive index section below). Such an embodiment is represented in FIG. 7, which shows a cross-sectional view of a polymeric layer 700 with nanocrystals 604 embedded in polymer 602 in such a way that they form a nanocrystal density gradient from high density (lower portion of FIG. 7) to low density (upper portion of FIG. 7) within polymer 602.

The photon-filtering polymeric layers and nanocomposites of the present invention can be used to coat, encapsulate, cover, be deposited on (or any other similar arrangement known to those skilled in the art) any substrate material. Suitably, the polymeric layers of the present invention can be used to coat optical devices. In other embodiment, the polymeric layers can be used to encapsulate active devices.

Figure 8:
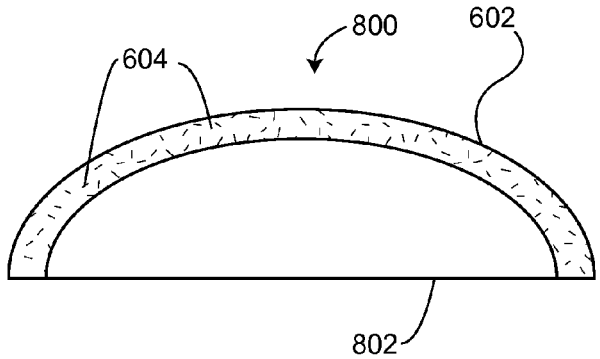
FIG. 8 is a cross-sectional view of an optical device with a polymeric layer coating the device in accordance with one embodiment of the present invention.

In embodiments of the present invention where the photon-filtering polymeric layers are used to coat optical devices, such optical devices can be refractive (e.g., lenses) or reflective (e.g., mirrors). FIG. 8 is a cross-sectional view of an optical device 802 coated with polymer 602 comprising nanocrystals 604. Coated optical devices 800 according to such an embodiment can be used in any application where a filter or anti-reflective coating is desired on a refractive or reflective device.

In embodiments of the present invention where the photon-filtering polymeric layers are used to encapsulate active devices, such active devices can be any device known to the skilled artisan. As used herein an "active device" is one that requires a source of energy for its operation and has an output that is a function of present and past input signals. Examples of active devices include, but are not limited to, controlled power supplies, transistors, diodes, including light emitting diodes (LEDs), light detectors, amplifiers, transmitters and other semiconductor devices.

By controlling the size and composition of the nanocrystals used in the practice of the present invention, the nanocrystals will absorb light of a particular wavelength, or a particular range of wavelengths, while not scattering light. The ability to make nanocrystals out of different semiconductors, and control their size, allows for polymeric layers to be fabricated with nanocrystals that will absorb light from the UV, to visible, to near infrared (NIR), to infrared (IR) wavelengths. Nanocrystals for use in the present invention will suitably be less than about 100 nm in size, and down to less than about 2 nm in size. In suitable embodiments, the nanocrystals of the present invention absorb visible light. As used herein, visible light is electromagnetic radiation with wavelengths between about 380 and about 780 nanometers that is visible to the human eye. Visible light can be separated into the various colors of the spectrum, such as red, orange, yellow, green, blue, indigo and violet. The photon-filtering nanocomposites of the present invention can be constructed so as to absorb light that makes up any one or more of these colors. For example, the nanocomposites of the present invention can be constructed so as to absorb blue light, red light, or green light, combinations of such colors, or any colors in between. As used herein, blue light comprises light between about 435 nm and about 500 nm, green light comprises light between about 520 nm and 565 nm and red light comprises light between about 625 nm and about 740 nm in wavelength. The ordinarily skilled artisan will be able to construct nanocomposites that can filter any combination of these wavelengths, or wavelengths between these colors, and such nanocomposites are embodied by the present invention.

Polymeric layers that comprise nanocrystals that can absorb light of a particular wavelength, or range of wavelengths, will act as edge pass filters, absorbing light that is less than a certain wavelength. For example, the photon-filtering nanocomposites can be constructed so as to absorb light that is less than about 565 nm (e.g., blue and green) and allowing wavelengths of light that are longer than about 565 nm (e.g., red) to pass through the polymeric layer.

In other embodiments, the nanocrystals have a size and a composition such that they absorb photons that are in the ultraviolet, near-infrared, and/or infrared spectra. As used herein, the ultraviolet spectrum comprises light between about 100 nm to about 400 nm, the near-infrared spectrum comprises light between about 750 nm to about 100 µm in wavelength and the infrared spectrum comprises light between about 750 nm to about 300 µm in wavelength.

While nanocrystals of any suitable material can be used in the practice of the present invention, in certain embodiments, the nanocrystals can be ZnS, InAs or CdSe nanocrystals. In one example, InAs nanocrystals (with a 1340 nm absorption peak) with TOP (tri-n-octylphosphine) ligands attached to their surface can be dissolved in a solvent such as toluene. Poly(vinyl butyral):poly(vinyl acetate) (PVB:PVA) polymer can also be dissolved in toluene and the two solutions can be mixed together. A substrate can then be coated or encapsulated with the mixture and the toluene evaporated off. A thin film results that is non-light-scattering due to the size of the non-aggregated nanocrystals. Polymeric layers produced in such a manner will have an effective refractive index between that of either material by itself (i.e., the polymer or the nanocrystal material), which can be adjusted by modifying the loading ratio of the nanocrystals and the density of the nanocrystals at various points in the polymeric layer (see Refractive Index section for additional disclosure). A polymeric layer comprising such nanocrystals can act as an antireflective filter, absorbing light that is less than about 1340 nm in wavelength.

In another example, CdSe nanocrystals (having an absorption peak at about 580 nm) with stearic acid ligands can be dissolved in a solvent such as toluene. In other embodiments, ZnS nanocrystals with amine, carboxylic acid, phosphonic acid, phosphonate, phosphine, phosphine oxide or sulfur ligands can be dissolved in a solvent. In the case of CdSe nanocrystals, a ligand exchange can then be performed in solution with a siloxane ligand and excess ligand can be removed. Nanocrystals can then be mixed with a polymer base, such as silicone, and a substrate material can then be coated or encapsulated. After curing, the film will have an effective refractive index between that of the polymer (e.g., silicone) and the nanocrystals, which can be adjusted by changing the loading ratio of the nanocrystals in the silicone. Such a polymeric layer will act as a filter absorbing light that is less than about 580 nm in wavelength (i.e., blue, green, yellow, orange, violet, UV light).

III. Refractive Index Matching Nanocomposites

Poor extraction caused by total internal light reflection due to index of refraction mismatches at interfaces is a problem for light emitting devices, including LEDs. It is well known that light impinging an interface between materials of index n and n'<n, at an angle θ relative to the vertical will be totally reflected, if sin θ>sin θc=n'/n. For a direct extraction from GaN with n=2.26 into air n'=1, this limits the extraction cone within a solid angle ΔΩ=2π(1-cos θc), where θc is the critical extraction angle, θc=26°, being just 10% of the total extraction angle 2π (upper half only). In the encapsulation arrangement shown in FIG. 2, overall light extraction relates to: (a) extraction from substrate 202 to phosphor encapsulant layer 206; and (b) from phosphor encapsulant layer 206 to air. The radius of the encapsulant layer is much larger than the emitting area (e.g., cm vs mm) thus light rays inside the encapsulant layer that reach out in the radial direction impinge almost perpendicular to the encapsulant layer surface θ<<θc and are extracted. Thus the overall extraction is mainly limited by extraction from the substrate to the phosphor plane interface, taking advantage of the higher phosphor critical angle, due to the higher than air index of refraction.

In one embodiment, as shown in FIG. 2, the present invention provides nanocomposite layers 208, that can bond to LED substrate 202, that have an effective refraction index of greater than 1.5. In suitable embodiments, by increasing the substrate effective refractive index to 1.8, an angle of θc=68° is generated and the extraction efficiency is doubled to 63%. In another embodiment, the present invention provides nanocomposites combining nanocrystals with a refractive index of about 2.0 to about 3 with host matrix materials, including polymers (e.g., $TiO_2$ with an effective refractive index 1.5 to 2, or silicone with a refractive index of about 1.49), to generate a nanocomposite material with an effective refractive index of about 2, with a critical extraction angle of about θc=77°, thereby increasing the extraction efficiency to 78%. In further embodiments, a matched-index passive layer (e.g., a hard shell polymer) can be added above the phosphor layer to take advantage of the radial incidence, thereby enhancing extraction from the phosphor layer into the air.

As used herein, the term "effective refractive index ($n_e$)" is used to indicate that the polymeric layers of the present invention are composite materials, and thus, their effective refractive index is a result of the refractive index of all components of the layer. The term refractive index as used herein indicates the degree to which the nanocomposites of the invention bend light. The refractive index of the nanocomposites can be determined by the ratio of the speed of light in a vacuum divided by the speed of light in the nanocomposites.

Figure 9:
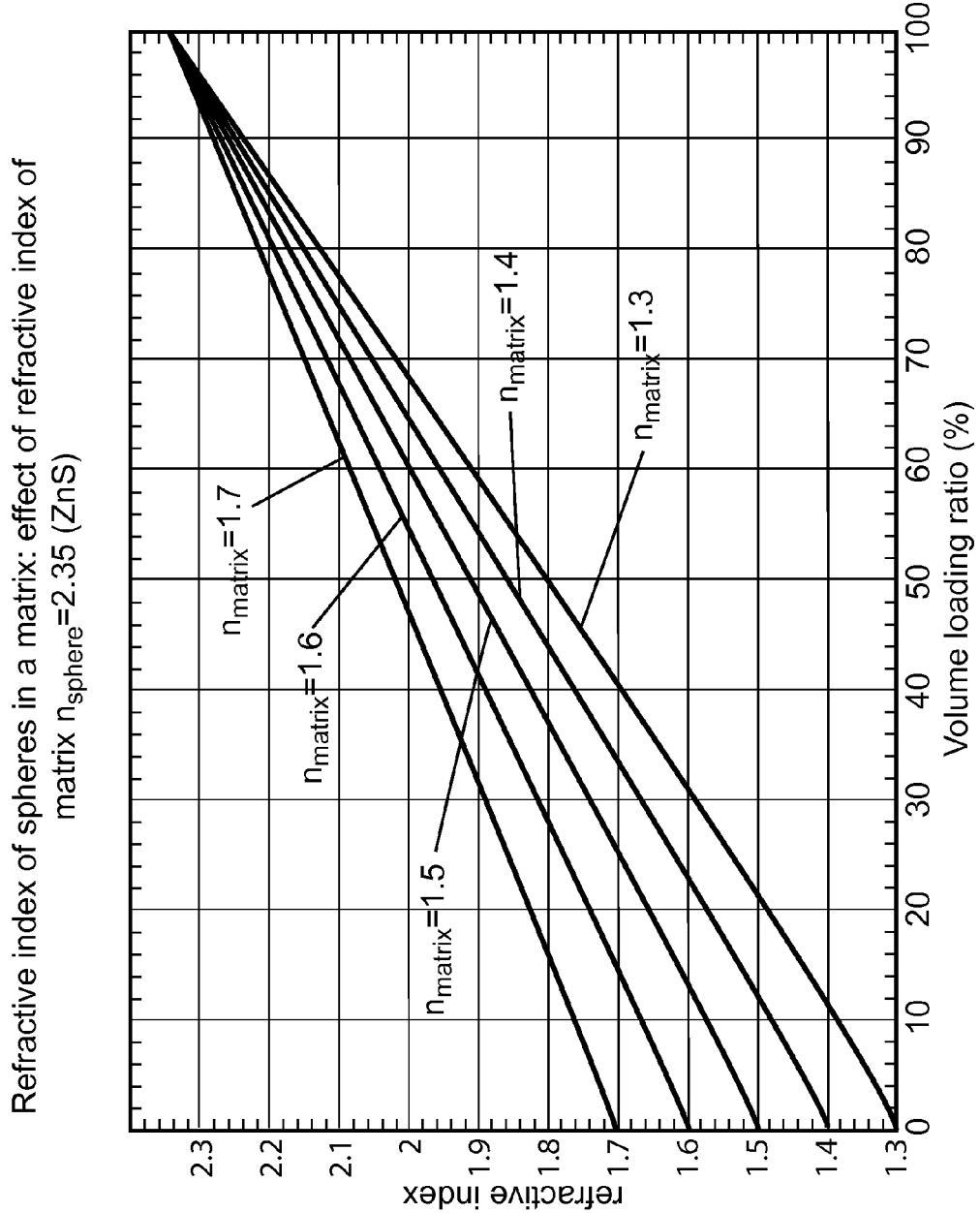
FIG. 9 is a plot showing the effective refractive index of various matrixes versus volume loading ratio of ZnS nanocrystals.
Figure 10:
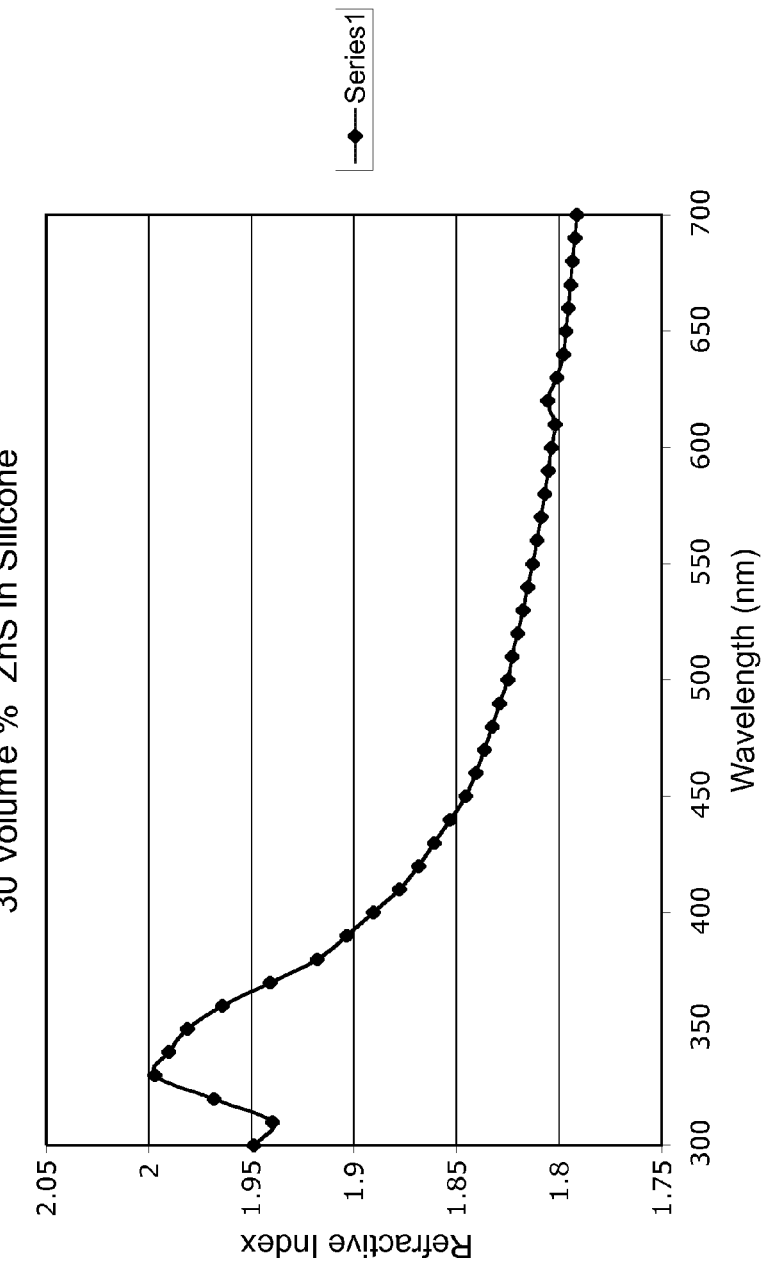
FIG. 10 is a plot showing the effective refractive index of a silicone nanocomposite comprising ZnS nanocrystals as a function of wavelength.

The polymeric layers of the present invention, whether down-converting, photon-filtering, or refractive index matching, have an effective refractive index that can be controlled by the ratio, density, composition and size of the nanocrystals embedded within the matrix. FIG. 9 shows the effect of loading ratio of ZnS nanocrystals (n=2.35) on the effective refractive index of various materials. For all matrixes, the effective refractive index increases linearly with the loading ratio (%) up to the refractive index of the pure ZnS nanocrystals. FIG. 10 shows the effective refractive index of a silicone nanocomposite comprising 3 nm ZnS nanocrystals at 30% by volume as a function of wavelength. An effective refractive index of greater than about 1.77 is observed for all wavelengths from 300 nm to 700 nm.

Figure 11:
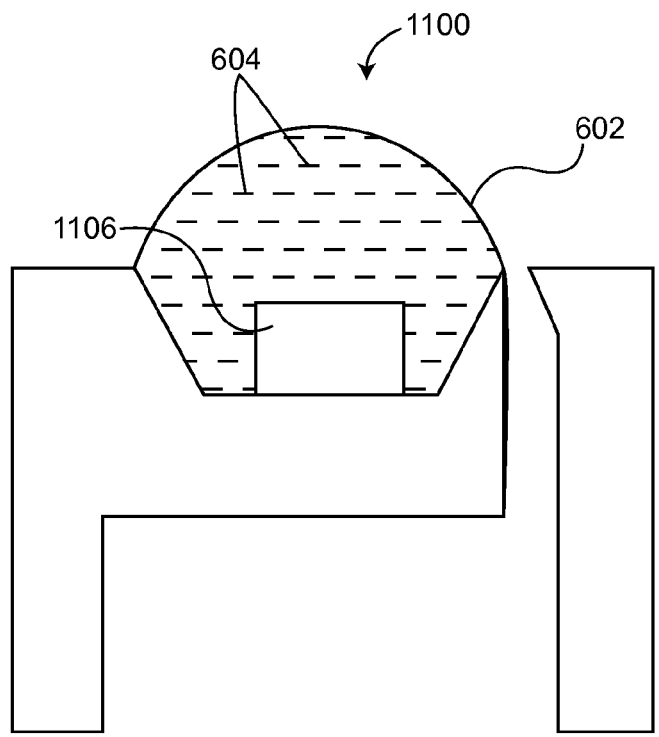
FIG. 11 is a cross-sectional view of a light emitting diode encapsulated within a polymeric layer in accordance with one embodiment of the present invention.
Figure 12:
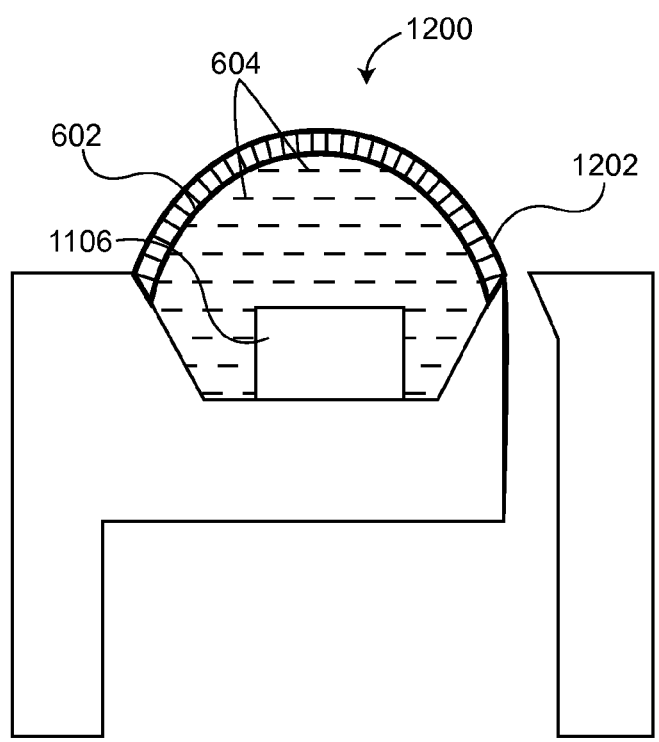
FIG. 12 is a cross-sectional view of a light emitting diode encapsulated within a polymeric layer having a nanocrystal density gradient in accordance with one embodiment of the present invention.

Control and tailoring of the effective refractive index allows the matrixes of the present invention to be utilized in applications where a layer having either a uniform or varying effective refractive index may be desired, for example as polymeric layers encapsulating LEDs. In such applications, a polymeric layer is used to encapsulate the light emitting diode chip of an LED to provide protection to the chip. As discussed above, due to refractive index (n) differences between the high n of the LED chip and the generally low n of the polymeric encapsulant, large amounts of light are lost due to light reflecting at the chip/polymer interface. The present invention therefore provides for a polymeric layer that has a refractive index higher than pure polymer that can approach or match the refractive index of the LED chip, thereby limiting the light lost at the chip/polymer interface. Such an embodiment is represented in FIG. 11, showing a cross-sectional view of an encapsulated light emitting diode 1100, in which polymer 602 comprising embedded nanocrystals 604 encapsulates LED chip 1106. Any active device, including those discussed throughout, can be encapsulated in a similar manner. Furthermore, FIGS. 11 and 12 showing specific LED structures are presented for illustrative purposes only, and any LED structure known to those skilled in the art can be similarly encapsulated.

The effective refractive index of the polymeric layer can be any value between that of the pure matrix material (e.g., silicone at about 1.49, $TiO_2$ at about 1.5) and the nanocrystals themselves (e.g., up to about 3). Suitably, the effective refractive index of the matrix will be greater than about 1.5, preferably between about 1.5 and about 2.5, and in certain embodiments the refractive index of the matrix will be about 1.8.

In other embodiments, in order to add further stability to an LED structure, a second polymeric layer can be added on top of the first layer. Often, this second layer will be a "hard-shell" polymer and will have a refractive index that is lower than the LED chip. Thus, if the refractive index of the first polymeric layer is matched to the refractive index of the LED chip, reflections will occur at the first polymeric layer/hard shell polymer interface. In order to overcome this problem, in another embodiment, the present invention provides for a polymeric layer or polymeric encapsulant which has a density gradient of nanocrystals such that the effective refractive index of the polymeric layer matches both the chip and the hard shell polymer at their respective interfaces.

In one such embodiment, the present invention provides polymeric layers that encapsulate an active device that has an effective refractive index, $n_1$. The layer comprises a polymer and semiconductor nanocrystals embedded within the polymer, and has an inner boundary in contact with the active device and an outer boundary in contact with a medium that has an effective refractive index, $n_2$. The layer has an effective refractive index less than or equal to $n_1$ at the inner boundary and an effective refractive index greater than or equal to $n_2$ at the outer boundary. Suitably, the active device will be an LED, though any active device, including those described throughout, can be encapsulated. In suitable embodiments, $n_1$ will be greater than $n_2$.

FIG. 12 shows a cross-sectional view of an LED encapsulated in such a polymeric layer. Encapsulated LED 1200 comprises polymeric layer 602 comprising embedded nanocrystals 604 encapsulating LED chip 1106. Hard shell polymer 1202 further coats polymeric layer 602 to provide additional structural integrity and protection to the LED. FIG. 12 illustrates the nanocrystal density gradient throughout the thickness of polymeric layer 602, this gradient being highest at the boundary with LED chip 1106 and lowest at the boundary with hard shell polymer 1202. In such embodiments, the effective refractive index is $n_1$ at the boundary with LED chip 1106 and the effective refractive index is $n_2$ at the boundary with hard shell polymer 1202. In certain embodiments, this nanocrystal density gradient will be substantially linear throughout the polymeric layer, though it can take any form throughout the thickness of the layer, e.g., cyclic, parabolic, etc. Suitably, the effective refractive index of polymeric layer 602 will be greater than about 1.5 throughout the layer, and in certain embodiments will be about 1.8 ($n_1$) at the interface with LED chip 1106 and about 1.5 ($n_2$) at the interface with hard shell polymer 1202.

Figure 13:
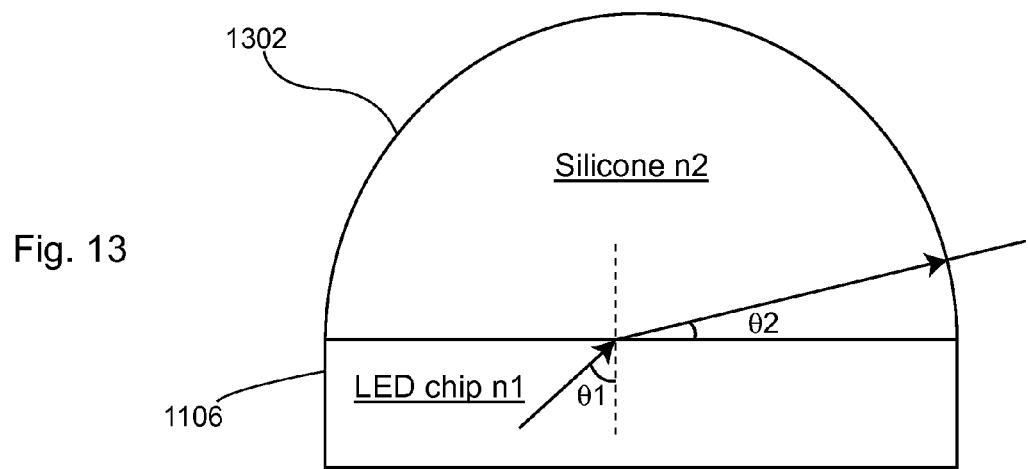
FIG. 13 is a traditional LED chip—silicon cap assembly.

As shown in FIG. 13, light emitting diodes often utilize LED chip 1106 covered by a drop or layer of silicone 1300 usually a few millimeters in diameter. As discussed throughout, by replacing the silicone cap in FIG. 13 with nanocrystal doped matrixes with enhanced refractive indexes, more light can be extracted from LED chip 1106. However, two issues may arise by doing so: (1) the amount of nanocrystals required for a doped matrix a few millimeters thick for each LED translates to rather large quantities of nanocrystals for mass production, thereby driving up the cost; and (2) the scattering from the nanocrystals throughout a thick layer may make the matrix opaque for a path-length of a few millimeters.

Figure 14:
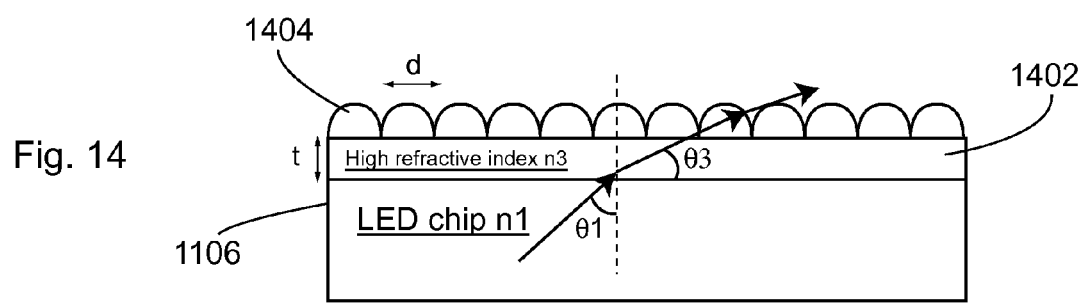
FIG. 14 is a nanocomposite—LED chip assembly in accordance with one embodiment of the present invention.

To resolve these issues, in another embodiment (see FIG. 14), the present invention provides for a thin film of nanocomposite 1402 formed on the surface of an LED chip 1106, this thin film is then further capped with small hemispheres 1404 of the same nanocomposite. All of the light that enters the nanocomposite hits the composite/air interface at 90° and therefore does not suffer from any internal reflection. The thickness of the film and the diameter of the small caps can be chosen to satisfy the thermal compliance and other mechanical/thermal requirements. The thickness, t, of the film, and the diameter, d, of the small hemispheres, can be in the range of 10's-100's of nms to microns to millimeters. Suitably, the thickness of the layer will be on the order of 10's of microns, for example about 10-50 microns. The diameter of the hemispheres is generally on the order of microns.

Figure 15:
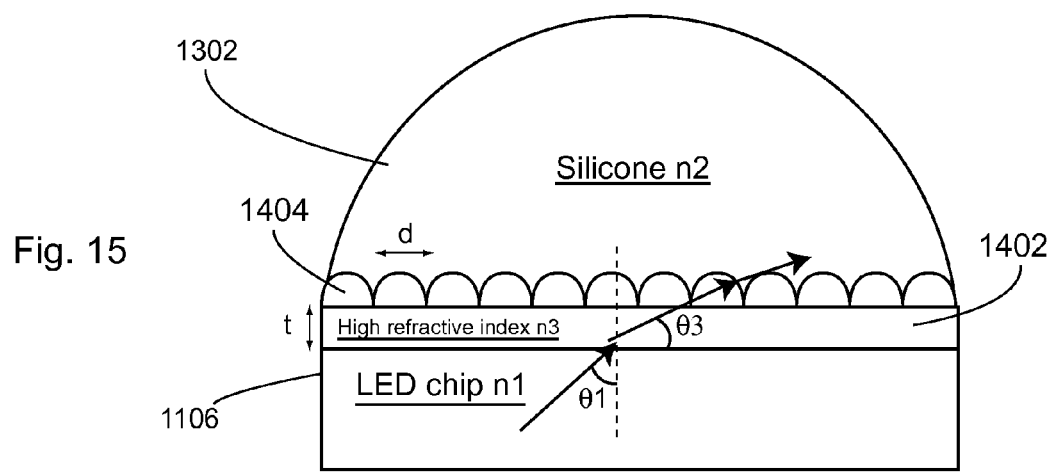
FIG. 15 is a nanocomposite—LED chip assembly in accordance with one embodiment of the present invention.

In other embodiments of the present invention, the small hemispheres 1404 of nanocomposite can be further capped with a large hemisphere of silicone 1302, as illustrated in FIG. 15. In this case, the refractive index of the large hemisphere of silicone is not required for light extraction. The critical angle is only determined by the refractive index of the LED chip 1106, n1, and that of the nanocrystal doped matrix (1402 and 1404), n3 as:

$$\theta_{critical} = \sin^{-1} \frac{n_1}{n_3}.$$

Preparation of nanocomposite films and hemispheres in this manner allows for the use of larger sized nanocrystals in comparison to those that can be used in conjunction with thicker pathlength films. For example, nanocrystals on the order of 5-7 nm could be used with the thin film/hemisphere embodiments of the present invention, while nanocrystals on the order of about 3-5 nm could be required for thicker pathlength nanocomposites.

As discussed throughout, the nanocrystals useful in the practice of the present invention can have a composition and a size such that they absorb light at a particular wavelength(s) and emit at a particular wavelength(s). In certain embodiments, the polymeric layers of the present invention can comprise combinations of nanocrystals that function in the various ways described herein. For example, a nanocomposite of the present invention can comprise nanocrystals having specific, enhanced emission properties, others having specific, enhanced absorption properties but low emission properties, and the entire nanocomposite can be constructed such that the layer has a specific refractive index that is matched or tailored for a specific purpose. Combined in such a way, the polymeric layers of the present invention can be used as encapsulants for active devices (e.g., LEDs) that emit light of a certain wavelength, filter out other wavelengths and have a refractive index appropriately matched to an active device and/or an additional substrate or coating.

IV. Exemplary Embodiments

In one aspect, the present invention provides matrix materials doped with nanocrystals that have specific emission and/or absorption characteristics and also allow for specific tailoring of refractive indexes of the nanocomposites.

In one embodiment, the present invention provides polymeric layers comprising a polymer and semiconductor nanocrystals embedded within the polymer, wherein the nanocrystals have a size and a composition such that they absorb visible, ultraviolet, near-infrared and/or infrared light, and wherein the polymeric layers scatter a minimal portion of light that enters the layers. In certain embodiments, the polymer is silicone. The polymeric layers of the present invention can be used to coat optical devices (e.g., refractive lenses or reflective elements) or can be used to encapsulate active devices, such as a light emitting diodes (LEDs). Suitably, the polymeric layers of the present invention that absorb visible light will absorb red light, blue light and/or green light.

The nanocrystals utilized throughout the embodiments of the present invention will suitably be between about 1-10 nm in size, about 1-4 nm in size or about 1-3 nm in size and can further comprise miscibility-enhancing ligands attached to their surface to aid in mixing with the polymers. The polymeric layers of the present invention can have any effective refractive index between that of the pure polymer and the pure nanocrystals, and will suitably have an effective refractive index greater than about 1.5 and in certain embodiments about 1.8. In certain embodiments, the polymeric layers of the present invention will be greater than about 0.5 mm in thickness. Suitable polymers include silicone.

In another embodiment, the present invention provides polymeric layers comprising a polymer and semiconductor nanocrystals embedded within the polymer, wherein the polymeric layer has an effective refractive index greater than the polymer alone, and wherein the polymeric layer scatters a minimal portion of light that enters the polymeric layer. Suitably, the polymeric layers will scatter less than about 50%, less than about 20% or less than about 15% of light that enters the polymeric layers. In suitable embodiments, the nanocrystals will be ZnS nanocrystals and the polymeric layers will be greater than about 0.5 mm in thickness.

In another embodiment, the present invention provides polymeric layers that encapsulate an active device (e.g., an LED) that has an effective refractive index, $n_1$. The layer comprises a polymer and semiconductor nanocrystals embedded within the polymer.

The layer has an inner boundary in contact with the active device and an outer boundary in contact with a medium having an effective refractive index, $n_2$, wherein the layer has an effective refractive index less than or equal to $n_1$ at the inner boundary and an effective refractive index greater than or equal to $n_2$ at the outer boundary. In certain embodiments, effective refractive index $n_1$ will be greater than $n_2$, suitably greater than about 1.5, and in certain embodiments about 1.8. In certain such embodiments, the layer will have a nanocrystal density gradient, being highest at the inner boundary and lowest at the outer boundary. Suitably this nanocrystal density gradient will be substantially linear throughout the polymeric layer. The nanocrystals optionally have a size and a composition such that they absorb visible (e.g., red, blue and/or green), ultraviolet, near-infrared and/or infrared light.

The present invention also provides processes for preparing polymeric layers, comprising mixing semiconductor nanocrystals at a first density with a solvent and a polymer to form a first mixture, coating a substrate material with the first mixture and evaporating the solvent to form the polymeric layer, wherein the polymeric layer has an effective refractive index of $n_1$.

The processes of the present invention can be used to prepare polymeric layers for coating active devices (e.g., LEDs), or optical devices (e.g., refractive lenses or reflective elements). The processes of the present invention can utilize nanocrystals which further comprise miscibility-enhancing ligands attached to their surface.

In suitable embodiments, the processes of the present invention can further comprise mixing semiconductor nanocrystals at a second density with a solvent and a polymer to form a second mixture, coating the substrate material with the second mixture and evaporating the solvent to form a second polymeric layer, wherein the second polymeric layer has an effective refractive index of $n_2$. In other embodiments, the processes can further comprise repeating these steps with a third through $i^{th}$ density of semiconductor nanocrystals to produce third through $i^{th}$ polymeric layers, wherein the third through $i^{th}$ polymeric layers have effective refractive indices, $n_3$ through $n_2$ respectively. In certain such embodiments, the effective refractive index $n_1$ will be greater than $n_2$ and the effective refractive index of the $i^{th}$ polymeric layer will be less than the effective refractive index of any other polymeric layer. The processes of the present invention can further comprise centrifuging the first mixture of semiconductor nanocrystals, solvent and polymer, to form a nanocrystal density gradient within the mixture prior to coating the substrate material.

In suitable embodiments of the processes of the present invention, the coating can be via spin coating or screen printing. As discussed throughout, the nanocrystals used in the processes of the present invention can have a size and a composition such that they absorb light at a particular wavelength. In other embodiments, the nanocrystals can be tuned so as to emit light at a particular wavelength. In other embodiments, the process of the present invention can utilize semiconductor nanocrystals that comprise two or more different sizes or compositions and therefore can have different properties. The polymeric layers produced by the processes of the present invention will suitably be greater than about 0.5 mm in thickness.

In another embodiment, the present invention provides solid state white lighting devices comprising a power efficiency greater than 25 lm/W, suitably greater than 50 lm/W, greater than 100 lm/W, greater than 150 lm/W, or greater than 200 lm/W.

In other embodiments, the solid state white lighting devices comprise a down converting nanocomposite that comprises two or more semiconductor nanocrystals tuned to emit light at one or more selected wavelengths. The solid state white lighting devices of the present invention will suitably provide a CRI of greater than about 80. In still other embodiments, the solid state white lighting devices comprise a matrix coupled to the two or more semiconductor nanocrystals via one or more chemical moieties.

Another embodiment the present invention provides down converting nanocomposite devices, comprising two or more semiconductor nanocrystal phosphors of two or more sizes, the nanocrystal phosphors tuned to emit light at one or more selected wavelengths, and providing a CRI of greater than about 80; a matrix with a high index of refraction, low UV degradation and/or matched thermal expansion; and a chemical structure coupling the matrix to the nanocrystal phosphors. Suitably, the two or more semiconductor nanocrystal phosphors will comprise a core-shell structure, wherein a shell (e.g., ZnS) provides a type I band gap with respect to a core. The core-shell nanocrystals of the present invention will suitably have a quantum efficiency of about 10% to about 90%.

In further embodiments of the present invention, the two or more semiconductor nanocrystal phosphors are color matched and the matrix can comprise $TiO_2$. In yet further embodiments, the nanocomposite can be layered on an LED substrate which comprises sapphire or SiC. Suitably, the matrix will be a compliant layer that can withstand the thermal expansion that results when the LED heats up, and suitably will be silicone. Suitably, the matrix has a refractive index that is the same as the LED substrate.

In another embodiment, the present invention provides polymeric layers, comprising a polymer; and semiconductor nanocrystals embedded within the polymer, wherein the nanocrystals have miscibility-enhancing ligands conjugated to their surface, and wherein the ligands comprise an alkane chain of between 6 and 18 carbons in length. In suitable embodiments, the ligands can comprise an alkane chain of between 12 and 18 carbons in length. The polymer will suitably be silicone, and the semiconductor nanocrystals will suitably have a size between about 1-10 nm (e.g., 1-4 nm or 1-3 nm), and in certain embodiments will be ZnS nanocrystals. In certain embodiments, the polymeric layers will scatter a minimal portion of light that enters said polymeric layer (e.g., less than about 50%, less than about 20%, or less than about 15% of light that enters said polymeric layer). Suitably, the layer will be greater than about 0.5 mm in thickness.

Additional exemplary polymeric layers and nanocomposites are described herein, for example, composites that include nanostructures with bound ligands and composites in which the matrix was formed from a polymeric molecule serving as the nanostructure ligand.

V. Size and Miscibility of Nanocrystals

In all embodiments of the present invention, it is desirable that the nanocrystals do not aggregate. That is, that they remain separate from each other in the polymeric layer and do not coalesce with one another to form larger aggregates. This is important, e.g., as individual crystals will not scatter light passing through the layer, while larger aggregated structures can create an opaque layer that can hinder the passage of light.

Suitably, whether functioning as down-converting layers, photon-filtering layers, refractive index matching layers, or combinations thereof, the nanocomposites of the present invention will scatter a minimal portion of light that enters the various layers. It is desirable that the nanocomposites of the present invention scatter as little light as possible, such that the layers are substantially transparent or clear.

As used herein, the phrase "scatter a minimal portion of light," means that the amount of light that enters the various nanocomposites of the invention from the incident side (the side that light is entering) is transmitted such that less than about 50% of this incident light is scattered by the nanocomposite. In suitable embodiments, the amount of light that is scattered by the nanocomposite will be less than about 20%, less than about 15%, and approaching 0% of the light being transmitted. The factors that impact most significantly on the amount of light that is scattered by the nanocomposites are the size of the nanocrystals and their miscibility in the polymeric matrix, and hence their ability to remain separated. It should be understood that in applications of the present invention where the nanocomposites function as filters, the amount of light that is transmitted through the polymeric layer will necessarily be reduced as certain wavelengths or ranges of wavelengths will absorbed by the nanocrystals and filtered out of the incident light.

Figure 16:
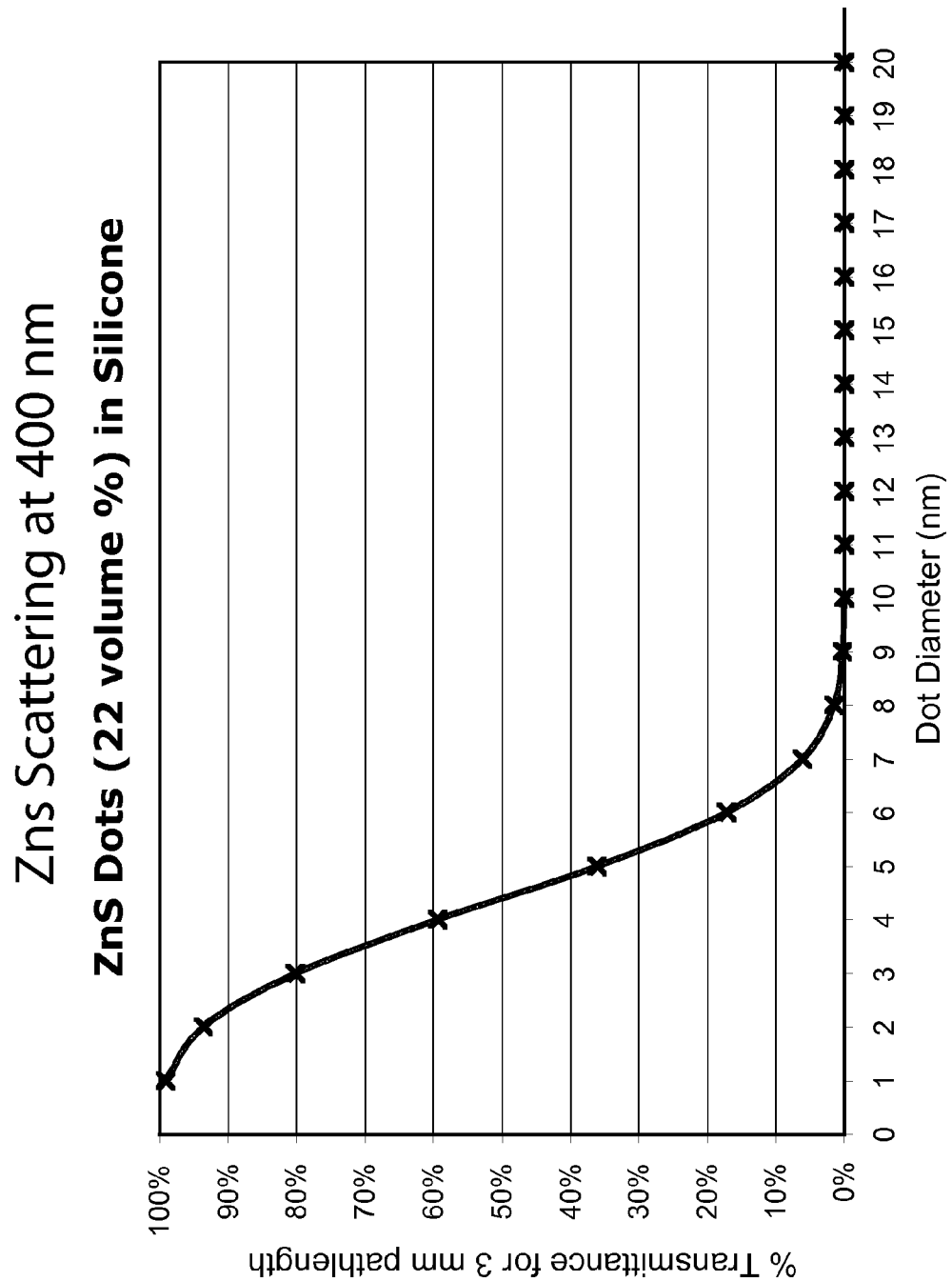
FIG. 16 is a plot of percent transmittance for a silicone nanocomposite comprising ZnS nanocrystals as a function of nanocrystal size.
Figure 17:
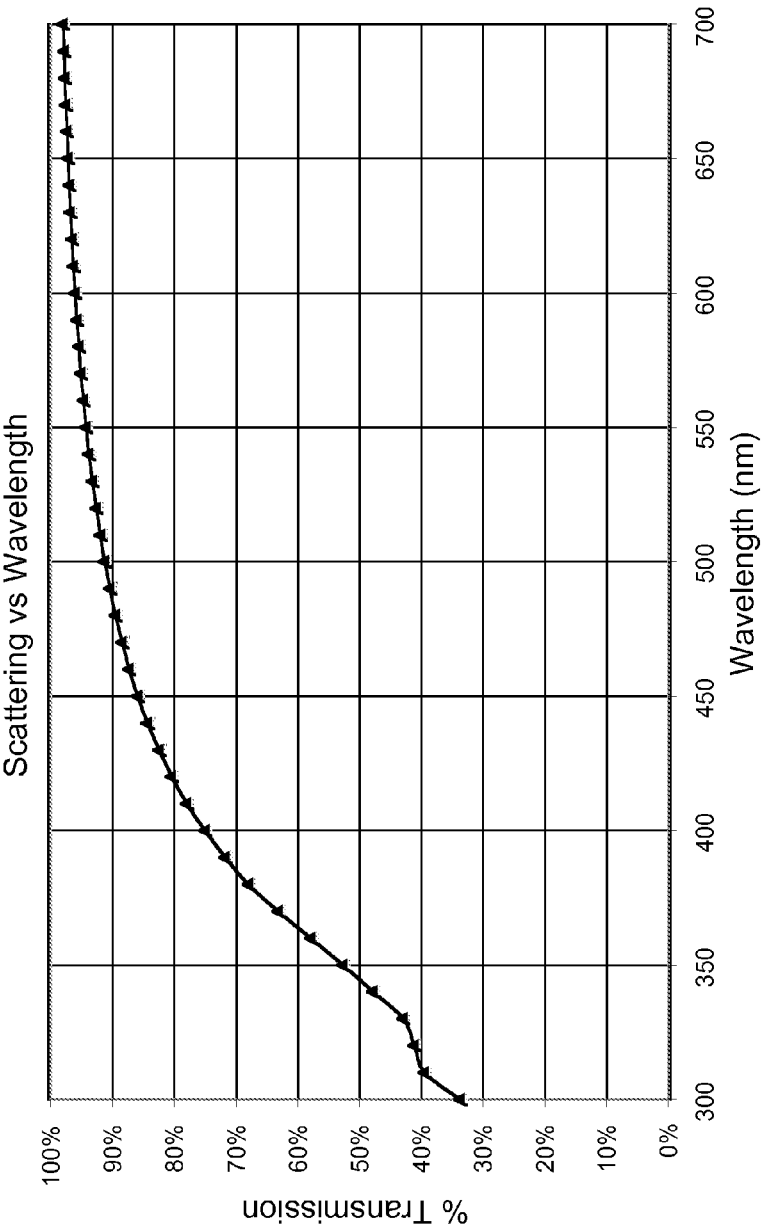
FIG. 17 is a plot of percent transmission for a silicone nanocomposite comprising ZnS nanocrystals as a function of wavelength.

As discussed above, the size of the nanocrystals can be tailored by selecting specific semiconductor materials and then generating and processing the nanocrystals until the desired size is attained. In the various embodiments of the present invention, the nanocrystals will suitably be between about 1 nm and about 20 nm in size, more suitably, between about 1 nm and about 10 nm, between about 1 nm and about 4 nm and most suitably between about 1 nm and about 3 nm. As shown in FIG. 16, using a constant loading volume of ZnS nanocrystals (22% by volume) in silicone, the percent transmittance of light can be tailored from between about 5% to about 100% (i.e. percent that is scattered can be tailored from between about 95% to about 0%). It is a significant advantage of the present invention that by generating nanocrystals that are between about 1 nm to about 4 nm, less than about 50% of the incident light is scattered by the nanocomposites of the present invention. As shown in FIG. 16, by creating nanocrystals that are between about 1 nm and about 3 nm, scattering of less than 20%, approaching 15%, 10%, 5% and 0%, can be achieved. As demonstrated in FIG. 17, a silicone nanocomposite, comprising 3 nm ZnS nanocrystals and a layer with a 3 mm pathlength will scatter less than about 50% (i.e. transmit more than about 50%) of the incident light over the wavelength range 350 nm to 700 nm, scatter less than about 30% over the wavelength range 400 nm to 700 nm and scatter less than about 15% over the wavelength range 500 nm to 700 nm.

Controlled Surface Chemistry For High Loading Density Nanocomposites

In the formation of the nanocomposites of the present invention, two critical issues are: (1) achieving high miscibility of the nanocrystals in the host matrix, and (2) prevention of aggregation of the nanocrystals at a high concentration. Aggregation results in quenching of the emission, hence a lowering of the amount of light transmitted, as well as light scattering from the aggregates. Tuning the index of refraction of the overall composite layer also occurs at different nanocrystal loading densities. Since the nanocrystals have a refractive index of about 2.5 to about 3 and the host matrix is about 1.5 to about 2, matching of the refractive index of the LED substrate (typically sapphire or SiC) will eliminate an optical interface and losses from total internal reflection.

As part of this approach, several issues are addressed, including determination of whether the necessary loading densities in the nanocomposites as determined by simulations are achieved; whether the nanocrystals are homogenously embedded in the host matrix with no (or minimized) aggregation or phase separation so that a high quantum yield is retained and scattering is prevented; whether the index of refraction of the composite layer can be tuned by adjusting the loading density (e.g., gradient) of nanocrystals in the host matrix; whether refractive indices close to the LED substrate are achieved and what the projected effect on the light extraction efficiency is; and at the nanocrystal loading density for refractive index matching, what is the layer thickness of the composite layer necessary to reach an optical density at the excitation wavelength to yield the optimized emission profile determined by the simulations. It can also be determined whether this thickness is compatible with low cost, thin film processing (e.g., thicknesses <1-2 microns).

In order to accomplish this, a tailored, miscibility-enhancing ligand can be designed to bind, associate, coordinate, attach or conjugate to a nanocrystal, and to allow for controlled mixing and miscibility in the host matrix. The performance characteristics, including quantifying the effects on the internal quantum efficiency and light extraction efficiency are measured on nanocomposites of various loading densities and thicknesses.

Surface Chemistry Modification

Figure 18:
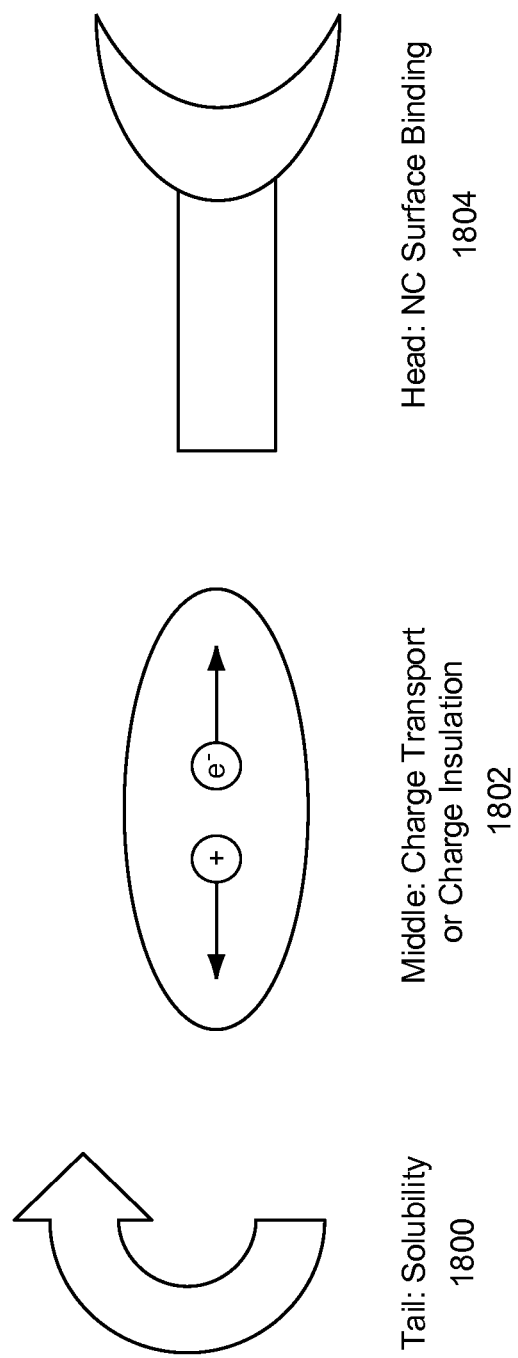
FIG. 18 shows a representation of a 3-part ligand, with a tail-group, a head group and a middle/body-group.

Dispersion of nanocrystals in a host matrix can be controlled by minimizing phase separation and aggregation that can occur when mixing the nanocrystals into the matrixes. A basic strategy is to design a novel 3-part ligand, in which the head-group, tail-group and middle/body-group can each be independently fabricated and optimized for their particular function, and then combined into an ideally functioning complete surface ligand (see FIG. 18; see FIG. 19 for an example ligand). As shown in FIG. 18, head group 1804 is selected to bind specifically to the semiconductor or other material of the nanocrystal (e.g., can be tailored and optimized for CdSe, ZnS, a metal, or any other nanocrystal material). Tail group 1800 is designed to interact strongly with the matrix material and be miscible in the solvent utilized (and can, optionally, contain a linker group to the host matrix) to allow maximum miscibility and loading density in the host matrix without nanocrystal aggregation. Middle or body group 1802 is selected for specific electronic functionality (e.g., charge isolation).

This multipart ligand strategy has been used for the fabrication of high loading density, non-fluorescent, polymer-CdSe nanorod composites in the development of hybrid inorganic-organic nanocomposite solar cells. In certain embodiments of the present invention, significant modifications to the ligand are made due to differences in the two applications. Specifically, the ligand is designed to be charge insulating (rather than charge conducting) and to provide retention of nanocrystal photoluminescence as well as to be compatible with a completely different matrix type (inorganic rather than organic polymers) and nanocrystal material type and shape.

With the development of the 3-part ligand, control of the loading density of the nanocrystals in the nanocomposite can be achieved for purposes of creating the nanoparticle density gradients as described. This permits evaluation of the influence of quantum yield and optical scattering in the nanocomposite. Additionally, tuning of the refractive index of the nanocomposite is possible since the index of refraction of the host matrix is known.

A benefit of this modular approach is the ability to rapidly evaluate new tail, head, and middle/body groups. In the area of head groups (binding with the nanocrystal), there are available methods developed for the development of CdSe synthetic techniques. This includes an understanding of the binding of nanocrystals with phosphonic acids, amines, thiols, phosphines, and phosphine oxides.

A tailored ligand can be optionally designed to bind strongly to the nanocrystal and to allow for mixing in a $TiO_2$ host medium. The new ligand allows for dispersion control (solubility and processability) to facilitate incorporation of the nanocrystals into solvents or host matrixes over a wide range of loading densities as necessary to achieve the optimal white light device performance characteristics and refractive index matching to the blue-LED. Similarly, as other examples, ligands can be designed to bind strongly to the nanocrystal and allow for mixing in a silicone or hydrocarbon polymer.

Ligand Synthesis

The ligand molecule can be synthesized using a generalized technique allowing three separate groups to be synthesized separately and then combined. Head groups of phosphonic acid, amines, carboxylic acids or thiol moieties can be used because of their affinity for the nanocrystal surface. Tail groups can contain terminal hydroxyl groups to tether the nanocrystal in a titania sol-gel matrix, silicon groups to match a silicone polymer matrix, or organic groups to match an organic matrix. The middle/body unit is selected, e.g., for charge insulation (e.g., large energy gap for both electrons and holes), and possible targets are optionally identified using computer modeling. The modeling is performed using a Density Functional Theory (DFT) to model the bandgap of various target molecular structures for ligand design. The confirmation of the chemical identity and purity will be done using mass spectrometry, NMR and FTIR analysis, or similar techniques.

The insulating group (middle/body unit) of the ligands can be selected from long-chain alkanes of various lengths and aromatic hydrocarbons, e.g., C6-C22 alkanes. Selection of the length of the body unit will depend on the desired characteristics of the final matrix and of the polymeric base being used. For example, in applications where it is desired that the matrix possess rheologic or other properties (e.g., mechanical/electrical) similar to that of the polymeric base substance, a shorter chain (e.g., C6-C18) body unit can be selected. For example, the use of a C12 body unit-based ligand on ZnS nanocrystals allows for increased loading of the ZnS nanocrystals at a ratio sufficient to achieve a refractive index of 1.7070 in a base of immersion oil (starting refractive index 1.5180), while still maintaining the grease like consistency of the oil. The use of shorter chain ligands allows for a lower volume fraction of nanocrystals to be used to achieve the same refractive index when compared to nanocrystals with longer chain ligands.

In other applications, the use of longer chain ligands (e.g., C18-C22) can be used when it is desired that the final matrix possess properties closer to that of the ligand itself, rather than the base material. In certain applications, the ligand itself could be used to form the matrix material. Longer chain ligands also allow for additional spacing between the nanocrystals to keep them from aggregating in the base substrate.

Figure 19:
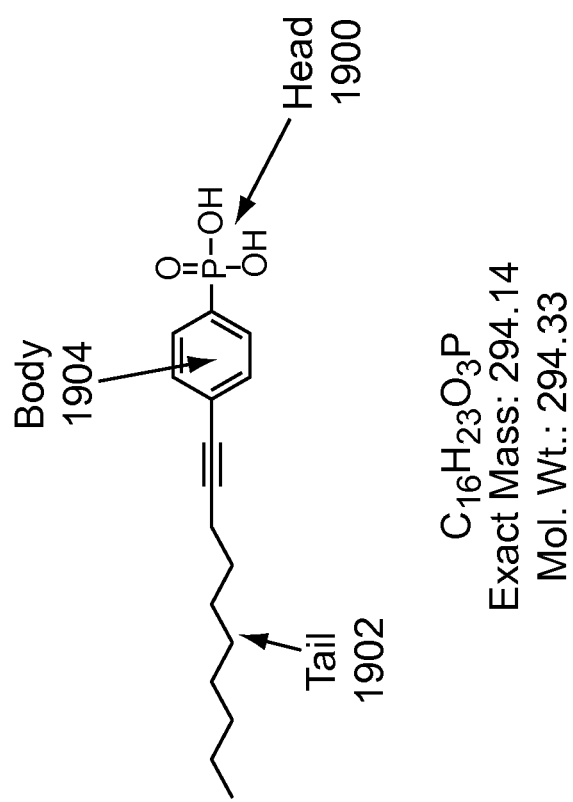
FIG. 19 is an example ligand that can be conjugated to the nanocrystals of the present invention.

FIG. 19 shows an example of a ligand with a phosphonic acid head group 1900, an aliphatic tail 1902 and an aromatic hydrocarbon body 1904. Appropriate choice of body and/or tail components are used to provide like functionality to the matrix to afford high concentrations of nanocrystals in siloxane polymer matrices. Refractive index (RI) tuning/matching can also be affected by the ligand. Independent tuning of the tail or body components of the ligand to obtain a particular RI match with the polymer matrix can be achieved by varying the ligand chemistry appropriately.

Figure 20A:
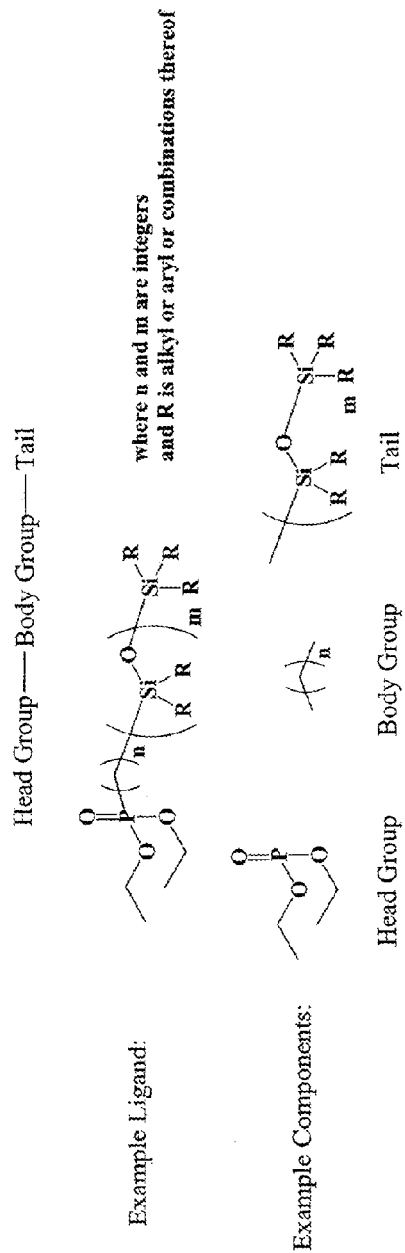
FIGS. 20a-20n show examples, chemical synthesis, and NMR characterization of several example ligands in accordance with the present invention.
Figure 20A:
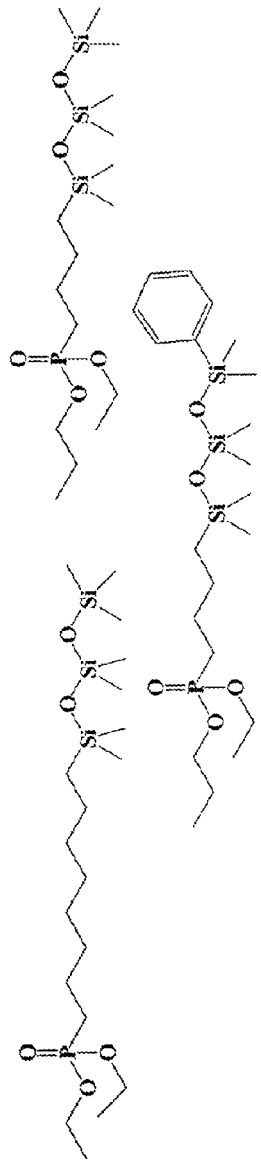
Figure 20B:
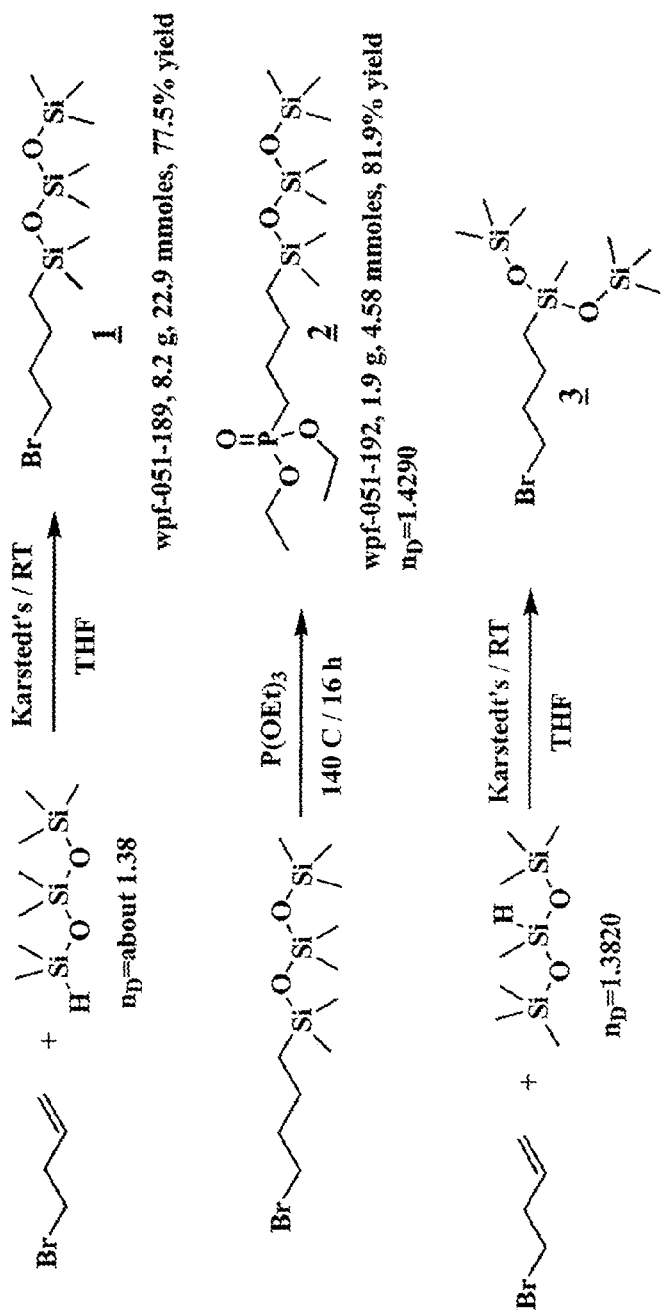
Figure 20C:
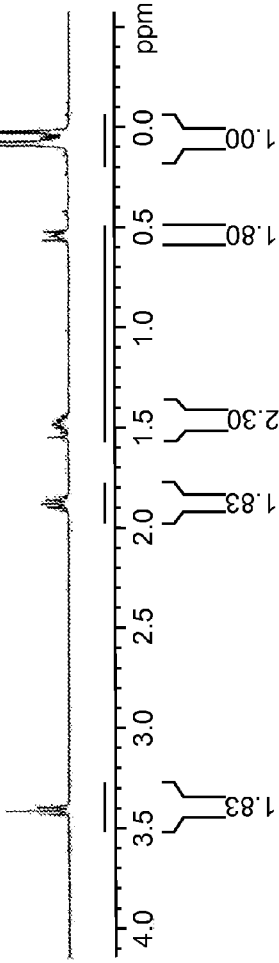
Figure 20D:
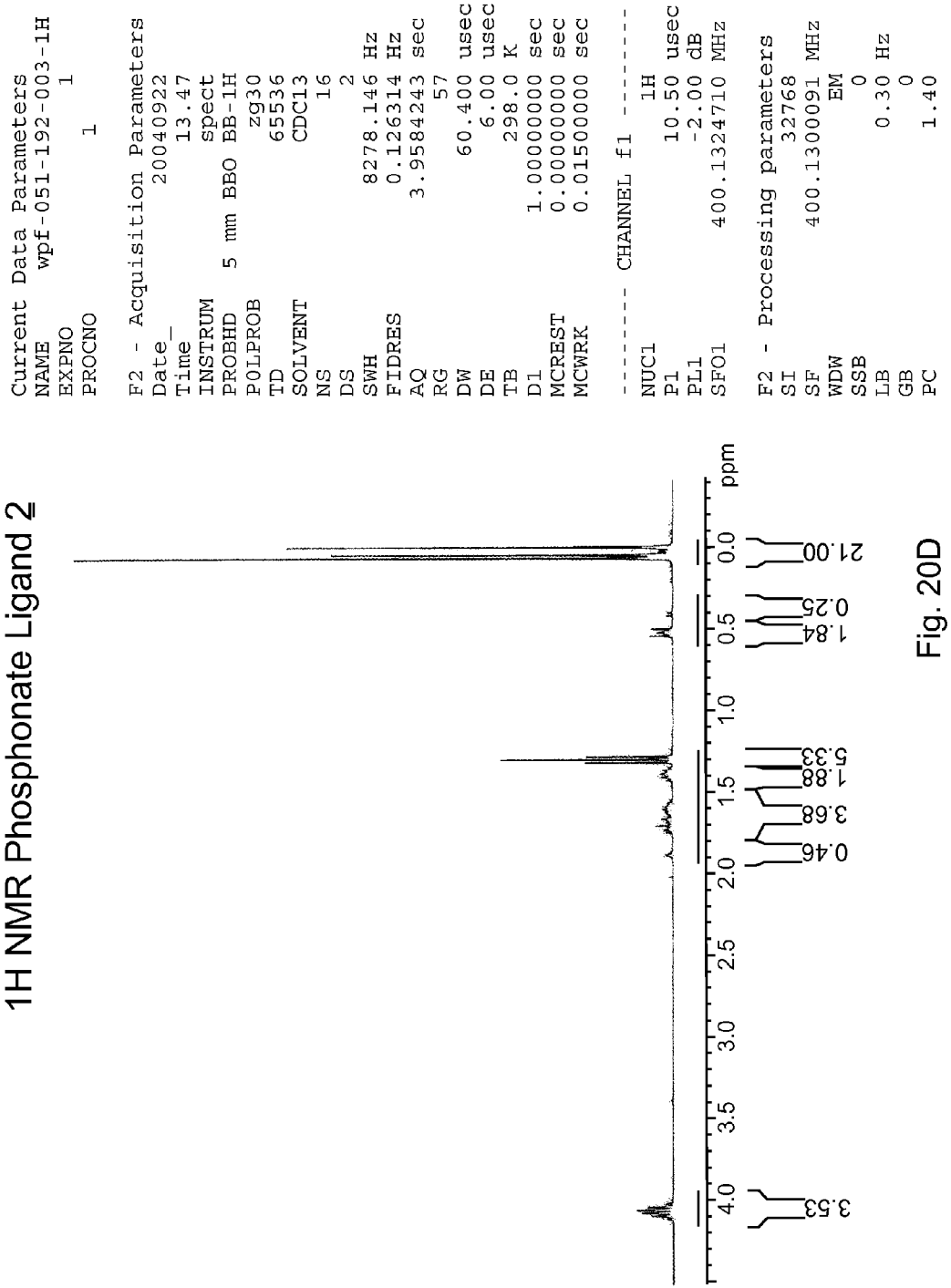
Figure 20E:
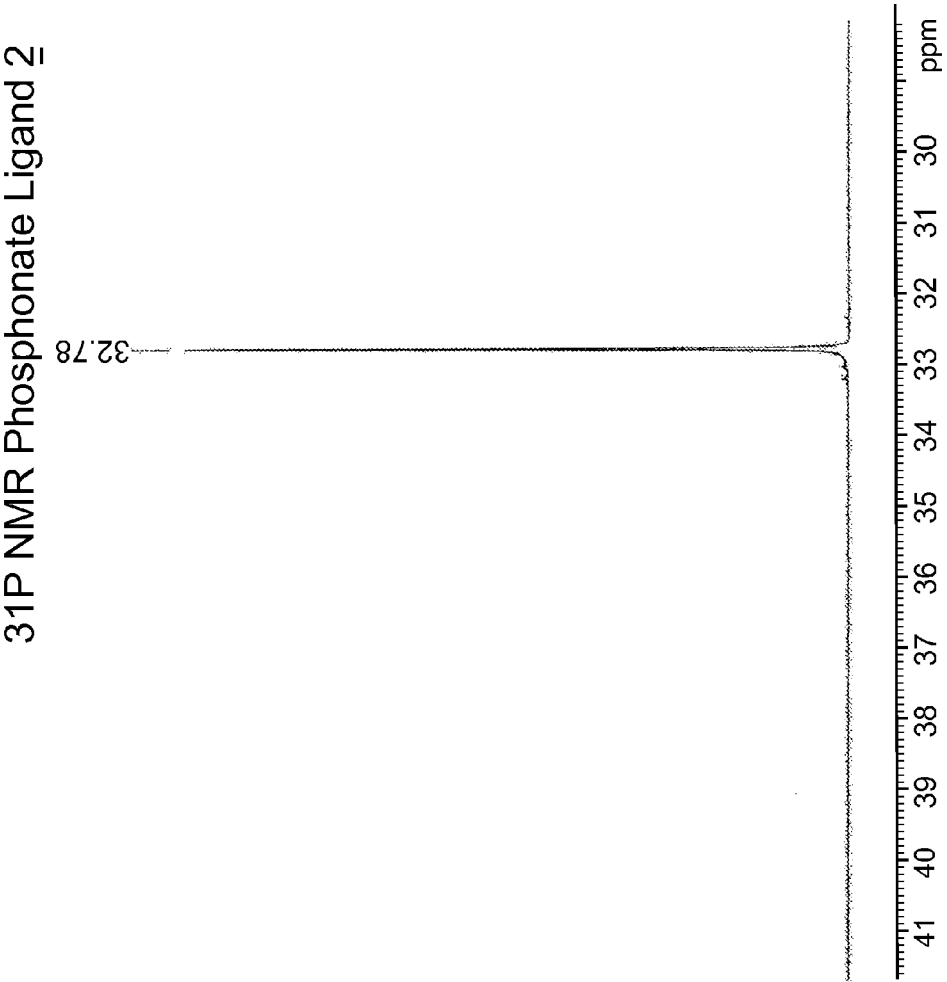
Figure 20F:
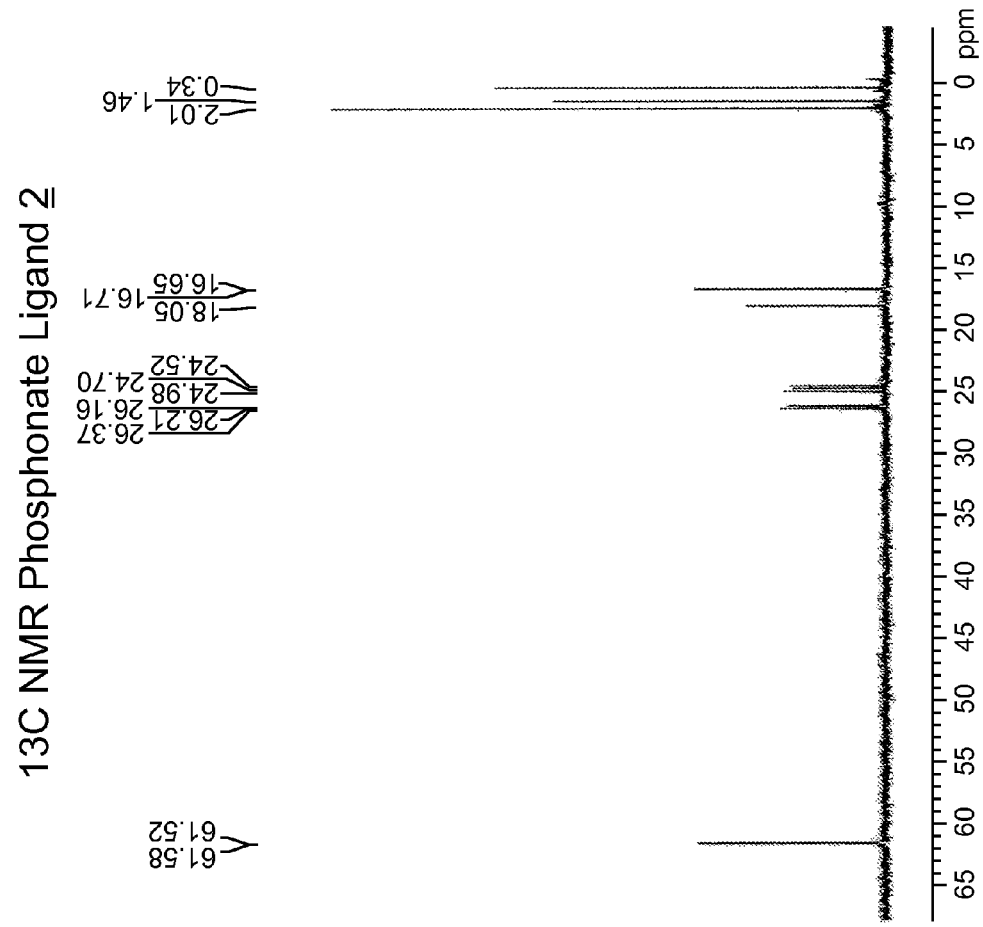

The general design "Head-Body-Tail" affords freedom from any particular ensemble limitations. For example: a phosphonate head group for nanocrystal binding, alkane body group for length adjustment/nanocrystal spacing and dimethyl silicone tail for silicone matrix compatibility can be synthesized as shown in FIG. 20b. An example of tuning the RI (increasing the value) can be realized by incorporation of phenyl groups shown in FIG. 20a (similar to silicone polymers (from vendor Gelest Inc., 612 William Leigh Drive Tullytown, Pa. 19007-6308): DMS-H21 dimethylsiloxane vs. HPM-502 phenyl-methylsiloxane, 1.403 and 1.500 refractive index values, respectively) in the siloxane tail. FIG. 20a illustrates several non-limiting example ligands with head-body-tail design. Matrix compatibility adjustments such as branching siloxane units can also be accommodated (FIG. 20b, molecule 3). Structure verification by NMR of synthesized precursors 1 and 2 in FIG. 20b is shown in FIGS. 20c-f.

Figure 20G:
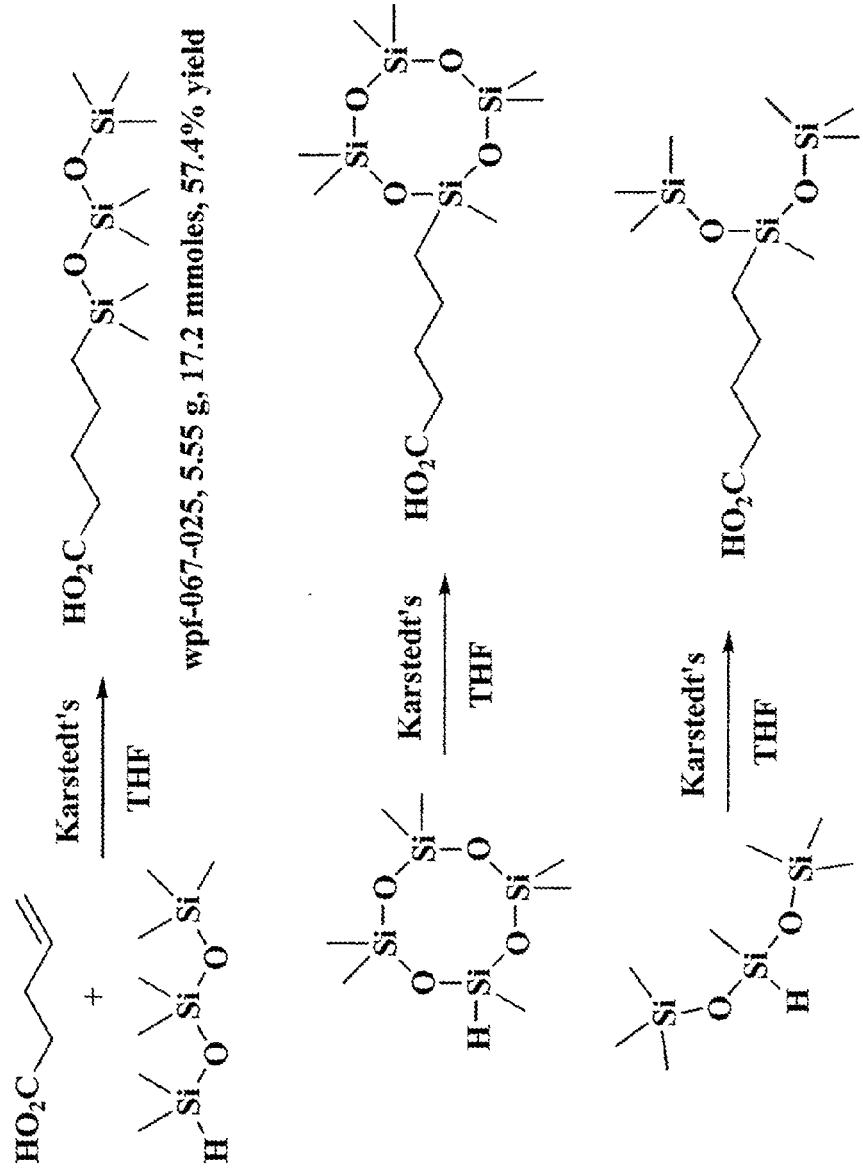
Figure 20H:
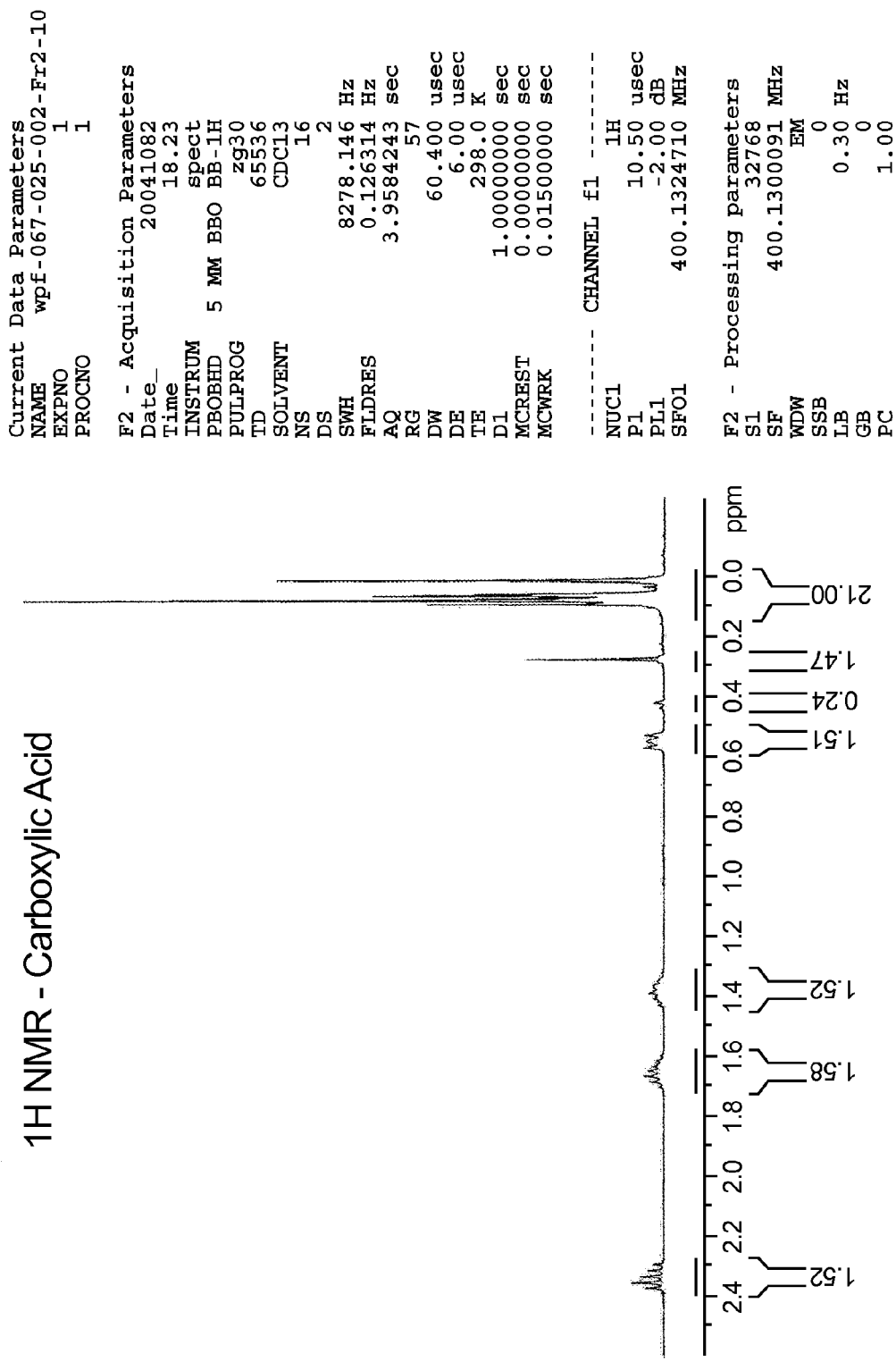
Figure 20I:
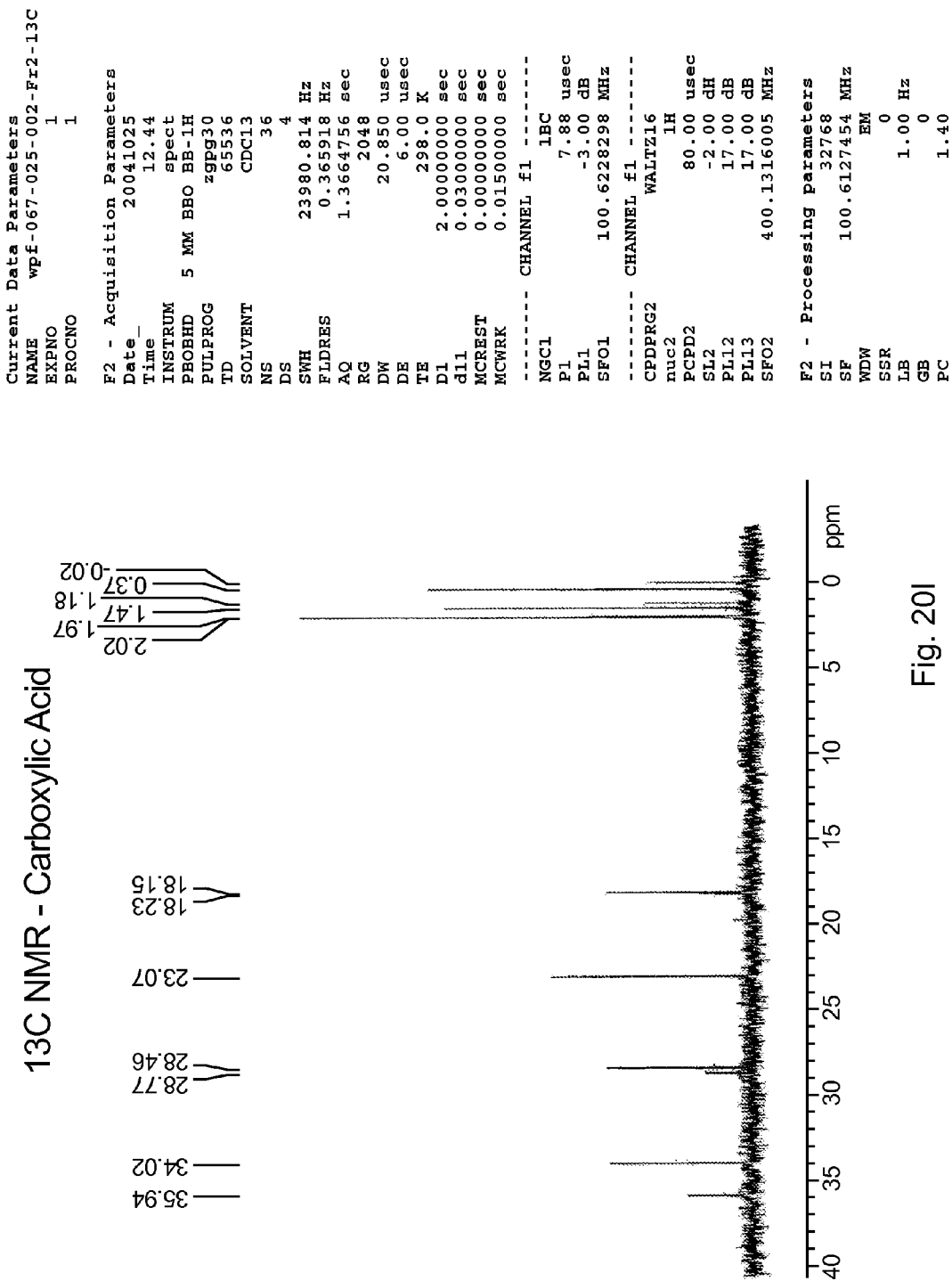

FIG. 20g shows additional examples of ligands and synthesis schemes, including (from top to bottom) the use of trisiloxane, cyclic tetrasiloxane and branched siloxane tail groups in the generation of ligands. Carboxylic acid functionalization of these silicone surfactants is illustrated in FIG. 20g. Structure verification by NMR of a carboxylated trisiloxane ligand shown in FIG. 20g (ligand at top of page) is represented in FIGS. 20h-i.

It is worth noting that although the ligands can be described in terms of three parts, head, body, and tail, they need not be synthesized from these three units. As noted above, three separate groups can be synthesized separately and then combined to produce the ligand. Other synthesis routes are, however, contemplated; for example, the head and body can be introduced into the synthesis procedure on a single molecule, as illustrated in the syntheses shown in FIGS. 20g, 20n, 25a-b, and 27.

Figure 20J:
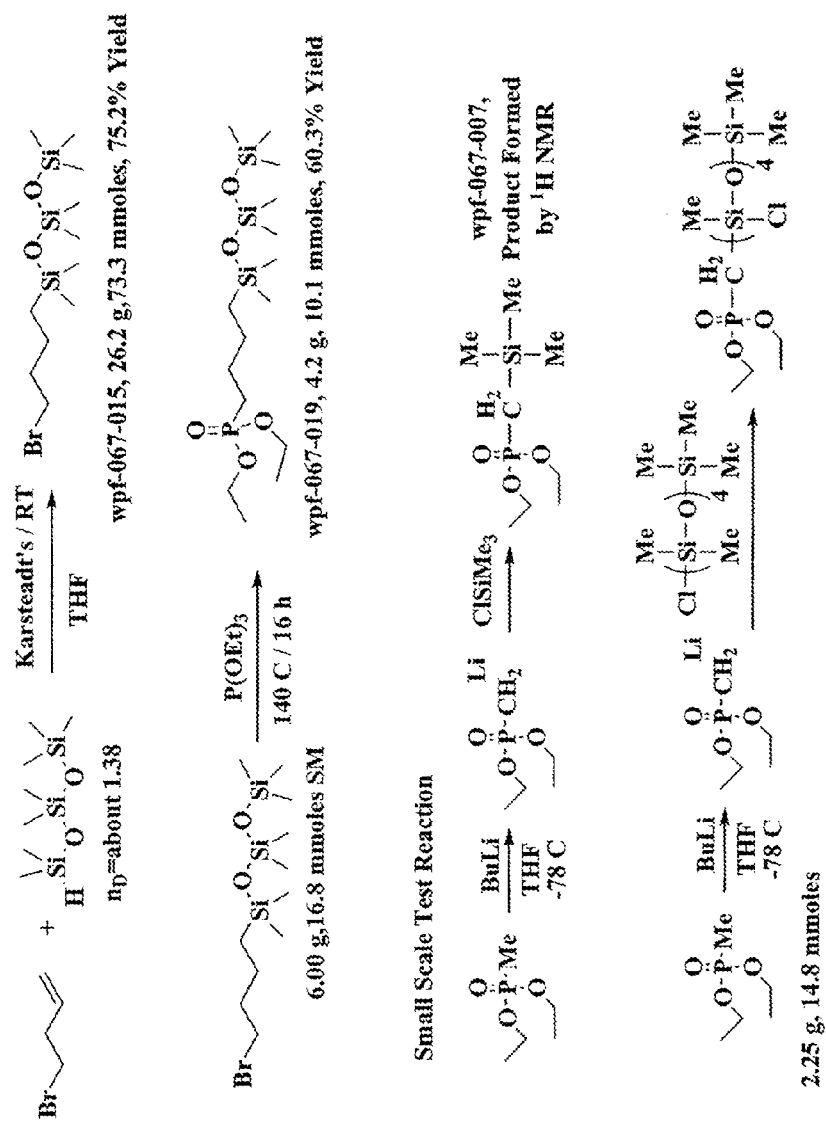
Figure 20K:
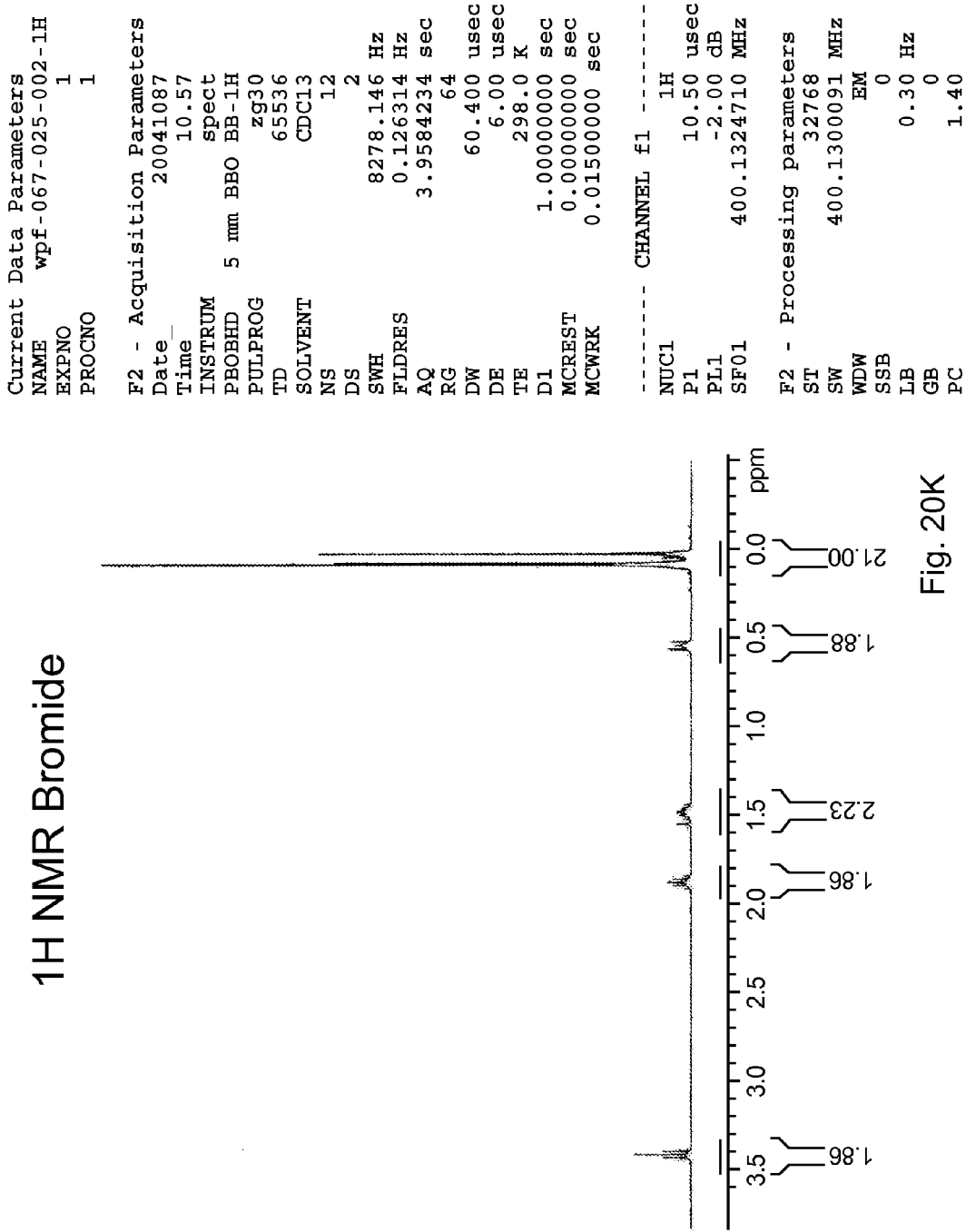
Figure 20L:
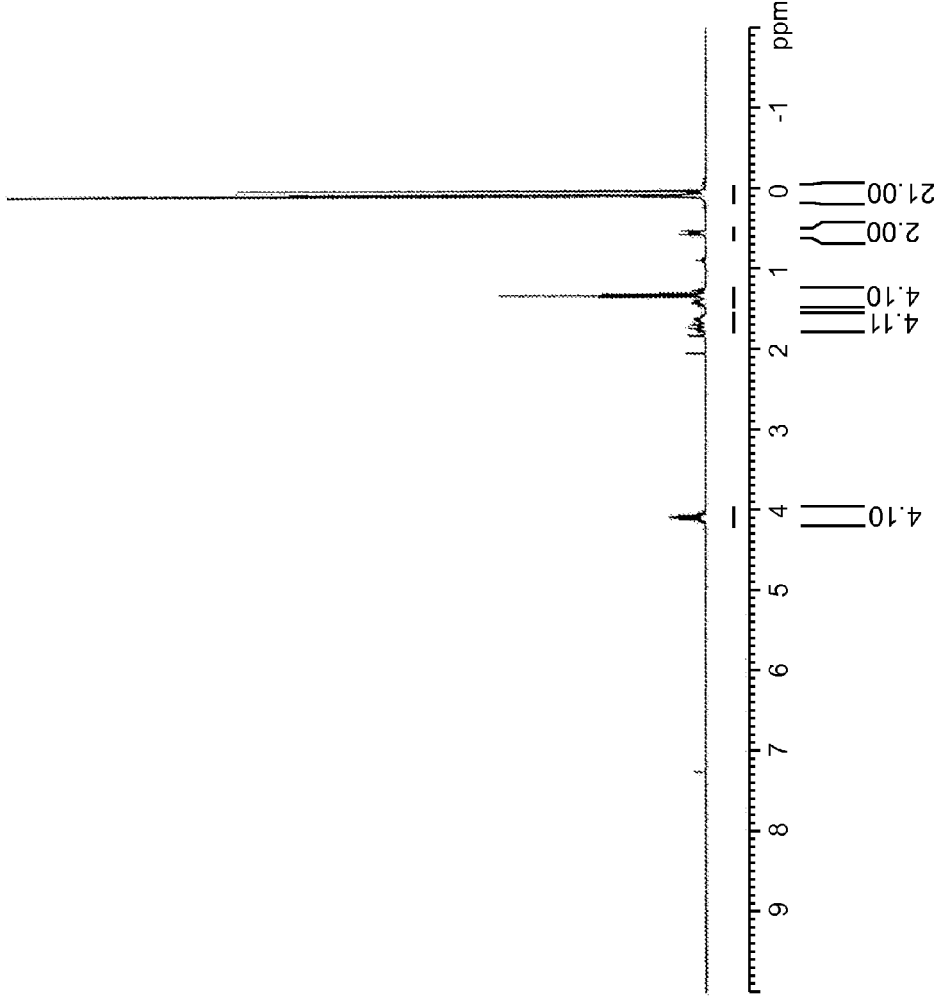
Figure 20M:
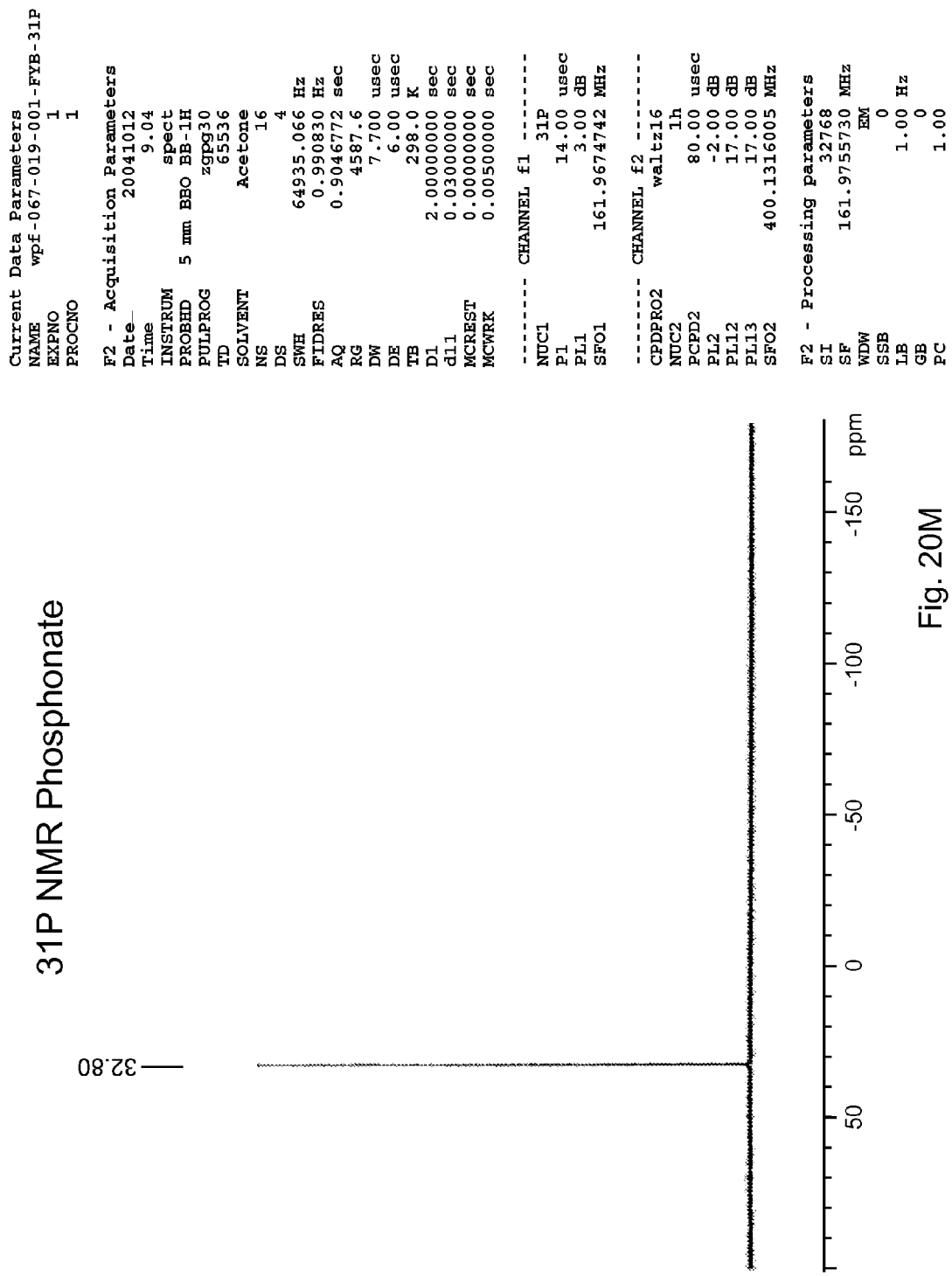
Figure 20N:
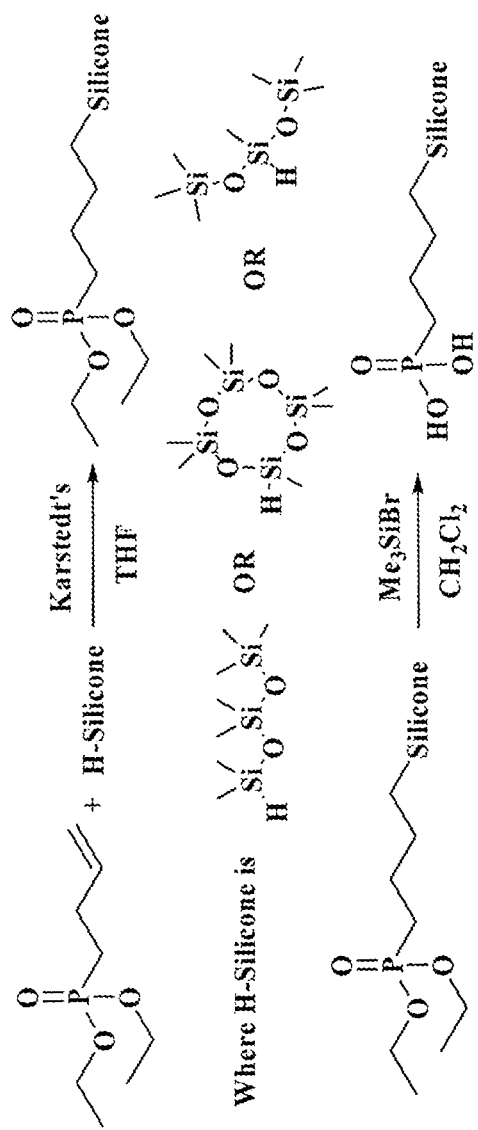

FIGS. 20j and 20n show further examples and synthesis schemes for the production of phosphonate functionalized silicone ligands. Structure verification by NMR of the bromide precursor shown in FIG. 20j is represented in FIG. 20k. FIGS. 20l and 20m represent NMR verification of the structure of the phosphonate ligand product.

Further examples of suitable ligands are presented below, for example in Table 1, and additional synthesis schemes are shown in FIGS. 25-31 and 34 and Examples 3-6 and 9 below.

Ligand exchange to displace the surfactants, which are used during nanocrystal synthesis, can be done by mass action exchange in solution. The nanocrystals and the new ligand (e.g., one of those described herein) are co-dissolved in solvent and allowed to react for a specified time at elevated temperatures. The product is optionally precipitated with alcohol to remove any excess unbound ligands and to remove the displaced synthesis surfactants. The attachment can be confirmed by NMR analysis by redissolving the product into a deuterated NMR compatible solvent. Complexation of the ligand with the nanocrystal causes a shift and broadening in the spectrum compared to the free unbound molecule due to a hindered rotation. As another example, nanostructures are optionally synthesized using one (or more) of the novel ligands described herein as the synthesis surfactant(s).

Nanostructure/Ligand Compositions

One aspect of the invention provides nanostructures having ligands of the invention bound to them (e.g., attached, conjugated, coordinated, associated, or otherwise bound to their surface). As described throughout, the nanostructures are optionally nanocrystals or quantum dots, e.g., inorganic, semiconductor, or metal nanocrystals. In certain embodiments, the nanostructures are core-shell nanostructures.

One general class of embodiments provides a composition comprising a nanostructure and a ligand bound to a surface of the nanostructure, which ligand comprises a body group comprising an organic moiety, a head group coupled to the body group, and a tail group coupled to the body group. The head group comprises a nanostructure binding moiety, and the tail group comprises a silicone moiety.

The body group optionally comprises an unsaturated moiety, an aryl moiety, an alkene moiety, an alkyne moiety, or the like. The body group is optionally a non-conjugated unsaturated moiety.

In other embodiments, the body group comprises an alkyl moiety. For example, the body group can be an alkane chain moiety that contains one or more carbons, e.g., 1-20 carbons. Examples include, but are not limited to, compounds 11-26 in Table 1. In one embodiment, the body group is a linear alkyl moiety three carbons or four carbons in length.

The nanostructure binding moiety can be essentially any moiety that binds or is capable of binding to the surface of the nanostructure. The binding can be, for example, covalent, non-covalent, electrostatic, dative, and/or the like. In one class of embodiments, the nanostructure binding moiety is a carboxylic acid moiety, a monocarboxylic acid moiety, a dicarboxylic acid moiety, a phosphonate moiety, a diethylphosphonate moiety, a bistrimethylsilylphosphonate moiety, a thiol moiety, or an amine moiety. In some embodiments, the head group is monodentate; in other embodiments, the head group is multidentate, which can result in higher affinity binding of the ligand to the nanostructure surface.

In one class of embodiments, the tail group comprises a linear silicone moiety. Exemplary ligands include, but are not limited to, compounds 11-13 and 16-25 in Table 1. In certain embodiments, the tail includes 7-12 dimethylsiloxane units; such compounds are readily soluble in silicone media but are not so large that a highly concentrated solution can not be prepared. In other embodiments, the tail group comprises a cyclic silicone moiety (e.g., compound 15), a branched silicone moiety (e.g., compound 14), or a silsesquioxane moiety (e.g., a polyhedral oligomeric silsesquioxane (POSS) moiety). Optionally, the silicone moiety is a moiety other than a silsesquioxane moiety or other than a POSS moiety. The ligand is optionally thermostable, e.g., to 300° C., 400° C., or even 500° C. or more.

One general class of embodiments provides a composition comprising a nanostructure and a polymeric ligand bound to a surface of the nanostructure. The polymeric ligand comprises a silicone backbone, e.g., a linear silicone backbone, and one or more nanostructure binding moieties coupled to the silicone backbone.

The polymeric ligand includes two or more monomer units. As just a few examples, a monomer unit can be a dimethylsiloxane group, a phenylmethylsiloxane group, a siloxane group bearing a polymerizable or other functional group (as discussed in greater detail below), or a siloxane group bearing a nanostructure binding moiety. The monomer units within the ligand can be of the same type or of different types. In ligands including two or more different types of monomer units, the ligand can, e.g., include a block copolymer of the units (such as in compounds 26-27 and 32-33 in Table 1) or a random copolymer of the units (such as in compounds 36-39).

As for the embodiments above, the nanostructure binding moiety can be essentially any moiety that binds or is capable of binding to the surface of the nanostructure, e.g., a carboxylic acid moiety, a monocarboxylic acid moiety, a dicarboxylic acid moiety, a phosphonate moiety, a diethylphosphonate moiety, a bistrimethylsilylphosphonate moiety, a thiol moiety, or an amine moiety. The ligand optionally comprises two or more nanostructure binding moieties, e.g., three or more, five or more, 10 or more, or even 20 or more.

In one class of embodiments, each of the one or more nanostructure binding moieties is coupled to the silicone backbone through an alkyl moiety. For example, a nanostructure binding moiety can be coupled to the silicon atom through a linear alkyl group (examples of such ligands include compounds 26-29 and 32-39 in Table 1). As another example, the nanostructure binding moiety can be coupled to the silicone backbone through an alkane chain and a silicone moiety (examples of such ligands include compounds 30-31). More generally, the nanostructure binding moiety can be coupled to the silicone backbone through essentially any suitable linker, including, e.g., an organic, aliphatic (saturated or unsaturated), aromatic, substituted, unsubstituted, and/or non-hydrolyzable group. In embodiments in which the ligand includes two or more nanostructure binding moieties, each of the moieties is optionally coupled to a different silicon atom in the silicone backbone.

One general class of embodiments provides a composition comprising a nanostructure and a ligand bound to a surface of the nanostructure, which ligand comprises a body group comprising an alkyl moiety, a head group coupled to the body group, and a tail group coupled to the body group. The head group comprises a nanostructure binding moiety, and the tail group comprises an unsaturated moiety or a silane moiety.

As for the embodiments above, the nanostructure binding moiety can be essentially any moiety that binds or is capable of binding to the surface of the nanostructure, e.g., a carboxylic acid moiety, a monocarboxylic acid moiety, a dicarboxylic acid moiety, a phosphonate moiety, a diethylphosphonate moiety, a bistrimethylsilylphosphonate moiety, a thiol moiety, or an amine moiety.

In one class of embodiments, the body group is a linear alkyl moiety. Examples include, but are not limited to, compounds 40-45 in Table 1. The linear alkyl moiety includes one or more carbons, for example, 1-20 carbons. In one embodiment, the body group is a linear alkyl moiety three carbons or four carbons in length.

In embodiments in which the tail group comprises an unsaturated moiety, the moiety can be an alkene moiety (e.g., a monoalkene, dialkene, or diene), an alkyne moiety, an aromatic moiety, an aryl moiety, or the like. Exemplary ligands in which the tail group is an alkene moiety include compounds 43 and 44 of Table 1. The tail group is optionally a non-conjugated moiety. It is worth noting that certain ligands can be described as alkenes or alkynes bearing one or more nanostructure binding groups, instead of or in addition to being described in terms of head, body, and tail groups.

In embodiments in which the tail group comprises a silane moiety, the silane moiety includes a silicon atom with three independently selected organic substituents. For example, the silicon atom can have three alkene substituents or three aromatic or aryl substituents. In one class of embodiments, the tail group comprises a trialkyl silane moiety. Exemplary ligands in which the tail group comprises a silane moiety include compounds 40-42 and 45 of Table 1.

TABLE 1

Exemplary ligands.

11 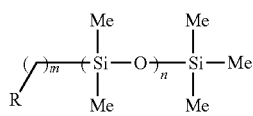

where m is an integer, e.g., between 1 and 20 (e.g., 3-4), where n is an integer, e.g., between 0 and 40 (e.g., 2; preferably 7-12), and where R is the head group 12 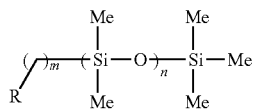

where m is an integer, e.g., between 1 and 20 (e.g., 3-4), where n is an integer, e.g., between 0 and 40 (preferably, 7-12), and where R is selected from the group consisting of

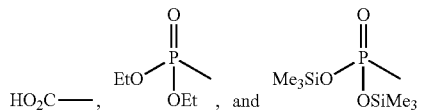

13 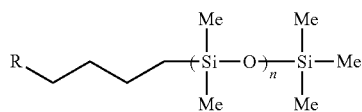

where n is an integer, e.g., between 0 and 40 (preferably, 7-12), and where R is selected from the group consisting of

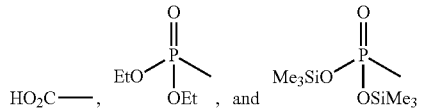

14 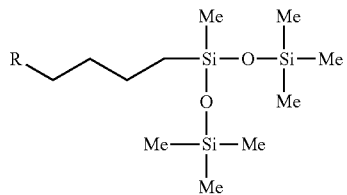

where R is selected from the group consisting of

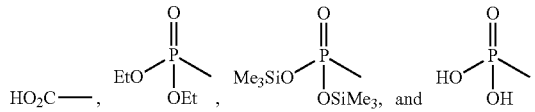

15 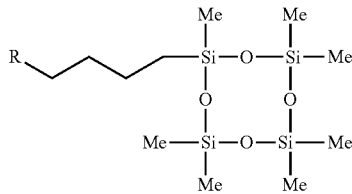

where R is selected from the group consisting of

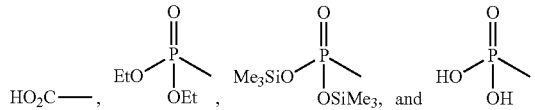

TABLE 1-continued

Exemplary ligands.

16 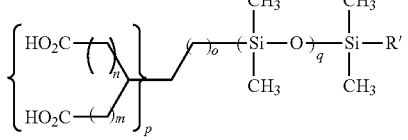

where m is an integer, e.g., between 0 and 20, where n is an integer, e.g., between 0 and 20, where o is an integer, e.g., between 0 and 20, where p is 1, 2, or 3, where q is an integer, e.g., between 0 and 40 (preferably, 7-12), and where R' is Me or Bu 17 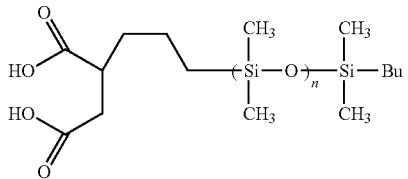

where n is an integer, e.g., between 0 and 40 (preferably, 7-12)

18 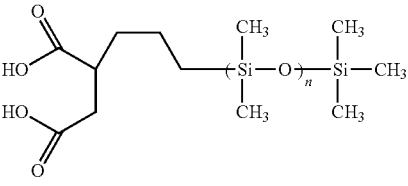

where n is an integer, e.g., between 0 and 40 (preferably, 7-12, e.g., 8-9)

19 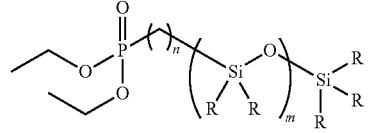

where n and m are integers, and where R is an alkyl group, an aryl group, or combinations thereof 20 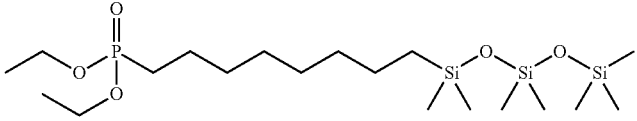 [SMILES: CCOP(=O)(CCCCCCCC[Si](C)(C)O[Si](C)(C)O[Si](C)(C)C)OCC]

21 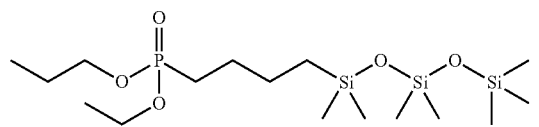 [SMILES: CCCOP(=O)(CCCC[Si](C)(C)O[Si](C)(C)O[Si](C)(C)C)OCC]

22 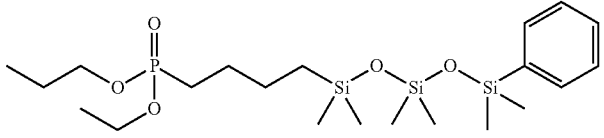 [SMILES: CCCOP(=O)(CCCC[Si](C)(C)O[Si](C)(C)O[Si](C)(C)c1ccccc1)OCC]

23 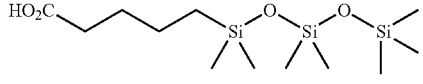 [SMILES: C[Si](C)(C)O[Si](C)(C)O[Si](C)(C)CCCCC(=O)O]

24 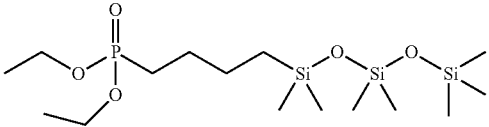 [SMILES: CCOP(=O)(CCCC[Si](C)(C)O[Si](C)(C)O[Si](C)(C)C)OCC]

TABLE 1-continued

Exemplary ligands.

25

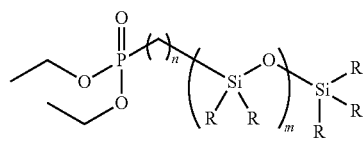

where n and m are integers, and where R is an alkyl group, an aryl group, or combinations thereof

26

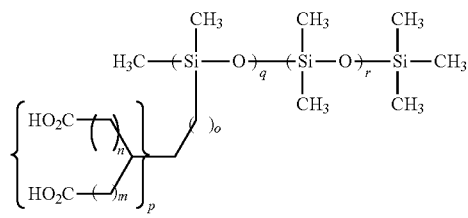

where m is an integer, e.g., between 0 and 20, where n is an integer, e.g., between 0 and 20, where o is an integer, e.g., between 0 and 20, where p is 1, 2, or 3, where q is an integer, e.g., between 1 and 40 (e.g., 2-40), and where r is an integer, e.g., between 0 and 40 (e.g., 2-40 or 3-40)

27

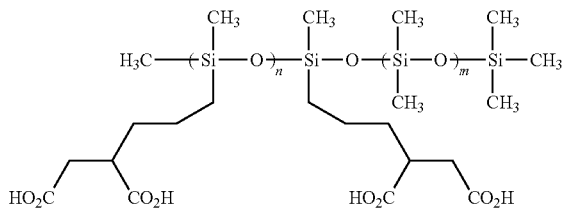

where n is an integer, e.g., between 1 and 40 (e.g., 2-40), and where m is an integer, e.g., between 0 and 40 (e.g., 2-40 or 3-40)

28

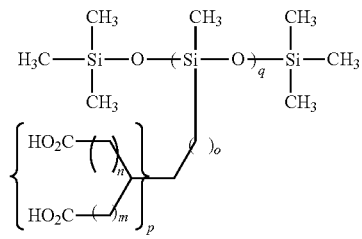

where m is an integer, e.g., between 0 and 20, where n is an integer, e.g., between 0 and 20, where o is an integer, e.g., between 0 and 20, where p is 1, 2, or 3, and where q is an integer, e.g., between 1 and 40

29

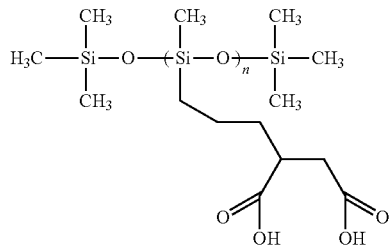

where n is an integer, e.g., between 1 and 40

TABLE 1-continued

Exemplary ligands.

30

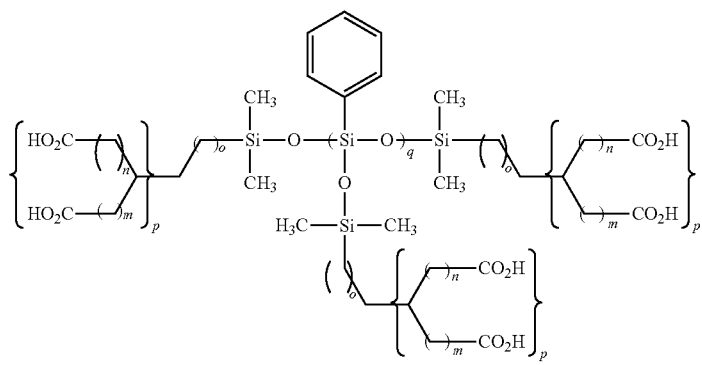

where m is an integer, e.g., between 0 and 20, where n is an integer, e.g., between 0 and 20, where o is an integer, e.g., between 0 and 20, where p is 1, 2, or 3, and where q is an integer, e.g., between 1 and 40

31

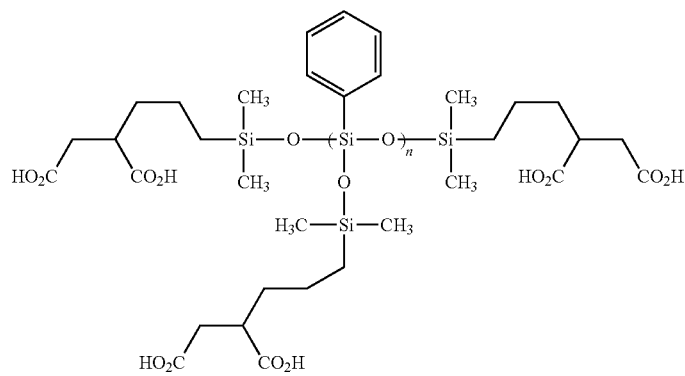

where n is an integer, e.g., between 1 and 40

32

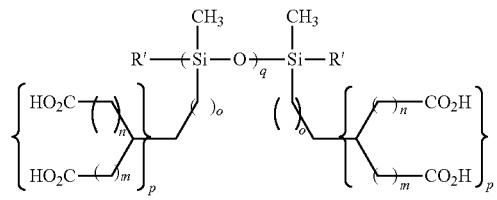

where R' is $-(OSiMe_2)_r SiMe_3$, where m is an integer, e.g., between 0 and 20, where n is an integer, e.g., between 0 and 20, where o is an integer, e.g., between 0 and 20, where p is 1, 2, or 3, where q is an integer, e.g., between 1 and 40, and where r is an integer, e.g., between 0 and 40

33

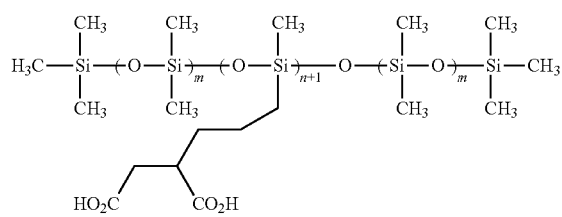

where n is an integer, e.g., between 1 and 40, and where m is an integer, e.g., between 0 and 40

TABLE 1-continued

Exemplary ligands.

34
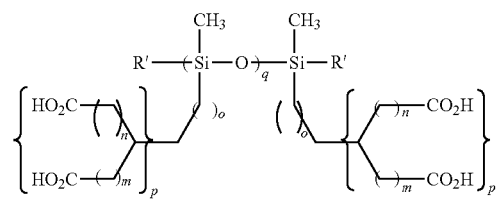

where R' is —(CH$_2$)$_r$CH$_3$, where m is an integer, e.g., between 0 and 20, where n is an integer, e.g., between 0 and 20, where o is an integer, e.g., between 0 and 20, where p is 1, 2, or 3, where q is an integer, e.g., between 1 and 40, and where r is an integer, e.g., between 0 and 40

35
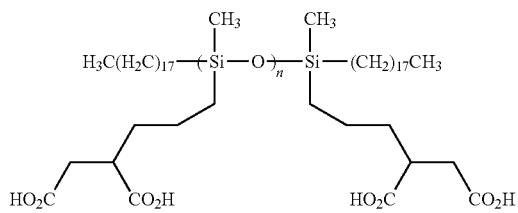

where n is an integer, e.g., between 1 and 40

36
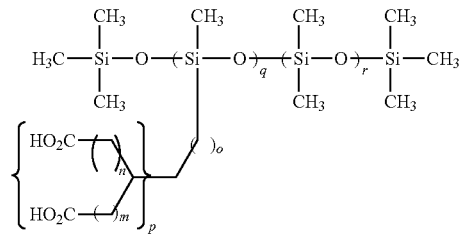

where m is an integer, e.g., between 0 and 20, where n is an integer, e.g., between 0 and 20, where o is an integer, e.g., between 0 and 20, where p is 1, 2, or 3, where q is an integer, e.g., between 1 and 40, where r is an integer, e.g., between 0 and 40, and where the dimethylsiloxane moiety and the moiety bearing the dicarboxylic acid nanostructure binding moiety are randomly situated along the silicone backbone 37
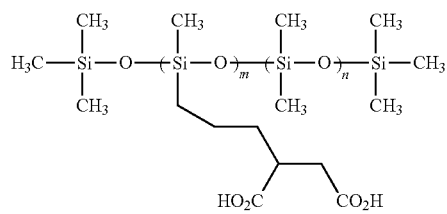

where m is an integer, e.g., between 1 and 40, where n is an integer, e.g., between 0 and 40, and where the dimethylsiloxane moiety and the moiety bearing the dicarboxylic acid nanostructure binding moiety are randomly situated along the silicone backbone

TABLE 1-continued

Exemplary ligands.

38

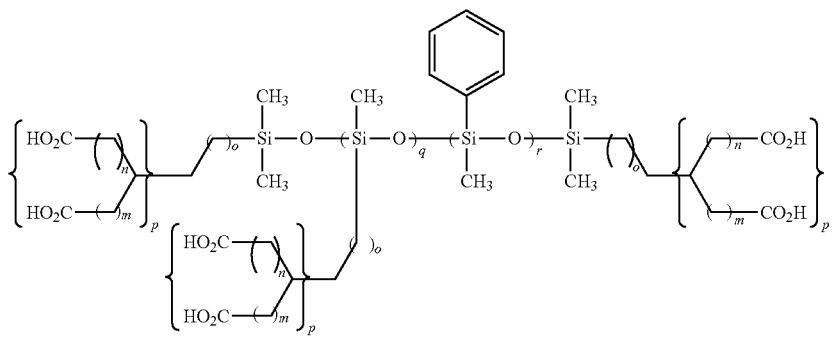

where m is an integer e.g., between 0 and 20, where n is an integer, e.g., between 0 and 20, where o is an integer, e.g., between 0 and 20, where p is 1, 2, or 3 where q is an integer, e.g., between 1 and 40, where r is an integer, e.g., between 0 and 40, and where the phenylmethylsiloxane moiety and the moiety bearing the dicarboxylic acid nanostructure binding moiety are randomly situated along the silicone backbone

39

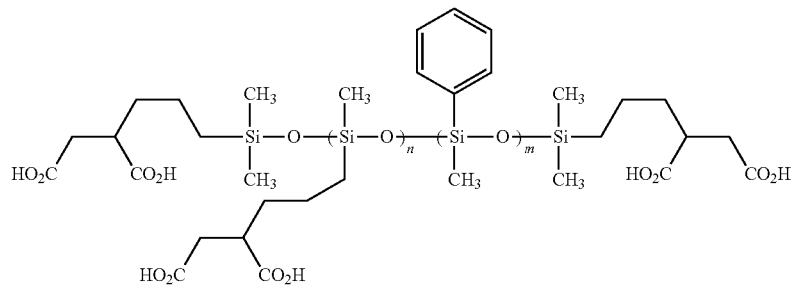

where m is an integer, e.g., between 0 and 40, where n is an integer, e.g., between 1 and 40, and where the phenylmethylsiloxane moiety and the moiety bearing the dicarboxylic acid nanostructure binding moiety are randomly situated along the silicone backbone

40

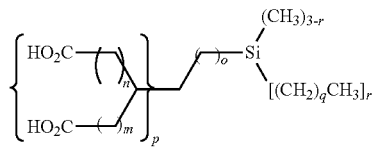

where m is an integer, e.g., between 0 and 20, where n is an integer, e.g., between 0 and 20, where o is an integer, e.g., between 0 and 20, where p is 1, 2, or 3, where q is an integer, e.g., between 0 and 40, and where r is 1, 2, or 3

41

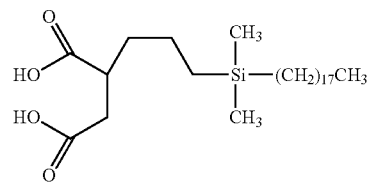

42

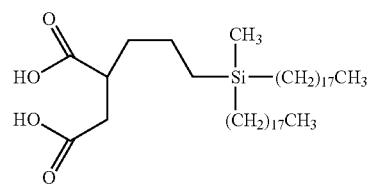

TABLE 1-continued

Exemplary ligands.

43 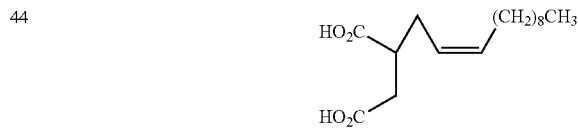

where m is an integer, e.g., between 0 and 20, where n is an integer, e.g., between 0 and 20, where o is an integer, e.g., between 0 and 20, where p is 1, 2, or 3, and where q is an integer, e.g., between 0 and 40

44 

45 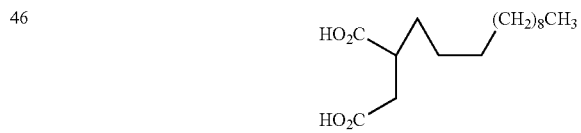

46 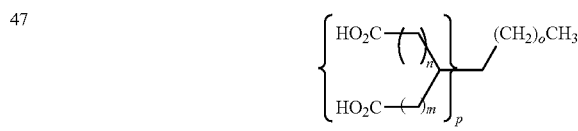

47 

where m is an integer, e.g., between 0 and 20, where n is an integer, e.g., between 0 and 20, where p is 1, 2, or 3, and where o is an integer, e.g., between 0 and 60 (e.g., between 0 and 30)

48 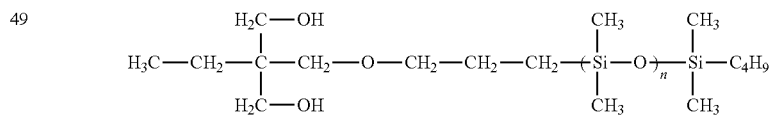

where n is an integer, e.g., between 0 and 60 (e.g., between 0 and 30)

49 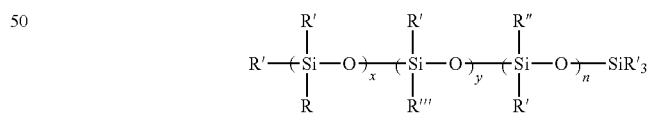

where n is an integer (e.g., n = 10)

50 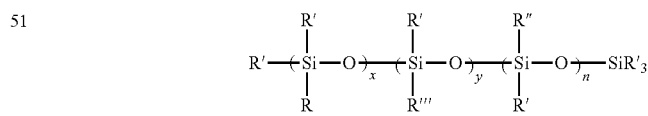

where R is a group comprising an alcohol (e.g., a dicarbinol) moiety, where R' and R'' are independently an alkyl or aryl group, where R''' is an alkyl group, a polymerizable group, a group comprising an epoxide group, a group comprising an amine group, or a group comprising a carboxylic acid group, where x is a positive integer, where y is zero or a positive integer, and where n is zero or a positive integer 51 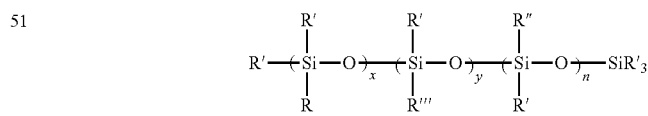

where R is a group comprising an alcohol (e.g., a dicarbinol) moiety, where R' and R'' are methyl groups or where R' is a methyl group and R'' is a phenyl group, where x is a positive integer, where y is zero, and where n is a positive integer TABLE 1-continued Exemplary ligands.

52
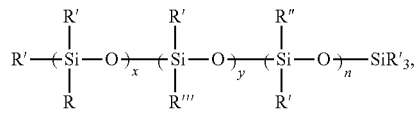

where R is a group comprising an alcohol (e.g., a dicarbinol) moiety, where R' and R" are methyl groups or where R' is a methyl group and R" is a phenyl group, where R''' is an alkyl group, a polymerizable group, a group comprising an epoxide group, a group comprising an amine group, or a group comprising a carboxylic acid group, where x is a positive integer, where y is a positive integer, and where n is a positive integer 53
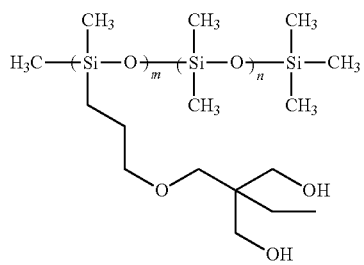

where m and n are positive integers

54
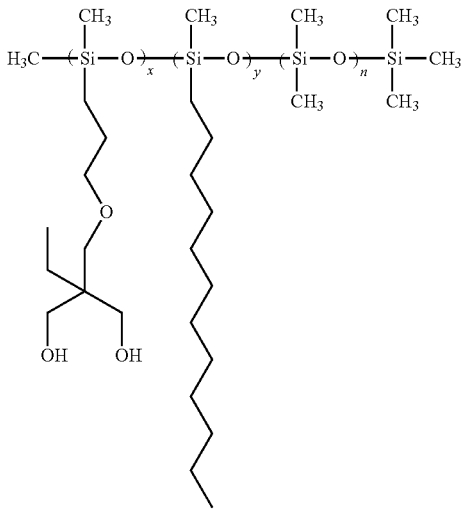

where n, x, and y are positive integers (e.g., x = 5, y = 1, and n = 75, or x = 4, y = 2, and n = 75)

55
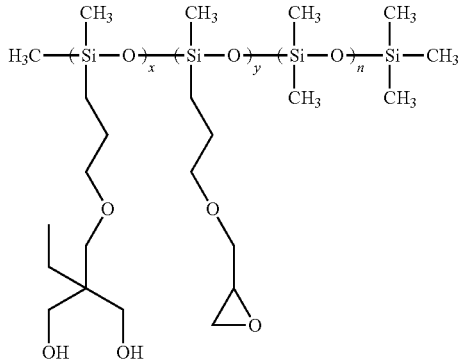

where n, x, and y are positive integers (e.g., x = 4, y = 2, and n = 75, or x = 5, y = 1, and n = 75)

TABLE 1-continued

Exemplary ligands.

56 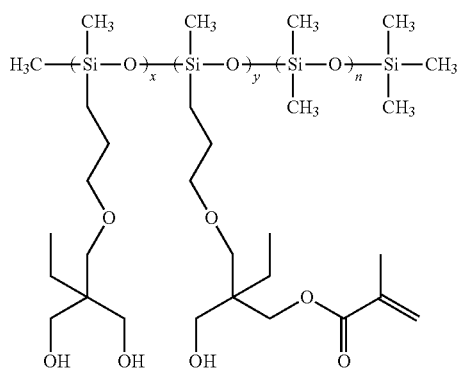

where n, x, and y are positive integers (e.g., x = 5, y = 1, and n = 75, or x = 4, y = 2, and n = 75)

57 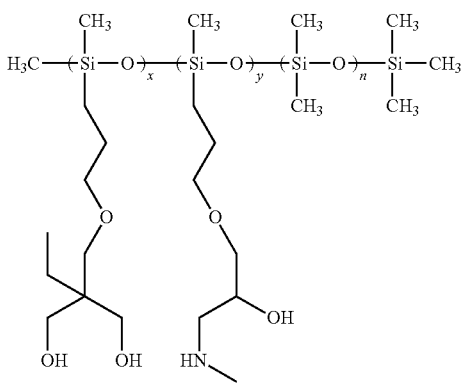

where n, x, and y are positive integers

58 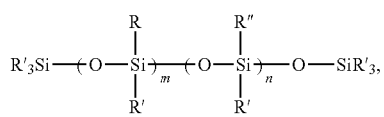

where R is a group comprising a primary and/or secondary amine moiety, where R' and R'' are independently an alkyl (e.g., methyl) or aryl (e.g., phenyl) group, where m is a positive integer, and where n is zero or a positive integer 59 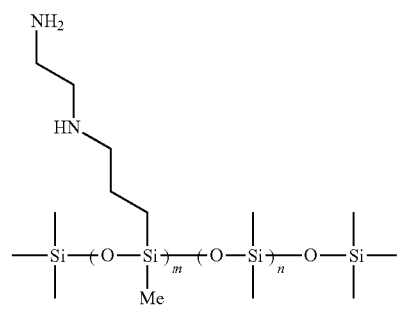

where m and n are positive integers

TABLE 1-continued

Exemplary ligands.

60 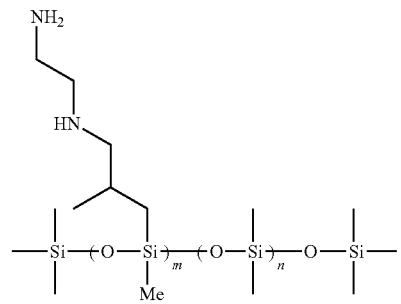

where m and n are positive integers

61 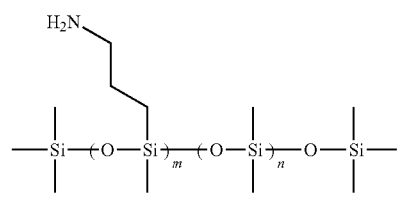

where m and n are positive integers

62 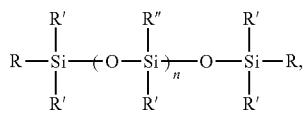

where R is a group comprising a primary and/or secondary amine moiety, where R' and R" are independently an alkyl or aryl group, and where n is a positive integer 63 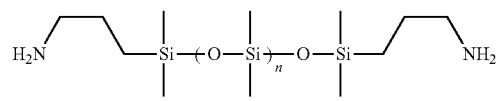

64 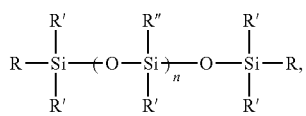

where R is a group comprising an alcohol (e.g., a dicarbinol) moiety, where R' and R" are independently an alkyl or aryl group, and where n is a positive integer 65 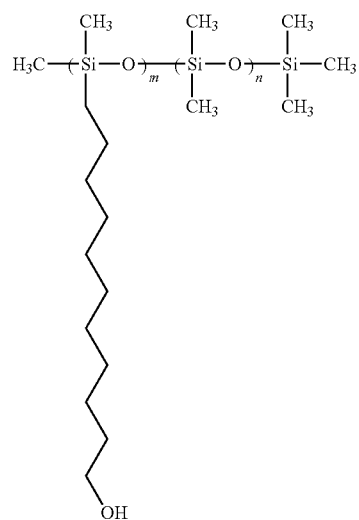

where m and n are positive integers

TABLE 1-continued

Exemplary ligands.

66

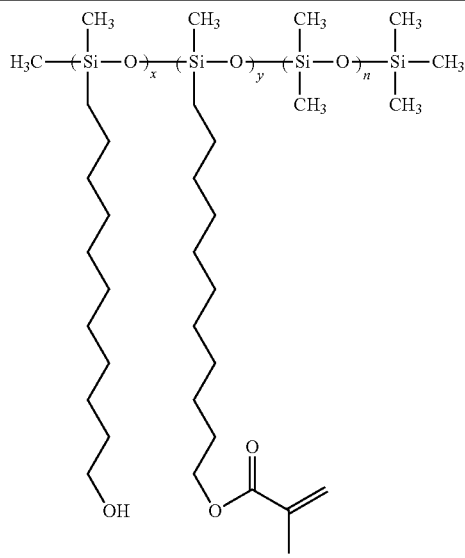

where n, x, and y are positive integers

67

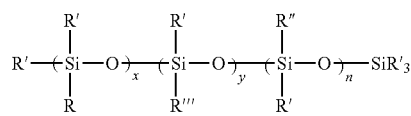

where R is a group comprising a primary and/or secondary amine moiety, where R' and R" are independently an alkyl or aryl group, where R'" is an alkyl group, a polymerizable group, a group comprising an epoxide group, a group comprising an amine group, or a group comprising a carboxylic acid group, where x is a positive integer, where y is zero or a positive integer, and where n is zero or a positive integer; typically R'" is different from R and R"

It will be evident that although certain exemplary ligands are shown with a particular nanostructure binding moiety, the depicted moiety can be replaced with any other nanostructure binding moiety to obtain another ligand of the invention (e.g., in compounds 49-67).

A wide variety of dicarboxylic and polycarboxylic acid nanostructure ligands are described. Thus, one general class of embodiments provides a composition including a nanostructure and a ligand bound to a surface of the nanostructure, where the ligand is a dicarboxylic or polycarboxylic acid other than a poly(norbornene)-poly(norbornene-dicarboxylic acid) diblock copolymer (e.g., any of the carboxylic acid ligands described herein). In one class of embodiments, the nanostructure comprises a semiconductor other than ZnO or ZnS; for example, the nanostructure can comprise a Group semiconductor, a Group IV semiconductor, etc. In another class of embodiments, the nanostructure is a metal nanostructure, e.g., a Ru, Pd, Pt, Ni, W, Ta, Co, Mo, Ir, Re, Rh, Hf, Nb, Au, Ag, Ti, Sn, Zn, Fe, FePt, or similar nanostructure. In one aspect, the nanostructure is a core-shell nanostructure. Optionally, a plurality of the ligand-bound nanostructures are embedded in a polymer, preferably, a polymer comprising a material different from the carboxylic acid ligand.

Ligands are optionally synthesized, for example, as described herein. Certain ligands are commercially available, e.g., compound 44 (dodecenyl succinic acid).

A composition of the invention optionally includes a plurality or population of the ligand-bound nanostructures. The nanostructures are optionally dispersed in a solvent or are optionally embedded in a polymer to form a polymer layer or nanocomposite. Accordingly, in one aspect, the composition comprises a plurality of the nanostructures, each of which has the ligand bound to its surface, and a polymer in which the nanostructures are embedded. The polymer can be, for example, a silicone polymer (e.g., in embodiments in which the ligand has a silicone tail group or substituent) or a hydrocarbon or other organic polymer (e.g., in embodiments in which the ligand has an alkyl, alkene, or other hydrocarbon tail or substituent). Suitable polymers are well known in the art and examples are described herein. Additional exemplary hydrocarbon polymers include polystyrene, polyethylene, acrylates, and the like.

In another embodiment, the present invention provides polymeric layers, comprising a polymer and semiconductor nanocrystals embedded within the polymer, wherein the nanocrystals have miscibility-enhancing ligands conjugated to their surface, and wherein the ligands comprise an alkane chain of between 6 and 18 carbons in length. In suitable embodiments, the ligands can comprise an alkane chain of between 12 and 18 carbons in length. The polymer will suitably be silicone, and the semiconductor nanocrystals will suitably have a size between about 1-10 nm, and in certain embodiments will be ZnS nanocrystals. In certain embodiments, the polymeric layers will scatter a minimal portion of light that enters said polymeric layer. Suitably, the layer will be greater than about 0.5 mm in thickness.

In one aspect, the invention provides a variety of polymeric molecules including alcohol nanostructure binding moieties that are useful as nanostructure ligands. Accordingly, one general class of embodiments provides a composition that includes a nanostructure and a polymeric ligand, where the ligand comprises a silicone backbone and one or more alcohol moieties coupled to the silicone backbone. The silicone backbone is typically linear but is optionally branched.

An alcohol moiety includes a hydroxyl group (—OH) attached to a carbon atom. The alcohol moiety is optionally part of a larger functional group. For example, particularly useful ligands in the context of the present invention include one or more dicarbinol moieties coupled to the silicone backbone. A dicarbinol moiety includes a saturated carbon atom to which two carbinol groups (—CH$_2$OH) are covalently bonded, typically directly but optionally through one or more other atoms (e.g., one or more other saturated or unsaturated carbon atoms).

Generally, as for the embodiments above, the polymeric ligand is bound to a surface of the nanostructure. Not all of the ligand in the composition need be bound to the nanostructure, however. In some embodiments, the polymeric ligand is provided in excess (e.g., in substantial excess, e.g., in an amount at least equal in weight to the amount provided to bind the nanostructure and typically much greater), such that some molecules of the ligand are bound to a surface of the nanostructure and other molecules of the ligand are not bound to the surface of the nanostructure. The excess ligand can optionally be polymerized into a silicone matrix in which the nanostructure is embedded, as described in greater detail hereinbelow. Similarly, not all of the hydroxyl groups in a given molecule need be bound to the nanostructure.

As noted above, the polymeric ligand includes two or more monomer units, which can be of the same type or different types. All of the monomer units can include the alcohol (e.g., dicarbinol) moiety, or some of the monomers can include the alcohol moiety while others lack it. One or more terminal and/or internal subunits can bear the alcohol group(s) (see, e.g., compounds 64 and 52 for terminal and internal examples, respectively).

In one class of embodiments, the polymeric ligand comprises at least two different types of monomer units, at least one of which comprises the alcohol (e.g., dicarbinol) moiety and at least one of which lacks the alcohol moiety. The ligand optionally includes three or more different types of monomers. The ligands can include either random copolymers (such as in compounds 50-57 and 65-66 in Table 1) or block copolymers. The number and/or percentage of monomers including the alcohol group can be varied. For example, monomer units comprising the alcohol (e.g., dicarbinol) moiety are optionally present in the ligand at a molar percentage between 0.5% and 99.5%, between 0.5% and 75%, between 0.5% and 50%, between 0.5% and 40%, between 0.5% and 30%, between 0.5% and 25%, preferably between 0.5% and 20%, and more preferably between 0.5% and 10% (inclusive). In embodiments in which the ligand comprises a dicarbinol nanostructure binding group, monomer units comprising the alcohol moiety optionally comprise a single dicarbinol moiety per monomer unit. Also in embodiments in which the ligand comprises a dicarbinol nanostructure binding moiety, the ligand optionally comprises 1-500 dicarbinol moieties per ligand molecule, e.g., 1-200, 2-200, or 2-100. In one exemplary embodiment, the ligand includes about 60 dicarbinol moieties per ligand molecule.

Subunits lacking the alcohol moiety can be, e.g., diphenylsiloxane, phenylmethylsiloxane, or dimethylsiloxane groups, as just a few examples. As another example, the monomer units lacking the alcohol group can include a longer alkyl group (e.g., to modify the glass transition temperature of a polymer formed from the ligand or to modify interactions between the ligand and the nanostructures). As yet another example, the monomer units can include other groups that impart additional functions to the ligand, for example, a polymerizable group, an epoxide group, an amine group, or a carboxylic acid group. A polymerizable group (a functional group which can undergo polymerization) can be employed to incorporate the ligand (whether bound to the nanostructure or provided in excess) into a polymeric matrix. For example, a (meth)acrylate group can polymerize when initiated by radicals, and an epoxide group can polymerize when initiated by cationic initiators.

Suitable polymeric ligands include, but are not limited to, compounds 49-57 and 64-66 in Table 1. The ligands are optionally synthesized, e.g., as described herein (see FIG. 34 and Example 9). Certain ligands are commercially available, e.g., compound 49 with n=10 is available from Gelest, Inc. (www dot gelest dot com).

As for the other embodiments herein, the nanostructures are optionally nanocrystals or quantum dots, e.g., inorganic, semiconductor (e.g., group II-VI, III-V, or IV), or metal nanocrystals. Optionally, the nanostructures are core-shell nanostructures, e.g., CdSe/ZnS quantum dots.

The composition optionally includes a plurality or population of the nanostructures, e.g., with bound ligand. The composition optionally includes a solvent (e.g., toluene), in which the nanostructure(s) and ligand can be dispersed. As noted, the nanostructures and ligand can be incorporated into a matrix to form a polymer layer or nanocomposite (e.g., a silicone matrix formed from the ligand). Thus, the composition can also include a crosslinker (e.g., 1,6-diisocyanatohexane) and/or an initiator, e.g., a radical or cationic initiator. Suitable crosslinkers include organic or polymeric compounds with two or more functional groups that can react with hydroxyl groups (or other groups on the ligand) to form covalent bonds. Such functional groups include, but are not limited to, isocyanate, epoxide, anhydride, and carboxylic acid groups, e.g., on a silicone or other molecule. The composition optionally includes a mixture of ligands.

In another aspect, the invention provides a variety of polymeric molecules including amine nanostructure binding moieties that are useful as nanostructure ligands. Accordingly, one general class of embodiments provides a composition that includes a nanostructure and a polymeric ligand, where the ligand comprises a silicone backbone and one or more primary and/or secondary amine moieties coupled to the silicone backbone. The silicone backbone is typically linear but is optionally branched.

Generally, as for the embodiments above, the polymeric ligand is bound to a surface of the nanostructure. Not all of the ligand in the composition need be bound to the nanostructure, however. In some embodiments, the polymeric ligand is provided in excess (e.g., in substantial excess, e.g., in an amount at least equal in weight to the amount provided to bind the nanostructure and typically much greater), such that some molecules of the ligand are bound to a surface of the nanostructure and other molecules of the ligand are not bound to the surface of the nanostructure. The excess ligand can optionally be polymerized into a silicone matrix in which the nanostructure is embedded, as described in greater detail hereinbelow. Similarly, not all of the amine groups in a given molecule need be bound to the nanostructure.

As noted above, the polymeric ligand includes two or more monomer units, which can be of the same type or different types. All of the monomer units can include the amine moiety, or some of the monomers can include the amine moiety while others lack it. One or more terminal and/or internal subunits can bear the amine group(s). Optionally, the ligand includes a primary amine group at the end of a linear chain substituent on the monomer, e.g., an internal (pendant) and/or terminal monomer. Optionally, the linear chain also includes a secondary amine group. More generally, monomer units comprising the amine moiety optionally comprise a single primary amine moiety per monomer unit. In one class of embodiments, monomer units comprising the amine moiety comprise a single primary amine moiety and a single secondary amine moiety per monomer unit.

In one class of embodiments, the polymeric ligand comprises at least two different types of monomer units, at least one of which comprises the amine (e.g., primary and/or secondary) moiety and at least one of which lacks the amine moiety. The ligand optionally includes three or more different types of monomers. The ligands can include either random copolymers (such as in compounds 58-61 and 67 in Table 1) or block copolymers. The number and/or percentage of monomers including the amine group can be varied. For example, monomer units comprising the amine moiety are optionally present in the ligand at a molar percentage between 0.5% and 99.5%, between 0.5% and 75%, between 0.5% and 50%, between 0.5% and 40%, between 0.5% and 30%, between 0.5% and 25%, and preferably between 0.5% and 20% (e.g., between 1% and 20%) or between 0.5% and 10% (e.g., between 1% and 10%) (inclusive). The range between 0.5% and 20% provides the best performance observed in terms of luminescence and stability of the nanostructures. As another example, the ligand optionally comprises 1-500 amine moieties (e.g., primary and/or secondary) per ligand molecule, e.g., 1-200, 2-200, or 2-100. In one exemplary embodiment, the ligand includes 1-20 primary amine moieties per ligand molecule (e.g., 1-15), and optionally also includes an equal number of secondary amine moieties per ligand molecule.

Subunits lacking the amine moiety can be, e.g., diphenylsiloxane, phenylmethylsiloxane, or dimethylsiloxane groups, as just a few examples. As another example, the monomer units lacking the amine group can include a longer alkyl group or other group that imparts additional functions to the ligand, for example, a polymerizable group, an epoxide group, or a carboxylic acid group (e.g., compound 67).

Suitable polymeric ligands include, but are not limited to, compounds 58-63 and 67 in Table 1. The ligands are optionally synthesized, and certain ligands are commercially available. For example, compound 63 with a formula weight of about 900 (product no. DMS-A11), compound 63 with a formula weight of about 25,000 (product no. DMS-A31), compound 63 with a formula weight of about 30,000 (product no. DMS-A32R), compound 60 with m to n ratio of about 4 to 100 and formula weight of about 7000 (product no. AMS-242), compound 61 with m to n ratio of about 6.5 to 100 and formula weight of about 4500 (product no. AMS-162), compound 61 with m to n ratio of 4.5 to 100 and formula weight of about 7500 (product no. AMS-152), and compound 59 with m to n ratio of about 3 to 100 and formula weight of about 21,000 (product no. AMS-233, see also product nos. ATM-1112 and ATM-1322) are available from Gelest, Inc. (www dot Gelest dot com). Compound 59 with m to n ratio of about 1 to 100 and formula weight of about 20,000 (product no. GP-344), compound 59 with m to n ratio of 2 to 100 and formula weight of about 45,000 (product no. GP-316), and compound 59 with m to n ratio of about 0.5 to 100 and formula weight of about 70,000 (product no. GP-345) are available from Genesee Polymers Corporation (www dot gpcsilicones dot com). Exemplary formula weights thus include, but are not limited to, those between about 900 and 70,000.

The composition optionally includes a mixture of ligands, for example, a mixture of a ligand having the amine group on internal subunits (pendant, e.g., compounds 58-61) and an additional ligand having the amine group on one or more terminal subunits (e.g., compounds 62-63). Thus, in one class of embodiments, the composition also includes a second polymeric ligand, which second polymeric ligand comprises a silicone backbone and one or more primary and/or secondary amine moieties coupled to the terminal subunits of the second polymeric ligand. The ratio of pendant to terminal amine ligand can be varied, for example, from 90% pendant (first) polymeric ligand:10% terminal (second) polymeric ligand to 50% pendant ligand:50% terminal ligand. As one example, the composition can include a mixture of compounds 58 and 62. In one class of embodiments, the composition includes a mixture of two (or more) ligands having the amine group on internal subunits (e.g., a mixture of compounds 59 and 60).

As for the other embodiments herein, the nanostructures are optionally nanocrystals or quantum dots, e.g., inorganic, semiconductor (e.g., group II-VI, III-V, or IV), or metal nanocrystals. Optionally, the nanostructures are core-shell nanostructures, e.g., CdSe/ZnSe/ZnS or CdSe/CdS/ZnS quantum dots.

The composition optionally includes a plurality or population of the nanostructures, e.g., with bound ligand. The composition optionally includes a solvent, in which the nanostructure(s) and ligand can be dispersed. As noted, the nanostructures and ligand can be incorporated into a matrix to form a polymer layer or nanocomposite (e.g., a silicone matrix formed from the ligand). Thus, the composition can also include a crosslinker and/or an initiator. Suitable crosslinkers include organic or polymeric compounds with two or more functional groups (e.g., two, three, or four) that can react with amine groups (or other groups on the ligand) to form covalent bonds. Such functional groups include, but are not limited to, isocyanate, epoxide (also called epoxy), succinic anhydride or other anhydride or acid anhydride, and methyl ester groups, e.g., on a silicone, hydrocarbon, or other molecule. In one class of embodiments, the crosslinker is an epoxy crosslinker, e.g., an epoxycyclohexyl or epoxypropyl crosslinker (e.g., compounds A-C or D-G in Table 2, respectively). The reactive groups on the crosslinker can be pendant and/or terminal (e.g., compounds B and D or compounds A, C, and E-G in Table 2, respectively). The crosslinker is optionally an epoxy silicone crosslinker, which can be, e.g., linear or branched. In certain embodiments, the crosslinker is a linear epoxycyclohexyl silicone or a linear epoxypropyl (glycidyl) silicone. A number of exemplary crosslinkers are listed in Table 2. Suitable crosslinkers are commercially available. For example, compounds H-K are available from Aldrich (www dot sigmaaldrich dot com) and compounds A-G are available from Gelest, Inc. (www dot gelest dot com), e.g., with a formula weight of about 900-1100 for compound A as product no. DMS-EC13, with a formula weight of about 18,000 and a molar percentage of 3-4% for m for compound B as product no. ECMS-327, with a formula weight of about 8000, m≈6, and n≈100 for compound D as product no. EMS-622, and as product no. DMS-E09 for compound E.

TABLE 2
Exemplary crosslinkers.
A
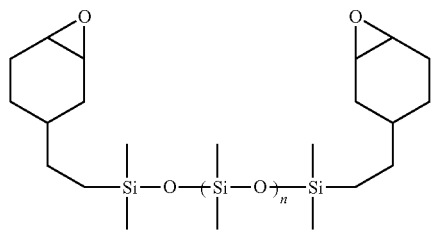
where n is a positive integer
B
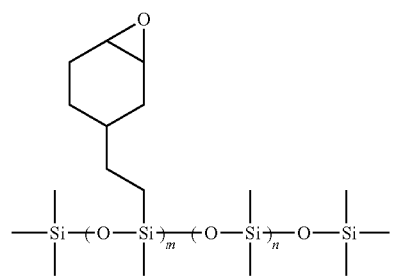
where m and n are positive integers
C
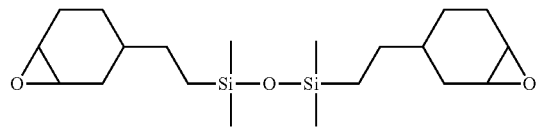
D
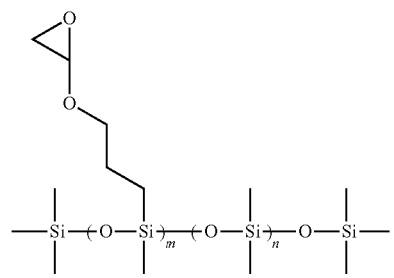
where m and n are positive integers (e.g., m≈6 and n≈100)
E
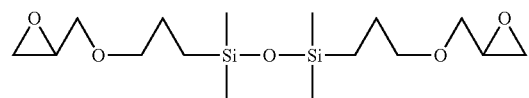 [SMILES: C[Si](C)(CCCOCC1CO1)O[Si](C)(C)CCCOCC1CO1]
F
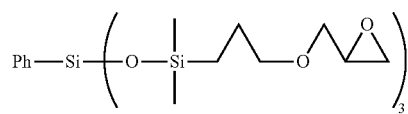
where Ph represents a phenyl group
G
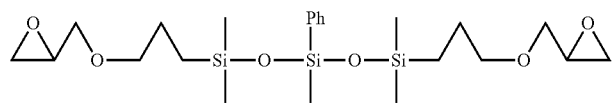
where Ph represents a phenyl group TABLE 2-continued
Exemplary crosslinkers.
H 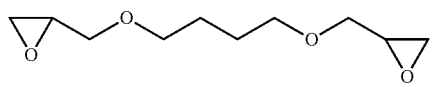
1,4-butanediol diglycidyl ether
I 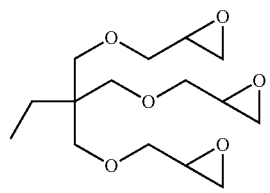 [SMILES: CCC(COCC1CO1)(COCC1CO1)COCC1CO1]
trimethylolpropane triglycidyl ether
J 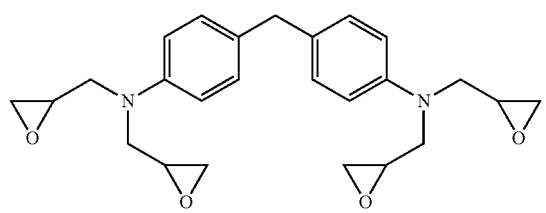 [SMILES: c1cc(N(CC2CO2)CC2CO2)ccc1Cc1ccc(N(CC2CO2)CC2CO2)cc1]
4,4'-methylenebis(N,N-diglycidylaniline)
K 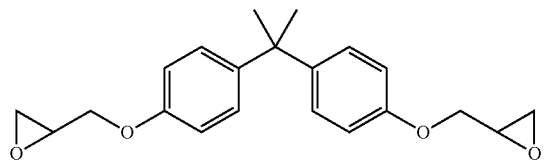 [SMILES: CC(C)(c1ccc(OCC2CO2)cc1)c1ccc(OCC2CO2)cc1]
bisphenol A diglycidyl ether
L 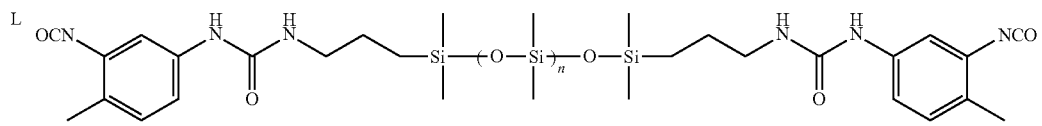
M 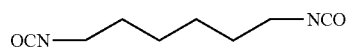
1,6-diisocyanate
N 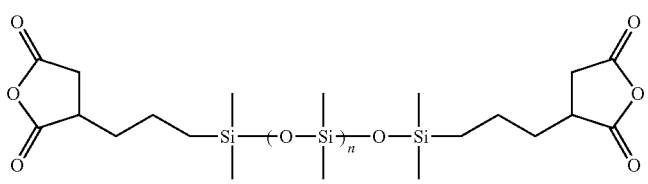
where n is a positive integer
O 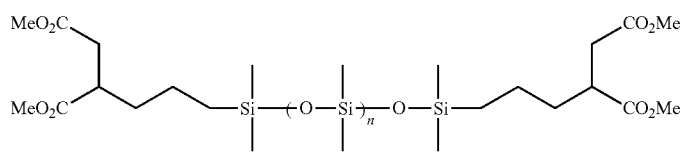
where n is a positive integer and where Me represents a methyl group

VI. Processes for Producing Nanocomposites

Figure 21:
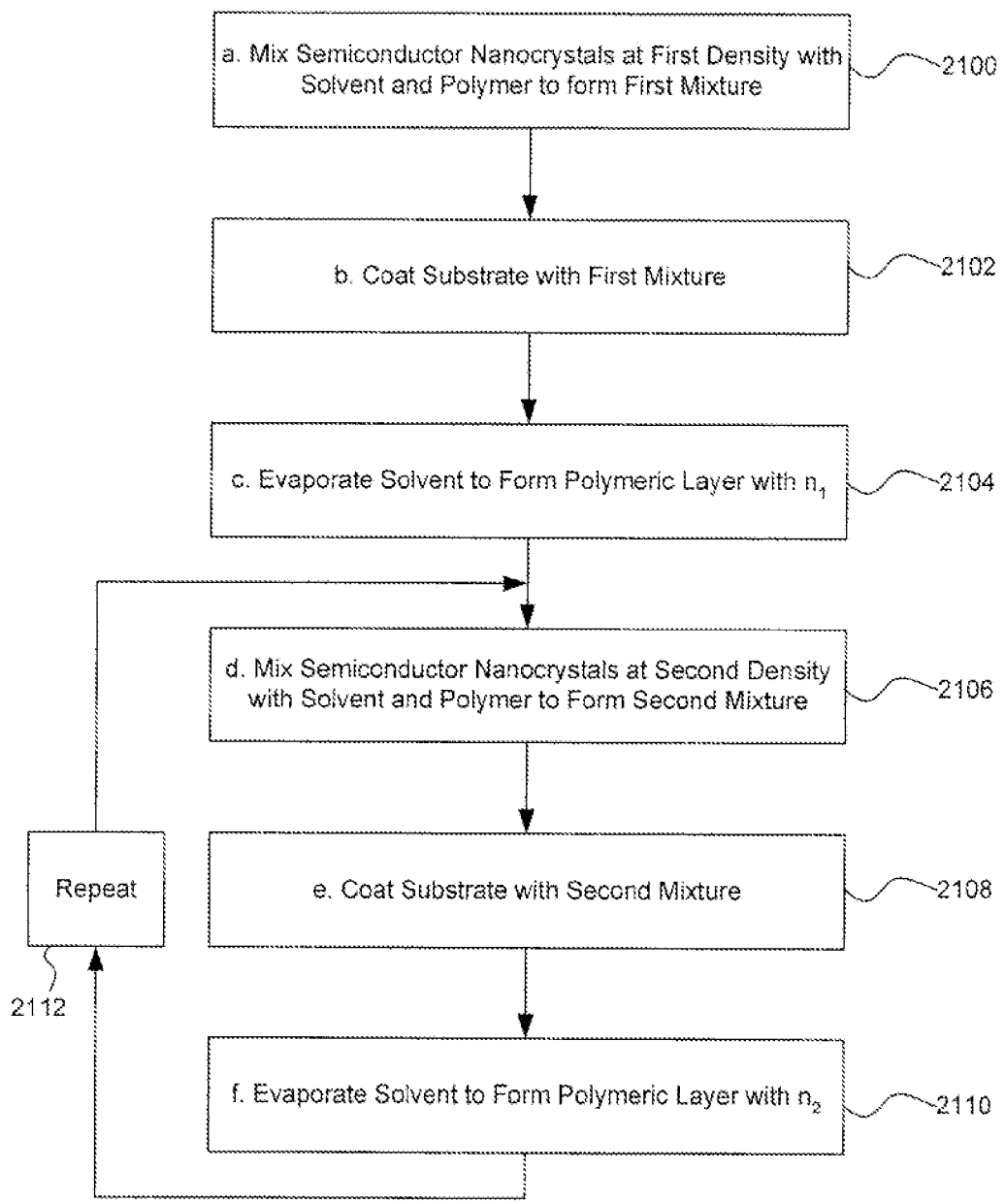
FIG. 21 is a flowchart depicting processes for preparing polymeric layers in accordance with the present invention.

In another embodiment, as represented in FIG. 21, the present invention provides processes for preparing polymeric layers, comprising (a) mixing semiconductor nanocrystals at a first density with a solvent and a polymer to form a first mixture (2100), (b) coating a substrate material with the first mixture (2102), and (c) evaporating the solvent to form the polymeric layer (2104), wherein the polymeric layer has an effective refractive index of $n_1$.

In suitable embodiments, the processes of the present invention can be used to coat active devices or optical devices. As discussed throughout, nanocrystals useful in the processes of the present invention can comprise miscibility-enhancing ligands conjugated, coordinated, attached, bound or otherwise associated to their surface. Any of the various types of nanocrystals discussed herein can be used in the processes of the present invention. For example, high emission nanocrystals, low emission/high absorption nanocrystals and low emission/low absorption nanocrystals can be used. In certain embodiments, two or more different types of nanocrystals can be mixed with the solvent and polymer, thereby creating a composite that has several or all of the properties described herein. Refractive index matching applications can utilize any of the nanocrystals discussed throughout, depending on if the nanocomposite is also required to function as a down-converting layer or a filtering layer. In other applications, nanocrystals that have low emission/low absorption properties are useful in refractive index matching applications where refractive index effects only are desired.

In other embodiments, as shown in FIG. 21, the processes of the present invention can further comprise (d) mixing semiconductor nanocrystals at a second density with a solvent and a polymer to form a second mixture (2106), (e) coating the substrate material with the second mixture (2108), and (f) evaporating the solvent to form a second polymeric layer (2110), wherein the second polymeric layer has an effective refractive index of $n_2$.

In other embodiments, the processes of the present invention can further comprise repeating steps (d) through (f) with a third through $i^{th}$ density of semiconductor nanocrystals to produce third through $i^{th}$ polymeric layers, wherein the third through $i^{th}$ polymeric layers have effective refractive indices, $n_3$ through $n_i$, respectively (2112). As used herein, "i" refers to an integer. The present invention encompasses processes for producing polymeric layers which comprise any number of separate layers used to produce an overall layer, coating, or encapsulant. Each individual layer, 1 through i, can comprise a different density of nanocrystals, nanocrystals of a different composition (i.e., high emission or high absorptive properties), and nanocrystals of different sizes. As such, each layer can have a different effective refractive index and can have multiple and/or different properties and characteristics.

Figure 22:
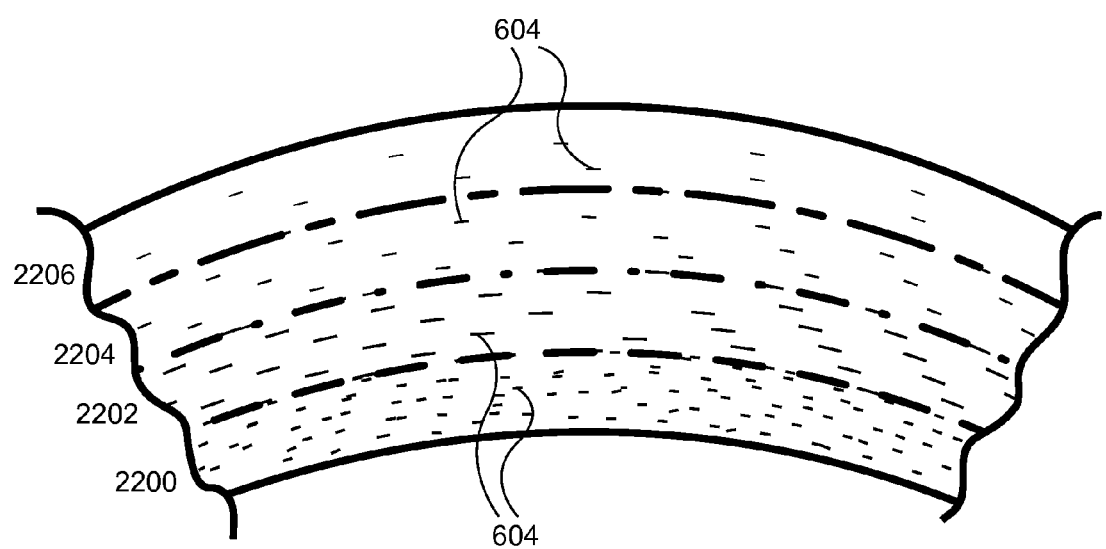
FIG. 22 is a cross-sectional view of a polymeric layer comprising individual layers each with a different nanocrystal density gradient according to one embodiment of the present invention.

By providing individual polymeric layers each with a potentially different effective refractive index, an overall polymeric layer (e.g., an encapsulating layer) can be generated that has a nanocrystal density gradient throughout the overall layer, and also an effective refractive index gradient throughout the overall layer. FIG. 22 illustrates that the effective refractive index of the $1^{st}$ layer, $n_1$ (2200), will be greater than any other layer (2202, 2204, 2206), and the effective refractive index of the $i^{th}$ layer, $n_i$ (2206), will be less than any other layer (2200, 2202, 2204). It should also be noted that the processes of the present invention can be performed in the reverse order, i.e., where the nanocrystal density and thus the effective refractive index of the $i^{th}$ layer is higher than any other layer, and the effective refractive index of the first layer prepared, $n_1$, is less than any other layer. In other embodiments, the density and effective refractive index of the individual layers can be the same, or can be prepared in such a manner that the overall effective refractive index of the polymeric layer varies throughout the layer, rather than in a graded fashion, as in FIG. 22.

As discussed throughout, various known processes can be used to coat a substrate material with the polymeric layers of the present invention, as would become apparent to people having ordinary skill in the art and based on the description herein. Suitable coating processes include, but are not limited to, spin coating and screen printing.

In general, spin coating consists of four stages. The first stage is the deposition of the coating fluid onto the substrate. It can be done using a nozzle that pours the coating solution out, or can be sprayed onto the surface, etc. Usually this dispense stage provides a substantial excess of coating solution compared to the amount that will ultimately be required in the final coating thickness. The second stage is when the substrate is accelerated up to its final, desired, rotation speed. The second stage is usually characterized by aggressive fluid expulsion from the substrate surface by the rotational motion. Ultimately, the substrate reaches its desired speed and the fluid is thin enough that the viscous shear drag exactly balances the rotational accelerations. The third stage is when the substrate is spinning at a constant rate and fluid viscous forces dominate fluid thinning behavior. This stage is characterized by gradual fluid thinning. Mathematical treatments of the flow behavior show that if the liquid exhibits Newtonian viscosity (i.e., is linear) and if the fluid thickness is initially uniform across the substrate (albeit rather thick), then the fluid thickness profile at any following time will also be uniform, leading to a uniform final coating. The fourth stage is when the substrate is spinning at a constant rate and solvent evaporation dominates the coating thinning behavior. As the prior stage advances, the fluid thickness reaches a point where the viscosity effects yield only rather minor net fluid flow. At this point, the evaporation of any volatile solvent species will become the dominant process occurring in the coating.

In another embodiment, the processes of the present invention can further comprise centrifuging the mixture produced in step 2100 to form a nanocrystal density gradient within the mixture prior to the coating in 2102. The use of centrifugation creates a gradient within the polymeric layer as nanocrystals separate in accordance with their inertia. Various centrifugation speeds or accelerations can be used to produce the nanocrystal density gradient in the polymeric layers and can readily be determined by those skilled in the art. The centrifugation speed selected depends on the size of the nanocrystals and the difference in density between the nanocrystals and the polymer solution prior to polymerization, and the centrifugal approach. Centrifugation can be for a short time at high speed and generate a gradient kinetically where the centrifugation step is timed based on a calculated or measured centrifugation rate. Alternatively, an equilibrium approach can be used where the flux of the nanocrystals toward the bottom of a centrifuge tube is matched to the flux of nanocrystals toward the top of the tube (due to diffusion). The diffusional flux is proportional to the concentration gradient of the nanocrystals. Suitably, accelerations can be in the range of a few hundred times g to 100,000 times g, where g is the acceleration due to gravity ($9.8 \text{ m/s}^2$) By selecting nanocrystals of different sizes and made from different materials, the nanocrystals will spread out through the polymeric layer according to their inertia in response to the centrifugation and generate a gradient in the layer. Any other process known to those skilled in the art to generate gradients within polymers may also be used to create the polymeric layers of the present invention.

In optical lenses, the optical path length varies with distance from its center, where optical path length is defined as the product of the physical path length, thickness, and the refractive index, n, of the lens material. In the most common lenses, the refractive index, n, is fixed and the thickness, varies. However, a lens can also be created by keeping the thickness, constant and varying the refractive index as a function of distance from the axis of the lens. Such a lens is called a Graded Index lens, or sometimes abbreviated as a GRIN lens. The methods of the present invention can also be used to create GRIN lenses. Polymer/nanocrystal blends can be used to make GRIN lenses due to the dramatic refractive index difference between nanocrystals (e.g., ZnS about 2.35) and optical plastics such as poly(methyl methacrylate) (PMMA) (refractive index about 1.45). With normal glass, a difference of about 0.05 refractive index units is achievable over about 8 mm. Utilizing the methods and processes of the present application, a difference of about 0.20 refractive index units over about 8 mm can be achieved to make much more powerful lenses.

In such embodiments, a gradient pump can be used to inject a solution containing polymer monomers and nanocrystals into the center of a mold, and then nanocrystal concentration can be varied during the fill. The lens can then be cured and removed.

The polymeric nanocomposites of the present invention can be used in any application where the down-conversion, filtering, and/or refractive index characteristics of the composites are desired. Non-limiting examples of applications of polymeric nanocomposites with increased refractive indexes include:

Super High Gloss Coatings: Increasing the refractive index of a transparent coating increases gloss. The addition of nanocrystals (e.g., ZnS nanocrystals) to polymeric coatings such as waxes and other coatings (e.g., car waxes, shoe waxes, floor coatings and related products) would increase the amount of light that is reflected from the coated surface and thus increase the glossiness of its appearance. Appropriate ligands, including C18, PEG and others discussed throughout could be used so as to allow the nanocrystals to be formulated with various polymers, waxes and coatings.

Plastic Eye Glass Lenses and Contacts: The thickness of a lens is proportional to the refractive index of the material of which it made. The higher the refractive index, the thinner the lens. Normal glass has a refractive index of about 1.523 while an example plastic, such as CR39, has refractive index of 1.49. A plastic lens, although lighter in weight, is thicker than a glass lens of equivalent power.

By incorporating nanocrystals, for example ZnS nanocrystals suitably with the appropriate ligands, into a plastic lens, the refractive index can be increased beyond the level of glass to make ultra-thin lenses. In applications such as contact lenses, there is an even more pressing need to create thin lenses due to the importance of oxygen transport through the lens to the eye. The refractive index of contact lenses are about 1.40. The addition of even a small percentage of nanocrystals (e.g., about 10% ZnS) would increase the refractive index to about 1.5, therefore allowing for thinner lenses. Ligands such as those discussed throughout can be used to lock the nanocrystals in place in the polymeric layer. The addition of nanocrystals with specific absorptive properties, e.g., ultraviolet (UV) absorbing nanocrystals, would allow for the creation of UV (or other wavelength) blocking lenses.

Functionalized Silicone Matrixes for Dispersion of Nanostructures

Dispersion of nanostructures in a polymer matrix is desirable for a number of applications, for example, application of quantum dots to light-emitting devices, where dispersion in an appropriate matrix can stabilize the quantum dots and facilitate device fabrication. Silicone polymers are generally preferred by the optical industry due to their transparency and stability to heat and high light fluxes. Unmodified silicone polymers, however, are generally not compatible with quantum dots. Ligands described herein can overcome this difficulty by facilitating dispersion of nanostructures in a silicone matrix. In one aspect, the matrix is formed from the ligand.

Accordingly, one general class of embodiments provides methods of making a composite material, in which a population of nanostructures having a polymeric ligand bound to a surface of the nanostructures is provided, and the polymeric ligand is incorporated into a silicone matrix in which the nanostructures are embedded.

Optionally, the matrix comprises a material different from the ligand (e.g., a different polymeric silicone molecule). Preferably, however, the matrix is formed from the ligand itself. Thus, in one class of embodiments, the methods include providing an excess of the polymeric ligand (e.g., a substantial excess), which excess polymeric ligand is not bound to the surface of the nanostructures, and incorporating the excess polymeric ligand and the polymeric ligand bound to the nanostructures into the silicone matrix. In embodiments in which no other precursors of the silicone matrix are provided, the matrix optionally consists essentially of the polymeric ligand and/or a cross-linked or further polymerized form thereof, as well as any residual solvent, crosslinker, initiator, and the like.

In some embodiments, to incorporate the polymeric ligand into the silicone matrix the population of nanostructures and any excess polymeric ligand are mixed with at least one solvent. The solvent is then evaporated, e.g., after application of the mixture to the desired location of the composite in or on a device. The polymeric ligand bound to the nanostructures and any excess polymeric ligand not bound to the nanostructures form the silicone matrix. This technique is suitable, e.g., for ligands that are initially gels or semi-solids. In some embodiments, e.g., useful for liquid ligands or where additional solidity is desired, a crosslinker is provided and reacted with moieties on the ligand (e.g., nanostructure binding moieties such as hydroxyl or amine moieties that are not bound to the surface of the nanostructures, on ligand molecules that are bound or not bound to the nanostructures). Exemplary crosslinking reactions are illustrated in FIG. 35, epoxy addition by amine in Panel A (the epoxy group can also react with other epoxy groups), epoxy addition by epoxy (initiated by an alcohol) in Panel B, amine-isocyanate in Panel C, amine-anhydride condensation in Panel D, and amine-methyl ester condensation in Panel E. Similarly, an initiator (e.g., a radical or cationic initiator) can be provided.

As yet another example, for polymeric ligands comprising at least two different types of monomer units, at least one of which comprises the nanostructure binding moiety and at least one of which lacks the nanostructure binding moiety but comprises a polymerizable group or an epoxide group, incorporating the polymeric ligand into the silicone matrix includes reacting the polymerizable or epoxide groups on different molecules of the polymeric ligand with each other.

Exemplary nanostructures and ligands have been described above. In one exemplary class of embodiments, the polymeric ligand comprises a silicone backbone and one or more alcohol (e.g., dicarbinol) moieties coupled to the silicone backbone. In another exemplary class of embodiments, the polymeric ligand comprises a silicone backbone and one or more primary and/or secondary amine moieties coupled to the silicone backbone. The backbone can be, e.g., linear or branched. Specific exemplary alcohol-, dicarbinol-, and amine-containing ligands have been described above. Also as described above, the nanostructures can be synthesized in the presence of the ligand or the polymeric ligand can be exchanged for another ligand that was employed during nanostructure synthesis.

More than one ligand can be employed. For example, in one class of embodiments, a mixture of pendant and terminal amine ligands is employed. In these embodiments, a second polymeric ligand is provided and incorporated into the silicone matrix along with the polymeric ligand. The second polymeric ligand comprises a silicone backbone and one or more primary and/or secondary amine moieties coupled to the terminal subunits. The first polymeric ligand generally has amine moieties coupled to internal subunits. The ratio of pendant to terminal amine ligand can be varied, for example, from 90% pendant (first) polymeric ligand:10% terminal (second) polymeric ligand to 50% pendant ligand:50% terminal ligand. In another exemplary class of embodiments, a mixture of two (or more) pendant amine ligands is employed.

Composite materials produced by any of the methods herein are a feature of the invention, as are devices comprising the composite materials (e.g., LEDs). For example, a composite material comprising nanostructures (e.g., nanocrystals) embedded in a silicone matrix, where the matrix is coordinated or otherwise associated with the surface of the nanostructures through hydroxyl (e.g., dicarbinol) groups, amine groups, or other nanostructure binding moieties of the matrix, is featured.

VII. Processes for Producing Nanostructures

Semiconductor nanocrystals, particularly with sizes on the scale of 1-10 nm, have emerged as a category of the most promising advanced materials for cutting-edge technologies because of their novel properties. Despite the technological advantages of this new generation of materials, concerns have arisen about potentially harmful interactions of nanocrystals with biological systems and the environment, for example, potential toxicity. Only a few semiconductor compounds are considered to be non-toxic, such as zinc sulfide (ZnS), indium phosphide (InP), gallium phosphide (GaP), indium nitride (InN), etc.

For many applications of quantum dots, two factors are typically considered. The first factor is the ability to absorb and emit visible light. This consideration makes InP a highly desirable base material. The second factor is the photoluminescence efficiency (quantum yield). Generally, II-VI quantum dots (such as cadmium selenide) have higher quantum yield than III-V quantum dots (such as InP). The quantum yield of InP cores produced previously has been very low (<<1%), and therefore the production of a core-shell structure with InP as the core and another semiconductor compound with higher bandgap (e.g. ZnS) as the shell has been pursued in attempts to improve the quantum yield. However, previous efforts in this direction have achieved a quantum yield of only 10-20% for two reasons. First, the cores used were of low quality; therefore, the growth process was accompanied by the appearance of precipitation. Second, the surfactants used in the syntheses, trioctylphosphine (TOP) and trioctylphosphine oxide (TOPO), are bound weakly with the nanocrystals and therefore provided weak protection to the nanocrystal surface. Although in one instance the quantum yield of InP dots was reportedly made as high 20-40% by means of photoetching, those etched dots have poor stability in terms of photoluminescence efficiency.

See, e.g., Micic et al. (1995) "Synthesis and characterization of InP, GaP, GaInP2 quantum dots" J. Phys. Chem. 99:7754-7759; Guzelian et al. (1996) "Synthesis of size-selected, surface-passivated InP nanocrystals" J. Phys. Chem. 100:7212-7219; Battaglia and Peng (2002) "Formation of high quality InP and InAs nanocrystals in a noncoordinating solvent" Nano Lett. 2:1027-1030; Lucey et al. (2005) "Monodispersed InP Quantum Dots Prepared by Colloidal Chemistry in a Noncoordinating Solvent" Chem. Mater. 17:3754-3762; Xu et al. (2006) "Rapid synthesis of high-quality InP nanocrystals" J. Am. Chem. Soc. 128:1054-1055; Haubold et al. (2001) "Strongly luminescent InP/ZnS core-shell nanoparticles" ChemPhysChem. 2:331; Micic et al. (2000) "Core-shell quantum dots of lattice matched ZnCdSe2 shells on InP cores: experiment and theory" J. Phys. Chem. B 104:12149-12156; Bharali et al. (2005) "Folate-Receptor-Mediated Delivery of InP Quantum Dots for Bioimaging Using Confocal and Two-Photon Microscopy" J. Am. Chem. Soc. 127: 11364; Talapin et al. (2002) "Etching of colloidal Inp nanocrystals with fluorides: photochemical nature of the process resulting in high photoluminescence efficiency" J. Phys. Chem. B 106:12659-12663; Hines and Guyot-Sionnest (1998) "Bright UV-Blue Luminescent Colloidal ZnSe Nanocrystals" J. Phys. Chem. B 102:3655; Li et al. (2004) "High quality ZnSe and ZnS nanocrystals formed by activating zinc carboxylate precursors" Nano Lett. 4:2261-2264; Chen et al. (2004) "Colloidal ZnSe, ZnSe/ZnS, and ZnSe/ZnSeS quantum dots synthesized from ZnO" J. Phys. Chem. B 108:17119-17123; Murray et al. (1993) "Synthesis and characterization of nearly monodisperse CdE (E=S, Se, Te) semiconductor nanocrystallites", J. Am. Chem. Soc. 115: 8706-8715; Dabbousi et al. (1997) J. Phys. Chem. B 101: 9463; and Cao and Banin (2000) "Growth and properties of semiconductor core/shell nanocrystals with InAs cores" J. Am. Chem. Soc. 122:9692-9702.

Methods for synthesizing high quality InP nanostructures, including high quality InP cores which can be used for production of high quality core-shell nanocrystals, are described below. In previously reported work, InP cores were prepared with indium chloride as the precursor for indium and TOPO (trioctyl phosphine oxide) as the solvent. The methods below use novel precursors, surfactants, and/or solvents to synthesize InP cores, for example, indium acetate as the precursor for indium, tris(trimethylsilyl)phosphine as the precursor for phosphorous, and a mixture of lauric acid and trioctylphosphine oxide as the growth solvent, which enables precise control of the resulting InP particle size and size distribution as well as the surface properties. In addition, the resulting cores are extremely stable and have higher quantum yield than has previously been achieved.

Also provided are methods of shell growth, also facilitating synthesis of high quality core-shell nanostructures. For example, a novel strategy for ZnS shell growth is provided, in which diethylzinc and hexamethyldisilthiane are used as precursors and a fatty acid is used as a part of the growth solvent. This enables further narrowing of the size distribution and significant increase of quantum yield. In other embodiments, dicarboxylic and polycarboxylic acids, including novel ligands described herein, are used as surfactants. For example, shells were grown using a monodicarboxylic acid terminated polydimethylsiloxane (DCASi-Me) as the surfactant. With this new surfactant, the surface of the nanocrystals was better passivated, and the quantum yield was boosted to greater than 50%.

One general class of embodiments provides methods for production of InP nanostructures. In the methods, a first precursor, e.g., indium acetate, and a second precursor, e.g., tris(trimethylsilyl)phosphine, are provided. The first and second precursors are reacted in the presence of an acid and a solvent to produce the nanostructures. The solvent is preferably a solvent other than octadecene. For example, the solvent can be TOPO, TOP, benzophenone, hexadecane, octadecane, or another solvent with a similarly high boiling point.

In one class of embodiments, the acid is a fatty acid, for example, lauric acid, capric acid, myristic acid, palmitic acid, or stearic acid. In other embodiments, the acid is a phosphonic acid, a dicarboxylic acid, or a polycarboxylic acid, for example, one of those described herein or known in the art. Examples include, but are not limited to, phosphonic acids such as hexylphosphonic acid and tetradecylphosphonic acid and carboxylic acids such as heptanedioic acid and dodecenylsuccinoic acid. Dicarboxylic acids are compounds having two carboxylic acid moieties (e.g., two monocarboxylic acid moieties or one dicarboxylic acid moiety). Polycarboxylic acids are compounds having three or more carboxylic acid moieties.

The resulting nanostructures are typically nanocrystals, optionally, small nanocrystals having a narrow distribution of sizes. For example, the average diameter of the resulting nanocrystals can be between 1 and 6 nm, e.g., between 1.5 and 5.5 nm, e.g., less than 2.5 nm or less than 2.0 nm. In one embodiment, the emission spectrum of the nanocrystals has an emission maximum of between 500 nm and 750 nm. In one embodiment, a luminescence spectrum of the nanocrystals has a full width at half maximum of less than 70 nm (e.g., less than 60 nm, less than 50 nm, or even 40 nm or less), indicating that the nanocrystals have a narrow size distribution.

The methods optionally include using the InP nanostructures as cores and growing one or more shells around them, for example, a ZnS, ZnSe, $ZnSe_xS_{1-x}$, ZnTe, or ZnO shell. Optionally, the resulting nanostructures have a high quantum efficiency, e.g., greater than 40%, greater than 50%, greater than 55%, or even 60% or higher.

Another general class of embodiments provides methods for production of core-shell nanostructures having Group II-VI semiconductor shells. In the methods, a nanostructure core is provided, and a shell surrounding the core is produced by providing a first precursor comprising a Group II atom, providing a second precursor comprising a Group VI atom, and reacting the first and second precursors in the presence of a ligand to produce the shell. The precursors are typically reacted in a solvent or mixture of solvents such as TOP, TOPO, etc. Conditions such as the reaction temperature and annealing time can be varied as is known in the art (for either core or shell synthesis).

The ligand is a dicarboxylic or polycarboxylic acid. Exemplary ligands are described herein, and additional examples can be found in the art. Exemplary ligands include, but are not limited to, compounds 16, 18 (DCASi-Me), 43, 44, 46, 47, and 48.

The cores can include essentially any material around which a II-VI shell is desirable. In one class of embodiments, the core comprises a Group II-VI semiconductor, e.g., CdS, ZnS, ZnSe, or ZnTe. In another class of embodiments, the core comprises a Group semiconductor, e.g., InP, InAs, or $In_{1-x}Ga_xP$.

Similarly, the shell can comprise essentially any desired II-VI semiconductor. For example, the shell can comprise ZnS, ZnSe, or $ZnSe_xS_{1-x}$. Exemplary core-shell combinations include, but are not limited to, InP/ZnS, InP/ZnSe/ZnS core/shell/shell, $InP/ZnSe_xS_{1-x}$ core/alloy shell, $In_{1-x}Ga_xP/ZnS$ alloy core/shell (optionally for better lattice matching between the cores and the shells so as to improve the quantum yield and making the shell thicker for improved environmental stability), and other non-toxic nanocrystals such as ZnSe/ZnS and ZnTe/ZnS core-shell nanocrystals whose emission can cover the blue to ultra-violet spectral range.

As noted above, the first precursor can be diethylzinc. Other exemplary first precursors include dimethyl zinc, zinc oxide, zinc stearate, and zinc acetate. The second precursor can be, e.g., hexamethyldisilthiane or elemental sulfur.

Compositions produced by or useful in practicing the methods are also featured. For example, a composition can include a first precursor, e.g., indium acetate, a second precursor, e.g., tris(trimethylsilyl)phosphine, an acid, and a solvent. The solvent is preferably a solvent other than octadecene. For example, the solvent can be TOPO, TOP, benzophenone, hexadecane, octadecane, or another solvent with a similarly high boiling point. In one class of embodiments, the acid is a fatty acid, for example, lauric acid, capric acid, myristic acid, palmitic acid, or stearic acid. In other embodiments, the acid is a phosphonic acid, a dicarboxylic acid, or a polycarboxylic acid, for example, one of those described herein or known in the art. The composition optionally includes InP nanostructures, e.g., nanocrystals, optionally, small nanocrystals having a narrow distribution of sizes. Another exemplary composition includes a nanostructure core, a first precursor comprising a Group II atom, a second precursor comprising a Group VI atom, and a dicarboxylic or polycarboxylic acid ligand. The composition optionally includes core-shell nanostructures having Group II-VI semiconductor shells. Essentially all of the features described for the methods above apply to these compositions as well, as relevant.

As noted above, use of the methods and/or ligands of the invention enable synthesis of nanostructures with high quantum efficiency. Quantum efficiency (also known in the literature as quantum yield) is the number of defined events which occur per photon absorbed (e.g., the number of photons emitted by the nanostructures per photon absorbed by the nanostructures).

Accordingly, one general class of embodiments provides a composition comprising a population of nanostructures, which population displays a quantum efficiency of 50% or greater. A member nanostructure of the population (typically, each member of the population) comprises a core and a shell, which core is other than a Cd-containing core or a Pb-containing core. Optionally, the population displays a quantum efficiency of 55% or greater, e.g., about 60% or more.

In one class of embodiments, a ligand is bound to a surface of the member nanostructure (e.g., each member). Exemplary ligands include, but are not limited to, those described herein, for example, dicarboxylic acid ligands such as compounds 16 or 18.

As noted, the core does not contain Cd or Pb. In certain embodiments, the core is a non-heavy-metal containing core, where the heavy metals are the group of elements between copper and lead on the periodic table of the elements, having atomic weights between 63.546 and 200.590 and specific gravities greater than 4.0. In one class of embodiments, the core comprises a Group III-V semiconductor, e.g., InP. The shell can comprise essentially any desired material, for example, a Group II-VI semiconductor such as ZnS, ZnSe, $ZnSe_xS_{1-x}$, ZnTe, or ZnO.

In one class of embodiments, the member nanostructure comprises an InP core. Optionally, the nanostructure comprises a ZnS, ZnSe, ZnSe$_x$S$_{1-x}$, ZnTe, or ZnO shell. A ligand can be bound to a surface of the member nanostructure, for example, compound 18.

Essentially all of the features described for the embodiments above apply to these embodiments as well, as relevant. For example, the nanostructures can be quantum dots. The nanocrystals can have a narrow size distribution, the cores can be small (e.g., between 1.5 and 5.5 nm in diameter), and/or the nanocrystals can cover the visible spectral range, e.g., having an emission wavelength between 500 nm and 750 nm. The nanostructures are optionally dispersed in a solvent, polymer, or the like. Such highly luminescent nanostructures have a variety of applications, e.g., in luminescent nanocomposites, etc.

As noted above, use of the methods and/or ligands of the invention enable synthesis of small InP nanostructures. Thus, one class of embodiments provides a composition comprising a population of InP nanocrystals, wherein the average diameter of the nanocrystals in the population is less than 5.5 nm. Preferably, the average diameter of the nanocrystals is less than 2.5 nm, e.g., less than 2.0 nm. In one embodiment, the average diameter is as small as 1.5 nm or 1 nm. The nanocrystals optionally have a narrow size distribution.

Also as noted above, use of the methods and/or ligands of the invention enable synthesis of InP nanostructures having a narrow size distribution. Accordingly, one class of embodiments provides a composition comprising a population of InP nanocrystals, wherein a luminescence spectrum of the population has a full width at half maximum of less than 70 nm. For example, the full width at half maximum can be less than 60 nm, less than 50 nm, or even 40 nm or less. The nanocrystals are optionally small, e.g., 1-6 nm or 1.5-5.5 nm in size; optionally, the emission spectrum of the population has an emission maximum between 500 nm and 750 nm.

VIII. Luminescent Nanocomposites

Incorporation of luminescent nanocrystals into a curable matrix is desirable for fabrication of luminescent, optically transparent solid state samples of desired shape. However, such incorporation has been difficult to achieve. In previous attempts at incorporating luminescent nanocrystals into a curable matrix, either the nanocrystals were incompatible with the matrix, leading to phase separation, or the luminescence was lost after curing, particularly for nanostructures that do not contain cadmium.

In one aspect, the present invention provides luminescent nanocomposites and methods for incorporating luminescent nanostructures into curable matrices while preserving the luminescent properties into the solid state. The nanostructures optionally have ligands bound to their surface, including novel ligands of the invention and/or other tightly binding ligands.

One general class of embodiments thus provides a luminescent nanocomposite comprising a population of luminescent nanocrystals, which nanocrystals are embedded in a matrix, and which nanocrystals substantially retain their luminescence when embedded in the matrix. The matrix is preferably an epoxy, polyurea, or polyurethane matrix. An "epoxy" is an epoxide polymer that polymerizes and crosslinks when mixed with a catalyzing agent. "Polyurea" is a polymer created by a chemical reaction between an isocyanate and an amine "Polyurethane" is a polymer created by a chemical reaction between an isocyanate and a polyol. A variety of suitable matrices are well known in the art.

As noted, the nanocrystals remain luminescent when embedded in the matrix. Thus, light output of the composite is optionally at least 5%, at least 10%, at least 20%, or at least 30% or more of light output of a comparable population of nanocrystals not embedded in the matrix. For example, the quantum yield of a luminescent nanocomposite can be 18%, compared to a quantum yield of 53% for corresponding nanocrystals in solution; light output of the composite would thus be 34% that of the free nanocrystals.

In one class of embodiments, a ligand is bound to a surface of a member nanocrystal (e.g., of each member nanostructure). The ligand can include a nanostructure binding moiety such as an amine moiety or a dicarboxylic acid moiety. Exemplary amine ligands include aliphatic amines, such as decylamine or octylamine, and polymeric amines. Exemplary dicarboxylic acid ligands include, but are not limited to, those described herein; for example, compounds 43, 44, and 46.

In one aspect, the nanocrystals are non-Cd containing nanocrystals. In embodiments in which the nanocrystals are core-shell nanocrystals, both the core and the shell are substantially cadmium free (i.e., are synthesized from precursors which comprise elements other than cadmium). The non-Cd containing nanocrystals are typically free of cadmium as determined by elemental analysis. In one embodiment, the nanocrystals are core-shell nanocrystals, and the cores comprise a Group III-V semiconductor. As just a few examples, the nanocrystals can be InP/ZnS, InP/ZnSe, or InP/ZnSe$_x$S$_{1-x}$ core-shell nanocrystals or InP/ZnSe/ZnS core/shell/shell nanocrystals, e.g., such as those described above.

A related general class of embodiments provides a luminescent nanocomposite comprising a population of luminescent nanocrystals embedded in a matrix, wherein a ligand is bound to a surface of a member nanocrystal. The ligand preferably comprises an amine moiety or a dicarboxylic acid moiety that binds to the surface of the member nanocrystal. Preferably, as for the embodiments above, the nanocrystals substantially retain their luminescence when embedded in the matrix.

The matrix can be essentially any desired matrix, for example, an optically transparent and/or curable matrix. A variety of matrices are well known in the art and can be adapted to practice of the present invention. In one embodiment, the matrix comprises epoxy, polyurea, or polyurethane.

Essentially all of the features noted for the embodiments above apply to these compositions as well, as relevant; for example, with respect to type of nanocrystal, type of ligand, and/or the like. For example, the nanocrystals are optionally non-Cd containing nanocrystals.

A luminescent composite of the invention is optionally formed into a desired three-dimensional shape, used as a coating, etc. Potential applications include luminescent solid state nanocrystal-based samples of any desirable shape, which can be used in toys, design applications, encapsulation applications, etc. It is worth noting that control over nanocrystal size allows for color tuning, which allows for color tuning while only one excitation source is needed. Also, the concentration and loading ratios of the nanocrystals in the composite can be varied.

The invention also provides methods of making such luminescent composites. Thus, one general class of embodiments provides methods of producing a luminescent nanocomposite, in which luminescent nanocrystals are provided and mixed with one or more matrix precursors to form a first mixture. The matrix precursors are cured to produce a matrix, e.g., an epoxy, polyurea, or polyurethane matrix, thereby providing the nanocomposite. The resulting nanocomposite comprises the luminescent nanocrystals embedded in the matrix, wherein the nanocrystals substantially retain their luminescence when embedded in the matrix. The methods optionally include casting or forming the first mixture into a desired shape prior to curing the matrix precursors.

Essentially all of the features noted for the embodiments above apply to these methods as well, as relevant; for example, with respect to light output, composition of the nanocrystals, associated ligands, and/or the like. For example, providing luminescent nanocrystals optionally comprises providing luminescent nanocrystals having a ligand bound to a surface of the nanocrystals. The ligand can include an amine moiety or a dicarboxylic acid moiety that binds to the surface of the nanocrystals. Exemplary ligands include those noted above, e.g., decylamine, octylamine, and compounds 43, 44, and 46.

A related general class of embodiments also provides methods of producing a luminescent nanocomposite. In the methods, luminescent nanocrystals having a ligand bound to a surface of the nanocrystals are provided. The ligand preferably comprises an amine moiety or a dicarboxylic acid moiety that binds to the surface of the nanocrystals. The nanocrystals are mixed with one or more matrix precursors to form a first mixture, and the matrix precursors are cured to produce a matrix, thereby providing the nanocomposite comprising the luminescent nanocrystals embedded in the matrix. Preferably, the nanocrystals substantially retain their luminescence when embedded in the matrix. The methods optionally include casting or forming the first mixture into a desired shape prior to curing the matrix precursors.

Essentially all of the features noted for the embodiments above apply to these methods as well, as relevant; for example, with respect to composition of the nanocrystals, light output, exemplary ligands, type of matrix, and/or the like.

EXAMPLES

The following examples are illustrative, but not limiting, of the method and compositions of the present invention. Other suitable modifications and adaptations of the variety of conditions and parameters normally encountered in nanocrystal synthesis, and which would become apparent to those skilled in the art, are within the spirit and scope of the invention.

Example 1

Core/Shell Nanocrystal Synthesis

Suitable nanocrystal synthesis procedures include fabricating nanocrystal samples with specific spectral characteristics matched to those prescribed by the theoretical models of the present invention. This can include fabricating nanocrystals with tunable sizes and size distributions (e.g., sizes ranging from 1-20 nm in diameter producing emission peak wavelengths tunable between 460 and 640 nm with FWHM tunable from about 15 to about 100 nm). This in turn is used to synthesize nanocrystal mixtures identified by simulations that have the optimal emission characteristics. The simulation and core/shell nanocrystal procedure is typically performed in an iterative process.

Type I core-shell nanocrystals of CdSe/ZnS (core/shell) can be synthesized by a two step process using a solution phase method, first with the fabrication of the core material followed by growth of the shell.

Core Synthesis

Stock solutions are prepared of Se powder dissolved in tri-n-butylphosphine (TBP), and $Cd(CH_3)_2$ dissolved in TBP. In an air-free environment, the Cd stock solution is added drop-wise to a mixture of trioctylphosphine oxide (TOPO), and trioctylphosphine (TOP), which was previously degassed at 120° C. The temperature is raised to 300° C., followed by a quick injection of the Se precursor. After injection, the temperature drops to around 260° C., which is held constant for a period of time to control the size of the particle. By controlling the temperature profile and starting reagents and conditions, the center-wavelength and size-distribution can be tuned independently. The identity of the product is confirmed using XRD and TEM analysis.

Shell Synthesis

Core CdSe nanocrystals are dispersed in TOPO and TOP to which a mixture of $ZnEt_2$ and $(TMS)_2S$ will be added at a temperature between 140° C. to 220° C. ZnS shell coating thickness will be varied by changing precursor ratios and growth temperatures to obtain a uniform surface coverage and to improve the quantum efficiency. The confirmation of shell growth will be done using XRD, EDX and TEM analysis.

The optical properties of the individual nanocrystals are characterized by measurement of the UV-Vis absorption and photoluminescence spectra using a commercial UV-Vis spectrophotometer and a fluorometer. The excitation wavelength is matched to the blue LED (about 460 nm). Internal quantum efficiency of the nanocrystals in solution are calculated using internal reference standards. Nanocrystal component mixtures (solution phase) are formed by mixing the appropriate concentration ratios to match the predictions from the theoretical model. The emission and absorption information of these actual mixtures is then back-fed as an input into the simulation to validate (and to refine, if necessary) the model.

The output of this procedure is a solution-phase mixture of nanocrystals that has the appropriate composition to produce white light with CRI and CTT matching that of the theoretical model when illuminated with blue excitation and total down-conversion efficiency comparable to that predicted by the model, assuming zero loss to other mechanisms in the process.

Example 2

ZnS Nanocrystal Synthesis

In the order listed, add the following to a 50 mL 3-neck round bottom flask:
1. $Zn(acetate)_2$: 76.5 mg Lot#12727BC
2. Stearic Acid: 484 mg Lot#06615MA
3. Tri-n-octylphosphine oxide (TOPO): 4.07 g Lot#21604LA In a glove box prepare the following:
3.9 g of distilled tri-n-octylphosphine (TOP) (#35-111) in 5 mL syringe;
116.4 mg of stock solution 02-190 (bis(trimethylsilyl)sulfide
$(TMS_2S)$:TOP) in 1 mL syringe; and
One 40 mL septa cap vial with 5.0 mL of MeOH
Place reactor under vacuum
Heat to 120° C.
Once at 120° C., allow to sit for 20 minutes
Place reactor under argon
Slowly inject TOP from 5 mL syringe
Change set point temperature to 250° C.
Once at 250° C., immediately inject the stock solution 02-190 (bis(trimethylsilyl)sulfide $(TMS_2S)$:TOP) from 1 mL syringe
Grow with temperature at 250° C. for 2 minutes
Remove the heating mantle and allow reaction to cool to 50° C.
At 50° C., use a syringe to remove the growth solution and inject it into the 40 mL vial with MeOH.

Figure 23:
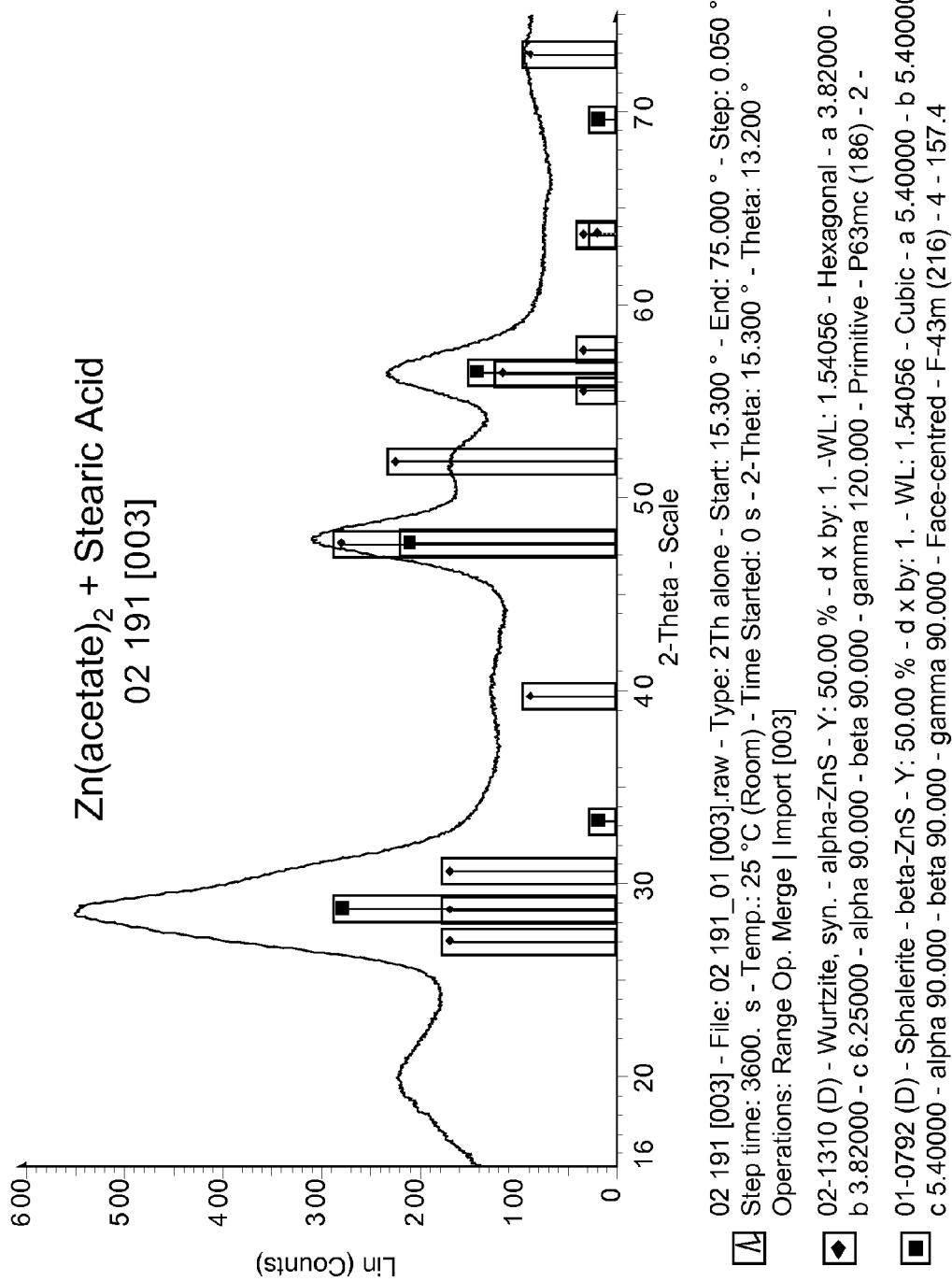
FIG. 23 shows an X-Ray diffraction analysis of ZnS nanocrystals.

FIG. 23 shows an X-Ray diffraction scan of ZnS nanocrystals produced according the present invention. The scan shows the presence of Zinc Sulfide with a mixture of wurtzite and zinc blend (sphalerite) crystals.

Figure 24:
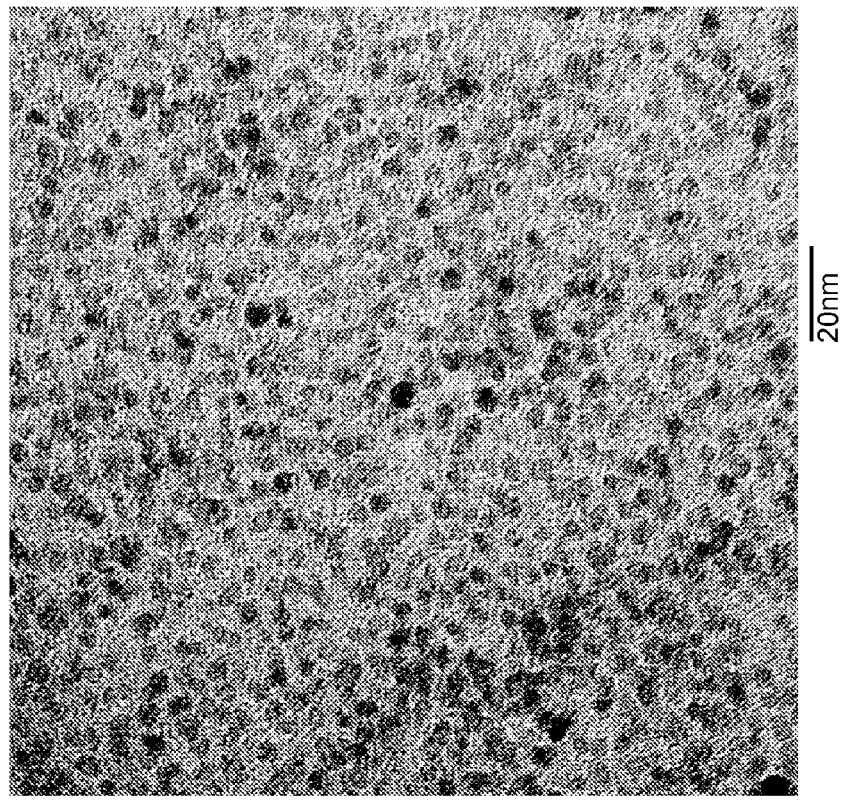
FIG. 24 shows Transmission Electron Micrographs of ZnS nanocrystals.
Figure 24:
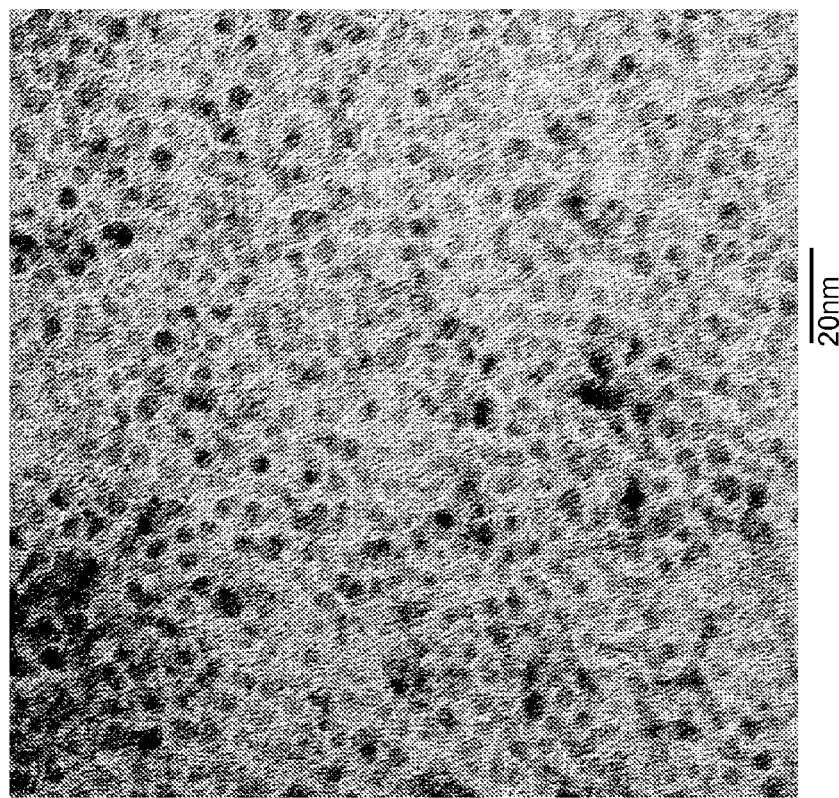
Figure 25A:
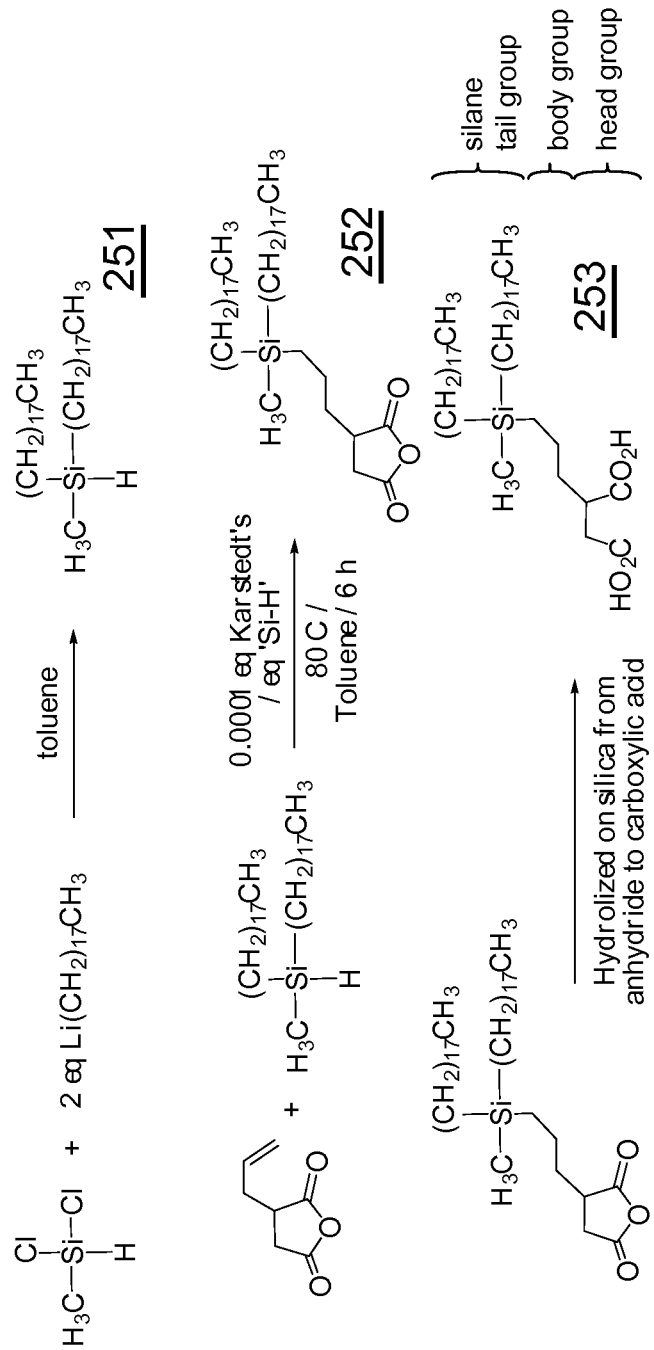
FIG. 25 A-B schematically illustrate chemical synthesis of an exemplary ligand in accordance with the present invention.
Figure 25B:
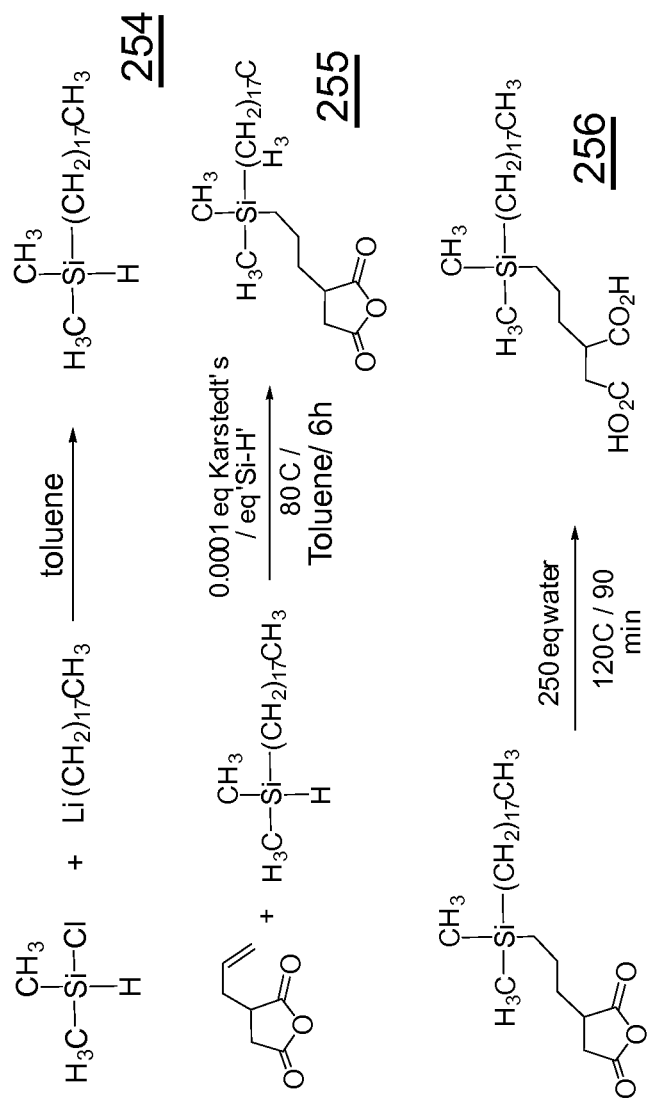

FIG. 24 shows a Transmission Electron Micrograph (TEM) of ZnS nanocrystals (about 4 nm diameter) produced according to the present invention.

The ZnS nanocrystals can be produced using any chain length hydrocarbon, for example C6-C22 alkane, depending on the application and desired properties.

Example 3

Carboxylic Acid-Silicone Ligand Synthesis

General Methods

All manipulations were carried out with strict exclusion of air and moisture by using Schlenk technique under an atmosphere of dry nitrogen, unless otherwise stated. THF, toluene, chloroform-$d_1$ and toluene-$d_8$ were dried over activated 4 A Molecular Sieves and de-gassed by three freeze-pump-thaw cycles. 4-pentenoic acid and 1,1,1,3,5,5,5-heptamethyltrisiloxane were purchased from Aldrich (St. Louis, Mo.), distilled and stored in a storage flask using Schlenk technique before use. Heptamethyl cyclotetrasiloxane and 1,1,1,3,3,5,5-heptamethyl trisiloxane were purchased from Gelest (Morrisville, Pa.), distilled and stored in a storage flask using Schlenk technique before use. Karstedt's catalyst or platinum divinyl tetramethyl disiloxane complex, 2.1 to 2.4% in xylenes, was purchased from Gelest, stored in the glove box and used without further purification. All products were stored in the glove box. NMR chemical shift data were recorded with a Bruker FT NMR at 400 MHz for $^1$H, 100 MHz for $^{13}$C{$^1$H}, 162 MHz for $^{31}$P{$^1$H} and 79.5 MHz for $^{29}$Si{$^1$H} and are listed in ppm.

General Synthesis Procedure (See FIG. 20g)

Synthesis of $HO_2C(CH_2)_4(SiMe_2O)_2SiMe_3$

In a glove box, the following reaction was set up in a 100 mL Schlenk flask by addition of Karstedt's catalyst (2.66 g solution, 0.300 mmol) followed by dilution in THF, 60 mL, on the Schlenk line. Then to the clear colorless solution, 1,1,1,3,3,5,5-heptamethyltrisiloxane (8.13 mL, 6.67 g, 30.0 mmol) was added by syringe over about 90 seconds and in about 30 seconds turned the solution clear green. The solution was stirred at room temperature for about 15 minutes. Then, with the reaction flask surrounded by a room temperature water bath, 4-pentenoic acid (3.07 mL, 3.00 g, 30.0 mmol) was added by syringe over about 90 seconds which slowly turned the solution light brown and produced a small amount of heat. After about 2 hours, the water bath was heated to 35° C. using a heater controlled by a thermostat and stirred overnight.

The volatiles were removed from the clear brown solution by rotational evaporator leaving an opaque brown oil. The product was distilled from the mixture by short path apparatus collecting the fraction with vapor temperature between 80 and 95° C. and pressure <20 mtorr. The product is a clear colorless oil (5.55 g or approximately 17 mmol and 57% yield) that typically contains about 50% acid and 50% anhydride. Complete conversion to the acid was accomplished by dissolution of the product mixture (2.00 g or approximately 6.2 mmol) in acetonitrile, 40 mL, followed by addition of pyridine (5.00 mL, 5.11 g, 64.6 mmol) and water (6.20 mL, 6.20 g, 33.4 mmol). The solution was stirred overnight in air. The volatiles were removed from the solution by rotational evaporator until the residue was reduced to an oil. Next, toluene, 100 mL, was added and the volatiles removed by rotational evaporator until the residue was reduced to an oil. The water removal using toluene azeotrope was performed twice. The resulting clear colorless oil was transferred into a beaker producing a layer about 3 mm thick and the product dried in a desiccator over phosphorous pentoxide under static vacuum of <10 mtorr overnight. The product was a clear colorless oil (1.35 g, 4.18 mmol, 67% yield) and was stored in the glove box.

Additional carboxylic acid-silicone ligands such as those shown in FIG. 20g and disclosed throughout the present specification, can be prepared using a procedure similar to that above.

Analysis of $HO_2C(CH_2)_4(SiMe_2O)_2SiMe_3$ $^1$H NMR (chloroform-$d_1$, δ): 0.10, 0.13, 0.14 (s, SiMe), 0.52, 1.39, 1.67 (m, CH2), 2.35 (t, 2H, CH2).

$^{13}$C{$^1$H} NMR (chloroform-$d_1$, δ): 1.5, 2.0, 2.0 (s, SiMe), 18.1, 23.1, 28.5, 34.1 (s, CH2), 180.5 (s, C=O).

$^{29}$Si {$^1$H} (1:1 $CDCl_3/Et_3N$, 0.02 M $Cr(acac)_3$, δ): −20.9, 7.1 (s, 1:2).

IR ($cm^{-1}$, diamond): 1050 s (Si—O—Si), 1700 m (C=O), 3030 w (CH aromatic), 2956 sh, 2928 s, 2854 m (CH aliphatic), 3400 to 2700 v br (acid).

Mass Spec ESI (m/z): 345 (MNa+).

Data for Synthesis and Analysis of $HO_2C(CH_2)_4SiMeO(SiMe_2)_3$ (cyclic tetrasiloxane)

The boiling point of the anhydride/acid mixture was 95 to 110° C. at a pressure of <10 mbar. The yield for synthesis of the acid/anhydride mixture was about 64% and the conversion to acid was 63%.

$^1$H NMR (chloroform-$d_1$, δ): 0.10, 0.12, 0.13 (s, SiMe), 0.48, 1.39, 1.65 (m, 2H, $CH_2$), 2.35 (t, 2H, $CH_2$).

$^{13}$C {$^1$H} NMR (chloroform-$d_1$, δ): −0.1, 1.9, 2.0 (s, SiMe), 17.5, 22.9, 28.3, 34.1 (s, $CH_2$), 180.4 (s, C=O).

$^{29}$Si{$^1$H} (1:1 $CDCl_3/Et_3N$, 0.02 M $Cr(acac)_3$, δ): −20.3, −19.1, −19.0 (s, 1:2:1).

IR ($cm^{-1}$, diamond): 1050 s (Si—O—Si), 1700 m (C=O), 3030 w (CH aromatic), 2956 sh, 2928 s, 2854 m (CH aliphatic), 3400 to 2700 v br (acid).

Data for Synthesis and Analysis of $HO_2C(CH_2)_4SiMe(OSiMe_3)_2$

The boiling point of the anhydride/acid mixture was 78 to 95° C. at a pressure of <10 mbar. The yield for synthesis of the acid/anhydride mixture was 63% and the conversion to acid was 62%.

$^1$H NMR (chloroform-$d_1$, δ): 0.10, 0.12, 0.13 (s, SiMe), 0.53, 1.43, 1.68 (m, 2H, $CH_2$), 2.35 (t, 2H, $CH_2$).

$^{13}$C {$^1$H} NMR (chloroform-$d_1$, δ): 0.9, 1.0 (s, SiMe), 16.9, 22.7, 28.1, 34.0 (s, CH2), 180.0 (s, C=O).

$^{29}$Si {$^1$H} (1:1 $CDCl_3/Et_3N$, 0.02 M $Cr(acac)_3$, δ): −22.0, −7.1, (s, 1:2).

IR ($cm^{-1}$, diamond): 1050 s (Si—O—Si), 1700 m (C=O), 3030 w (CH aromatic), 2956 sh, 2928 s, 2854 m (CH aliphatic), 3400 to 2700 v br (acid).

Mass Spec ESI TOF 381 ($MH^+$) and ESI TOF 379 (M-H).

Example 4

Phosphonic Acid—Silicone Ligand Synthesis

General Synthesis Procedure

Synthesis of $(EtO)_2P(O)(CH_2)_4(SiMe_2O)_2SiMe_3$

In a glove box, Karstedt's catalyst (0.450 g solution, 0.052 mmol) was added to a 250 mL Schlenk flask. On the Schlenk line, THF, 100 mL, was added and followed by 1,1,1,3,5,5,5-heptamethyl trisiloxane (14.0 mL, 11.5 g, 51.8 mmol) by syringe over about 90 seconds. The clear colorless solution turned clear green in about 30 seconds. The reaction solution was stirred for about 15 minutes before addition of diethyl 3-butenyl phosphonate (10.0 mL, 9.95 g, 51.8 mmol) by syringe over about 90 seconds. The reaction solution then slowly turned light brown and produced a small amount of heat. After about 2 hours, the reaction flask was surrounded by a thermostat controlled water bath that was heated to 35° C. The reaction solution was heated overnight.

The volatiles were removed from the clear brown solution by rotational evaporator leaving an opaque brown oil. A column was packed with silica (230-400 mesh) in hexanes that was 30 mm in diameter and 150 mm long. After placing the crude product on the column, the column was eluted with hexane, 250 mL, followed by a mixed solvent of 1:1 ratio of ethyl acetate to hexane, 1500 mL. The elutant was collected in one fraction. Next the volatiles were then removed by rotational evaporator leaving a light brown oil. The product was then distilled using a simple distillation at pressure of <20 mtorr and pot temperature of 120° C. The product was a clear colorless oil (17.6 g, 42.5 mmol, 82.1% yield).

Additional phosphonic acid-silicone ligands such as those shown in FIGS. 20a, 20j and 20n and disclosed throughout the present specification can be prepared using a procedure similar to that above.

Analysis of $(EtO)_2P(O)(CH_2)_4(SiMe_2O)_2SiMe_3$ $^1$H NMR (chloroform-$d_1$, δ): 0.00 (s, 6H, SiMe), 0.05 (s, 6H, SiMe), 0.07 (s, 9H, SiMe), 0.53, 1.39, 1.60, 1.70 (m, 2H, $CH_2$), 1.30 (t, 6H, $CH_2CH_3$), 4.06 (m, 4H, $CH_2CH_3$).

$^{13}$C {$^1$H} NMR (chloroform-$d_1$, δ): −0.34, 1.46, 2.01 (s, SiMe), 16.68, 61.52 (d, JP-C=6 Hz, $CH_2CH_3O$), 18.05 (s, $CH_2$), 24.62 (d, JP-C=18 Hz, $CH_2$), 26.19 (d, JP-C=5 Hz, $CH_2$), 25.69 (d, JP-C=140 Hz, $CH_2P$).

$^{31}$P {$^1$H} NMR (chloroform-$d_1$, δ): 32.

$^{29}$Si{$^1$H} (1:1 $CDCl_3$, 0.02 M $Cr(acac)_3$, δ): −22.00, 7.12 (s, 1:2). IR ($cm^{-1}$, diamond): 1030 (s, Si—O—Si), 1260 (m, Si-Me), 1380, 1400 1430 (w, Et-O—P). Data for Synthesis and Analysis of $(EtO)_2P(O)(CH_2)_4SiMe(OSiMe_3)_2$ The pot was heated to 120° C. at a pressure of <20 mtorr to distill the product as a clear colorless oil in 81% yield.

$^1$H NMR (chloroform-$d_1$, δ): −0.32 (s, 3H, SiMe), 0.06 (s, 18H, SiMe), 0.44, 1.37, 1.60, 1.70 (m, 2H, $CH_2$), 1.30 (t, 6H, $CH_2CH_3$), 4.08 (m, 4H, $CH_2CH_3$).

$^{13}$C {$^1$H} NMR (chloroform-$d_1$, δ): −0.15, 2.01 (s, SiMe), 16.65, 61.49 (d, JP-C=6 Hz, $CH_2CH_3O$), 17.38 (s, $CH_2$), 24.48 (d, JP-C=18 Hz, $CH_2$), 25.97 (d, JP-C=5 Hz, $CH_2$), 25.71 (d, JP-C=140 Hz, $CH_2P$).

$^{31}$P {$^1$H} NMR (chloroform-$d_1$, δ): 33.

$^{29}$Si {$^1$H} (1:1 $CDCl_3$, 0.02 M $Cr(acac)_3$, δ): −17.96, 9.94, 10.00 (s, 1:1:1).

IR ($cm^{-1}$, diamond): 1030 (s, Si—O—Si), 1250 (m, Si-Me), 1380, 1400, 1430 (w, Et-O—P).

Data for Synthesis and Analysis of $(EtO)_2P(O)(CH_2)_4SiMeO(SiMe_2)_3$ (cyclic tetrasiloxane)

For the distillation the vapor temperature was 84 to 96° C. at a pressure of <10 mtorr. The product was isolated as a clear colorless oil in 44% yield.

$^1$H NMR (chloroform-$d_1$, δ): 0.50, 0.70 (s, 21H total, SiMe), 0.51 1.41, 1.61, 1.69 (m, 2H each, $CH_2$), 1.30 (t, 6H, $CH_2CH_3$), 4.08 (m, 4H, $CH_2CH_3$).

$^{13}$C {$^1$H} NMR (chloroform-$d_1$, δ): −0.57, 0.91, 0.94 (s, SiMe), 16.66, 61.50 (d, JP-C=6 Hz, $CH_2CH_3O$), 16.86 (s, $CH_2$), 24.29 (d, JP-C=18 Hz, $CH_2$), 25.88 (d, JP-C=5 Hz, $CH_2$), 25.70 (d, JP-C=140 Hz, $CH_2P$).

$^{31}$P {$^1$H} NMR (chloroform-$d_1$, δ): 33.

$^{29}$Si{1H} (1:1 $CDCl_3$, 0.02 M $Cr(acac)_3$, δ): −20.39, −19.17, −19.08 (s, 1:2:1).

IR ($cm^{-1}$, diamond): 1015, 1050 (s, Si—O—Si), 1250 (m, Si-Me), 1380, 1400, 1430 (w, Et-O—P).

General Synthesis Procedure for the Phosphonic Acid, $(HO)_2P(O)(CH_2)_4(SiMe_2O)_2SiMe_3$ In a 50 mL Schlenk flask, $CH_2Cl_2$, 15 mL, was added followed by $(EtO)_2P(O)(CH_2)_4(SiMe_2O)_2SiMe_3$ (1.00 g, 2.42 mmol) and the solution stirred until homogenous. Then trimethylsilyl bromide (0.671 mL, 0.778 g, 5.08 mmol) was added and the solution was stirred for 15 minutes.

The volatiles were removed by vacuum transfer and 10.0 mL of methanol was added followed by 0.25 mL of water. After stirring for 30 minutes, the volatiles were removed by vacuum transfer and 10.0 mL of toluene was added and the solution was stirred for 1 minute. The volatiles were removed by vacuum transfer and 10 ml of toluene was added, the solution stirred and the volatiles removed again, as before. The product was a slightly cloudy viscous oil.

Analysis of $(HO)_2P(O)(CH_2)_4(SiMe_2O)_2SiMe_3$

ESI (m/z): 359 (MH+) and 381 (MNa+).

Example 5

Synthesis of Aliphatic Carboxylic Acid Ligands

Synthesis of Di-Aliphatic (C18) Mono-Succinic Acid Ligand

Synthesis of the ligand is schematically illustrated in FIG. 25 Panel A.

General Methods

All manipulations were carried out with strict exclusion of air and moisture by using Schlenk technique under an atmosphere of dry nitrogen, unless otherwise stated. Toluene was dried with an M Braun solvent system that incorporated molecular sieves and alumina as drying agents. Acetone-$d_6$ was purified by stirring with anhydrous calcium (II) sulfate (Drierite) for 7 days then distilled 'trap-to-trap'. Chloroform and dichloromethane were purchased from Fisher Chemical and used as received. Octadecyl lithium was purchased from FMC Lithium, stored in the refrigerator and assayed by titration against biphenylmethanol before use. Allyl succinic anhydride was purchased from TCI America, distilled and stored using Schlenk technique until used. Dichloro methyl silane and dimethyl chloro silane were purchased from Acros Organics and transferred by cannula to a storage flask before use. Karstedt's catalyst precursor, or platinum divinyl tetramethyl disiloxane complex 2.1 to 2.4% in xylenes—low color, was purchased from Gelest, stored in the glove box and used without further purification. Silica gel 60 (230-400 mesh) was purchased from EM Science and used as received. Phosphorous pentoxide was purchased from Fisher Chemical and used as received. Activated carbon (coconut shell) and 4 A Molecular Sieves were purchased from Aldrich and used as received. NMR chemical shift data was recorded with a Bruker FT NMR at 400 MHz for $^1$H and 100 MHz for $^{13}$C{$^1$H} and are listed in ppm. NMR chemical shifts were referenced using proton impurities in the deuterium solvent. Silicone formula weight was determined by comparison of end-group to repeat unit integration using $^1$H NMR using a post acquisition delay (d1) of at least 60 seconds for accuracy. IR analysis was recorded on a Nicolet 6700 FTIR standardized with polypropylene.

Synthesis of 251

To a 500 mL Schlenk flask was added toluene (200 mL) and methyl dichloro silane (3.93 mL, 3.25 g, 28.2 mmoles). The solution was stirred at room temperature and octadecyl lithium (160 mL, 56.5 mmoles, 0.353 M in toluene) added by syringe over 10 minutes. During the addition the reaction solution turned from clear colorless to opaque white. About 30 minutes after the addition, toluene (100 mL) was added and the reaction solution was heated with thermostat controlled water bath to 50° C. It was held at this temperature for 4 h, then the heat was turned off and the reaction solution cooled to room temperature overnight. Then the reaction solution was filtered with a filter tip cannula (Fisherbrand P5 with particle retention of 5 to 10 μm) and the volatiles removed by rotational evaporator which left an opaque colorless oil. The residue was dissolved in hexane (250 mL) and filtered again with filter tip canula. Then the volatiles were removed by vacuum transfer to leave a clear colorless oil, 14.5 g, 26.4 mmoles, 93.5% yield.

It is worth noting that this reaction also works with a less expensive Grignard reagent. With the Grignard reagent, however, the reaction solution is heated for 2 days for completion and the product is washed thoroughly to remove the magnesium halide salts.

Analysis of 251

$^1$H NMR (chloroform-d$_1$, δ): 0.20, 0.3 (m, SiCH$_3$, 3H), 0.57 (m, CH$_2$(CH$_2$)$_{16}$CH$_3$, 4H), 0.88 (t, CH$_2$(CH$_2$)$_{16}$CH$_3$, 6H), 1.30 (m, CH$_2$(CH$_2$)$_{16}$CH$_3$, 64H), 3.75 (m, Si—H, 1H).

IR (cm$^{-1}$, diamond): 2108 m (Si—H), 2852 s, 2917 s, 2958 m (sp$^3$ C—H).

Synthesis of 252 and 253 (Compound 42)

To a 250 mL Schlenk flask was added toluene (80 mL) and silane 251 (7.00 g, 12.7 mmoles) that produced a clear colorless reaction solution with stirring. The reaction solution was heated to 80 C using a thermostat controlled oil bath. Then allyl succinic anhydride (1.78 g, 12.7 mmoles) was added followed by Karstedt's catalyst precursor (11.3 mg of 2.2 wt % solution, 0.0013 mmol or 0.0001 eq Pt metal). After about 1 h, a sample of the reaction solution was prepared for analysis by removal of the volatiles. IR analysis showed a large Si—H absorbance without an anhydride or vinyl absorbance, indicating that allyl succinic anhydride had probably been removed during sample preparation via azeotropic distillation with toluene. Additionally, that the reaction had not initiated was confirmed by $^1$H NMR. Another 0.0001 eq of Karstedt's catalyst precursor (low color) was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. Initiation occurred in about a day and a half when the color of the reaction solution abruptly changed from clear yellow to clear brown. Sampling followed by IR analysis indicated that the Si—H absorbance was replaced by two succinic anhydride C═O absorbances (symmetrical and asymmetrical stretches). Following initiation, the reaction solution was heated about 90 minutes to insure complete conversion of starting material. The progress of the reaction was monitored by $^1$H NMR analysis using the disappearance of the vinyl resonances and Si—H peak and the appearance of a multiplet for the methylene on the propyl chain bonded to the silicone.

To work up the reaction, the volatiles were removed by rotational evaporator and the resulting clear brown oil dissolved in chloroform (300 mL). Then 2 g of activated carbon was added and the solution stirred overnight in air. The solution was filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in chloroform (200 mL) and sent through a 0.45 um nylon syringe filter. The complete de-colorization procedure (with activated carbon and syringe filter etc) was performed twice. The volatiles were removed to leave clear light brown oily anhydride 252 (~8 g) which was dissolved in chloroform (200 mL) and combined with silica gel 60 (11 g). The volatiles were removed on a roto-evaporator and the dry powder that was isolated was transferred to a chromatography column (55 mm in diameter and 200 mm long). The column was eluted with 500 mL toluene and then the product 253 was eluted with 500 mL of ethyl acetate (20%)/toluene (80%). Removal of the volatiles gave 1.30 g, 1.80 mmoles, 14.4% yield of white waxy dicarboxylic acid 253.

Analysis of 252

$^1$H NMR (CDCL$_3$, δ): −0.06 (s, SiCH$_3$), 0.50, 0.57 (br m, SiCH$_2$(CH$_2$)$_{16}$CH$_3$) and SiCH$_2$CH$_2$CH$_2$C(H)(C═O)(CH$_2$)C═O), 0.88 (t, CH$_2$(CH$_2$)$_{16}$CH$_3$), 1.26 (br m, CH$_2$(CH$_2$)$_{16}$CH$_3$ and SiCH$_2$CH$_2$CH$_2$C(H)(C═O)(CH$_2$)C═O), 1.67 and 1.96 (d-m, SiCH$_2$CH$_2$CH$_2$C(H)(C═O)(CH$_2$)C═O), 2.70, 3.1 (d-m, SiCH$_2$CH$_2$CH$_2$C(H)(C═O)(CH$_2$)C═O), 3.3 (m, SiCH$_2$CH$_2$CH$_2$C(H)(C═O)(CH$_2$)C═O).

IR (cm$^{-1}$, diamond): 1781 and 1863 s (C═O).

Analysis of 253

$^1$H NMR (acetone-d$_6$, δ): −0.08 (s, SiCH$_3$, 3H), 0.49 (m, CH$_2$(CH$_2$)$_{16}$CH$_3$), SiCH$_2$CH$_2$CH$_2$CH(CO$_2$H)CH$_2$CO$_2$H, 6H), 0.89 (t, CH$_2$(CH$_2$)$_{16}$CH$_3$, 6H), 1.26 (m, CH$_2$(CH$_2$)$_{16}$CH$_3$, 64H), 1.63 (d-m, J$_{HH}$=68 Hz, SiCH$_2$CH$_2$CH$_2$CH(CO$_2$H)CH$_2$CO$_2$H, 4H), 2.43 (d-m, J$_{HH}$=99 Hz, SiCH$_2$CH$_2$CH$_2$CH(CO$_2$H)CH$_2$CO$_2$H, 4H), 2.81 (d-m, J$_{HH}$=64 Hz, SiCH$_2$CH$_2$CH$_2$CH(CO$_2$H)CH$_2$CO$_2$H, 4H), 2.96 (m, SiCH$_2$CH$_2$CH$_2$CH(CO$_2$H)CH$_2$CO$_2$H, 1 H), 12.21 (m, CO$_2$H, 2H).

IR (cm$^{-1}$, diamond): 1703 s (acid C═O), 2852 m, 2917 m, 2954 w, (sp$^3$ C—H), 2500 to 3500 broad m (acid OH).

Synthesis of Mono-Aliphatic (C18) Succinic Acid Ligand

Synthesis of the ligand is schematically illustrated in FIG. 25 Panel B. Substitution of dimethyl chloro silane for methyl dichloro silane into the synthesis above produced the mono aliphatic (C18) monosuccinic acid ligand (compound 41), as schematically illustrated in FIG. 25 Panel B. The reactions were performed analogously to the synthesis of other ligands. Analysis of the intermediates and products are below. Synthesis of 254 resulted in 14.7 g, 20.3 mmoles, 91.9% yield; of 255, 12.8 g, 28.0 mmoles, 87.7% yield; of 256, 4.00 g, 8.50 mmoles, 30.3% yield.

Analysis of 254

$^1$H NMR (acetone-d$_6$, δ): 0.08 (s, SiCH$_3$, 3H), 0.62 (m, SiCH$_2$(CH$_2$)$_{16}$CH$_3$, 2 H), 0.89 (t, SiCH$_2$(CH$_2$)$_{16}$CH$_3$, 3H), 1.30 (s, SiCH$_2$(CH$_2$)$_{16}$CH$_3$, 32H), 3.89 (m, Si—H, 1H).

IR (cm$^{-1}$, diamond): 2112 m (Si—H), 2852s, 2921 s, 2958 sh (sp$^3$ C—H).

Analysis of 255

$^1$H NMR (acetone-d$_6$, δ): −0.01 (m, SiCH3, 6H), 0.55, 0.57 (m, SiCH$_2$(CH$_2$)$_{16}$CH$_3$ and SiCH$_2$CH$_2$CH$_2$CH(C═O)(CH$_2$)C═O), 4H), 0.88 (t, CH$_2$(CH$_2$)$_{16}$CH$_3$), 1.29 (m, SiCH$_2$(CH$_2$)$_{16}$CH$_3$, 32H), 1.50 (m, SiCH$_2$CH$_2$CH$_2$CH(C═O)(CH$_2$)C═O), 2H), 1.84 (d-m, J$_{HH}$=64 Hz, SiCH$_2$CH$_2$CH$_2$CH(C═O)(CH$_2$)C═O), 2H), 3.03 (d-m, J$_{HH}$=127 Hz, SiCH$_2$CH$_2$CH$_2$C(H)(C═O)(CH$_2$)C═O), 2H), 3.34 (m, SiCH$_2$CH$_2$CH$_2$C(H)(C═O)(CH$_2$)C═O), 1H).

IR (cm$^{-1}$, diamond): 1781 s, 1963 m (anhydride C═O symm. and asymm.), 2852 s, 2917 s, 2958 sh (sp$^3$ C—H).

Analysis of 256

$^1$H NMR (acetone-d$_6$, δ): −0.2 (s, SiCH$_3$, 6H), 0.54, 0.55 (m, SiCH$_2$(CH$_2$)$_{16}$CH$_3$, SiCH$_2$CH$_2$CH$_2$CH(CO$_2$H)CH$_2$CO$_2$H, 4H), 0.88 (t, SiCH$_2$(CH$_2$)$_{16}$CH$_3$, 3 H), 1.29 (m, SiCH$_2$(CH$_2$)$_{16}$CH$_3$, 32H), 1.40 (m, SiCH$_2$CH$_2$CH$_2$CH(CO$_2$H)CH$_2$CO$_2$H, 2H), 1.64 (d-m, J$_{HH}$=40 Hz, SiCH$_2$CH$_2$CH$_2$CH(CO$_2$H)CH$_2$CO$_2$H, 2H), 2.55 (d-m, J$_{HH}$=80 Hz, SiCH$_2$CH$_2$CH$_2$CH(CO$_2$H)CH$_2$CO$_2$H, 2H), 2.82 (m, SiCH$_2$CH$_2$CH$_2$CH(CO$_2$H)CH$_2$CO$_2$H, 1 H), 10.69 (m, CO$_2$H, 2H).

IR (cm$^{-1}$, diamond): 1691 s (acid C═O), 2852 s, 2917 s, 2954 sh (sp$^3$ C—H), 2500 to 3500 (CO$_2$H).

Synthesis of Aliphatic (C18) Two-Tail Poly-Carboxylic Acid Ligand

Figure 26:
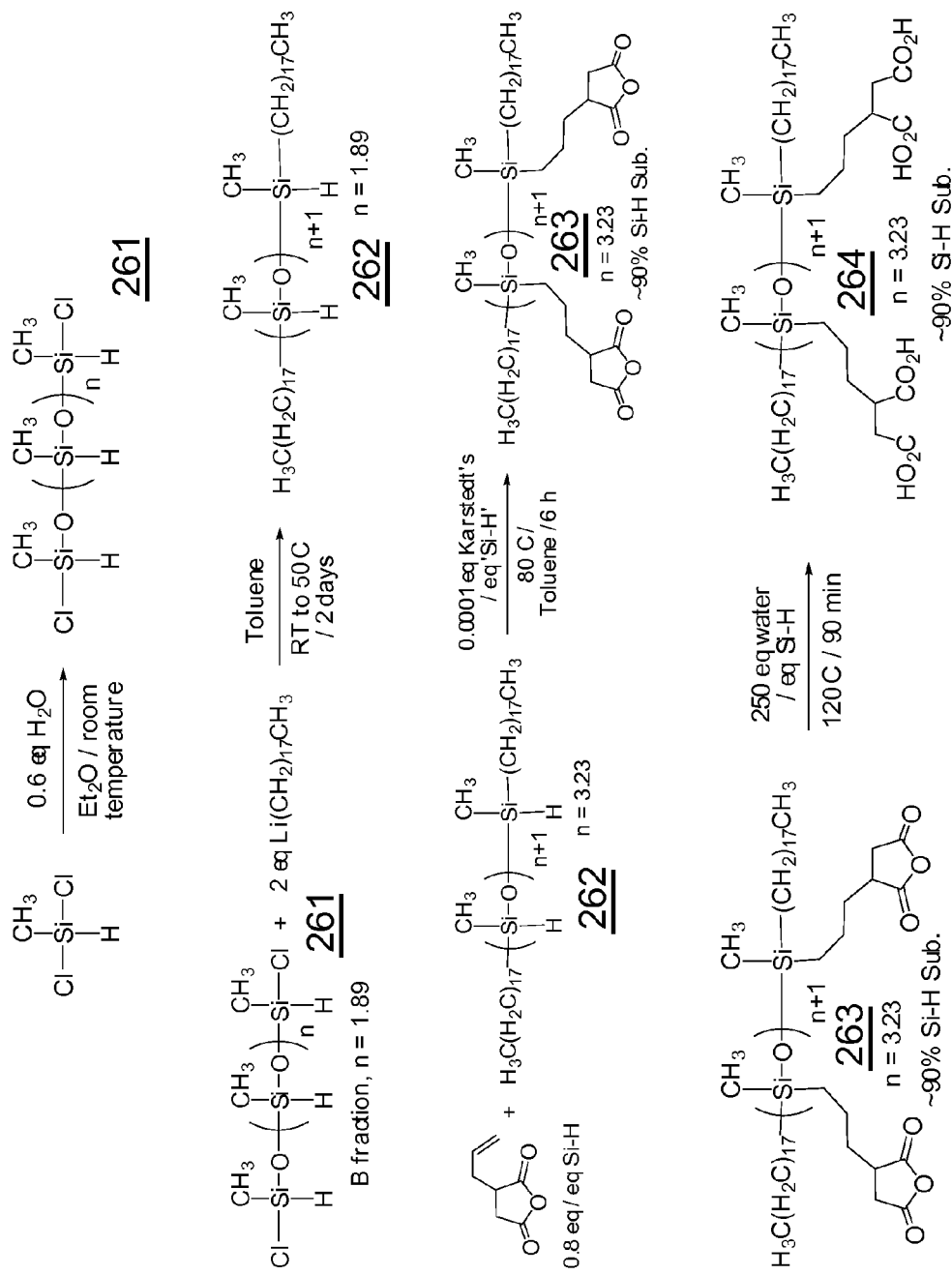
FIG. 26 schematically illustrates chemical synthesis of an exemplary ligand in accordance with the present invention.

Synthesis of the ligand is schematically illustrated in FIG. 26.

General Methods

All manipulations were carried out with strict exclusion of air and moisture by using Schlenk technique under an atmosphere of dry nitrogen, unless otherwise stated. Toluene was dried in an M Braun solvent system that incorporated molecular sieves and alumina as drying agents. Acetone-$d_6$ was purified by stirring with anhydrous calcium (II) sulfate (Drierite) for 7 days then distilled 'trap-to-trap'. Chloroform and dichloromethane were purchased from Fisher Chemical and used as received. Triethylamine was purchased from Aldrich dry in sure-seal bottles and transferred by cannula (or double tipped needle) into storage flasks until used. Allyl succinic anhydride was purchased from TCI America, distilled and stored using Schlenk technique until used. Dichloro methyl silane was purchased from Acros Organics and a new, previously un-opened bottle was used for each synthesis. Monosilanol terminated silicone was special ordered from Gelest. Karstedt's catalyst precursor, or platinum divinyl tetramethyl disiloxane complex 2.1 to 2.4% in xylenes—low color, was purchased from Gelest, stored in the glove box and used without further purification. Phosphorous pentoxide was purchased from Fisher Chemical and used as received. Octadecyl magnesium chloride (in THF), anhydrous diethyl ether, activated carbon (coconut shell) and 4 A Molecular Sieves were purchased from Aldrich and used as received. NMR chemical shift data was recorded with a Bruker FT NMR at 400 MHz for $^1$H and 100 MHz for $^{13}$C {$^1$H} and are listed in ppm. NMR chemical shifts were referenced using proton impurities in the deuterium solvent. Silicone formula weight was determined by comparison of end-group to repeat unit integration using $^1$H NMR using a post acquisition delay (d1) of at least 60 seconds for accuracy. IR analysis was recorded on a Nicolet 6700 FTIR standardized with polypropylene.

Synthesis of 261

Synthesis of 261 is adapted from U.S. Pat. No. 2,381,366 to Patnode, W. I., 1942, and Manami, H. et al. (1958) Nippon Kagaku Zasski 79:60-65.

A 2000 mL, 3-neck round bottom flask was equipped with an addition funnel, mechanical stirrer, reflux condenser and nitrogen atmosphere. The nitrogen bubbler consisted of a piece of glass tubing placed into a 1 L Erlenmeyer flask containing about 800 mL of water to absorb the HCl gas generated in the reaction. To the reaction flask was added diethyl ether (1 L) and methyl dichloro silane (500 mL, 533 g, 4.80 moles). Water (51.9 mL, 2.88 moles, 0.6 eq) was transferred into the addition funnel. The reaction was stirred rapidly while water was added over about 45 minutes and the reaction solution refluxed gently during the addition. Following the addition the reaction solution was stirred at room temperature for about 1 h and under positive nitrogen flow the reaction flask was re-fitted for vacuum distillation. The mechanical stirrer was exchanged for a magnetic stirrer and the reflux condenser was replaced with an inverted 'U' tube connected to a 2 L receiver. Also the reaction flask was fitted with a heating mantle with temperature controller that used a thermocouple between reaction flask and heating mantle. Then the pot was heated to 25° C. and vacuum gradually applied to the system using a Teflon lined vacuum pump with vacuum controller (Buchi V-800). During evacuation the receiver was cooled in a dry ice/ethanol bath while the vacuum was gradually increased to 200 mtorr. Removing the volatiles at this stage required about 4 h and removed ~75% of the solution volume. Then the receiver was changed to a 1 L Schlenk flask and product was separated from nonvolatile material by distillation with the same apparatus (an inverted 'U' tube connected to a receiver). In this case the receiver was cooled with liquid nitrogen while the pressure was gradually dropped to ~20 mtorr and the temperature of the pot was gradually increased to 200° C. That distillate was transferred by cannula to a pot connected to a fraction cutter and the product carefully distilled to separate the oligomeric products. On this reaction scale a fraction cutter with 24/40 standard taper joints is most convenient. All fractions were clear colorless oils and were stored in the glove box. Total reaction yield was 57.8% and the fractions are detailed below.

Fraction A, 26.5 g, n=1.38, fwt 258.1, 7.2% yield, collected between 23 C at 125 torr to 24 C at 300 mtorr Fraction B, 22.1 g, n=1.89, fwt 288.8, 6.2% yield, collected between 24 C at 300 mtorr and 24 C at 180 mtorr Fraction C, 27.5 g, n=2.73, fwt 339.9, 8.0% yield, collected between 24 C at 180 mtorr and 25 C at 65 mtorr Fraction D, 23.5 g, n=2.62, fwt 332.7, 6.8% yield, collected between 25 C at 65 mtorr and 22 C at 50 mtorr Fraction E, 37.0 g, n=3.63, fwt 393.4, 11.0% yield, collected between 22 C at 50 mtorr and 29 C at 25 mtorr Fraction F, 16.9 g, n=4.82, fwt 465.0, 5.1% yield, collected between 29 C at 25 mtorr and 37 C at 25 mtorr Fraction G, 22.8 g, n=5.39, fwt 499.3, 7.8% yield, collected between 33 C at 25 mtorr and 30 C at 23 mtorr Fraction H, 17.7 g, n=7.34, fwt 623.8, 5.5% yield, collected between 30 C at 23 mtorr and 63 C at 20 mtorr It is worth noting that the procedure can be optimized and the yield may be increased somewhat by accurate metering of the water addition rate by using a syringe pump or similar fluid metering device. Additionally, the yield may be further optimized by increasing the number of equivalents of water. It is also worth noting that the diethyl ether removed from the reaction in the first stage of the work-up will contain unreacted silicon chlorides and should be disposed of carefully, since silicon chlorides react exothermically with water.

Analysis of 261 (fraction A)

$^1$H NMR (acetone-$d_6$, δ): 0.26, 0.29, 0.32 (m, ClSi(CH$_3$)(H)O[Si(CH$_3$)(H)O]$_n$Si(CH$_3$)(H)Cl, 4.4H), 0.60, 0.65 (m, ClSi(CH$_3$)(H)O[Si(CH$_3$)(H)O]$_n$Si(CH$_3$)(H)Cl, 6H), 4.71, 4.74 (m, ClSi(CH$_3$)(H)O[Si(CH$_3$)(H)O]$_n$Si(CH$_3$)(H)Cl, 1.4H), 5.23 (m, ClSi(CH$_3$)(H)O[Si(CH$_3$)(H)O]$_n$Si(CH$_3$)(H)Cl, 2H).

IR (cm$^{-1}$, diamond): 497 m (Si—Cl), 1066 m (Si—O—Si), 1266 m (Si-Me), 2190 m (Si—H).

Synthesis of 262

To a 500 mL Schlenk flask was added toluene (200 mL) and dichloro polysilane 261 (15.7 g, 54.5 mmoles) that produced a clear colorless reaction solution with stirring. The reaction solution was immersed in a tap water bath at ~20° C. and octadecyl magnesium chloride (218 mL, 109 mmoles, 0.50 M in THF) was added by syringe which turned the reaction solution opaque white. About 30 minutes after the addition a thermostat controlled water bath was set to 50° C. to warm the reaction solution for about 6 hrs. The heat was turned off to let the reaction solution cool to room temperature overnight. The next day the water bath was to 50° C. to heat the reaction solution for another 9 hrs. Then after cooling to room temperature overnight the reaction solution was filtered using a filter tip canula and Fisherbrand Q8 (particle retention 20 to 25 μm). Then the white residue was extracted with hexane (2×150 mL and 1×100 mL) and the organic phase combined. The organic phase was washed with water (8×100 mL) to remove the residual Grignard reaction salts. In the first water wash the aqueous phase turned opaque white after mixing but by the last wash the water was clear without any turbidity after mixing. The volatiles were removed by vacuum transfer to leave a clear colorless oil (37.3 g, 49.5 mmoles, 90.9% yield). Proton NMR analysis gave n=1.74 for a formula weight of 743.9 g/mole.

Analysis of 262

$^1$H NMR (chloroform-d$_1$, δ): 0.14, 0.15, 0.16, 0.19 (m, [OSi(CH$_3$)(H)]$_x$CH$_2$(CH$_2$)$_{16}$CH$_3$, 12H), 0.64 (m, [OSi(CH$_3$)(H)]$_x$CH$_2$(CH$_2$)$_{16}$CH$_3$, 4H), 0.88 (t, [OSi(CH$_3$)(H)]$_x$CH$_2$(CH$_2$)$_{16}$CH$_3$, 6H), 1.26 (m, [OSi(CH$_3$)(H)]$_x$CH$_2$(CH$_2$)$_{16}$CH$_3$, 64 H), 4.64 (m, [OSi(CH$_3$)(H)]$_x$CH$_2$(CH$_2$)$_{16}$CH$_3$, 4H). $^{13}$C{$^1$H} (chloroform-d$_1$, δ): −0.9 (m, SiCH3), 1.2, 14.4, 17.1, 22.9, 23.1, 29.6, 29.8, 29.9, 30.0, 32.2, 33.3 (m, [OSi(CH$_3$)(H)]$_x$CH$_2$(CH$_2$)$_{16}$CH$_3$).

IR (cm$^{-1}$, diamond): 1054 s (Si—O—Si), 1258 m (Si—CH$_3$), 2128 m (Si—H), 2852 s, 2917 s, 2958 m (sp3 C—H).

Synthesis of 263

To a 500 mL Schlenk flask equipped with a reflux condenser was added polysilane 262 (15.7 g, 18.8 mmoles) and toluene (150 mL). The reaction solution was heated to 80° C. using a thermostat controlled oil bath. Then allyl succinic anhydride (10.6 g, 75.7 mmoles, 0.80 eq/eq Si—H) was added followed by Karstedt's catalyst precursor (6.71 mg of 2.2 wt % solution, 0.0076 mmol or 0.0001 eq Pt metal). After about 1 h, a sample of the reaction solution was prepared for analysis by removal of the volatiles. IR analysis showed a large Si—H absorbance without an anhydride or vinyl absorbance, indicating that allyl succinic anhydride had probably been removed during sample preparation via azeotropic distillation with toluene. Additionally, that the reaction had not initiated was confirmed by $^1$H NMR. Another 0.0001 eq of Karstedt's catalyst precursor (low color) was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. Initiation occurred in about a day and a half when the color of the reaction solution abruptly changed from clear yellow to clear brown. Sampling followed by IR analysis indicated that the Si—H absorbance was replaced by two succinic anhydride C=O absorbances (symmetrical and asymmetrical stretches). Following initiation, the reaction solution was heated about 90 minutes to insure complete conversion of starting material. The progress of the reaction was monitored by $^1$H NMR analysis using the disappearance of the vinyl resonances and Si—H peak and the appearance of a multiplet for the methylene on the propyl chain bonded to the silicone.

To work up the reaction, the volatiles were removed by rotational evaporator and the resulting clear brown oil dissolved in chloroform (800 mL). Then 4.0 g of activated carbon was added and the solution stirred overnight in air. The solution was filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in dichloromethane (200 mL) and sent through a 0.45 um nylon syringe filter. The complete de-colorization procedure (with activated carbon and syringe filter etc) was performed twice. The volatiles were removed to leave clear very light yellow oil (25.1 g, 18.0 mmoles, 95.7% yield).

Analysis of 263

$^1$H NMR (chloroform-d$_1$, δ): 0.06, 1.0, 0.12, 0.18 (m, SiCH3, 9H), 0.56, 0.57 (m, SiCH$_2$CH$_2$CH$_2$C(H)(C=O)(CH$_2$)C=O and/or SiCH$_2$(CH$_2$)$_{16}$CH$_3$, 10H), 0.89 (t, SiCH$_2$(CH$_2$)$_{16}$CH$_3$, 6H), 1.27 (m, SiCH$_2$(CH$_2$)$_{16}$CH$_3$, 64H), 1.45 (m, SiCH$_2$CH$_2$CH$_2$C(H)(C=O)(CH$_2$)C=O, 6H), 1.83 (d-m, J$_{HH}$=92 Hz, SiCH$_2$CH$_2$CH$_2$C(H)(C=O)(CH$_2$)C=O, 6H), 2.87 (d-m, J$_{HH}$=176 Hz, SiCH$_2$CH$_2$CH$_2$C(H)(C=O)(CH$_2$)C=O, 6H), 3.16 (m, SiCH$_2$CH$_2$CH$_2$C(H)(C=O)(CH$_2$)C=O, 3H). $^{13}$C{$^1$H} (chloroform-d$_1$, δ): partial listing 170.4, 174.0 (m, C=O anhydride).

IR (cm$^{-1}$, diamond): 1013 s (Si—O—Si), 1262 m (Si—CH$_3$), 1789 m, 1867 w, (C=O, sym. and asym.), 2962 m and 2905 w (CH aliphatic).

Synthesis of 264 (see Compound 35)

To a 1000 mL RBF in air was added polyanhydride 263 (25.1 g, 18.0 mmoles) and water (340 mL, 18.9 moles). The solution was heated to 120° C. using a heating mantle with temperature control monitored by a thermocouple positioned between the flask and heating mantle. The solution was stirred rapidly and a temperature of 120° C. was maintained for 90 minutes during which time the reaction solution gradually thickened to opaque white mousse. After cooling to room temperature the volatiles were removed using trap to trap distillation with an inverted 'U' shaped tube to connect reaction flask and receiver. During distillation the reaction flask was gently heated with a thermostat controlled heating mantle (as above) to 30° C. while the receiver was cooled in a dry ice/ethanol bath. The vacuum was maintained at <30 mtorr. To remove the last traces of water the product was placed in a desiccator with fresh phosphorous pentoxide and static vacuum of <30 mtorr for at least 16 h. This desiccation step was performed twice with fresh phosphorous pentoxide each time. The product was ground into a rough white powder before the last overnight in the desiccator. It was taken into the glove box, weighed and transferred into vials for storage (23.9 g, 16.2 mmoles, 90.1% yield).

Analysis of 264

$^1$H NMR (acetone-d$_6$, δ): −0.04 (br m, SiCH3), 0.48 (br m, SiCH$_2$(CH$_2$)$_{16}$CH$_3$ and SiCH$_2$CH$_2$CH$_2$CH(CO$_2$H)CH$_2$CO$_2$H), 0.88 (t, CH$_2$(CH$_2$)$_{16}$CH$_3$), 1.29 (m, SiCH$_2$(CH$_2$)$_{16}$CH$_3$, 32H), 1.70 (m, SiCH$_2$CH$_2$CH$_2$CH(CO$_2$H)CH$_2$CO$_2$H), 2.45 (br SiCH$_2$CH$_2$CH$_2$CH(CO$_2$H)CH$_2$CO$_2$H), 2.9 (br m, SiCH$_2$CH$_2$CH$_2$CH(CO$_2$H)CH$_2$CO$_2$H and SiCH$_2$CH$_2$CH$_2$CH(CO$_2$H)CH$_2$CO$_2$H), 11.8 (br s, CO$_2$H).

IR (cm$^{-1}$, diamond): 1033 s (Si—O—Si), 1262 m (Si—CH$_3$), 1732 s (C=O), 2848, 2917 s (sp3 C—H), 2500 to 3500 broad m (carboxylic acid OH).

It will be evident that additional ligands can be prepared using procedures similar to those above.

Example 6

Figure 27:
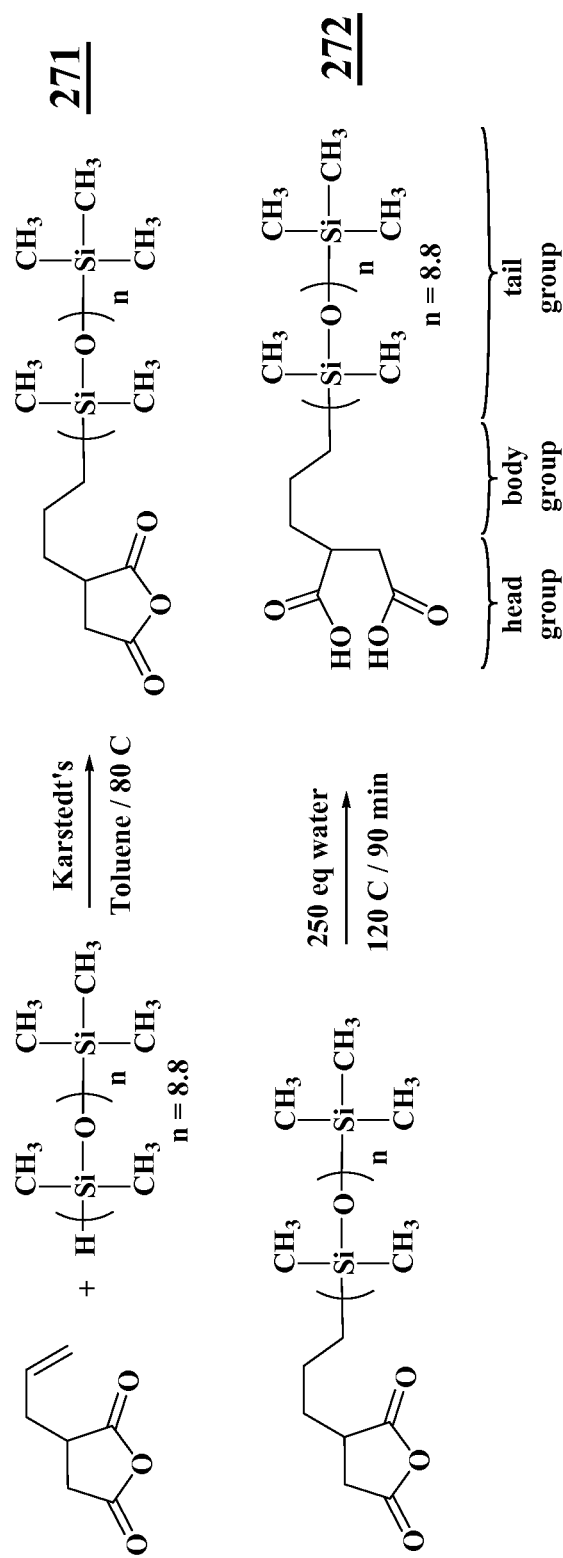
FIG. 27 schematically illustrates chemical synthesis of an exemplary ligand in accordance with the present invention.

Synthesis of Polycarboxylic Acid Ligands
Synthesis of Silicone Di-Carboxylic Acid (DCASi-Me)
Synthesis of the ligand is schematically illustrated in FIG. 27.

General Methods

All manipulations were carried out with strict exclusion of air and moisture by using Schlenk technique under an atmosphere of dry nitrogen, unless otherwise stated. Toluene, chloroform-d$_1$ and toluene-d$_8$ were dried over activated 4 A Molecular Sieves and de-gassed by three freeze-pump-thaw cycles. Acetone-d$_6$ was purified by stirring with anhydrous CaSO$_4$ (Drierite) for 7 days then distilled trap-to-trap. Chloroform was purchased from Fisher chemical and used as received. Allylsuccinic anhydride was purchased from TCI America, distilled and stored using Schlenk technique. The monosilane terminated silicone was special ordered from Gelest. Monosilane silicone formula weight was determined by $^1$H NMR using a post acquisition delay (d1) of at least 60 seconds for accurate integration. Karstedt's catalyst, or platinum divinyl tetramethyl disiloxane complex 2.1 to 2.4% in xylenes—low color, was purchased from Gelest, stored in the glove box and used without further purification. Activated carbon was purchased from Aldrich and used without purification. NMR chemical shift data was recorded with a Bruker FT NMR at 400 MHz for $^1$H and 100 MHz for $^{13}$C{$^1$H} and are listed in ppm. NMR chemical shifts were referenced on proton impurities in the deuterium solvent. IR analysis was recorded on a Nicolet 6700 FTIR standardized with polypropylene.

Synthesis Procedure for 271 (n=8.8)

To a 1000 mL Schlenk flask with nitrogen atmosphere, reflux condenser and thermostat controlled oil bath was added allylsuccinic anhydride (55.0 g, 0.392 moles), toluene, 200 mL, and monosilane terminated silicone (286 g, 0.392 moles, fwt 728.2). The reaction solution was stirred and when the oil bath temperature reached 80° C. Karstedt's catalyst precursor was added (355 mg of 2.2 wt % solution, 0.040 mmol or 0.0001 eq Pt metal). After about 1 h a sample of the reaction solution was prepared for analysis by removal of the volatiles. IR analysis showed a large Si—H absorbance without an anhydride or vinyl absorbance, indicating that allylsuccinic anhydride had probably been removed during sample preparation via azeotropic distillation with toluene. Additionally, the analysis indicated the reaction had not initiated, which was confirmed by $^1$H NMR. Another 0.001 eq of Karstedt's catalyst precursor was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. After about a day and a half, the color of the reaction solution abruptly changed from clear yellow to clear brown. Then IR analysis indicated that the Si—H absorbance was replaced by two succinic anhydride C=O absorbances (symmetrical and asymmetrical stretches). About 90 minutes following the color change, complete conversion of starting material was confirmed by $^1$H NMR analysis using the disappearance of the vinyl resonances and Si—H peak as well as appearance of a multiplet for the methylene on the propyl chain bonded to the silicone.

To work up the reaction, the volatiles were removed by rotational evaporator and the resulting clear brown oil decolorized in two parts, each half dissolved in 800 mL chloroform. Then to each solution activated carbon, 20 g, was added and the solutions stirred in the air for 90 minutes. The solutions were filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in 300 mL of chloroform and sent through a 0.45 um nylon syringe filter followed by removal of volatiles to leave a clear, very light yellow oil (280 g, 0.323 moles, 82.4% yield).

Analysis of 271 (n=8.8)

$^1$H NMR (acetone-d$_6$, δ): 0.13 (m, SiMe, 61.9H), 0.65 (m, O$_2$CCH$_2$CH(CO)CH$_2$CH$_2$CH$_2$Si, 2H), 1.56 (m, O$_2$CCH$_2$CH(CO)CH$_2$CH$_2$CH$_2$Si, 2H), 1.86 (d-m, J=76 Hz, O$_2$CCH$_2$CH(CO)CH$_2$CH$_2$CH$_2$Si, 2H), 2.91 (d-q, J$_{H-H}$=148 Hz, J$_{H-H}$=10 Hz, O$_2$CCH$_2$CH(CO)CH$_2$CH$_2$CH$_2$Si, 2H), 3.32 (m, O$_2$CCH$_2$CH(CO)CH$_2$CH$_2$CH$_2$Si, 1H). $^{13}$C{$^1$H} (chloroform-d$_1$, δ): 1.5 (m, SiMe), 18.5, 21.7, 34.8, 34.9, 41.4 (s, O$_2$CCH$_2$CH(CO)CH$_2$CH$_2$CH$_2$Si), 175.6, 172.0 (s, O$_2$CCH$_2$CH(CO)CH$_2$CH$_2$CH$_2$Si).

IR (cm$^{-1}$, diamond): 1017 s (Si—O—Si), 1262 m (Si—CH$_3$), 1789 m and 1867 w (C=O, sym. and asym.), 2962 m and 2905 w (CH aliphatic).

Synthesis of 272, HO$_2$CCH$_2$CH(CO$_2$H)(CH$_2$)$_3$(SiMe$_2$O)$_n$SiMe$_3$(n=8.8) (see compound 18)

The reaction solution was divided in half and each part transferred into a 2000 mL RBF equipped with a reflux condenser in air. To the reaction flask was then added water (730 mL, 40.5 moles or 250 eq) and the solution heated to 120° C. using a heating mantle with temperature control monitored by thermocouple positioned between the flask and heating mantle. The solution was rapidly stirred using a mechanical stirrer as the temperature of 120° C. was maintained for 90 minutes. As the reaction proceeded the solution gradually attained the consistency of mousse and was opaque white. After cooling to room temperature the volatiles were removed using trap to trap distillation with an inverted 'U' shaped tube to connect reaction flask and receiver. During distillation the reaction flask was gently heated with a thermostat controlled heating mantle (as above) to 30° C. while the receiver was cooled in a dry ice/ethanol bath and the vacuum was maintained at <30 mtorr. Then the product was dissolved in chloroform, 100 mL, and filtered again with 0.45 um syringe filter before final removal of volatiles to <30 mtorr for a period of 4 h using dynamic vacuum. To remove the last traces of water the product was placed in a desiccator with fresh P$_4$O$_{10}$ and static vacuum of <30 mtorr for at least 16 h. This desiccation step was performed twice with fresh P$_4$O$_{10}$ each time. The clear, very light yellow oil was taken into the glove box, weighed and transferred into vials for storage (272 g, 0.307 moles, 95.2% yield).

Analysis of HO$_2$CCH$_2$CH(CO$_2$H)(CH$_2$)$_3$(SiMe$_2$O)$_n$SiMe$_3$ (n=8.8)

$^1$H NMR (acetone-d$_6$, δ): 0.11 (m, SiMe, 61.9H), 0.62 (m, HO$_2$CCH$_2$CH(CO$_2$H)CH$_2$CH$_2$CH$_2$Si, 2H), 1.48 (m, HO$_2$CCH$_2$CH(CO$_2$H)CH$_2$CH$_2$CH$_2$Si, 2H), 1.61 (d-m, J$_{H-H}$=16 Hz, HO$_2$CCH$_2$CH(CO$_2$H)CH$_2$CH$_2$CH$_2$Si, 2H), 2.55 (d-q, J$_{H-H}$=92 Hz, J$_{H-H}$=10 Hz, HO$_2$CCH$_2$CH(CO$_2$H)CH$_2$CH$_2$CH$_2$Si, 2H), 2.83 (m, HO$_2$CCH$_2$CH(CO$_2$H)CH$_2$CH$_2$CH$_2$Si, 1H), 10.71 (s, HO$_2$C, 2H). $^{13}$C{$^1$H} (chloroform-d$_1$, δ): 1.8 (m, SiMe), 18.8, 21.6, 36.1, 36.3, 41.5 (s, HO$_2$CCH$_2$CH(CO$_2$H)CH$_2$CH$_2$CH$_2$Si), 173.5, 176.4 (s, HO$_2$CCH$_2$CH(CO$_2$H)CH$_2$CH$_2$CH$_2$Si).

IR (cm$^{-1}$, diamond): 1017 s (Si—O—Si), 1258 m (Si—CH$_3$), 1716 m (acid C=O), 2905 m and 2962 w (CH aliphatic), 2500 to 3300 w broad (carboxylic acid).

Synthesis of an Alkene Di-Carboxylic Acid Ligand (DDSA, compound 44)

Figure 28:
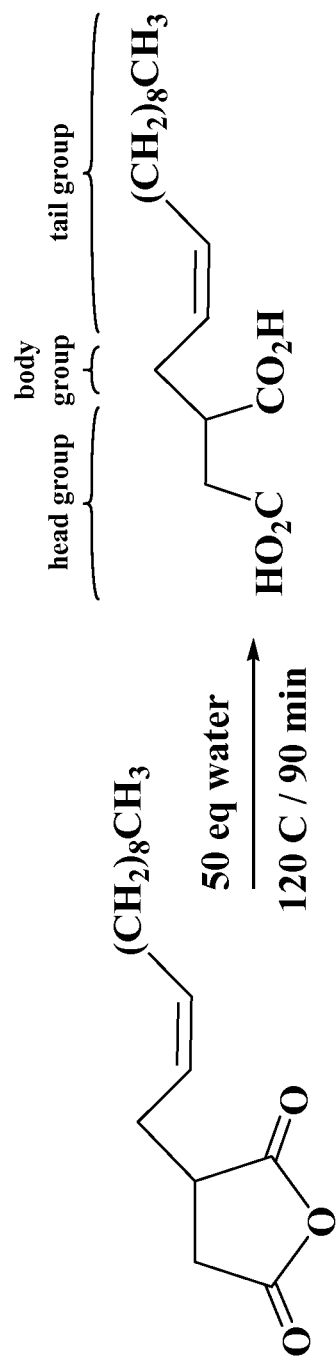
FIG. 28 schematically illustrates chemical synthesis of an exemplary ligand in accordance with the present invention.

Synthesis of the ligand is schematically illustrated in FIG. 28.

General Methods

The starting anhydride (2-dodecen-1-ylsuccinic anhydride) was purchased from Aldrich. Acetone-d$_6$ was purified by stirring with anhydrous CaSO$_4$ (Drierite) for 7 days then distilled trap-to-trap. NMR chemical shift data was recorded with a Bruker FT NMR at 400 MHz for $^1$H and 100 MHz for $^{13}$C{$^1$H} and are listed in ppm. NMR chemical shifts were referenced from proton impurities in the deuterium solvent. IR analysis was recorded on a Nicolet 6700 FTIR standardized with polypropylene.

Synthesis Procedure

To a 2000 mL round bottom flask equipped with mechanical stirrer and heating mantle (thermocouple between the flask and heating mantle) was added anhydride (100 g, 0.375 moles, a waxy white solid) and water (337 mL, 18.7 moles) in air. The flask was fitted with a reflux condenser and heated to 120 C using the thermostat to control the temperature with a temperature controller. The reaction solution was stirred rapidly giving it an opalescent appearance initially but as heating was continued it became opaque white and thickened a bit. After about 90 minutes at 120 C the heat was turned off and the solution cooled to room temperature overnight. The product was isolated by removing the water by vacuum transfer.

An inverted 'U' tube was used to connect the reaction flask to a 1000 mL round bottom flask used as a distillation receiver. The receiving flask was cooled with a dry ice/ethanol bath and the vacuum applied to the system gradually to avoid excessive foaming of the reaction solution. During the distillation the reaction flask was heated to 30 C using the thermostat controlled heating mantle. The vacuum was gradually increased until <30 mtorr was reached to remove available water. As the water was removed the product turned into a white solid containing some powder. Then the product was transferred to a crystallizing dish and the larger chunks broken up to facilitate drying. Then last traces of water were removed at <30 mtorr in a vacuum desiccator over $P_2O_5$ overnight under static vacuum. The $P_2O_5$ was replaced and the process repeated again in a desiccator producing a flocculent white powder (97.5 g, 0.343 moles, 91.4% yield).

Analysis $^1$H NMR (acetone-$d_6$, δ): 0.88 (m, $CH_3$, 3H), 1.28 (m, $HO_2CCH_2CH(CO_2H)CH_2CH=CHCH_2(CH_2)_7CH_3$, 14H), 2.00 (q, $HO_2CCH_2CH(CO_2H)CH_2CH=CHCH_2(CH_2)_7CH_3$, 2H), 2.28, 2.37 (d-q, $HO_2CCH_2CH(CO_2H)CH_2CH=CHCH_2(CH_2)_7CH_3$ 2H), 2.43, 2.63 (d-m, $HO_2CCH_2CH(CO_2H)CH_2CH=CHCH_2(CH_2)_7CH_3$, 2H), 2.84 (m, $HO_2CCH_2CH(CO_2H)CH_2CH=CHCH_2(CH_2)_7CH_3$, 1H), 5.40, 5.51 (d-m, $HO_2CCH_2CH(CO_2H)CH_2CH=CHCH_2(CH_2)_7CH_3$, 2H), 10.75 (s, $CO_2H$, 2H). $^{13}C\{^1H\}$ (acetone-$d_6$, δ): 127, 134 (s, CH=CH), 173, 176 (s, $CO_2H$), (incomplete listing).

IR ($cm^{-1}$, diamond): 1691 s (C=O), 2848 m, 2921 m, 2958 w (C—H aliphatic), 3019 w (C=C), 2400-3400 br w (acid OH). It is worth noting that IR analysis is a reliable tool for distinguishing acid from anhydride.

Synthesis of a Silicone One-Tail Poly-Carboxylic Acid Ligand

Figure 29:
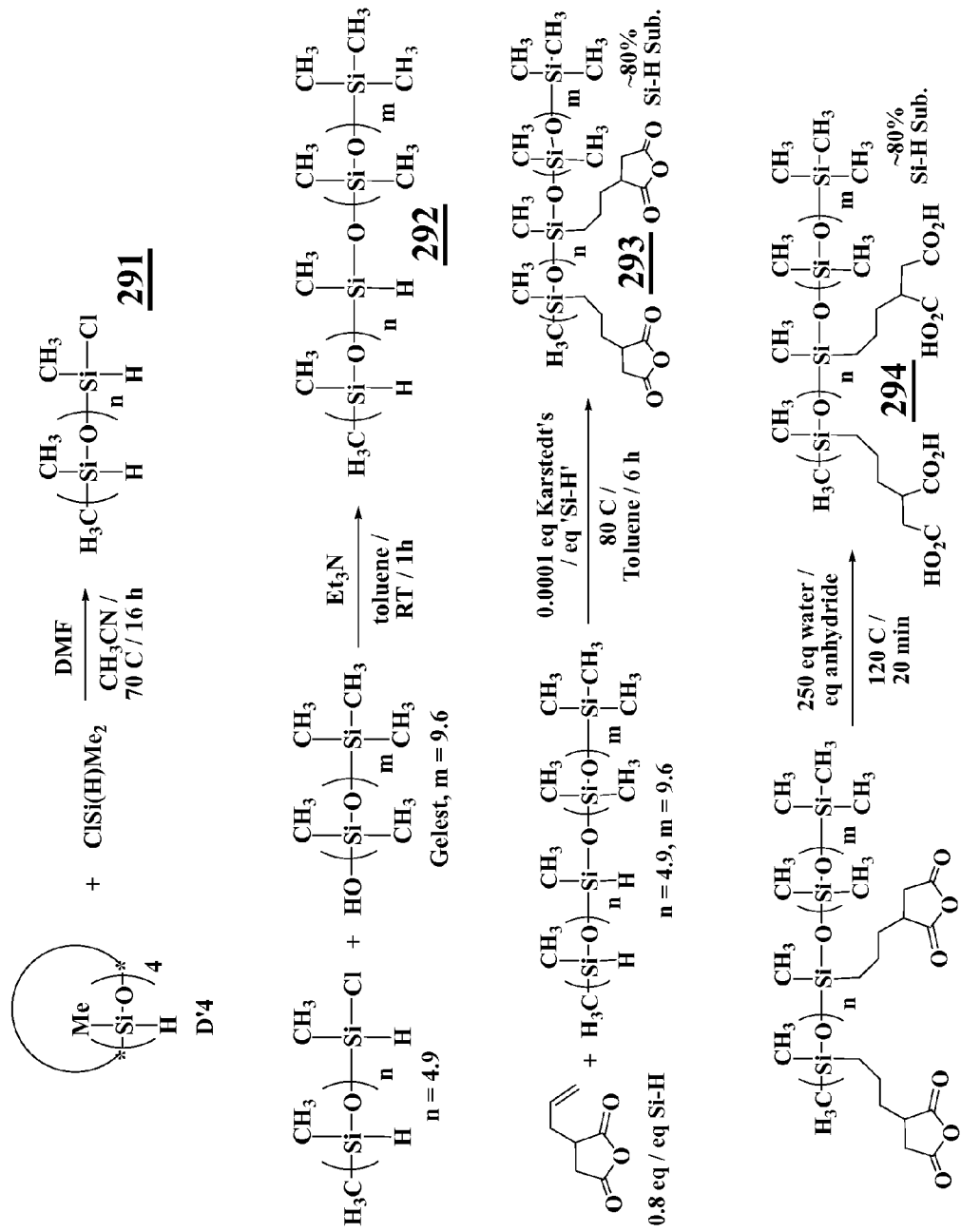
FIG. 29 schematically illustrates chemical synthesis of an exemplary ligand in accordance with the present invention.

Synthesis of the ligand is schematically illustrated in FIG. 29.

General Methods

All manipulations were carried out with strict exclusion of air and moisture by using Schlenk technique under an atmosphere of dry nitrogen, unless otherwise stated. Toluene was dried over activated 4 A Molecular Sieves and de-gassed by three freeze-pump-thaw cycles. Acetone-$d_6$ was purified by stirring with anhydrous calcium (II) sulfate (Drierite) for 7 days then distilled 'trap-to-trap'. Chloroform and dichloromethane were purchased from Fisher Chemical and used as received. Dimethylformamide (DMF), triethylamine and acetonitrile were purchased from Aldrich dry in sure-seal bottles and transferred by cannula (double tipped needle) to storage flasks until used. Allyl succinic anhydride was purchased from TCI America, distilled and stored using Schlenk technique until used. Methylhydrocyclosiloxanes (D'4) was purchased from Gelest. The material was used as received and was a mixture of ring sizes containing between 3 and 5 SiH (CH3)-O units with the average ring size being 4. Dimethyl chloro silane was purchased from Aldrich, distilled and stored in a storage flask until used. Monosilanol terminated silicone was special ordered from Gelest. Karstedt's catalyst precursor, or platinum divinyl tetramethyl disiloxane complex 2.1 to 2.4% in xylenes—low color, was purchased from Gelest, stored in the glove box and used without further purification. Phosphorous pentoxide was purchased from Fisher Chemical and used as received. Activated carbon (coconut shell) and 4 A Molecular Sieves were purchased from Aldrich and used as received. NMR chemical shift data was recorded with a Bruker FT NMR at 400 MHz for $^1$H and 100 MHz for $^{13}C\{^1H\}$ and are listed in ppm. NMR chemical shifts were referenced using proton impurities in the deuterium solvent. Silicone formula weight was determined by comparison of end-group to repeat unit integration using $^1$H NMR using a post acquisition delay (d1) of at least 60 seconds for accuracy. IR analysis was recorded on a Nicolet 6700 FTIR standardized with polypropylene.

Synthesis of 291

Synthesis of 291 is adapted from Suzuki, Toshio et al. (1989) Polymer 30:333-337 and Cella, James A. et al. (1994) J. Organomet. Chem. 480:23-26.

To a 250 mL Schlenk flask on the vacuum line was added DMF (0.651 mL, 0.017 moles), acetonitrile (15.9 mL, 0.304 moles) and D'4 (40 g, 0.166 mol) which formed a colorless cloudy solution initially that became clear colorless after stirring for about 3 minutes. Then dimethyl chloro silane (18.0 ml, 15.7 g, 0.166 moles) was added and the reaction solution did not appear to generate any heat. The reaction solution was heated to 70° C. using a thermostat controlled oil bath for about 16 h (overnight). The product was then isolated from the reaction solution by distillation. First the solvent was distilled with pot temperature of 70° C. which was attained by fitting the flask directly with a short path distillation apparatus. The apparatus was not cooled to room temperature after heating overnight but the pressure was gradually decreased with a vacuum regulator (Buchi V-400) and Teflon diaphragm vacuum pump. At about 120 torr the receiver was cooled with an ice bath and when the pressure reached about 40 torr the distillation apparatus was re-configured. The distillate was discarded and a 14/20 (standard taper joint) fraction-cutter distillation apparatus was set up and connected to the vacuum line for a more efficient vacuum. The contents of the reaction flask were transferred to the fraction cutter distillation pot by cannula and the temperature of the oil bath (heating the pot) was dropped to 35° C. and maintained at 35° C. Vacuum was applied to the distillation apparatus and as the pressure reached about 40 torr some distillate was collected in the receiver. That distillate evaporated as the pressure was dropped to 500 mtorr. Then below about 300 mtorr product was collected in three fractions: fraction A between 24° C. at 310 mtorr to 27° C. at 80 mtorr (0.68 g); fraction B at 27° C. at 80 mtorr to 23° C. at 45 mtorr (3.17 g); and then fraction C (1.70 g). The apparatus was re-configured to collect fraction C. Distillate was collected by heating the pot to 100° C., the vacuum at <30 mtorr and the pot connected directly to the receiver using an inverted 'U' tube. By $^1$H NMR it was determined that B fraction had 4.9 repeat units (MW=389.5). Based on this molecular weight the yield of fraction B was 5.7% (8.14 mmoles). All fractions were clear-colorless oils and were stored in a nitrogen atmosphere.

Analysis of 291

$^1$H NMR (acetone-$d_6$, δ): 0.24 (m, $ClSiHCH_3(OSiCH_3H)_nCH_3$, 17.7H), 0.61 (s, $ClSiHCH_3(OSiCH_3H)_nCH_3$, 3H), 4.70, 4.75 (m, $ClSiHCH_3(OSiCH_3H)_nCH_3$, 4.7H), 5.24 (m, $ClSiHCH_3(OSiCH_3H)_nCH_3$, 1H). $^{13}C\{^1H\}$ (acetone-$d_6$, δ): 0.4, 0.7, 1.0, 1.2, 1.3, 3.6 (m, SiMe).

IR ($cm^{-1}$, diamond): 502 m (Si—Cl), 1046 m (Si—O—Si), 1262 m (Si-Me), 2165 m (Si—H).

Synthesis of 292

To a 50 mL Schlenk flask was added toluene (20 mL) and chloropolysilane 291 (1.00 g, 2.57 mmoles) that produced a clear colorless reaction solution with stirring. Then the silanol (2.06 g, 2.57 mmoles) was added and in less than 15 sec triethylamine (0.430 mL, 0.312 g, 3.08 mmoles) was added. The reaction solution turned opaque white almost instantaneously and produced a little white vapor but did not appear to produce any heat. As the reaction solution was stirred for 1 h it became a bit thicker but continued to stir freely at room temperature. After 1 h the volatiles were removed by vacuum transfer. The white residue was extracted with toluene (3×5 mL) and the filtrate transferred by filter tip cannula (using Fisherbrand P2 filter paper with particle retention 1-5 μm) to a separate Schlenk flask. Removal of the volatiles from the filtrate by vacuum transfer produced as a clear-colorless oil (2.07 g, 1.79 mmoles, 60.3% yield). It was taken into the glove box and after a couple of days storage at room temperature turned slightly cloudy. The oil was filtered again through a 0.45 μm syringe filter before the next reaction.

Analysis of 292

$^1$H NMR (acetone-$d_6$, δ): 0.15 (m, $CH_3$, 67H), 4.70 (m, SiH, 5.9H). $^{13}C\{^1H\}$ (acetone-$d_6$, δ): 0.7, 1.27, 1.46, 2.03 (m, SiMe).

IR ($cm^{-1}$, diamond): 1021 s (Si—O—Si), 1262 m (Si—$CH_3$), 2165 m (Si—H).

Synthesis of 293

To a 50 mL Schlenk flask equipped with a reflux condenser was added polysilane 292 (2.07 g, 1.79 mmoles), toluene (15 mL) and allyl succinic anhydride (1.19 g, 8.46 mmoles). The reaction solution was stirred and when the oil bath temperature reached 80° C. Karstedt's catalyst precursor was added (7.49 mg of 2.2 wt % solution, 0.0008 mmol or 0.0001 eq Pt metal). After about 1 h, a sample of the reaction solution was prepared for analysis by removal of the volatiles. IR analysis showed a large Si—H absorbance without an anhydride or vinyl absorbance, indicating that allyl succinic anhydride had probably been removed during sample preparation via azeotropic distillation with toluene. Additionally, that the reaction had not initiated was confirmed by $^1$H NMR. Another 0.0001 eq of Karstedt's catalyst precursor (low color) was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. Initiation occurred in about a day and a half when the color of the reaction solution abruptly changed from clear yellow to clear brown. Sampling followed by IR analysis indicated that the Si—H absorbance was replaced by two succinic anhydride C=O absorbances (symmetrical and asymmetrical stretches). Following initiation, the reaction solution was heated about 90 minutes to insure complete conversion of starting material. The progress of the reaction was monitored by $^1$H NMR analysis using the disappearance of the vinyl resonances and Si—H peak and the appearance of a multiplet for the methylene on the propyl chain bonded to the silicone.

To work up the reaction the volatiles were removed by rotational evaporator and the resulting clear brown oil dissolved in dichloromethane (100 mL). Then 5 g of activated carbon was added and the solution stirred overnight in air. The solution was filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in chloroform (300 mL) and sent through a 0.45 um nylon syringe filter. The complete de-colorization procedure (with activated carbon and syringe filter etc) was performed twice. The volatiles were removed to leave clear very light yellow oil (2.19 g, 1.21 mmoles, 67.4% yield).

Analysis of 293

$^1$H NMR (acetone-$d_6$, δ): 0.90, 0.12, 0.16 (m, $SiCH_3$, 149H), 0.69 (m, $O_2CCH_2CH(CO)CH_2CH_2CH_2Si$, 12H), 1.58 (m, $O_2CCH_2CH(CO)CH_2CH_2CH_2Si$, 12H), 1.88 (d-m, $J_{HH}$=88 Hz, $O_2CCH_2CH(CO)CH_2CH_2CH_2Si$, 12H), 3.01 (d-q, $J_{H-H}$=148 Hz, $J_{H-H}$=10 Hz, $O_2CCH_2CH(CO)CH_2CH_2CH_2Si$, 12H), 3.34 (m, $O_2CCH_2CH(CO)$ $CH_2CH_2CH_2Si$, 6H), 4.78 (m, Si—H, 1H, 80% substitution). $^{13}C\{^1H\}$ (acetone-$d_6$, δ): 0.2, 0.6, 1.5, 2.0 (m, $SiCH_3$), 17.8, 18.6, 21.6, 34.9, 41.4 (m, $O_2CCH_2CH(CO)CH_2CH_2CH_2Si$) 172.0, 175.6 (m, anhydride).

IR ($cm^{-1}$, diamond): 1017 s (Si—O—Si), 1262 m (Si—$CH_3$), 1785 m, 1867 w, (C=O, sym. and asym.), 2962 m and 2905 w (CH aliphatic).

Synthesis of 294 (see Compound 27)

To a 100 mL RBF in air was added silicone polyanhydride 293 (2.19 g, 1.21 moles) and water (25.7 mL, 1.43 moles). The solution was heated to 120° C. using a heating mantle with temperature control monitored by a thermocouple positioned between the flask and heating mantle. The solution was stirred rapidly and a temperature of 120° C. was maintained for 90 minutes during which time the reaction solution gradually thickened to opaque white mousse. After cooling to room temperature the volatiles were removed using trap to trap distillation with an inverted 'U' shaped tube to connect reaction flask and receiver. During distillation the reaction flask was gently heated with a thermostat controlled heating mantle (as above) to 30° C. while the receiver was cooled in a dry ice/ethanol bath. The vacuum was maintained at <30 mtorr. To remove the last traces of water the product was placed in a desiccator with fresh phosphorous pentoxide and static vacuum of <30 mtorr for at least 16 h. This desiccation step was performed twice with fresh phosphorous pentoxide each time. The clear, very light yellow oil was taken into the glove box, weighed and transferred into vials for storage (1.68 g, 0.874 mmoles, 72.2% yield).

Analysis of 294

$^1$H NMR (acetone-$d_6$, δ): 0.70, 0.12 (m, $SiCH_3$, 149H), 0.62 (m, $HO_2CCH_2CH(CO_2H)CH_2CH_2CH_2Si$, 12H), 1.50 (m, $HO_2CCH_2CH(CO_2H)CH_2CH_2CH_2Si$, 12H), 1.67 (d-m, $J_{HH}$=32 Hz, $HO_2CCH_2CH(CO_2H)CH_2CH_2CH_2Si$, 12H), 2.4 (d-m, $J_{HH}$=88 Hz, $HO_2CCH_2CH(CO_2H)CH_2CH_2CH_2Si$, 12H), 2.84 (m, $HO_2CCH_2CH(CO_2H)CH_2CH_2CH_2Si$, 6H), 10.75 (m, $HO_2C$, 12H). $^{13}C\{^1H\}$ (acetone-$d_6$, δ): 2.0 (m, $SiCH_3$), 18.3, 18.8, 21.6, 36.2, 36.4, 41.6 (m, $HO_2CCH_2CH(CO_2H)CH_2CH_2CH_2Si$), 173.7, 176.9 (m, $HO_2C$).

IR ($cm^{-1}$, diamond): 1017 s (Si—O—Si), 1262 m (Si—$CH_3$), 1712 (C=O), 2500 to 3500 br ($HO_2C$).

Synthesis of Silicone Two-Tail Poly-Carboxylic Acid Ligand

Figure 30:
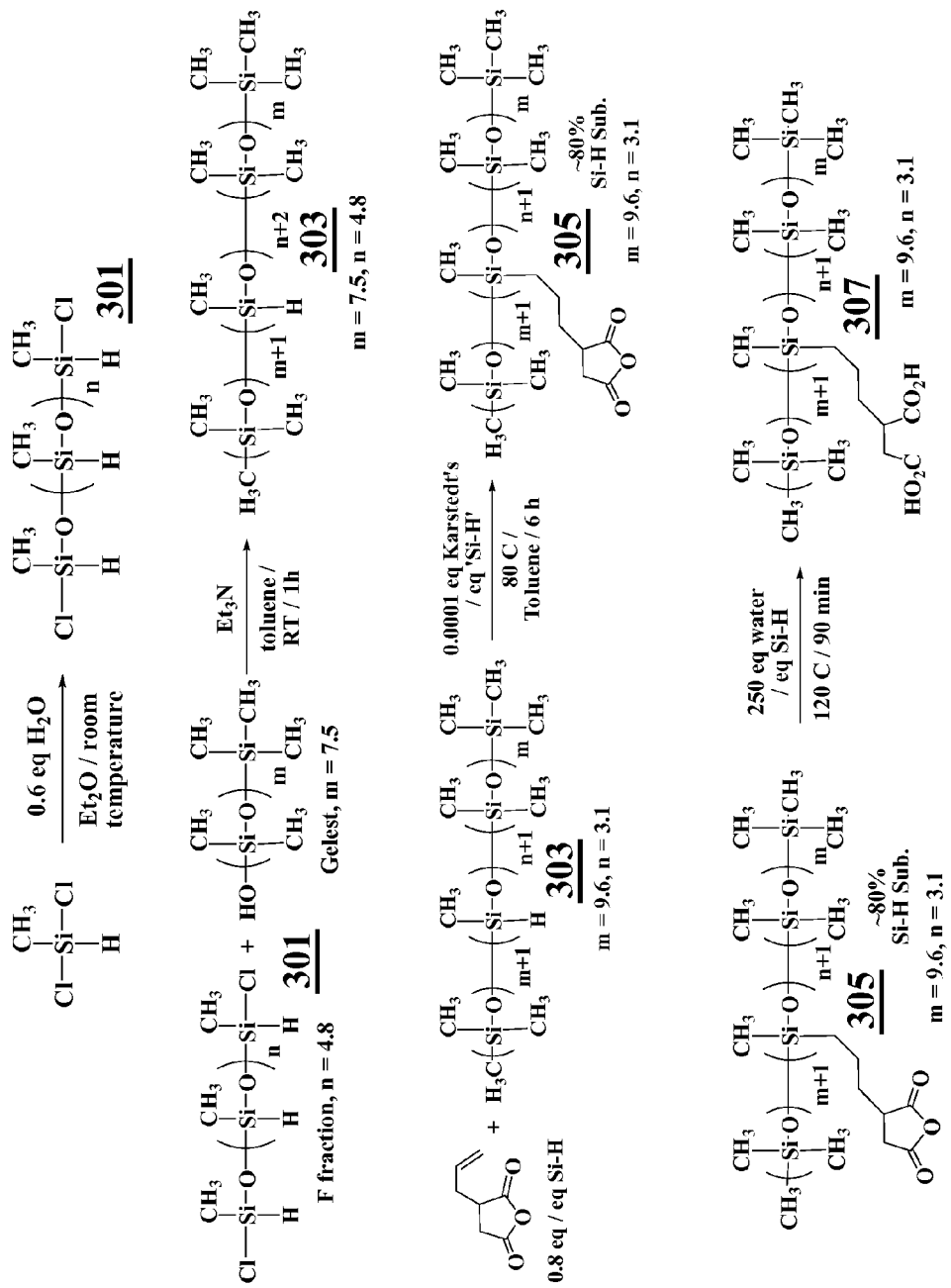
FIG. 30 schematically illustrates chemical synthesis of an exemplary ligand in accordance with the present invention.

Synthesis of the ligand is schematically illustrated in FIG. 30.

General Methods

All manipulations were carried out with strict exclusion of air and moisture by using Schlenk technique under an atmosphere of dry nitrogen, unless otherwise stated. Toluene was dried in an M Braun solvent system that incorporated molecular sieves and alumina as drying agents. Acetone-$d_6$ was purified by stirring with anhydrous calcium (II) sulfate (Drierite) for 7 days then distilled 'trap-to-trap'. Chloroform and dichloromethane were purchased from Fisher Chemical and used as received. Triethylamine was purchased from Aldrich dry in sure-seal bottles and transferred by cannula (or double tipped needle) into storage flasks until used. Allyl succinic anhydride was purchased from TCI America, distilled and stored using Schlenk technique until used. Dichloro methyl silane was purchased from Acros Organics and a new, previously un-opened bottle was used for each synthesis. Monosilanol terminated silicone was special ordered from Gelest. Karstedt's catalyst precursor, or platinum divinyl tetramethyl disiloxane complex 2.1 to 2.4% in xylenes—low color, was purchased from Gelest, stored in the glove box and used without further purification. Phosphorous pentoxide was purchased from Fisher Chemical and used as received. Activated carbon (coconut shell) and 4 A Molecular Sieves were purchased from Aldrich and used as received. NMR chemical shift data was recorded with a Bruker FT NMR at 400 MHz for $^1$H and 100 MHz for $^{13}$C{$^1$H} and are listed in ppm. NMR chemical shifts were referenced using proton impurities in the deuterium solvent. Silicone formula weight was determined by comparison of end-group to repeat unit integration using $^1$H NMR using a post acquisition delay (d1) of at least 60 seconds for accuracy. IR analysis was recorded on a Nicolet 6700 FTIR standardized with polypropylene.

Synthesis of 301

Synthesis of 301 is adapted from U.S. Pat. No. 2,381,366 to Patnode, W. I., 1942, and Manami, H. et al. (1958) Nippon Kagaku Zasski 79:60-65.

A 2000 mL, 3-neck round bottom flask was equipped with an addition funnel, mechanical stirrer, reflux condenser and nitrogen atmosphere. The nitrogen bubbler consisted of a piece of glass tubing placed into a 1 L Erlenmeyer flask containing about 800 mL of water to absorb the HCl gas generated in the reaction. To the reaction flask was added diethyl ether (1 L) and methyl dichloro silane (500 mL, 533 g, 4.80 moles). Water (51.9 mL, 2.88 moles, 0.6 eq) was transferred into the addition funnel. The reaction was stirred rapidly while water was added over about 45 minutes and the reaction solution refluxed gently during the addition. Following the addition the reaction solution was stirred at room temperature for about 1 h and under positive nitrogen flow the reaction flask was re-fitted for vacuum distillation. The mechanical stirrer was exchanged for a magnetic stirrer and the reflux condenser was replaced with an inverted 'U' tube connected to a 2 L receiver. Also the reaction flask was fitted with a heating mantle with temperature controller that used a thermocouple between reaction flask and heating mantle. Then the pot was heated to 25 C and vacuum gradually applied to the system using a Teflon lined vacuum pump with vacuum controller (Buchi V-800). During evacuation the receiver was cooled in a dry ice/ethanol bath while the vacuum was gradually increased to 200 mtorr. Removing the volatiles at this stage required about 4 h and removed ~75% of the solution volume. Then the receiver was changed to a 1 L Schlenk flask and product was separated from nonvolatile material by distillation with the same apparatus (an inverted 'U' tube connected to a receiver). In this case the receiver was cooled with liquid nitrogen while the pressure was gradually dropped to ~20 mtorr and the temperature of the pot was gradually increased to 200 C. That distillate was transferred by cannula to a pot connected to a fraction cutter and the product carefully distilled to separate the oligomeric products. On this reaction scale a fraction cutter with 24/40 standard taper joints is most convenient. All fractions were clear colorless oils and were stored in the glove box. Total reaction yield was 57.8% and the fractions are detailed below.

Fraction A, 26.5 g, n=1.38, fwt 258.1, 7.2% yield, collected between 23 C at 125 torr to 24 C at 300 mtorr Fraction B, 22.1 g, n=1.89, fwt 288.8, 6.2% yield, collected between 24 C at 300 mtorr and 24 C at 180 mtorr Fraction C, 27.5 g, n=2.73, fwt 339.9, 8.0% yield, collected between 24 C at 180 mtorr and 25 C at 65 mtorr Fraction D, 23.5 g, n=2.62, fwt 332.7, 6.8% yield, collected between 25 C at 65 mtorr and 22 C at 50 mtorr Fraction E, 37.0 g, n=3.63, fwt 393.4, 11.0% yield, collected between 22 C at 50 mtorr and 29 C at 25 mtorr Fraction F, 16.9 g, n=4.82, fwt 465.0, 5.1% yield, collected between 29 C at 25 mtorr and 37 C at 25 mtorr Fraction G, 22.8 g, n=5.39, fwt 499.3, 7.8% yield, collected between 33 C at 25 mtorr and 30 C at 23 mtorr Fraction H, 17.7 g, n=7.34, fwt 623.8, 5.5% yield, collected between 30 C at 23 mtorr and 63 C at 20 mtorr It is worth noting that the procedure can be optimized and the yield may be increased somewhat by accurate metering of the water addition rate by using a syringe pump or similar fluid metering device. Additionally, the yield may be further optimized by increasing the number of equivalents of water. It is also worth noting that the diethyl ether removed from the reaction in the first stage of the work-up will contain unreacted silicon chlorides and should be disposed of carefully, since silicon chlorides react exothermically with water.

Analysis of 301

$^1$H NMR (acetone-$d_6$, δ): 0.26, 0.29, 0.32 (m, ClSi(CH$_3$)(H)O[Si(CH$_3$)(H)O]$_n$Si(CH$_3$)(H)Cl, 4.4H), 0.60, 0.65 (m, ClSi(CH$_3$)(H)O[Si(CH$_3$)(H)O]$_n$Si(CH$_3$)(H)Cl, 6H), 4.71, 4.74 (m, ClSi(CH$_3$)(H)O[Si(CH$_3$)(H)O]$_n$Si(CH$_3$)(H)Cl, 1.4H), 5.23 (m, ClSi(CH$_3$)(H)O[Si(CH$_3$)(H)O]$_n$Si(CH$_3$)(H)Cl, 2H).

IR (cm$^{-1}$, diamond): 497 m (Si—Cl), 1066 m (Si—O—Si), 1266 m (Si-Me), 2190 m (Si—H).

Synthesis of 303

To a 250 mL Schlenk flask was added toluene (100 mL) and dichloro polysilane 301 (5.00 g, 10.7 mmoles) that produced a clear colorless reaction solution with stirring. Then the silanol (13.9 g, 21.5 mmoles) was added and in less than 15 sec triethylamine (3.58 mL, 2.60 g, 25.7 mmoles) was added. The reaction solution turned opaque white almost instantaneously and produced a little white vapor but did not appear to produce any heat. As the reaction solution was stirred for 5 h it became a bit thicker but continued to stir freely at room temperature. After 18 h the reaction solution was filtered by filter tip canula (using Fisherbrand P5 filter paper with particle retention 5-10 μm) to a separate Schlenk flask. Then hexane (120 mL) was added and the solution filtered again using a filter tip canula with Fisherbrand P5 filter paper to a separate Schlenk flask. The volatiles were removed by vacuum transfer to <30 mtorr and the resulting oil filtered with a 0.45 μm syringe filter to leave clear colorless oil (15.9 g, 9.79 mmoles, 91.5% yield) that was stored in the glove box.

Analysis of 303

$^1$H NMR (acetone-$d_6$, δ): 0.08, 0.12, 0.17, 0.22 m, (CH$_3$)$_3$SiO[Si(CH$_3$)$_2$O]$_m$[Si(H)(CH$_3$)O]$_{n+2}$[Si(CH$_3$)$_2$O]Si(CH$_3$)$_3$, 122H), 4.77 (m, (CH$_3$)$_3$SiO[Si(CH$_3$)$_2$O]$_m$[Si(H)(CH$_3$)O]$_{n+2}$[Si(CH$_3$)$_2$O]Si(CH$_3$)$_3$, 6.8H). $^{13}$C{$^1$H} (acetone-$d_6$, δ): 1.2, 1.4, 1.5, 2.1 (m, SiCH$_3$).

IR (cm$^{-1}$, diamond): 1017 s (Si—O—Si), 1258 m (Si—CH$_3$), 2165 m (Si—H), 2966, 2909 m (sp3 C—H).

Synthesis of 305

To a 50 mL Schlenk flask equipped with a reflux condenser was added polysilane 303 (3.73 g, 2.03 mmoles) and toluene (15 mL). The reaction solution was heated to 80° C. using a thermostat controlled oil bath. Then allyl succinic anhydride (0.933 g, 6.66 mmoles) was added followed by Karstedt's catalyst precursor (5.09 mg of 2.2 wt % solution, 0.00033 mmol or 0.0001 eq Pt metal). After about 1 h, a sample of the reaction solution was prepared for analysis by removal of the volatiles. IR analysis showed a large Si—H absorbance without an anhydride or vinyl absorbance, indicating that allyl succinic anhydride had probably been removed during sample preparation via azeotropic distillation with toluene. Additionally, that the reaction had not initiated was confirmed by $^1$H NMR. Another 0.0001 eq of Karstedt's catalyst precursor (low color) was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. Initiation occurred in about a day and a half when the color of the reaction solution abruptly changed from clear yellow to clear brown. Sampling followed by IR analysis indicated that the Si—H absorbance was replaced by two succinic anhydride C=O absorbances (symmetrical and asymmetrical stretches). Following initiation, the reaction solution was heated about 90 minutes to insure complete conversion of starting material. The progress of the reaction was monitored by $^1$H NMR analysis using the disappearance of the vinyl resonances and Si—H peak and the appearance of a multiplet for the methylene on the propyl chain bonded to the silicone.

To work up the reaction the volatiles were removed by rotational evaporator and the resulting clear brown oil dissolved in dichloromethane (200 mL). Then 5 g of activated carbon was added and the solution stirred overnight in air. The solution was filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in dichloromethane (200 mL) and sent through a 0.45 um nylon syringe filter. The complete de-colorization procedure (with activated carbon and syringe filter etc) was performed twice. The volatiles were removed to leave clear very light yellow oil (3.41 g, 1.49 mmoles, 73.3% yield).

Analysis of 305

$^1$H NMR (acetone-$d_6$, δ): 0.90, 0.13, 0.15 (m, SiCH3, 122H), 0.68 (m, SiCH$_2$CH$_2$CH$_2$C(H)(C=O)(CH$_2$)C=O, 8H), 1.60 (m, SiCH$_2$CH$_2$CH$_2$C(H)(C=O)(CH$_2$)C=O, 8H), 1.87 (d-m, $J_{HH}$=76 Hz, SiCH$_2$CH$_2$CH$_2$C(H)(C=O)(CH$_2$) C=O, 8H), 3.00 (d-m, $J_{HH}$=159 Hz, SiCH$_2$CH$_2$CH$_2$C(H) (C=O)(CH$_2$)C=O, 8H), 3.33 (m, SiCH$_2$CH$_2$CH$_2$C(H) (C=O)(CH$_2$)C=O, 4H), 4.97 (m, Si—H, 80% substitution). $^{13}$C{$^1$H} (acetone-$d_6$, δ): 0.14, 0.8, 1.5, 2.0 (m, SiCH$_3$), 17.9, 21.5, 34.8, 34.9, 41.4 (m, SiCH$_2$CH$_2$CH$_2$C(H)(C=O)(CH$_2$) C=O), 171.9, 175.6 (m, C=O anhydride).

IR (cm$^{-1}$, diamond): 1013 s (Si—O—Si), 1262 m (Si—CH$_3$), 1789 m, 1867 w, (C=O, sym. and asym.), 2962 m and 2905 w (CH aliphatic).

Synthesis of 307 (see Compound 33)

To a 100 mL RBF in air was added silicone polyanhydride 305 (3.41 g, 1.49 mmoles) and water (25.7 mL, 1.53 moles). The solution was heated to 120° C. using a heating mantle with temperature control monitored by a thermocouple positioned between the flask and heating mantle. The solution was stirred rapidly and a temperature of 120° C. was maintained for 90 minutes during which time the reaction solution gradually thickened to opaque white mousse. After cooling to room temperature the volatiles were removed using trap to trap distillation with an inverted 'U' shaped tube to connect reaction flask and receiver. During distillation the reaction flask was gently heated with a thermostat controlled heating mantle (as above) to 30° C. while the receiver was cooled in a dry ice/ethanol bath. The vacuum was maintained at <30 mtorr. To remove the last traces of water the product was placed in a desiccator with fresh phosphorous pentoxide and static vacuum of <30 mtorr for at least 16 h. This desiccation step was performed twice with fresh phosphorous pentoxide each time. The clear, very light yellow oil was taken into the glove box, weighed and transferred into vials for storage (3.18 g, 1.34 mmoles, 90.2% yield).

Analysis of 307

$^1$H NMR (acetone-$d_6$, δ): 0.80, 0.12 (m, SiCH$_3$, 122H), 0.63 (m, HO$_2$CCH$_2$CH(CO$_2$H)CH$_2$CH$_2$CH$_2$Si, 8H), 1.50 (m, HO$_2$CCH$_2$CH(CO$_2$H)CH$_2$CH$_2$CH$_2$Si, 8 H), 1.67 (d-m, $J_{HH}$=32 Hz, HO$_2$CCH$_2$CH(CO$_2$H)CH$_2$CH$_2$CH$_2$Si, 8H), 2.53 (d-m, $J_{HH}$=88 Hz, HO$_2$CCH$_2$CH(CO$_2$H)CH$_2$CH$_2$CH$_2$Si, 8H), 2.84 (m, HO$_2$CCH$_2$CH(CO$_2$H)CH$_2$CH$_2$CH$_2$Si, 6H), 10.73 (m, HO$_2$C, 12H). $^{13}$C{$^1$H} (acetone-$d_6$, δ): 1.5, 2.0 (m, SiCH$_3$), 18.2, 21.4, 36.2, 36.3, 41.6 (m, HO$_2$CCH$_2$CH (CO$_2$H)CH$_2$CH$_2$CH$_2$Si), 173.6, 176.7 (m, HO$_2$C).

IR (cm$^{-1}$, diamond): 1017 s (Si—O—Si), 1262 m (Si—CH$_3$), 1716 (C=O), 2500 to 3500 br (HO$_2$C).

Figure 31C:
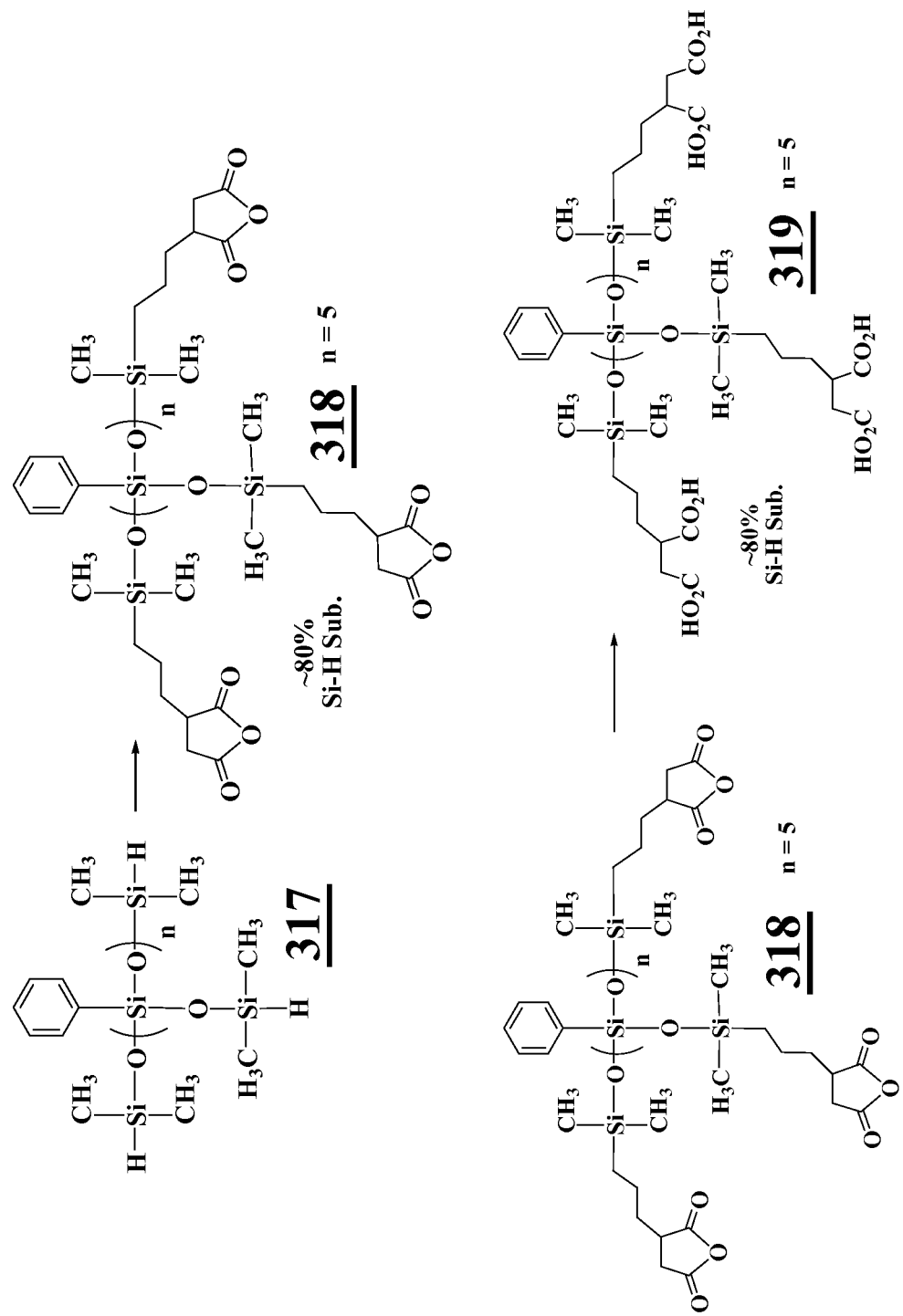
FIG. 31 A-C schematically illustrate chemical synthesis of an exemplary ligand in accordance with the present invention.

Synthesis of Silicone Two-Tail Poly-Carboxylic Acid Ligand with Random Silicone Backbones Synthesis of the ligand is schematically illustrated in FIG. 31 Panel A.

General Methods

All manipulations were carried out with strict exclusion of air and moisture by using Schlenk technique under an atmosphere of dry nitrogen, unless otherwise stated. Toluene was dried in an M Braun solvent system that incorporated molecular sieves and alumina as drying agents. Acetone-$d_6$ was purified by stirring with anhydrous calcium (II) sulfate (Drierite) for 7 days then distilled 'trap-to-trap'. Chloroform and dichloromethane were purchased from Fisher Chemical and used as received. Allyl succinic anhydride was purchased from TCI America, distilled and stored using Schlenk technique until used. Polyhydride silicones 311, 314 and 317 were purchased from Gelest. Karstedt's catalyst precursor, or platinum divinyl tetramethyl disiloxane complex 2.1 to 2.4% in xylenes—low color, was purchased from Gelest, stored in the glove box and used without further purification. Phosphorous pentoxide was purchased from Fisher Chemical and used as received. Activated carbon (coconut shell) and 4 A Molecular Sieves were purchased from Aldrich and used as received. NMR chemical shift data was recorded with a Bruker FT NMR at 400 MHz for $^1$H and 100 MHz for $^{13}$C {$^1$H} and are listed in ppm. NMR chemical shifts were referenced using proton impurities in the deuterium solvent. Silicone formula weight was determined by comparison of end-group to repeat unit integration using $^1$H NMR using a post acquisition delay (d1) of at least 60 seconds for accuracy. IR analysis was recorded on a Nicolet 6700 FTIR standardized with polypropylene.

Synthesis of 312

To a 50 mL Schlenk flask equipped with a reflux condenser was added polysilane 311 (6.69 g, 6.69 mmoles) and toluene (10 mL). The reaction solution was heated to 80° C. using a thermostat controlled oil bath. Then allyl succinic anhydride (3.00 g, 21.4 mmoles) was added followed by Karstedt's catalyst precursor (19 mg of 2.2 wt % solution, 0.00214 mmol or 0.0001 eq Pt metal). After about 1 h, a sample of the reaction solution was prepared for analysis by removal of the volatiles. IR analysis showed a large Si—H absorbance without an anhydride or vinyl absorbance, indicating that allyl succinic anhydride had probably been removed during sample preparation via azeotropic distillation with toluene. Additionally, that the reaction had not initiated was confirmed by $^1$H NMR. Another 0.0001 eq of Karstedt's catalyst precursor (low color) was added and the progress of the reaction monitored by IR using the Si—H absorbance to indicate consumption of silane starting material. This cycle was repeated about every 90 minutes, i.e. catalyst addition followed in 90 minutes by analysis, until the reaction had initiated. Initiation occurred in about a day and a half when the color of the reaction solution abruptly changed from clear yellow to clear brown. Sampling followed by IR analysis indicated that the Si—H absorbance was replaced by two succinic anhydride C=O absorbances (symmetrical and asymmetrical stretches). Following initiation, the reaction solution was heated about 90 minutes to insure complete conversion of starting material. The progress of the reaction was monitored by $^1$H NMR analysis using the disappearance of the vinyl resonances and Si—H peak and the appearance of a multiplet for the methylene on the propyl chain bonded to the silicone.

To work up the reaction the volatiles were removed by rotational evaporator and the resulting clear brown oil dissolved in dichloromethane (300 mL). Then 5 g of activated carbon was added and the solution stirred overnight in air. The solution was filtered through a coarse filter followed by a filter tip cannula equipped with Fisherbrand P5 filter paper (particle retention 5-10 um) and the volatiles removed by rotational evaporator leaving a turbid light yellow-gray oil. The product was then dissolved in dichloromethane (200 mL) and sent through a 0.45 um nylon syringe filter. The complete de-colorization procedure (with activated carbon and syringe filter etc) was performed twice. The volatiles were removed to leave clear very light yellow oil (8.22 g, 5.67 mmoles, 84.7% yield).

Analysis of 312

$^1$H NMR (acetone-$d_6$, δ): 0.15 (m, SiCH$_3$, 78H), 0.66 (m, SiCH$_2$CH$_2$CH$_2$C(H)(C=O)(CH$_2$)C=O, 6H), 1.79 (m, SiCH$_2$CH$_2$CH$_2$C(H)(C=O)(CH$_2$)C=O, 6H), 1.89 (d-m, $J_{HH}$=83 Hz, SiCH$_2$CH$_2$CH$_2$C(H)(C=O)(CH$_2$)C=O, 6H), 3.02 (d-m, $J_{HH}$=155 Hz, SiCH$_2$CH$_2$CH$_2$C(H)(C=O)(CH$_2$)C=O, 6H), 3.34 (m, SiCH$_2$CH$_2$CH$_2$C(H)(C=O)(CH$_2$)C=O, 3H), 4.75 (m, Si—H, 80% substitution). $^{13}$C{$^1$H} (acetone-$d_6$, δ): 1.5, 2.0, (m, SiCH$_3$), 17.8, 21.6, 34.8, 34.9, 41.4 (m, SiCH$_2$CH$_2$CH$_2$C(H)(C=O)(CH$_2$)C=O), 171.9, 175.6 (m, C=O anhydride).

IR (cm$^{-1}$, diamond): 1013 s (Si—O—Si), 1258 m (Si—CH$_3$), 1785 m, 1867 w, (C=O, sym. and asym.), 2153 w (Si—H), 2962 m (sp$^3$ C—H).

Synthesis of 313 (see Compound 37)

To a 100 mL RBF in air was added silicone polyanhydride 312 (8.22 g, 5.67 mmoles) and water (81.6 mL, 5.34 moles). The solution was heated to 120° C. using a heating mantle with temperature control monitored by a thermocouple positioned between the flask and heating mantle. The solution was stirred rapidly and a temperature of 120° C. was maintained for 90 minutes during which time the reaction solution gradually thickened to opaque white mousse. After cooling to room temperature the volatiles were removed using trap to trap distillation with an inverted 'U' shaped tube to connect reaction flask and receiver. During distillation the reaction flask was gently heated with a thermostat controlled heating mantle (as above) to 30° C. while the receiver was cooled in a dry ice/ethanol bath. The vacuum was maintained at <30 mtorr. To remove the last traces of water the product was placed in a desiccator with fresh phosphorous pentoxide and static vacuum of <30 mtorr for at least 16 h. This desiccation step was performed twice with fresh phosphorous pentoxide each time. The clear, very light yellow oil was taken into the glove box, weighed and transferred into vials for storage (7.95 g, 5.39 mmoles, 95.1% yield).

Analysis of 313

$^1$H NMR (acetone-$d_6$, δ): 0.10, 0.13 (m, SiCH$_3$, 78H), 0.62 (m, HO$_2$CCH$_2$CH(CO$_2$H)CH$_2$CH$_2$CH$_2$Si, 6H), 1.50 (m, HO$_2$CCH$_2$CH(CO$_2$H)CH$_2$CH$_2$CH$_2$Si, 6 H), 1.68 (d-m, $J_{HH}$=46 Hz, HO$_2$CCH$_2$CH(CO$_2$H)CH$_2$CH$_2$CH$_2$Si, 6H), 2.58 (d-m, $J_{HH}$=82 Hz, HO$_2$CCH$_2$CH(CO$_2$H)CH$_2$CH$_2$CH$_2$Si, 6H), 2.83 (m, HO$_2$CCH$_2$CH(CO$_2$H)CH$_2$CH$_2$CH$_2$Si, 3H), 10.77 (m, HO$_2$C, 12H). $^{13}$C{$^1$H} (acetone-$d_6$, δ): 1.5, 2.0 (m, SiCH$_3$), 18.2, 21.4, 36.2, 36.3, 41.6 (m, HO$_2$CCH$_2$CH(CO$_2$H)CH$_2$CH$_2$CH$_2$Si), 173.6, 176.8 (m, HO$_2$C).

IR (cm$^{-1}$, diamond): 1009 s (Si—O—Si), 1258 m (Si—CH$_3$), 1712 (C=O), 2157 w, (Si—H), 2500 to 3500 br (HO$_2$C).

Another random backbone silicone poly-carboxylic acid, with m=4 and n=75, was synthesized using similar techniques.

Other silicone poly-carboxylic acid ligands were synthesized analogously, e.g., as schematically illustrated in FIG. 31 Panels B and C. Their analyses are provided below. Synthesis of 318 resulted in 5.37 g, 2.82 mmoles, 74.0% yield; of 319, 5.33 g, 2.66 mmoles, 94.4% yield.

Analysis of 315

$^1$H NMR (acetone-$d_6$, δ): 0.21 (m, SiCH$_3$, 93H), 0.70 (m, SiCH$_2$CH$_2$CH$_2$C(H)(C=O)(CH$_2$)C=O, 40H), 1.60 (m, SiCH$_2$CH$_2$CH$_2$C(H)(C=O)(CH$_2$)C=O, 40H), 1.88 (d-m, $J_{HH}$=70 Hz, SiCH$_2$CH$_2$CH$_2$C(H)(C=O)(CH$_2$)C=O, 40H), 3.04 (d-m, $J_{HH}$=163 Hz, SiCH$_2$CH$_2$CH$_2$C(H)(C=O)(CH$_2$)C=O, 40H), 3.34 (m, SiCH$_2$CH$_2$CH$_2$C(H)(C=O)(CH$_2$)C=O, 20H). $^{13}$C{$^1$H} (acetone-$d_6$, δ): 0.3 (m, SiCH$_3$), 18.1, 21.6, 34.9, 41.4 (m, SiCH$_2$CH$_2$CH$_2$C(H)(C=O)(CH$_2$)C=O), 172.0, 175.8 (m, C=O anhydride).

IR (cm$^{-1}$, diamond): 1009 s, 1054 sh (Si—O—Si), 1258 m (Si—CH$_3$), 1777 m, 1859 w, (C=O, sym. and asym.), 2154 w (Si—H), 2868 w, 2929 m (sp$^3$ C—H).

Analysis of 316 (see Compound 29)

$^1$H NMR (acetone-$d_6$, δ): 0.10, 0.16 (m, SiCH$_3$, 93H), 0.62 (m, HO$_2$CCH$_2$CH(CO$_2$H)CH$_2$CH$_2$CH$_2$Si, 40H), 1.50 (m, HO$_2$CCH$_2$CH(CO$_2$H)CH$_2$CH$_2$CH$_2$Si, 40H), 1.68 (d-m, $J_{HH}$=25 Hz, HO$_2$CCH$_2$CH(CO$_2$H)CH$_2$CH$_2$CH$_2$Si, 40H), 2.60 (d-m, $J_{HH}$=90 Hz, HO$_2$CCH$_2$CH(CO$_2$H)CH$_2$CH$_2$CH$_2$Si, 40H), 2.85 (m, HO$_2$CCH$_2$CH(CO$_2$H)CH$_2$CH$_2$CH$_2$Si, 20H), 10.87 (m, HO$_2$C, 40H). $^{13}$C{$^1$H} (acetone-$d_6$, δ): −0.6, 0.3 (m, SiCH$_3$), 17.7, 18.3, 21.4, 36.3, 41.7 (m, HO$_2$CCH$_2$CH(CO$_2$H)CH$_2$CH$_2$CH$_2$Si), 174.6, 178.3 (m, HO$_2$C).

IR (cm$^{-1}$, diamond): 1008 s, 1082 sh (Si—O—Si), 1254 m (Si—CH$_3$), 1695 (C=O), 2872 w, 2933 w (sp$^3$ C—H), 2500 to 3500 br (HO$_2$C).

Analysis of 318

$^1$H NMR (acetone-$d_6$, δ): 0.13, 0.14, 0.15, 0.23 (m, SiCH$_3$, 42H), 0.64 (m, SiCH$_2$CH$_2$CH$_2$C(H)(C=O)(CH$_2$)C=O, 8H), 1.45 (m, SiCH$_2$CH$_2$CH$_2$C(H)(C=O)(CH$_2$)C=O, 8H), 1.76 (d-m, $J_{HH}$=73 Hz, SiCH$_2$CH$_2$CH$_2$C(H)(C=O)(CH$_2$)C=O, 8H), 2.91 (d-m, $J_{HH}$=144 Hz, SiCH$_2$CH$_2$CH$_2$C(H)(C=O)(CH$_2$)C=O, 8H), 3.23 (m, SiCH$_2$CH$_2$C(H)(C=O)(CH$_2$)C=O, 4H), 7.43, 7.61, 7.67 (m, Ph, 25H). $^{13}$C{$^1$H} (acetone-$d_6$, δ): 0.4, 0.5, 0.9, 2.2 (m, SiCH$_3$), 18.4, 21.7, 34.8, 34.9, 41.4 (m, SiCH$_2$CH$_2$CH$_2$C(H)(C=O)(CH$_2$)C=O), 171.9, 175.6 (m, C=O anhydride).

IR (cm$^{-1}$, diamond): 1037 s, 1131 sh (Si—O—Si), 1254 m ($S_1$—CH$_3$), 1781 m, 1867 w, (C=O, sym. and asym.), 2133 w (Si—H), 2864 w, 2958 m (sp$^3$ C—H), 3011 w, 3052 w, 3077 w (phenyl).

Analysis of 319 (see Compound 31)

$^1$H NMR (acetone-$d_6$, δ): 0.10, 0.16 (m, SiCH$_3$, 93H), 0.62 (m, HO$_2$CCH$_2$CH(CO$_2$H)CH$_2$CH$_2$CH$_2$Si, 40H), 1.50 (m, HO$_2$CCH$_2$CH(CO$_2$H)CH$_2$CH$_2$CH$_2$Si, 40H), 1.68 (d-m, $J_{HH}$=25 Hz, HO$_2$CCH$_2$CH(CO$_2$H)CH$_2$CH$_2$CH$_2$Si, 40H), 2.60 (d-m, $J_{HH}$=90 Hz, HO$_2$CCH$_2$CH(CO$_2$H)CH$_2$CH$_2$CH$_2$Si, 40H), 2.85 (m, HO$_2$CCH$_2$CH(CO$_2$H)CH$_2$CH$_2$CH$_2$Si, 20H), 10.87 (m, HO$_2$C, 40H). $^{13}$C{$^1$H} (acetone-$d_6$, δ): −0.6, 0.3 (m, SiCH$_3$), 17.7, 18.3, 21.4, 36.3, 41.7 (m, HO$_2$CCH$_2$CH(CO$_2$H)CH$_2$CH$_2$CH$_2$Si), 174.6, 178.3 (m, HO$_2$C).

IR (cm$^{-1}$, diamond): 1008 s, 1082 sh (Si—O—Si), 1254 m ($S_1$—CH$_3$), 1695 (C=O), 2872 w, 2933 w (sp$^3$ C—H), 2500 to 3500 br (HO$_2$C).

It will be evident that additional ligands can be prepared using procedures similar to those above.

Example 7

Synthesis of Highly Luminescent InP Nanocrystals

A. InP Nanocrystals with Green Emission λ~530 nm

Chemicals: Indium(III) acetate, Aldrich 99.99%; Tris(trimethylsilyl)phosphine (TMS$_3$P), Strem 98+%; Laurie acid (LA), Aldrich 99.5+%; Trioctylphosphine oxide (TOPO), Aldrich 99%; Trioctylphosphine (TOP), Aldrich, purified.

For preparing 580 mg (supposing 100% production yield):

A1. Prepare a growth solution (Growth A1) comprised of the following chemicals in air and place it in a 100 ml 3-neck flask.

Growth A1
2.33 g indium acetate
4 g TOPO
4.8 g LA

A2. Connect the flask with a straight condenser on Schlenk line. Use septa to stop the two side-necks of the flask.

A3. Evacuate the flask and then purge it with N$_2$. Repeat this step for 3 times.

A4. Heat the solution to 160° C. and keep this temperature for 40 min under evacuation.

A5. Increase the temperature to 250° C. and keep this temperature for 20 min, keep evacuating the system.

A6. Refill the system with N$_2$ and set temperature to 300° C.

A7. Prepare a stock solution (Stock A1) containing the following chemicals in the glovebox. Place the mixture in a 20 ml vial and stop it with a septum.

Stock A1
1 g tris(trimethylsilyl)phosphine
3 g TOP

A8. Nucleation: When the temperature of the growth solution in the flask reaches 300° C., the room temperature stock solution is loaded into a 10 ml glass syringe (with gauge 12, 2 in. needle), and injected into the flask swiftly. Upon injection, temperature should drop to ~250° C. and this temperature is maintained for the entire growth process.

A9. Growth: In order to prepare small dots (~1-2 nm, with green emission), the reaction is stopped by removing the heater 1 min after the injection. Maintaining good stirring is essential for size distribution control.

A10. Monitor the reaction using UV-Vis absorption spectroscopy.

A11. After cooling down, transfer the flask into the glovebox under the protection of N$_2$. Move the product to a 20 ml vial (with essential amount of toluene to wash off the crystals in the flask).

A12. Isolation of the nanocrystals: the original solution from the synthesis is diluted with toluene by a factor of two, and the dots are precipitated by adding ethanol (volume of ethanol is twice the diluted dot solution). By centrifugation the dots are separated. These separated dots are redissolved in toluene for further treatment (e.g. additional washing).

Note A1: Focusing and defocusing of size distribution. Size distribution (SD) is typically one of the most important parameters of concern. A size focusing technique is employed to obtain dots with narrow SD. Upon injection, SD is broad but since there are enough free precursors to maintain a high saturation concentration, SD can be improved by continued heating under a lower temperature (which is low enough to prohibit second nucleation). This is because smaller dots grow faster than the bigger ones. With the size being focused more and more precursors are consumed, the saturation concentration goes down and therefore SD turns broad again. This is referred to as defocusing. To ban defocusing, additional precursors can be introduced to maintain a high saturation concentration.

B. InP nanocrystals with red emission λ~630 nm

Chemicals: The same chemicals as used in Procedure A.

For preparing 1.8 g dots in terms of InP (supposing 100% production yield based on the amount of tris(trimethylsilyl) phosphine used; indium acetate is supplied in excess):

B1. Prepare a growth solution (Growth B1) comprised of the following chemicals in air and place it in a 100 ml 3-neck flask.

Growth B1
3.496 g indium acetate
5 g TOPO
7.196 g LA

B2. Repeat steps A2-A6.

B3. Prepare a stock solution (Stock B1) containing the following chemicals in the glovebox. Place the well mixed components in a 20 ml vial and stop it with a septum.

Stock B1
0.8 g tris(trimethylsilyl)phosphine
3 g TOP

B4. Nucleation: When the temperature of Growth B1 in the flask reaches 300° C., inject Stock B1 into the flask swiftly. Upon injection temperature should drop to ~250° C. and this temperature is maintained for 10 min to allow the crystals grow. Take aliquots to check the peak position of the absorption spectrum.

B5. Prepare additional growth and stock solutions for further growth.

Stock B2
1.5 g tris(trimethylsilyl)phosphine
6 g TOP.

B6. Add 1 ml StockB2 dropwise to the growth solution 12 min after the injection, then add 1 ml additional StockB2 each time with an interval of ~15 min until it is used up. Monitor the growth through UV-Vis absorption spectroscopy.

B7. After finishing Stock B2, the absorption peak of the crystals was at 566 nm, so more indium and phosphorous precursors are needed.

Growth B2
1.119 g indium acetate
2 g TOPO
2.303 g LA

Stock B3
0.8 g tris(trimethylsilyl)phosphine
3 g TOP

B8. Place Growth B2 in a 25 ml 3-neck flask. Repeat steps A2-A6.

B9. Cool the solution (Growth B2) to 70° C. and transfer it into the reaction flask with a 20 ml syringe.

B10. Add StockB3 in the same manner described in step B6.

B11. Finished adding StockB3. The absorption peak is at 590 nm. Wait for 1 h and cool the flask to RT.

B12. Repeat steps A11-A12.

C. InP/ZnS core-shell nanocrystals

Materials and Chemicals:

InP dots as synthesized (absorption peak 480-500 nm), isolated from the original reaction solution Diethylzinc (ZnEt$_2$), Aldrich 1M solution in hexanes
Hexamethyldisilathiane (TMS$_2$S, Aldrich purum grade)
TOPO, Aldrich 99%
LA, Aldrich 99.5%
Dicarboxylic acid (DCASi-Me) functionalized silicones (MW~800), made, e.g., as described above in Example 6
TOP, Aldrich, purified C1. Prepare the growth (Growth C1) and the stock (Stock C1) solutions.

Growth C1 is placed in a 100 ml 3-neck flask and connected to the Schlenk line. The stock is placed in a 25 ml vial and stopped with a septum.

Growth C1

120 mg InP (dots washed one time with ethanol/toluene) in 5 ml toluene
3 g TOP
3 g TOPO
1 g LA Stock C1

1.037 g (1.43 ml) $ZnEt_2$/hexane
3.083 g $TMS_2S$ in TOP (9.09 wt. %)
5.4 g TOP C2. Pump out toluene in the flask and refill it with $N_2$, repeat the pumping-refilling for 3 times.

C3. Set temperature to 180° C. Begin adding the stock solution when temperature reaches 80° C. Add 0.5 ml stock solution within 1 min (T increased to 140° C. after the addition).

C4. When T reaches 180° C., add another 0.5 ml Stock Cl.

C5. Add 0.5 ml Stock Cl in every 10 min until it is finished.

C6. Wait 10 min and cool the solution down to RT. Transfer it into the glovebox. Move the product in a 20 ml vial.

Note C1: The weight of InP is determined by the optical density of its diluted solution in toluene. The amount of $ZnEt_2$ and $TMS_2S$ calculated for growing two monolayer thick (one monolayer of ZnS equals about 0.31 nm) ZnS shells on the InP cores (diameter 2 nm).

Note C2: DCASi-Me is used instead of LA for preparing highly luminescent nanocrystals.

Note C3: S/Zn ratio is varied from 1.1 to 0.5. The stock may be divided into two parts where Zn and S are in separated stock solutions.

Note C4: to make oxide shell, after step C5, the solution is cooled to and maintained at 100° C. and air is pumped into the solution. The oxidation process lasts 1-3 h.

Note C5: The shelling is monitored through absorption and photoluminescence spectra. At the end, the crystals are kept in its growth solution without being diluted, and the solution is kept in air for storage.

It is worth noting that choice of ligand can affect quantum yield of the resulting nanostructures. For example, a dicarboxylic acid ligand (DCASi-Me) results in nanocrystals with a quantum yield of greater than 50%, phosphonic acid, about 40%, and fatty acids, about 30%.

Figure 32:
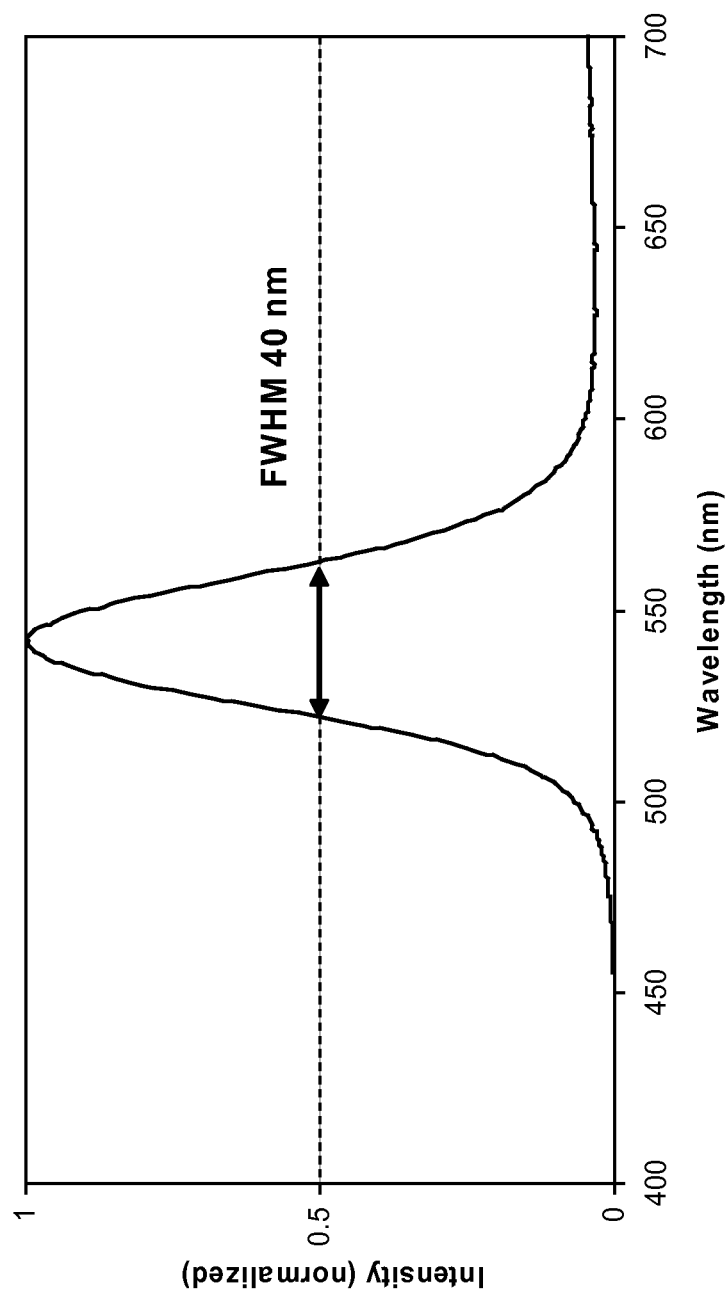
FIG. 32 presents a photoluminescence spectrum of a typical InP/ZnS nanocrystal sample with green emission. The FWHM of the spectrum is indicated.

A photoluminescence spectrum of a typical InP/ZnS nanocrystal sample with green emission is presented in FIG. 32. As noted above, the line width (Full Width at Half Maximum, FWHM) of the spectrum is a signature of the particle size distribution; the smaller the FWHM, the narrower the size distribution. The FWHM of the spectrum illustrated in FIG. 32 is 40 nm.

Figure 33:
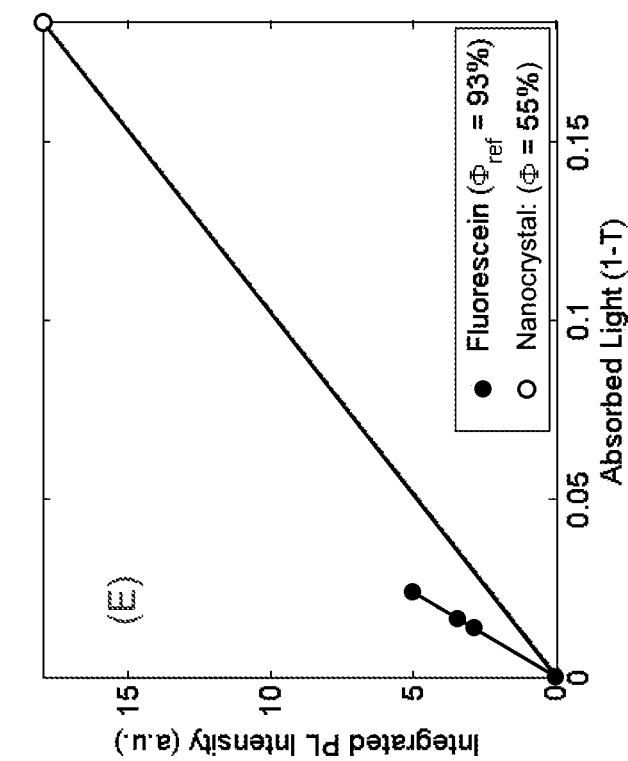
FIG. 33 Panel A presents absorption spectra of fluorescein dye. Panel B presents photoluminescence spectra of the dye. Panel C presents an absorption spectrum of the InP/ZnS nanocrystals of FIG. 32. Panel D presents a photoluminescence spectrum of the nanocrystals. Panel E shows the quantum yield deduced from Panels A-D.
Figure 33:
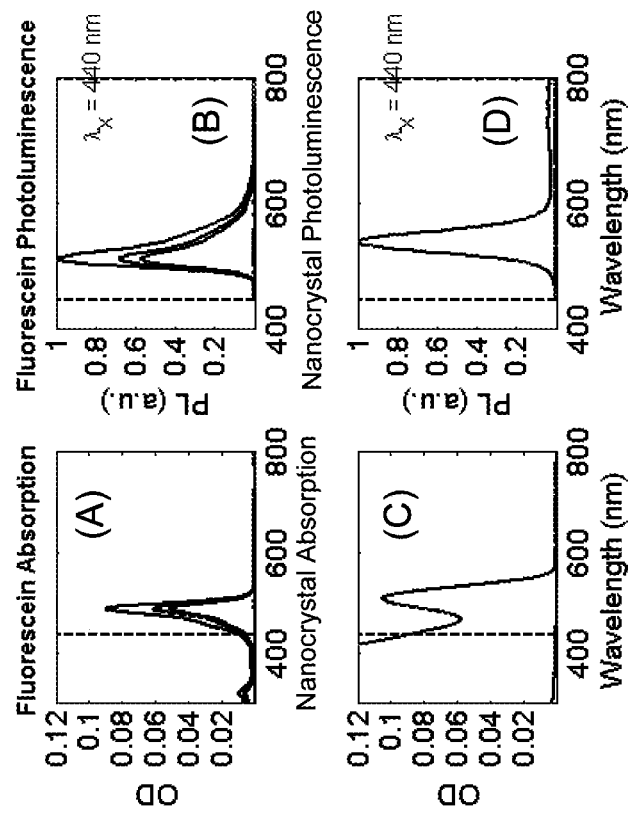

FIG. 33 illustrates determination of quantum yield (D) of the InP/ZnS nanocrystal sample described in FIG. 32. Panel A presents absorption spectra of fluorescein dye, with known quantum yield value, used as the reference. Panel B presents photoluminescence spectra of the dye. Panel C presents an absorption spectrum of the nanocrystals, and Panel D presents a photoluminescence spectrum of the nanocrystals. Panel E shows the quantum yield result deduced from the data of Panels A-D. The quantum yield of the InP/ZnS nanocrystals in this example is 55%.

Example 8

Luminescent Nanocomposites

Luminescent InP/ZnSe/decylamine nanocrystals were incorporated into a curable epoxy while preserving the luminescent properties into the solid state, as follows. InP/ZnSe core/shell nanocrystals were synthesized with decylamine as the surface ligand. The addition of decylamine strongly increased the luminescence of the InP/ZnSe nanocrystals. The nanocrystals were washed once using toluene and methanol and resuspended in 0.5 ml octylamine yielding a concentration of approximately 9 mg/ml. Octylamine was chosen for compatibility with the epoxy matrix and may prevent the surface ligands of the nanocrystals from coming off the surface, which may have happened when nanocrystals with other ligands were previously blended with epoxy. The above described nanocrystal solution was added to approximately 300-500 mg degassed Part 2 of Loctite epoxy E-30CL. After that, degassed Part 1 of the same epoxy was added in a ratio of approximately 3:1 with respect to Part 2. The sample was placed on a hot plate at 60° C. for 15 min in order to cure the epoxy matrix precursors. The entire sample preparation was done in inert atmosphere in a glovebox.

As another example, InP/ZnS nanocrystals were synthesized with the dicarboxylic acid DDSA (compound 44) as the surface ligand. The crystals were added in a similar fashion to Part B of the non-yellowing epoxy Epo-Tek 301-2 from Epoxy Technology at similar concentration as described above. After that, Part A of the same epoxy was added such that A:B was 3:1, and the sample was heated in the glovebox at 60° C. for 2 hours. All work was done in the glovebox. The resulting sample was solid, clear and luminescent of green color (when the crystals were washed 1×) or green-yellow (unwashed nanocrystals). Green InP/ZnSe nanocrystals with a decylamine ligand were similarly successfully incorporated into an Epo-Tek epoxy matrix.

As another example, InP/ZnS nanocrystals were synthesized with DDSA as the surface ligand and added into a urethane matrix. The nanocrystals were added directly from the growth solution into Part A of urethane set WC783 (BJB Enterprises), such that the resulting optical density was about 0.1 at the peak of the emission wavelength. (The concentration of the nanocrystals can also be varied to achieve stronger luminescence.) After vortexing, aniline was added, replacing Part B of the urethane set, and the ratio A:aniline was 3.3:1. After vortexing, the mixture was centrifuged for a few seconds to remove bubbles from the mixture. In a final step, the mixture was cured at room temperature for less than 5 minutes. All work was done in air. The resulting sample was solid, clear, and luminescent of green color. As another example, red nanocrystals were successfully mixed into the urethane matrix. All resulting samples were clear and luminescent. The samples still showed luminescence after keeping in air in an oven at 60° C. for 3 months.

Optical properties of the nanocrystals can be characterized by measurement of the UV-Vis absorption and photoluminescence spectra using a commercial UV-Vis spectrophotometer and a fluorometer. Internal photoluminescence quantum efficiency of the nanocrystals in solution are calculated using reference standards of known quantum yields. Photoluminescence quantum efficiencies of the nanocrystals in a solid matrix are determined using an integrating sphere. The quantum yield of an exemplary luminescent nanocomposite is 18%, compared to a quantum yield of 53% for corresponding nanocrystals in solution.

Example 9

Polydimethylsiloxane Bearing Multiple Dicarbinol Groups as a Dispersion Matrix for Quantum Dots Initial experiments demonstrated that a new class of silicone polymer, monodicarbinol terminated polydimethylsiloxanes (MDC), could be used to dissolve CdSe/ZnS quantum dots to obtain a transparent solution and that the quantum dot/MDC solution had good stability upon illumination by blue LEDs. These results were obtained with a low molecular weight MDC, compound 49 with n=10, molecular weight about 1000, viscosity 50-60 (commercially available from Gelest, Inc. as product no. MCR-C61). The initial experiments also demonstrated that a higher molecular weight MDC, compound 49 with n=64, molecular weight about 5000, viscosity 100-125 (commercially available from Gelest, Inc. as product no. MCR-C62), was not compatible with the CdSe/ZnS quantum dots. Previous results had indicated that simple silicones without any functional groups are also not compatible with the CdSe/ZnS quantum dots. This indicated that the presence of the dicarbinol group and its content in the polymer play an important role in dispersing quantum dots.

Since solid polymer/quantum dot formulations are generally preferred over liquid formulations in device fabrication, and since the lower molecular weight MDC is a liquid at ambient temperature and is not applicable to solid/gel formation, other, solid silicone polymers with multiple dicarbinol groups were explored (polydimethylsiloxanes bearing multiple dicarbinol groups, PDC). The PDC silicone polymers exhibit good stability and optical transparency, and the multiple dicarbinol groups render them compatible with quantum dots.

Figure 34:
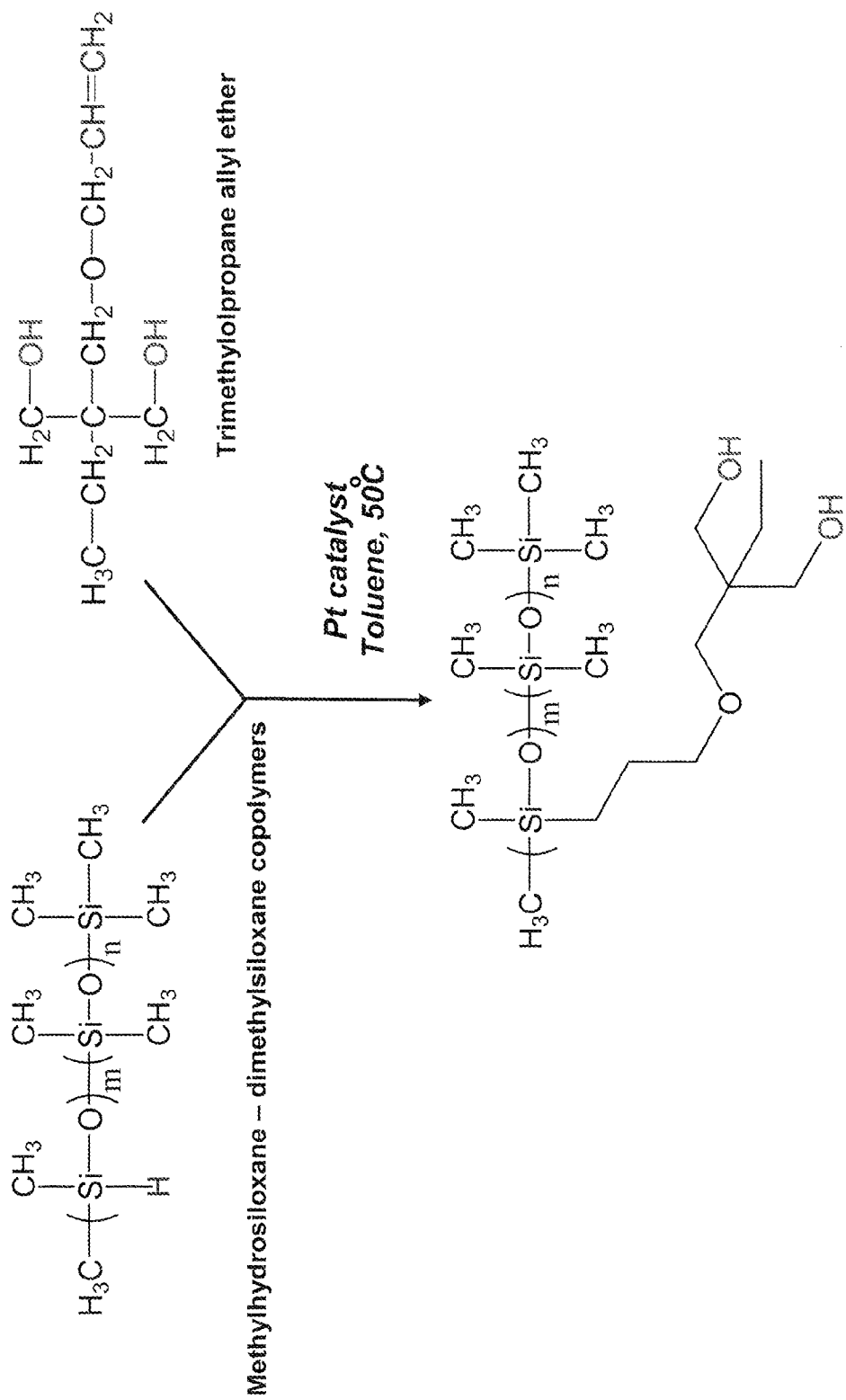
FIG. 34 schematically illustrates synthesis of an exemplary silicone ligand bearing multiple dicarbinol groups.
Figure 35A:
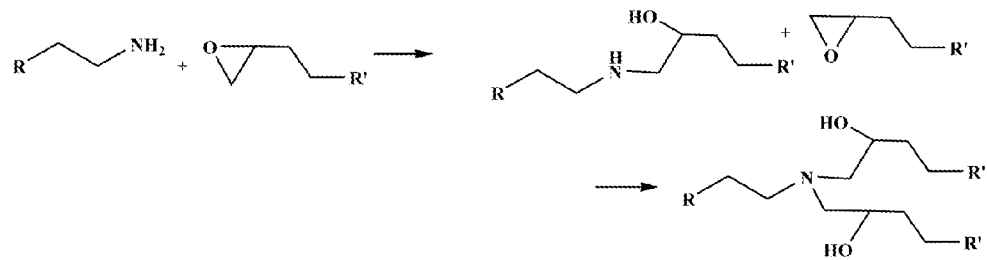
FIG. 35 schematically illustrates exemplary cross-linking reactions, epoxy addition by amine in Panel A, epoxy addition by epoxy (initiated by an alcohol) in Panel B, amine-isocyanate in Panel C, amine-anhydride condensation in Panel D, and amine-methyl ester condensation in Panel E.
Figure 35B:
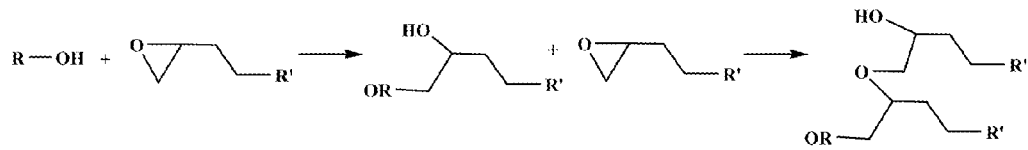
Figure 35C:
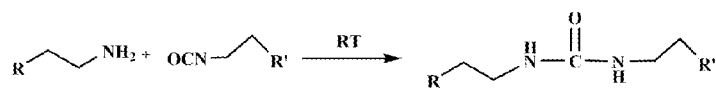
Figure 35D:
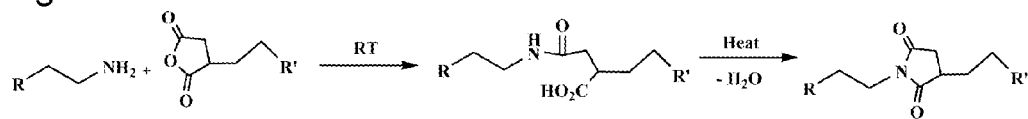
Figure 35E:
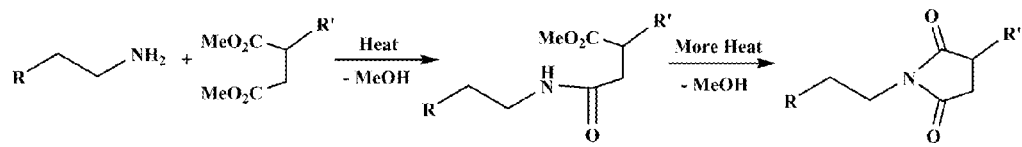

As illustrated in FIG. 34, a new polymer (compound 53 in Table 1) was synthesized by a hydrosilylation reaction between a silicone polymer with Si—H groups on its backbone (methylhydrosiloxane-dimethylsiloxane copolymer) and a small molecule with a diol and a vinyl group (trimethylolpropane allyl ether). Two starting silicone polymers, molecular weight 5500-6500 with 7-8 mole percent MeHSiO (commercially available from Gelest, Inc. as product no. HMS-082) and molecular weight 55000-65000 with 5-7 mole percent MeHSiO (commercially available from Gelest, Inc. as product no. HMS-064), were tested. The lower molecular weight starting material afforded a liquid product (low MW PDC), and the higher molecular weight starting material afforded a gel-like product (high MW PDC). The gel-like product was used directly as a solid matrix for quantum dot dispersion, but the liquid product required a crosslinking step to transform the polymer from liquid to solid form.

The PDC polymers showed very good compatibility with CdSe/ZnS quantum dots made with different ligands. Since toluene was a good solvent for both PDC polymer and quantum dots, it was chosen as the solvent for mixing the polymer and quantum dots. For high MW PDC, dissolving the polymer and quantum dots in toluene resulted in a transparent solution. Upon evaporation of the solvent, a transparent solid gel composite material was obtained, and the composite displayed the distinct colors of the quantum dots used in the material. No phase separation was observed in the composites. For low MW PDC, the polymer, quantum dots, and a crosslinker (hexamethylene diisocyanate) were first mixed in toluene with magnetic stirring, and toluene was removed by vacuum, affording a transparent liquid mixture. To the liquid mixture was then added a catalyst (dibutyltin dilaurate), and the liquid turned into solid gel in about 20 min.

In addition to the direct crosslinking to transform the low MW PDC from liquid into solid form as mentioned above, polymerizable groups (vinyl, epoxide, etc.) were introduced into the polymer structure (e.g., compounds 55 and 56), and an ensuing polymerization reaction converted the liquid into a solid. Compound 55 was prepared by mixing silicone polymer HMS-082, trimethylolpropane allyl ether, and allyl glycidyl ether in toluene at 50° C. in the presence of a platinum catalyst. Compound 56 was prepared by reacting low MW PDC with methacryloyl chloride in the presence of triethylamine using dichloromethane as a solvent. Compound 56 was polymerized into a solid gel using thermal radical initiators (e.g. 2,2'-azobis(2-methylpropionitrile)) or photoinitiators (e.g. 2,2-dimethoxy-2-phenyl-acetophenone). The polymerization process was simple. For example, compound 56, quantum dots, and a photoinitiator were first mixed in toluene, and evaporation of toluene by vacuum afforded a viscous liquid bearing the distinct color of the quantum dots used. Upon illumination by a UV light, the liquid turned into a solid gel material.

The polymer/quantum dot composites were readily fabricated into devices such as disks between two glass slides. For example, the solution of high MW PDC and quantum dots in toluene was first dispensed onto a glass slide, and toluene was then evaporated at 80° C., leaving a solid gel on the glass slide. A second glass slide was placed on top of the gel material, and an epoxy adhesive was applied between the two glass slides to glue the slides together. As a result, the composite material was sealed between the two glass slides.

Testing indicated that the composite materials exhibited good light-emitting properties upon excitation by blue LEDs. For example, the disks prepared above were illuminated by blue LEDs, and the disks emitted light based on the quantum dots used in the composite material and maintained more than 90% of initial light output after over 1000 hours at room temperature.

Example 10

Amino-Functionalized Silicone Matrix for Nanocrystal Dispersion and Stabilization Nanocrystals used in lighting applications (e.g., LEDs) typically absorb higher energy light, e.g., from an LED or other source in the UV and blue region, and re-emit in the visible region. The efficiency of absorption and emission can be expressed as the quantum yield. As noted above, the nanocrystals are desirably dispersed in a matrix for LED fabrication. This example presents a series of experiments illustrating that amino-functionalized silicone matrixes can be employed to disperse nanocrystals, e.g., CdSe/ZnSe/ZnS nanocrystals, to provide stability and quantum yield enhancement.

The CdSe/ZnSe/ZnS nanocrystals employed in these experiments are synthesized in a two step process of CdSe core synthesis and washing followed by ZnSe/ZnS shell synthesis and washing. The ZnSe/ZnS shell reaction uses decylamine, a primary amine, in the synthesis mixture Amines are considered to enhance stability and quantum yields of ZnS shelled nanocrystals by bonding to the nanocrystal surface. Initial experiments demonstrated that primary amines produced the highest quantum yield compared to secondary or tertiary amines in the shelling reaction. Additionally, results indicated that a small amount of primary amine improves nanocrystal solubility in hexane and toluene. Extra primary amine added during formulation, however, caused the nanocrystals to blue shift upon testing. Without limitation to any particular mechanism, the blue shift was thought to be caused by ligands sequestering surface nanocrystal atoms and dissolving the nanocrystals, and that for significant nanocrystal dissolution the solution needed to be fluid enough for the amine/metal atom complex to diffuse from the nanocrystal surface so free amine can approach the nanocrystal surface to sequester and remove other surface atoms.

A matrix composed of amines that could not sequester surface atoms was therefore considered to be desirable, as it would be able to provide stability and quantum yield enhancement without dissolving the nanocrystals Amine functional silicones can provide those properties. Amine functional silicones are commercially available or can be synthesized, for example, with primary amines protruding from a polydimethylsiloxy (PDMS) backbone with linkers. Excess amines not bonded to the nanocrystals can be crosslinked into a network polymer with a variety of functional groups; curing of the silicone backbone to rubber can prevent the nanocrystals from being dissolved and blue shifting.

Incorporation of CdSe/ZnSe/ZnS nanocrystals into an amine functional silicone matrix was performed in two steps: 1) nanocrystal ligand exchange with an amino functional silicone, followed by 2) curing the amino functional silicone/nanocrystal combination to a network polymer with crosslinking molecules.

Ligand exchange was accomplished by dissolving the nanocrystals in hexane or toluene, adding an amino functional silicone, heating at 50° to 60° C. for 16 to 36 h, and removing the volatiles by vacuum transfer. (In general, ligand exchange is typically accomplished at 50° to 130° C. for 2 to 72 h.) The quantum yield and other parameters were maintained, and the nanocrystals were left in silicone as a clear oil. The following five examples used a degassed amine functional silicone commercially available from Gelest, Inc. (product no. AMS-242, compound 60 with formula weight about 7000 and m to n ratio of about 4 to 100).

The first example of matrix cure used di-isocyanate as the crosslinker. Ligand exchanged nanocrystals in the amine functional silicone were combined with a small amount of 1,6-diisocyanatohexane in monodicarbanol (both distilled) which produced a clear silicone rubber instantly. The crosslinking reaction proved that the amine functional silicone matrix system would crosslink with isocyanate.

Another example used ligand exchanged nanocrystals in the amine functional silicone, an epoxy functional silicone from Gelest (product no. DMS-E09 degassed, crosslinker E from Table 2), and an iodonium tetrafluoroborate UV initiated catalyst (also from Gelest, OMB0037). The solution was mixed and placed out in the sunlight where it cured, proving the system would crosslink with epoxide.

Another example used ligand exchanged nanocrystals in the amine functional silicone, and an epoxy functional silicone from Gelest (product no. DMS-E09, crosslinker E from Table 2). After mixing, the system cured in 5 days at room temperature, proving the system would cure thermally with epoxide.

Still another example used ligand exchanged nanocrystals in the amine functional silicone, an epoxy functional silicone from Gelest (product no. SIB1110.0, crosslinker G from Table 2), and dimethylaminomethyl phenol catalyst. It cured in 30 min at 150° C., proving a thermal catalyst would cure the system.

The fifth example used ligand exchanged nanocrystals in the amine functional silicone, an epoxy functional silicone from Gelest (product no. SIB1110.0, crosslinker G from Table 2), and dimethylaminomethyl phenol catalyst. It was converted to a grease with fume silica, applied to glass disks, and cured at 150° C. in 3 h, proving the system would cure thermally with catalyst and fume silica.

Another exemplary composite was produced, this one having CdSe/CdS/ZnS nanocrystals in a matrix formed from pendant amine functional silicones. Separate batches of red and green CdSe/CdS/ZnS nanocrystals dissolved in toluene (two batches with different sizes and emission peaks for each color) were exchanged with amino silicone (50:50 mixture of degassed AMS-242 and AMS-233, Gelest, Inc.) at 50° C. for about 66 h. Nanocrystal concentration was between about 3 and 50 OD in toluene, with the amino silicone at 0.01-0.1 ml per ml toluene. The solutions were then cooled to 30° C. and the volatiles removed to p<60 mtorr for about 90 min. Samples were dissolved in toluene at 25 mg (nanocrystals plus amino silicone)/mL. The OD/g (at 1 cm path length) was determined for each batch of red and green nanocrystals at 460 nm using a UV-Vis instrument. The neat solution was calculated by assuming the density of neat nanocrystals in aminosilicone was 1 (i.e., multiplied by 40), to ensure the ODs measured were close to the projected values. Then nanocrystals from the two batches of red and two of green nanocrystals in amino silicone were combined, along with additional amino silicone. The amount of red nanocrystals added from the two red batches was adjusted to obtain a final OD of about 10, and the amount of green nanocrystals added from the two green batches was adjusted to obtain a final OD of about 30. In this example, 6.8 mL of each batch of green nanocrystals and 2.5 mL of each batch of red nanocrystals were combined, along with an additional 11.49 g of the amino silicone (again a 50:50 mixture of degassed AMS-242 and AMS-233). An equal volume of toluene (30 mL) was also added. Ligand exchange was performed on the mixture at 60° C. for 16 h. After heating the mixture was cooled to 30° C. and the volatiles removed to p<35 mtorr for 2 h. After volatiles removal the product was an orange paste. It was combined with 4.0 wt % of fumed silica and 20 wt % cross linker (degassed EMS-622, Gelest, Inc.) and mixed with a planetary mixer (THINKY ARV-310) until homogeneous. The product was cured by heating at 100° C. for 4 h.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:
   a nanostructure;
   a polymeric ligand, which ligand comprises
      a silicone backbone, and
      one or more alcohol moieties coupled to the silicone backbone, and
   a radical or cationic initiator, wherein the polymeric ligand comprises one or more dicarbinol moieties coupled to the silicone backbone.

2. The composition of claim 1, wherein the silicone backbone of the polymeric ligand is linear.

3. The composition of claim 1, wherein the polymeric ligand is provided in excess, whereby some molecules of the ligand are bound to a surface of the nanostructure and other molecules of the ligand are not bound to the surface of the nanostructure.

4. The composition of claim 1, wherein the polymeric ligand comprises at least two different types of monomer units, at least one of which comprises the alcohol moiety and at least one of which lacks the alcohol moiety.

5. The composition of claim 4, wherein monomer units comprising the alcohol moiety are present in the ligand at a molar percentage between 0.5% and 20%.

6. The composition of claim 4, wherein monomer units comprising the alcohol moiety are present in the ligand at a molar percentage between 0.5% and 10%.

7. The composition of claim 4, wherein monomer units comprising the alcohol moiety comprise a single dicarbinol moiety per monomer unit.

8. The composition of claim 4, wherein the at least one type of monomer unit which lacks the alcohol moiety comprises a monomer unit that comprises an alkyl group, a polymerizable group, an epoxide group, an amine group, or a carboxylic acid group.

9. The composition of claim 1, wherein the polymeric ligand comprises 1-200 dicarbinol moieties per ligand molecule.

10. The composition of claim 1, wherein the nanostructures are semiconductor nanocrystals.

11. The composition of claim 1, comprising a solvent.

12. The composition of claim 1, comprising a crosslinker.

13. A composition comprising:
   a nanostructure;
   a polymeric ligand, which ligand comprises
      a silicone backbone, and
      one or more alcohol moieties coupled to the silicone backbone, and
   a radical or cationic initiator,
   wherein the polymeric ligand is $$R'-(-Si(R')(R)-O-)_x-(-Si(R')(R''')-O-)_y-(-Si(R'')(R')-O-)_n-SiR'_3,$$

where R comprises a dicarbinol moiety and is a group comprising the alcohol moiety, where R' and R''' are independently an alkyl or aryl group, where R" is an alkyl group, a polymerizable group, a group comprising an epoxide group, a group comprising an amine group, or a group comprising a carboxylic acid group, where x is a positive integer, where y is zero or a positive integer, and where n is zero or a positive integer.

14. The composition of claim 13, wherein y is zero, n is a positive integer, and R' and R" are methyl groups.

15. The composition of claim 13, wherein y and n are positive integers and R' and R" are methyl groups.

16. A composition comprising:
   a nanostructure;
   a polymeric ligand, which ligand comprises
      a silicone backbone, and
      one or more alcohol moieties coupled to the silicone backbone, and
   a radical or cationic initiator,
   wherein the polymeric ligand is selected from the group consisting of:

[chemical structure]

-continued

[chemical structures]

-continued

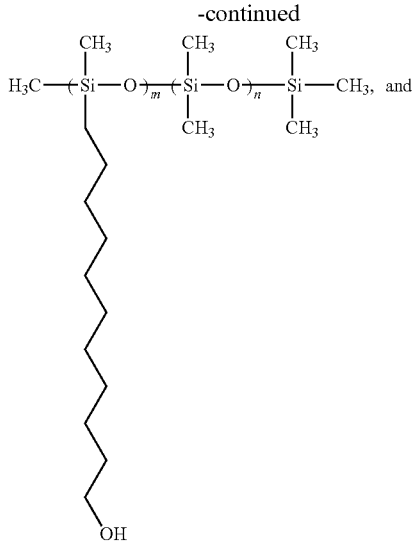
and

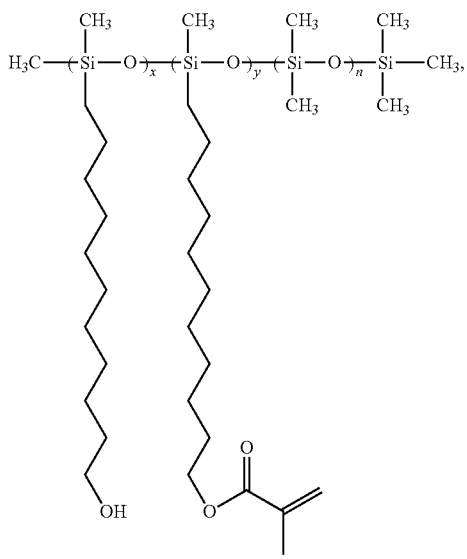

where m, n, x, and y are positive integers.

17. A method of making a composite material, the method comprising:
 providing a population of nanostructures, wherein the nanostructures have a polymeric ligand bound to a surface of the nanostructures, which ligand comprises a silicone backbone and one or more alcohol moieties coupled to the silicone backbone;
 incorporating the polymeric ligand into a silicone matrix in which the nanostructures are embedded;
 providing an excess of the polymeric ligand, which excess polymeric ligand is not bound to the surface of the nanostructures; wherein incorporating the polymeric ligand into the silicone matrix comprises incorporating the excess polymeric ligand and the polymeric ligand bound to the nanostructures into the silicone matrix; and
 wherein incorporating the polymeric ligand into the silicone matrix comprises providing a crosslinker and reacting the crosslinker with hydroxyl moieties on the ligand.

18. The method of claim 17, wherein the polymeric ligand comprises one or more dicarbinol moieties coupled to the silicone backbone.

19. A composite material produced by the method of claim 17.

20. A device comprising the composite material of claim 19.

21. A method of making a composite material, the method comprising:
 providing a population of nanostructures, wherein the nanostructures have a polymeric ligand bound to a surface of the nanostructures, which ligand comprises a silicone backbone and one or more alcohol moieties coupled to the silicone backbone;
 incorporating the polymeric ligand into a silicone matrix in which the nanostructures are embedded;
 providing an excess of the polymeric ligand, which excess polymeric ligand is not bound to the surface of the nanostructures; wherein incorporating the polymeric ligand into the silicone matrix comprises incorporating the excess polymeric ligand and the polymeric ligand bound to the nanostructures into the silicone matrix; and
 wherein the polymeric ligand comprises at least two different types of monomer units, at least one of which comprises the alcohol moiety and at least one of which lacks the alcohol moiety but comprises a polymerizable group or an epoxide group; wherein incorporating the polymeric ligand into the silicone matrix comprises reacting the polymerizable or epoxide groups on different molecules of the polymeric ligand with each other.

* * * * *